(12) United States Patent
Deonarain et al.

(10) Patent No.: US 8,703,427 B2
(45) Date of Patent: Apr. 22, 2014

(54) BIOLOGICAL MATERIALS AND USES THEREOF

(75) Inventors: Mahendra Deonarain, Surrey (GB); Gokhan Yahioglu, London (GB); Manpreet Bhatti, London (GB)

(73) Assignee: PhotoBiotics Limited, London (GB)

(*) Notice: Subject to any disclaimer, the term of this patent is extended or adjusted under 35 U.S.C. 154(b) by 730 days.

(21) Appl. No.: 12/089,406

(22) PCT Filed: Oct. 6, 2006

(86) PCT No.: PCT/GB2006/003733
§ 371 (c)(1),
(2), (4) Date: Sep. 23, 2008

(87) PCT Pub. No.: WO2007/042775
PCT Pub. Date: Apr. 19, 2007

(65) Prior Publication Data
US 2009/0053247 A1    Feb. 26, 2009

(30) Foreign Application Priority Data

Oct. 7, 2005    (GB) .................. 0520436.7

(51) Int. Cl.
*A61K 39/395*    (2006.01)
*A61K 47/00*    (2006.01)
*A61K 47/48*    (2006.01)
*A61K 49/00*    (2006.01)

(52) U.S. Cl.
USPC ...... 435/7.1; 424/178.1; 530/402; 530/391.1; 530/391.3

(58) Field of Classification Search
None
See application file for complete search history.

(56) References Cited

U.S. PATENT DOCUMENTS

| 4,803,170 | A | 2/1989 | Stanton et al. |
|---|---|---|---|
| 5,556,992 | A | 9/1996 | Gaboury et al. |
| 6,147,195 | A | 11/2000 | Scherz et al. |
| 7,655,753 | B2* | 2/2010 | Deonarain et al. ............ 530/350 |
| 2002/0137901 | A1 | 9/2002 | Cavanaugh |
| 2002/0197262 | A1* | 12/2002 | Hasan et al. ............... 424/178.1 |

FOREIGN PATENT DOCUMENTS

| EP | 0984282 | 3/2000 |
|---|---|---|
| WO | WO 88/04777 | 6/1988 |
| WO | 96/31237 | 10/1996 |
| WO | 01/08704 | 2/2001 |
| WO | 01/78606 | 10/2001 |
| WO | 02/067850 | 9/2002 |
| WO | 02/080754 A2 | 10/2002 |
| WO | WO 02/090361 | 11/2002 |
| WO | 02/100326 | 12/2002 |
| WO | 03/015825 | 2/2003 |
| WO | 2004/046151 | 6/2004 |
| WO | 2004/076461 | 9/2004 |
| WO | 2004/080284 A2 | 9/2004 |
| WO | 2005/030254 | 4/2005 |

OTHER PUBLICATIONS

The International Preliminary Report on Patentability for PCT/GB2006/003733, issued Apr. 9, 2008.*
Glazer et al., "Targeted MRI Contrast Agent Using Bioengineered scFv Fragments with Gadolinium Labelled Metal Binding Domain," Proc. Intl. Soc. Mag. Reson. Med., 2004, 11, p. 1713.*
Rajagopalan et al., "Targeted Type 1 phototherapeutic agents using azido-peptide bioconjugates," in Biomarkers and Biological Spectral Imaging, Eds. Bearman et al., 2001, pp. 129-132.*
Co et al., "Humanized antibodies for antiviral therapy," Proc. Natl. Acad. Sci., 1991, vol. 88, pp. 2869-2873.*
Affleck, K. et al., (1992). Br J Cancer 65, 838-844, Monoclonal antibody targeting of methotrexate (MTX) against MTX-resistant tumour cell lines.
Ahmad, N. et al., (1998) PNAS USA 95, 6977-6982, Photodynamic therapy results in induction of WAF1/CIP1/P21 leading to cell cycle arrest and apoptosis.
Akhlynina, TV. et al., (1997) J Biol Chem 272, 20328-20331, Nuclear targeting of chlorin e6 enhances its photosensitizing activity.
Ancey, C. et al., (2003) J Biol Chem 278, 16968-16972, A fusion protein of the gp130 and interleukin-6Ralpha ligand-binding domains acts as a potent interleukin-6 inhibitor.
Baas, P. et al., (1995) Lasers Surg Med 16, 359-367, Effect of N-acetylcysteine on Photofrin-induced skin photosensitivity in patients.
Batra et al., (2002) Curr Opin Biolechno 13, 603-608, Pharmacokinetics and biodistribution of genetically engineered antibodies.
Beers, R. et al., (Jul. 2000) Clin Cancer Res 6, 2835-2843, Immunotoxins with increased activity against epidermal growth factor receptor vIII-expressing cells produced by antibody phage display.
Begent, RH. et al., (1996. Nat Med 2, 979-984, Clinical evidence of efficient tumor targeting based on single-chain Fv antibody selected from a combinatorial library.
Better et al., (1988) Science 240, 1041-1043, *Escherichia coli* secretion of an active chimeric antibody fragment.
Binz, HK. et al., (2004) Nat Biolechnol. 22, 575-582, High-affinity binders selected from designed ankyrin repeat protein libraries.
Birchler, M. et al., (1999) Nat Biotechnol 17, 984-988, Selective targeting and photocoagulation of ocular angiogenesis mediated by a phage-derived human antibody fragment.
Bird et al., (1988) Science 242, 423-426, Single-Chain antigen-binding proteins.
Boehm, MK. et al., (2000) Biochem J 346, 519-528, Crystal structure of the anti-(carcinoembryonic antigen) single-chain Fv antibody MFE-23 and a model for antigen binding based on intermolecular contacts.
Bonifacino, JS. et al., (2003) Annu Rev Biochem 72, 395-447, Signals for sorting of transmembrane proteins to endosomes and lysosomes.
Borsi et al., (2003) Blood 102(13), 4384-92, Selective targeted delivery of TNFalpha to tumor blood vessels.
Boxer, GM. et al., (1994) Br J Cancer 69, 307-314, Localisation of monoclonal antibodies reacting with different epitopes on carcinoembryonic antigen (CEA)-implications for targeted therapy.
Brown, S. et al., (2004) Lancet Oncology 5, 497-508. The present and future rule of photodynamic therapy in cancer treatment.
Cavanaugh, PG. (2002) Breast Cancer Res Treat. 72, 117-130, Synthesis of chlorin e6-transferrin and demonstration of its light-dependent in vitro breast cancer cell killing ability.
Chen, SY. et al., (1995) Gene Ther 2, 116-123, Design of a genetic immunotoxin to eliminate toxin immunogenicity.

Cuenca, RE. et al., (2004) Annals Surg Oncol 11(3), 322-327, Breast cancer with chest wall progression: treatment with photodynamic therapy.
Dellinger, M. et al., (1996) Photochem Photobiol 64(1),182-187, Apoptosis or necrosis following Photofrin photosensitization: Influence of the incubation protocol.
Demidova, TN. et al., (2004) Pharmacol 17, 245-254, Photodynamic therapy targeted to pathogens.
Deonarain et al., (1997) Protein Eng 10(1), 89-98, Redesigned anti-human placental alkaline phosphatase single-chain Fv: soluble expression, characterization and in vivo tumour targeting.
Deonarain, MP. et al., (1998) Br J Cancer 77(4), 537-546, Design, characterization and anti-tumour cytotoxicity of a panel of recombinant, mammalian ribonuclease-based immunotoxins.
Dolmans, DE. et al., (2002) Cancer Res 62, 4289-4294, Targeting tumor vasculature and cancer cells in orthotopic breast tumor by fractionated photosensitizer dosing photodynamic therapy.
Dolmans et al., (May 2003) Nature Rev Cancer 3, 380-386, Photodynamic therapy for cancer.
Embleton, ML. et al., (2002) J Antimicrob Chemother 50, 857-864, Selective lethal photosensitization of methicillin-resistant *Staphylococcus aureus* using an IgG-tin(IV) chlorin e6 conjugate.
Enever, C. et al., (2005) J Mol Biol 347, 107-120, Engineering high affinity superantigens by phage display.
Epenetos, AA. et al., (Jun. 1986) Cancer Res 46, 3183-3191. Limitations of radiolabeled monoclonal antibodies for localization of human neoplasms.
Felici et al., (1995) Biotechnol Annual Rev 1, 149-183, Peptide and Protein Display on the Surface of Filamentous Bacteriophage.
Fiers, W. et al., (1999) Oncogene 18, 7719-7730, More than one way to die: apoptosis, necrosis and reactive oxygen damage.
Gangopadhyay, A. et al., (1996) Nucl Med Biol 23, 257-261, Modification of antibody isoelectric point affects biodistribution of 111-indium-labeled antibody.
Ghettie, V. et al.,. (1994) Pharmacol Ther 63, 209-234, Immunotoxins in the therapy of cancer: from bench to clinic.
Harris, M. (May 2004) Lancet Oncol 5, 292-302, Monoclonal antibodies as therapeutic agents for cancer.
Holliger et al., (Sep. 2005) Nature Biotechnology 23(9), 1126-1136, Engineered Antibody Fragments and the Rise of Single Domains.
Hoogenboom, HR. et al., (1991) Nucleic Acids Res 19(15), 4133-4137, Multi-subunit proteins on the surface of filamentous phage: methodologies for displaying antibody (Fab) heavy and light chains.
Hoogenboom, HR.. (Sep. 2005) Nature Biotechnology 23, 1105-1116, Selecting and screening recombinant antibody libraries.
Holt, LJ. et al., (Nov. 2003) Trends Biotechnol 21(11), 484-490, Domain antibodies: proteins for therapy.
Hopper, C. (Dec. 2000) Lancet Oncology 1, 212-219, Photodynamic therapy: a clinical reality in the treatment of cancer.
Hudson, PJ. (2000) Expert Opin Investig Drugs 9, 1231-1242, Recombinant antibodies: a novel approach to cancer diagnosis and therapy.
Hudson, R. et al., (2005) Br J Cancer 92, 1442-1449, The development and characterisation of porphyrin isothiocyanate-monoclonal antibody conjugates for photoimmunotherapy.
Huston et al., (Aug. 1988) Proc Natl Acad Sci USA 85, 5879-5883, Protein Engineering of antibody binding sites: Recovery of specific activity in an anti-digoxin single-chain Fv analogue produced in *Escherichia coli*.
Jager, HR. et al., (May 2005) AJNR Am J Neuroradiol 26, 1193-1200, MR imaging-guided interstitial photodynamic laser therapy for advanced head and neck tumors.
Katz, B. (1997) Annual Rev. Biophys Biomol Struct 26, 27-45, Structural and Mechanistic Determinants of Affinity and Specificity of Ligands Discovered by Engineered by Phage Display.
Kessel, D. et al., (2003) Photochem Photobiol 78(5), 431-435, Localization and photodynamic efficacy of two cationic porphyins varying in charge distributions.
Kim, JI. et al., (2005) J Neuroimmunol 158, 112-119, Simple and specific detection of abnormal prion protein by a magnetic bead-based immunoassay coupled with laser-induced fluorescence spectrofluorometry.
Khadem, J. et al., (Dec. 1999) Invest Ophthalmol Vis Sci 40(13), 3132-3137, Photodynamic tissue adhesion with chlorin(e6) protein conjugates.
Koide, A. et al., (1998) J Mol Biol. 284, 1141-1151, The fibronectin type III domain as a scaffold for novel binding proteins.
Korner, M. et al., (2005) Int J Cancer 115, 734-741, Neuropeptide Y receptors in renal cell carcinomas and nephroblastomas.
Koudinova et al., (2003) Int J Cancer 104, 782-789, Photodynamic Therapy with Pd-Bacteriopheophorbide (TOOKAD): Successful in vivo Treatment of Human Prostatic Small Cell Carcinoma Xenografts.
Kuby (2000) Immunology, 4th Ed. W. H. Freeman, p. 118, Combinatorial antibody diversity in humans and mice.
Harlow and Lane, 1990, Antibodies, p. 386-389, Epitope Mapping— Mapping by competition assay.
Leman, JA. et al., (2002) Expert Opin Bioi Ther 2, 45-53, Photodynamic therapy: applications in dermatology.
Li, Y. et al., (Mar. 2005) Nat Biotechnol 23(3), 349-354, Directed evolution of human T-cell receptors with picomolar affinities by phage display.
Linardou, H. et al., (2000) Int J Cancer 86, 561-569, A Recombinant Cytotoxic Chimera Based on Mammalian Deoxyribonuclease-I.
Lipschultz et al., (2000) Methods 20, 310-318, Experimental Design for Analysis of Complex Kinetics Using Surface Plasmon Resonance.
Little, M. et al., (2000) Immunol Today 21(8), 364-370, of mice and men: hybridoma and recombinant antibodies.
Lou, PJ. et al., (2004). Br J Cancer. 91, 441-446, Interstitial photodynamic therapy as salvage treatment for recurrent head and neck cancer.
Lutsenko, SV. et al., (1999) Tumour Biol 20, 218-224, Targeting phthalocyanines to tumor cells using epidermal growth factor conjugates.
McCafferty et al., (1990) Nature vol. 348, 552-554, Phage Antibodies: filamentous phage displaying antibody variable domains.
Meade, C. et al., (2004) Br J Opthal 88, 212-217, Photodynamic therapy with verteporfin is effective, but how big is its effect? Results of a systematic review.
Melnikova, VO. et al., (2000) Int J Cancer 88, 798-803, Enhancement of meta-tetrahydroxyphenylchlorin-sensitized photodynamic treatment on human tumor xenografts using a water-soluble vitamin E analogue, Trolox.
Milenic, DE. et al., (Jun. 2004) Nat Rev Drug Discov. 3, 488-499, Antibody-targeted radiation cancer therapy.
Mayo, GL. et al., (2003) Am J Opthalmol 136, 1151-1152, Antibody-targeted photodynamic therapy.
Moan, J. et al., (1992) Photochem Photobiol 55(6), 931-948, Photochemotherapy of cancer-experimental research.
Moriwaki, SI. et al., (2001) Photodermatol Photoimmunol Photomed. 17, 241-243, Analysis of photosensitivity in Japanese cancer-bearing patients receiving photodynamic therapy with porfimer sodium (Photofrin™).
Murrer, LH. et al., (1999) Br J Cancer 80(5/6), 744-755, Short- and long-term normal tissue damage with photodynamic therapy in pig trachea: a fluence-response pilot study comparing Photofrin and mTHPC.
Nseyo, UO. et al., (Jul. 1998) J Urol. 160, 39-44, Photodynamic therapy using porfimer sodium as an alternative to cystectomy in patients with refractory transitional cell carcinoma in situ of the bladder.
Oseroff et al., (Nov. 1986) Proc. Natl. Acad. Sci. USA 83: 8744-8748, Antibody-targeted photolysis: Selective photodestruction of human T-cell leukemia cells using monoclonal antibody-chlorin $e_6$ conjugates.
Oseroff et al., (1987) Photochemistry and Photobiology 46(1), 83-96, Strategies for Selective Cancer Photochemotherapy: Antibody-Targeted and Selective Carcinoma Cell Photolysis.
Pasqualini, R. et al., (Jun. 1997) Nat Biotechnol. 15, 542-546, αv Integrins as receptors for tumor targeting by circulating ligands.
Pericleous, LM. et al., (2005) Br J Cancer. 93 pp. 1257-1266, Characterisation and internalisation of recombinant humanised HMFG-I antibodies against MUCI.

Pfitzner, A. et al., (Oct. 2004). J Periodontol. 75(10), 1343-1349, Killing of periodontopathogenic bacteria by photodynamic therapy.
Polo, L. et al., (1992) Cancer Letters 66, 217-223, The distribution of the tumour photosensitizers Zn(II)-phthalocyanine and Sn (IV)-etiopurpurin among rabbit plasma proteins.
Press, OW. et al., (Dec. 2000) Semin Oncol vol. 27 No. 6 Suppl 12, 62-73, Principles of Radioimmunotherapy for hematologists and oncologists.
Renno, RZ. et al., (Jul. 2004) Arch Opthalmol 122, 1002-1011, Selective photodynamic therapy by targeted verteporfin delivery to experimental choroidal neovascularization mediated by a homing peptide to vascular endothelial growth factor receptor-2.
Rosenkranz, A. et al., (2000) Immunol and Cell Biol 78, 452-464, Targeted intracellular delivery of photosensitizers to enhance photodynamic efficiency.
Rusckowski, M. et al., (1997) J Pept Res 50, 393-401, Technetium-99m labeled epidermal growth factor-tumor imaging in mice.
Savellano, MD. et al., (Jul. 2005) Cancer Res 65, 6371-6379, Multiepitope Her2 targeting enhances photoimmunotherapy of Her2' expressing cancer cells with pyropheophorbide-a immunoconjugates.
Savellano, MD. et al., (Feb. 2005) Clin Cancer Res 11, 1658-1668, Photochemical targeting of epidermal growth factor receptor: a mechanistic study.
Schlehuber, S. et al., (Sep. 2001) Biol Chem 382, 1335-1342, Duocalins: engineered ligand-binding proteins with dual specificity derived from the lipocalin fold.
Schmidt-Erfurth, U. et al., (Oct. 1999) Arch Ophthalmo. 117, 1329-1345, Photodynamic Therapy of Subfoveal Choroidal Neovascularization in Age-Related Macular Degeneration with Verteporfin.
Schneider, R. et al., (2005) Bioorgan Med Chem 13, 2799-2808, Design, synthesis, and biological evaluation of folic acid targeted tetraphenylporphyrin as novel photosensitizers for selective photodynamic therapy.
Skerra et al., (1988) Science 240, 1038-1041, Assembly of a Functional Immunoglobulin Fv Fragment in *Escherichia coli*.
Smith (1985) Science 228, 1315-1317, Filamentous Fusion Phage: Novel Expression Vectors That Display Cloned Antigens on the Virion Surface.
Soukos, NS. et al., (2001) Proceedings of SPIE, 4259, 115, Biomarkers and Biological Spectral imaging, Eds. Bearman GH, Levenson RM and Bornhop DJ, Monoclonal antibody tagged receptor targeted contrast agents for detection of cancer.
van Dongen, G. et al., (2004) Adv Drug Del Rev 56, 31-52, Photosensitizer-antibody conjugates for detection and therapy of cancer.
van Nostrum (2004) Advances in Drug Delivery Rev. 56, 9-16, Polymeric micelles to deliver photosensitizers for photodynamic therapy.
Vasserot, AP. et al., (Feb. 2003) Drug Discovery Today 8, 118-126, Optimization of protein therapeutics by directed evolution.
Verhaar, MJ. et al., (1995) Int J Cancer 61, 497-501, A single chain Fv derived from a filamentous phage library has distinct tumor targeting advantages over one derived from a hybridoma.
Vrouenraets, MS. et al., (Apr. 1999) Cancer Res 59, 1505-1513, Development of meta-tetrahydroxypheneylchlorin-monoclonal antibody conjugates for photoimmunotherapy.
Vrouenraets, MB. et al., (2000) Int J Cancer 88, 108-114, Targeting of a hydrophilic photosensitizer by use of internalizing monoclonal antibodies: A new possibility for use in photodynamic therapy.
Vrouenraets, MB. et al., (Mar. 2001) Cancer Research 61 , 1970-1975, Targeting pf aluminum (III) phthalocyanine tetrasulfonate by use of internalizing monoclonal antibodies: Improved efficacy in photodynamic therapy.
Wagnieres, G. et al., (1998) Photochem Photobiol. 68(3), 382-387, Clinical evaluation of the cutaneous phototoxicity of 5,10,15,20-tetra (m-hydroxyphenyl)chlorin.
Ward et al., (1989) Nature 341, 544-546, Binding activities of a repertoire of single immunoglobulin variable domains secreted from *Escherichia coli*.
Ward, ES., (1992) FASEB J 6, 2422-2427, Antibody engineering: the use of *Escherichia coli* as an expression host.
Sambrook et al., (1990) Molecular Cloning Protocol 25, Preparation and Transformation of Competent *E. coli* using Calcium Chloride.
Weissleder, R. et al, (1999) Nat Biotechnol 17, 375-378, In vivo imaging of tumors with protease-activated nearinfrared fluorescent probes.

Westerman, P. et al., (1998) Int J Cancer 76, 842-850, Long circulating half-life and high tumor selectivity of the photosensitizer meta-tetrahydroxyphenylchlorin conjugated to polyethylene glycol in nude mice grafted with a human colon carcinoma.
Wu, AM. et al., (Sep. 2005) Nature Biotechnology 23, 1137-1146, Arming antibodies: Prospects and challenges for Immunoconjugates.
Wyss, P. et al., (2001) Int J Cancer 93, 720-724, Photodynamic therapy of locoregional breast cancer recurrences using a chlorin-type photosensitizer.
Yamaguchi, A. et al., (Jun. 2001) Transplantation 71(11), 1526-1532, Photodynamic therapy with motexafin lutetium (Lu-Tex) reduces experimental graft coronary artery disease.
Yamamoto et al., (Oct. 1999) Current Science 77(7), 894-903, Photodynamic therapy for cancers.
Harlow et al., (Eds) Antibodies A Laboratory Manual; Cold Spring Harbor Laboratory; Cold Spring Harbor, N.Y. (1988), Chapter 6 Staining Tissues.
Steward, et al., Price & Sikora (eds) Treatment of Cancer Chapman & Hall 1995 Chapter 7 Principles of Chemotherapy.
Malatesi et al, (2006), "Synthesis and in vitro investigation of cationic 5,15-diphenyl porphyrin-monoclonal antibody conjugates as targeted Photodynamic Sensitisers", International Journal of Oncology 28, pp. 1561-1569.
Bedel-Cloutour et al, (1991), "Synthesis of a monoclonal antibody-indium-111-porphyrin conjugate", Journal of Immunological Methods 144, pp. 35-41.
Roberts et al, (1987), "Preparation and Characterization of Copper-67 Porphyrin-Antibody Conjugates", Journal of Immunological Methods 105, pp. 153-164.
Carey and Sundberg, "Advanced Organic Chemistry, Part A, Fifth Edition", published 2007 by Springer Sciences, pp. 358-376.
Reichardt "Solvents and Solvent Effects in Organic Chemistry, Third Edition", published 2003 by Wiley-VCH, pp. 38-42.
Savellano et al., "Targeting Cells that Overexpress the Epidermal Growth Factor . . . Photosensitizer Immunoconjugates", Photochemistry and Photobiology, 2003, 77(4): 431-439.
Satoh et al., The Effect of Organic Solvents on Rabbit Antibody, Biochimica et Biophysica Acts 115, 455-463, 1966.
Chin et al., Communication to the Editor on Protein Solubility in Organic Solvents; Biotechnology and Bioengineering 44, 140-145, 1994.
Solvent Miscibility Table, Phenomenex HPLC Column Protection Guide Version 0610, 2010.
Reichardt, C.; Welton, T.; Solvents and Solvent Effects in Organic Chemistry, 4th ed. Dec. 6, 2010, pp. 75-83, Appendix A.1, and Table A-10.
Appendix 1: supplementary co-solvent solubility . . . , cited by Deonarain et al. in EP06794684.8 & JP2008-534076 both deriving from PCT/GB06/03733, priority dates of Oct. 7, 2005.
Hackbarth et al., (2001) Photophysical properties of pheophorbide-a-substituted diaminobutane poly-propylene-imine dendrimer. Chemical Physics, 269:339-346.
Haugland, R., (2000); Antibodies as cell biological tools. Current Protocols in Cell Biology, 16.5.1-16.5.22.
Rajagopalan et al., (2001) Biomarkers and Biological Spectral Imaging 4259:129-132.
Boyle, R.W., et al., Structure and biodistribution relationships of photodynamic sensitizers. Photochemistry and Photobiology, 1996, 64(3): 469-485 .
Campo, M.A., et al., Polymeric photosensitizer prodrugs for photodynamic therapy. Photochemistry and Photobiology, 2007, 83: 958-965.
Carcenac, M., et al., Internalisation enhances photo-induced cytotoxicity of monoclonal antibody-phthalocyanine conjugates. British Journal of Cancer, 2001, 85(11), 1787-1793.
Cho, H., et al., Structure of the extracellular region of HER2 alone and in complex with the Herceptin Fab. Nature, Feb. 13, 2003, vol. 421, pp. 756-760.
Hackbarth, S., et al., Interaction of pheophorbide a molecules covalently linked to DAB dendrimers. Optics Communications 248(2005) 295-306.
Li, S., et al., Structural basis for inhibition of the epidermal growth factor receptor by cetuximab. Cancer Cell, Apr. 2005, vol. 7, pp. 301-311.
RCSB Protein Data Bank, 1N8Z structure summary: Crystal structure of extracellular domain of human HER2 complexed with Herceptin Fab, Oct. 14, 2013.

RCSB Protein Data Bank, 1YY8 structure summary: Crystal structure of the Fab fragment from the monoclonal antibody cetuximab/Erbitux/IMC-C225, Oct. 14, 2013.
Rae, M., et al., Fluorescence quenching with exponential distance dependence: Application to the external heavy-atom effect. J. Chem. Phys, Jul. 22, 2003, vol. 119(4):2223-2231.
Soukos, N.S., et al., Epidermal growth factor receptor-targeted immunophotodiagnosis and photoimmunotherapy of oral precancer in vivo, Cancer Res 2001; 61:4490-4496.
Price et al., Exploring Proteins: a student's guide to experimental skills and methods.Oxford University Press, 2009, Chap 1.4 The Secondary Structure of Proteins, p. 23.
Thermo Fisher Scientific GmbH, Thermoscientific application note TI-PEP08-0708, copyright 2008.

\* cited by examiner

*Primary Examiner* — Shafiqul Haq
*Assistant Examiner* — Galina Yakovleva
(74) *Attorney, Agent, or Firm* — Ryan Kromholz & Manion, S.C.

(57) ABSTRACT

The invention provides a compound comprising a photosensitizing agent coupled to a carrier molecule with a minimum coupling ratio of 3:1 wherein the carrier molecule has a binding specificity for a target cell. There is also provided a process of conjugation comprising the use of a first and second aprotic solvent and uses of the conjugated compounds.

Figure 1:
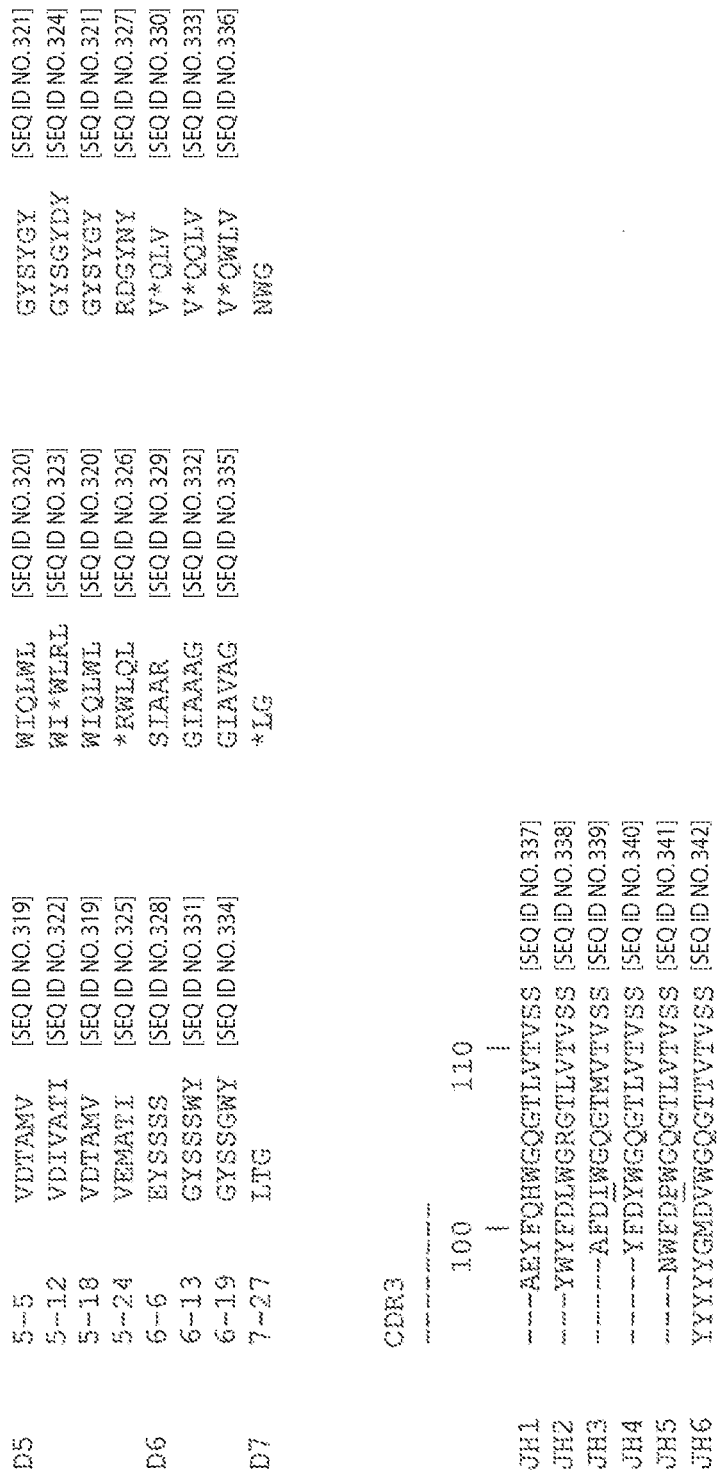

|  | H1-H2 | Locus | FR1<br>1         2         3<br>12345678901234567890 |
|---|---|---|---|
| VH1 | 1-3 | 1-02 | QVQLVQSGAEVKKPGASVKVSCKASGYTFT |
|  | 1-3 | 1-03 | QVQLVQSGAEVKKPGASVKVSCKASGYTFT |
|  | 1-3 | 1-08 | QVQLVQSGAEVKKPGASVKVSCKASGYTFT |
|  | 1-2 | 1-18 | QVQLVQSGAEVKKPGASVKVSCKASGYTFT |
|  | 1-U | 1-24 | QVQLVQSGAEVKKPGASVKVSCKVSGYTLT |
|  | 1-3 | 1-45 | QMQLVQSGAEVKKTGSSVKVSCKASGYTFT |
|  | 1-3 | 1-46 | QVQLVQSGAEVKKPGASVKVSCKASGYTFT |
|  | 1-3 | 1-58 | QMQLVQSGPEVKKPGTSVKVSCKASGFTFT |
|  | 1-2 | 1-69 | QVQLVQSGAEVKKPGSSVKVSCKASGGTFS |
|  | 1-2 | 1-e | QVQLVQSGAEVKKPGSSVKVSCKASGGTFS |
|  | 1-2 | 1-f | EVQLVQSGAEVKKPGATVKISCKVSGYTFT |
| VH2 | 3-1/2-1 | 2-05 | QITLKESGPTLVKPTQTLTLTCTFSGFSLS |
|  | 3-1 | 2-26 | QVTLKESGPVLVKPTETLTLTCTVSGFSLS |
|  | 3-1 | 2-70 | QVTLKESGPALVKPTQTLTLTCFSCFSLS |
| VH3 | 1-3 | 3-07 | EVQLVESGGGLVQPGGSLRLSCAASGFTFS |
|  | 1-3 | 3-09 | EVQLVESGGGLVQPGRSLRLSCAASGFTFD |
|  | 1-3 | 3-11 | QVQLVESGGGLVKPGGSLRLSCAASGFTFS |
|  | 1-1 | 3-13 | EVQLVESGGSLVQPGGSLRLSCAASGFTFS |
|  | 1-U | 3-15 | EVQLVESGGGLVKPGGSLRLSCAASGFTFS |
|  | 1-3 | 3-20 | EVQLVFSGGSVVRPGGSLRLSCAASGFTFD |
|  | 1-3 | 3-21 | EVQLVESGGGLVKPGGSLRLSCAASGFTFS |
|  | 1-3 | 3-23 | EVQLLESGGGLVQPGGSLRLSCAASGFTFS |
|  | 1-3 | 3-30 | QVQLVESSGGVVQPGRSLRLSCAASGFTFS |
|  | 1-3 | 3-30.3 | QVQLVESGGGVVQPGRSLRLSCAASGFTFS |
|  | 1-3 | 3-30.5 | QVQLVESGGGVVQPGRSLRLSCAASGFTFS |

|  | H1-H2 | Locus | CDR1<br>1ab2345 | FR2<br>4<br>67890123456789 |
|---|---|---|---|---|
| VH1 | 1-3 | 1-02 | G--YYMH | WVRQAPGQGLEWMG |
|  | 1-3 | 1-03 | S--YAMH | WVRQAPGQRLEWMG |
|  | 1-3 | 1-08 | S--YDIN | WVRQATGQGLEWMG |
|  | 1-2 | 1-18 | S--YGIS | WVRQAPGQGLEWMG |
|  | 1-U | 1-24 | E--LSMH | WVRQAPGKGLEWMG |
|  | 1-3 | 1-45 | Y--RYLH | WVRQAPGQALEWMG |
|  | 1-3 | 1-46 | S--YYMH | WVRQAPGQGLEWMG |
|  | 1-3 | 1-58 | S--SAVQ | WVRQARGQRLEWIG |
|  | 1-2 | 1-69 | S--YAIS | WVRQAPGQGLEWMG |
|  | 1-2 | 1-e | S--YAIS | WVRQAPGQGLEWMG |
|  | 1-2 | 1-f | D--YYMH | WVQQAPGKGLEWMG |
| VH2 | 3-1/2-1 | 2-05 | TSGVGVG | WIRQPPGKALEWLA |
|  | 3-1 | 2-26 | NARMGVS | WIRQPPGKALEWLA |
|  | 3-1 | 2-70 | TSGMRVS | WIRQPPGKALEWLA |
| VH3 | 1-3 | 3-07 | S--YWMS | WVRQAPGKGLEWVA |
|  | 1-3 | 3-09 | D--YAMH | WVRQAPGKGLEWVS |
|  | 1-3 | 3-11 | D--YYMS | WIRQAPGKGLEWVS |
|  | 1-1 | 3-13 | S--YDMH | WVRQATGKGLEWVS |
|  | 1-U | 3-15 | N--AWMS | WVRQAPGKGLEWVG |
|  | 1-3 | 3-20 | D--YGMS | WVRQAPGKGLEWVS |
|  | 1-3 | 3-21 | S--YSMN | WVRQAPGKGLEWVS |
|  | 1-3 | 3-23 | S--YAMS | WVRQAPGKGLEWVS |
|  | 1-3 | 3-30 | S--YGMH | WVRQAPGKGLEWVA |
|  | 1-3 | 3-30.3 | S--YAMH | WVRQAPGKGLEWVA |
|  | 1-3 | 3-30.5 | S--YGMH | WVRQAPGKGLEWVA |

16 Claims, 42 Drawing Sheets

| | Locus | FR1<br>1         2         3<br>1234567890123456789012345678901234567890 | CDR1<br>1ab2345 | FR2<br>4<br>67890123456789 |
|---|---|---|---|---|
| VH1 H1-H2 | | | | |
| 1-3 | 1-02 | QVQLVQSGARVKKPGASVKVSCKASGYTFT [SEQ ID NO.11] | G---YYMH [SEQ ID NO.12] | WVRQAPGQGLEWMG [SEQ ID NO.13] |
| 1-3 | 1-03 | QVQLVQSGAEVKKPGASVKVSCKASGYTFT [SEQ ID NO.14] | S---YAMH [SEQ ID NO.15] | WVRQAPGQRLEWMG [SEQ ID NO.16] |
| 1-3 | 1-08 | QVQLVQSGAEVKKPGASVKVSCKASGYTFT [SEQ ID NO.17] | S---YDIN [SEQ ID NO.18] | WVRQATGQGLEWMG [SEQ ID NO.19] |
| 1-2 | 1-18 | QVQLVQSGAEVKKPGASVKVSCKVSGYTFT [SEQ ID NO.20] | S---YGIS [SEQ ID NO.21] | WVRQAPGQGLEWMG [SEQ ID NO.22] |
| 1-0 | 1-24 | QVQLVQSGAEVKKPGASVKVSCKVSGYTLT [SEQ ID NO.23] | E---LSMH [SEQ ID NO.24] | WVRQAPGQALEWMG [SEQ ID NO.25] |
| 1-3 | 1-45 | QMQLVQSGAEVKKTGSSVKVSCKASGYTFT [SEQ ID NO.26] | Y---RYLH [SEQ ID NO.27] | WVRQAPGQGLEWMG [SEQ ID NO.28] |
| 1-3 | 1-46 | QVQLVQSGAEVKKPGASVKVSCKASGYTFT [SEQ ID NO.29] | S---YYMH [SEQ ID NO.30] | WVRQAPGQGLEWMG [SEQ ID NO.31] |
| 1-3 | 1-58 | QMQLVQSGPEVKKPGTSVKVSCKASGFTFT [SEQ ID NO.32] | S---SAVQ [SEQ ID NO.33] | WVRQARGQRLEWIG [SEQ ID NO.34] |
| 1-2 | 1-69 | QVQLVQSGAEVKKPGSSVKVSCKASGGTFS [SEQ ID NO.35] | S---YAIS [SEQ ID NO.36] | WVRQAPGQGLEWMG [SEQ ID NO.37] |
| 1-2 | 1-e | QVQLVQSGAEVKKPGSSVKVSCKASSGTFS [SEQ ID NO.38] | S---YAIS [SEQ ID NO.39] | WVQQAPGKGLEWMG [SEQ ID NO.40] |
| 1-2 | 1-f | EVQLVQSGAEVKKPGATVKISCKVSGYTFT [SEQ ID NO.41] | D---YYMH [SEQ ID NO.42] | WVQQAPGKGLEWLA [SEQ ID NO.43] |
| VH2 3-1/2-1 | 2-05 | QITLKESGPTLVKPTQTLTLTCTFSGFSLS [SEQ ID NO.44] | TSGVGVG [SEQ ID NO.45] | WIRQPPGKALEWLA [SEQ ID NO.46] |
| 3-1 | 2-26 | QVQLQESGPVLVKPTETLTLTCTVSGFSLS [SEQ ID NO.47] | NARMGVS [SEQ ID NO.48] | WIRQPPGKALEWLA [SEQ ID NO.49] |
| 3-1 | 2-70 | QVTLKESGPALVKPTQTLTLTCTFSGFSLS [SEQ ID NO.50] | TSGMRVS [SEQ ID NO.51] | WVRQPPGKGLEWVS [SEQ ID NO.52] |
| VH3 1-3 | 3-07 | EVQLVESGGGLVQPGGSLRLSCAASGFTFS [SEQ ID NO.53] | S---YWMS [SEQ ID NO.54] | WVRQAPGKGLEWVS [SEQ ID NO.55] |
| 1-3 | 3-09 | EVQLVESGGGLVQPGRSLRLSCAASGFTFD [SEQ ID NO.56] | D---YAMH [SEQ ID NO.57] | WVRQAPGKGLEWVS [SEQ ID NO.58] |
| 1-3 | 3-11 | QVQLVESGGGLVKPGGSLRLSCAASGFTFS [SEQ ID NO.59] | D---YYMS [SEQ ID NO.60] | WIRQAPGKGLEWVS [SEQ ID NO.61] |
| 1-1 | 3-13 | EVQLVESGGGLVKPGGSLRLSCAASGFTFS [SEQ ID NO.62] | S---YDMH [SEQ ID NO.63] | WVRQATGKGLEWVS [SEQ ID NO.64] |
| 1-0 | 3-15 | EVQLVESGGGLVKPGGSLRLSCAASGFTFS [SEQ ID NO.65] | N---AWMS [SEQ ID NO.66] | WVRQAPGKGLEWVG [SEQ ID NO.67] |
| 1-3 | 3-20 | EVQLVESGGGLVQPGGSLRLSCAASGFTFD [SEQ ID NO.68] | D---YGMS [SEQ ID NO.69] | WVRQAPGKGLEWVS [SEQ ID NO.70] |
| 1-3 | 3-21 | EVQLVESGGGLVKPGGSLRLSCAASGFTFS [SEQ ID NO.71] | S---YSMN [SEQ ID NO.72] | WVRQAPGKGLEWVS [SEQ ID NO.73] |
| 1-3 | 3-23 | EVQLLESGGGLVQPGGSLRLSCAASGFTFS [SEQ ID NO.74] | S---YAMS [SEQ ID NO.75] | WVRQAPGKGLEWVS [SEQ ID NO.76] |
| 1-3 | 3-30 | QVQLVESGGGVVQPGRSLRLSCAASGFTFS [SEQ ID NO.77] | S---YGMH [SEQ ID NO.78] | WVRQAPGKGLEWVA [SEQ ID NO.79] |
| 1-3 | 3-30.3 | QVQLVESGGGVVQPGRSLRLSCAASGFTFS [SEQ ID NO.80] | S---YAMH [SEQ ID NO.81] | WVRQAPGKGLEWVA [SEQ ID NO.82] |
| 1-3 | 3-30.5 | QVQLVESGGGVVQPGRSLRLSCAASGFTFS [SEQ ID NO.83] | S---YGMH [SEQ ID NO.84] | WVRQAPGKGLEWVA [SEQ ID NO.85] |

*Figure 1*

| | | | |
|---|---|---|---|
| | 1-3 | QVQLVESGGGVVQPGRSLRLSCAASGFTFS [SEQ ID NO.86] | S---YGMH [SEQ ID NO.87] WVRQAPGKGLEWVA [SEQ ID NO.88] |
| | 3-33 | EVQLVESGGGVVQPGGSLRLSCAASGFTED [SEQ ID NO.89] | D---YTMH [SEQ ID NO.90] WVRQAPGKGLEWVS [SEQ ID NO.91] |
| | 3-43 | EVQLVESGGGLVQPGGSLRLSCAASGFTFS [SEQ ID NO.92] | S---YSMN [SEQ ID NO.93] WVRQAPGKGLEWVS [SEQ ID NO.94] |
| | 3-48 | EVQLVESGGGLVQPGRSLRLSCTASGFTFG [SEQ ID NO.95] | D---YAMS [SEQ ID NO.96] WFRQAPGKGLEWVG [SEQ ID NO.97] |
| | 3-49 | EVQLVETGGGLIQPGGSLRLSCAASGFTVS [SEQ ID NO.98] | S---NYMS [SEQ ID NO.99] WVRQAPGKGLEWVS [SEQ ID NO.100] |
| | 3-53 | EVQLVESGGGLVQPGGSLRLSCAASGFTES [SEQ ID NO.101] | S---YAMH [SEQ ID NO.102] WVRQAPGKGLEYVS [SEQ ID NO.103] |
| | 3-64 | EVQLVESGGGLVQPGGSLRLSCAASGFTVS [SEQ ID NO.104] | S---NYMS [SEQ ID NO.105] WVRQAPGKGLEWVS [SEQ ID NO.106] |
| | 3-66 | EVQLVESGGGLVQPGGSLRLSCAASGFTFS [SEQ ID NO.107] | D---HYMD [SEQ ID NO.108] WVRQAPGKGLEWVG [SEQ ID NO.109] |
| | 3-72 | EVQLVESGGGLVQPGGSLKLSCAASGFTFS [SEQ ID NO.110] | G---SAMH [SEQ ID NO.111] WVRQASGKGLEWVG [SEQ ID NO.112] |
| | 3-73 | EVQLVESGGGLVQPGGSLRLSCAASGFTFS [SEQ ID NO.113] | S---YWMH [SEQ ID NO.114] WVRQAPGKGLVWVS [SEQ ID NO.115] |
| | 3-74 | EVQLVESRGGLVQPGGSLRLSCAASGFTVS [SEQ ID NO.116] | S---NEMS [SEQ ID NO.117] WVRQAPGKGLEWVS [SEQ ID NO.118] |
| | 3-d | QVQLQESGPGLVKPSGTLSLTCAVSGGSIS [SEQ ID NO.119] | SS-NWWS [SEQ ID NO.120] WVRQPPGKGLEWIG [SEQ ID NO.121] |
| VH4 | 2-1/1-1 | QVQLQESGPGLVKPSDTLSLTCAVSGGYSIS [SEQ ID NO.122] | SS-NWWG [SEQ ID NO.123] WIRQPPGKGLEWIG [SEQ ID NO.124] |
| | 4-04 | QVQLQESGPGLVKPSQTLSLTCTVSGGSIS [SEQ ID NO.125] | SGGYYWS [SEQ ID NO.126] WIRQHPGKGLEWIG [SEQ ID NO.127] |
| | 4-28 | QLQLQESGPGLVRPSQTLSLTCAVSGGSIS [SEQ ID NO.128] | SGGYSWS [SEQ ID NO.129] WIRQPPGKGLEWIG [SEQ ID NO.130] |
| | 4-30.1 | QVQLQESGPGLVKPSQTLSLTCTVSGGSIS [SEQ ID NO.131] | SGDYYWS [SEQ ID NO.132] WIRQPPGKGLEWIG [SEQ ID NO.133] |
| | 4-30.2 | QVQLQESGPGLVKPSETLSLTCTVSGGSFS [SEQ ID NO.134] | SGGYWS [SEQ ID NO.135] WIRQHPGKGLEWIG [SEQ ID NO.136] |
| | 4-30.4 | QLQLQQWGAGLLKPSETLSLTCAVYGGSFS [SEQ ID NO.137] | G---YWS [SEQ ID NO.138] WIRQPPGRGLEWIG [SEQ ID NO.139] |
| | 4-31 | QVQLQESGPGLVRPSETLSLTCTVSGGSIS [SEQ ID NO.140] | SSSYYWG [SEQ ID NO.141] WIRQPPGKGLEWIG [SEQ ID NO.142] |
| | 4-34 | QVQLQESGPGLVKPSETLSLTCTVSGGSIS [SEQ ID NO.143] | S---YYWS [SEQ ID NO.144] WIRQPPGKGLEWIG [SEQ ID NO.145] |
| | 4-39 | QVQLQESGPGLVKPSETLSLTCTVSGGSVS [SEQ ID NO.146] | SGGYYWS [SEQ ID NO.147] WIRQPPGKGLEWIG [SEQ ID NO.148] |
| | 4-59 | QVQLQESGPGLVKPSETLSLTCAVSGYSIS [SEQ ID NO.149] | SG-YYWG [SEQ ID NO.150] WIRQPPGKGLEWIG [SEQ ID NO.151] |
| | 4-61 | EVQLVQSGAEVKKPGESLKISCKGSGYSGYETT [SEQ ID NO.152] | S---YWIG [SEQ ID NO.153] WVRQMPGKGLEWMG [SEQ ID NO.154] |
| | 4-b | EVQLVQSGAEVKKPGESLRISCKGSGYSFT [SEQ ID NO.155] | S---YWIS [SEQ ID NO.156] WVRQMPGKGLEWMG [SEQ ID NO.157] |
| VH5 | 5-51 | QVQLVQSGSELKKPGASVKVSCKASGYIFT [SEQ ID NO.158] | SNSAAWN [SEQ ID NO.159] WIRQSPSRGLEWLG [SEQ ID NO.160] |
| VH6 | 1-2 | QVQLVQSGSELKKPGASVKVSCKASGYTFT [SEQ ID NO.161] | | |
| VH7 | 3-5 | | S---YAMN [SEQ ID NO.162] WVRQAPGQGLEWMG [SEQ ID NO.163] |

*Figure 1 (cont'd)*

Figure 1 (cont'd)

| | | | CDR2 | | FR3 | | |
|---|---|---|---|---|---|---|---|
| | | | 5     6<br>012abc3456789012345 | | 678901234567890123456789012abc345678901234<br>7     8     9 | | |
| VH1 | 1-3 | 1-02 | WINP---NSGGTNYAQKFQG | [SEQ ID NO.164] | RVTMTRDTSISTAYMELSRLRSDDTAVYYCAR | [SEQ ID NO.165] |
| | 1-3 | 1-03 | WINA---GNGNTKYSQKFQG | [SEQ ID NO.166] | RVTITRDTSASTAYMELSSLRSEDTAVYYCAR | [SEQ ID NO.167] |
| | 1-3 | 1-08 | WMNP---NSGNTGYAQKFQG | [SEQ ID NO.168] | RVTMTRNTSISTAYMELSLRSEDTAVYYCAR | [SEQ ID NO.169] |
| | 1-2 | 1-18 | WISA---YNGNTNYAQKLQG | [SEQ ID NO.170] | RVTMTTDTSTSTAYMELRSLRSDDTAVYYCAR | [SEQ ID NO.171] |
| | 1-U | 1-24 | GFDP---EDGETIYAQKFQG | [SEQ ID NO.172] | RVTMTEDTSDTAYMELSSLRSEDTAVYYCAT | [SEQ ID NO.173] |
| | 1-3 | 1-45 | WITP---FMGNTNYAQKFQD | [SEQ ID NO.174] | RVTITRDRSMSTAYMELSSLRSEDTAMYYCAR | [SEQ ID NO.175] |
| | 1-3 | 1-46 | LINP---SGGSTSYAQKFQG | [SEQ ID NO.176] | RVTMTRDTSTSTVMELSSLRSEDTAVYYCAR | [SEQ ID NO.177] |
| | 1-3 | 1-58 | WIVV---GSCNTNYAQKFQE | [SEQ ID NO.178] | RVTMTRDMSTSTAYMELSSLRSEDTAVYYCAR | [SEQ ID NO.179] |
| | 1-2 | 1-69 | GIIP---IFGTANIAQKFQG | [SEQ ID NO.180] | RVTITADESTSTAYMELSSLRSEDTAVYYCAR | [SEQ ID NO.181] |
| | 1-2 | 1-e | GIIP---IFGTANYAQKFQG | [SEQ ID NO.182] | RVTITADKSTSTAYMELSSLRSEDTAVYYCAR | [SEQ ID NO.183] |
| | 1-2 | 1-e | LVDP---EDGETIYAEKFQG | [SEQ ID NO.184] | RVTIIADTSDTAYMELSSLRSEDTAVYYCAT | [SEQ ID NO.185] |
| VH2 | 3-1/2-1 | 2-05 | LIY-----WNDDKRYSPSLKS | [SEQ ID NO.186] | RLTITKDTSKNQVVLTMTNMDEVDTATYYCAR | [SEQ ID NO.187] |
| | 3-1 | 2-26 | HIF-----SMDEKSYSTSLKS | [SEQ ID NO.188] | RLTISKDTSKSQVVLTMTNMDPVDTATYYCARI | [SEQ ID NO.189] |
| | 3-1 | 2-70 | RID-----WDDKFYSTSLKT | [SEQ ID NO.190] | RLTISKDTSKNQVVLIMTNMDPVDTATYYCARI | [SEQ ID NO.191] |
| VH3 | 1-3 | 3-07 | NIKQ----DGSEKYYVDSVKG | [SEQ ID NO.192] | RFTISRDNAKNSLYLQMNSLRAEDTAVYYCAR | [SEQ ID NO.193] |
| | 1-3 | 3-09 | GISW----NSGSIGYADSVKG | [SEQ ID NO.194] | RFTISRDNAKNSLYLQMNSLRAEDTALYYCAKD | [SEQ ID NO.195] |
| | 1-3 | 3-11 | VISS----SGSTIYYADSVKG | [SEQ ID NO.196] | RFTISRDNAKNSLYLQMNSLRAEDTAVYYCAR | [SEQ ID NO.197] |
| | 1-1 | 3-13 | AIG-----TAGDTYYPGSVKG | [SEQ ID NO.198] | RFTISRENAKNSLYLQMNSLRAGDTAVYYCAR | [SEQ ID NO.199] |
| | 1-U | 3-15 | RIKSKTDGGTTDYAAPVKG | [SEQ ID NO.200] | RFTISRDDSKNTLYLQMNSLKTEDTAVYYCTT | [SEQ ID NO.201] |
| | 1-3 | 3-20 | GINW----NGGSTGYADSVKG | [SEQ ID NO.202] | RFTISRDNAKNSLYLQMNSLRAEDTALYFCAR | [SEQ ID NO.203] |
| | 1-3 | 3-21 | SISS----SSSYIYYADSVKG | [SEQ ID NO.204] | RFTISRDNAKNSLYLQMNSLRAEDTAVYYCAR | [SEQ ID NO.205] |

*Figure 1 (cont'd)*

| | | | | | |
|---|---|---|---|---|---|
| 1-3 | 3-23 | AISG----SGGSTYYADSVKG | [SEQ ID NO.206] | RFTISRDNSKNTLYLQMNSLRAEDTAVYYCAK | [SEQ ID NO.207] |
| 1-3 | 3-30 | VISY----DGSNKYYADSVKG | [SEQ ID NO.208] | RFTISRDNSKNTLYLQMNSLRAEDTAVYYCAK | [SEQ ID NO.209] |
| 1-3 | 3-30.3 | VISY----DGSNKYYADSVKG | [SEQ ID NO.210] | RFTISRDNSKNTLYLQMNSLRAEDTAVYYCAR | [SEQ ID NO.211] |
| 1-3 | 3-30.5 | VISY----DGSNKYYADSVKG | [SEQ ID NO.212] | RFTISRDNSKNTLYLQMNSLRAEDTAVYYCAR | [SEQ ID NO.213] |
| 1-3 | 3-33 | VIWY----DGSNKYYADSVKG | [SEQ ID NO.214] | RFTISRDNSKNTLYLQMNSLRTEDTALYYCAR | [SEQ ID NO.215] |
| 1-3 | 3-43 | LISW----DGGSTYYADSVKG | [SEQ ID NO.216] | RFTISRDNSKNSLYLQMNSLRTEDTAVYYCAK | [SEQ ID NO.217] |
| 1-3 | 3-48 | YISS----SSSTIYYADSVKG | [SEQ ID NO.218] | RFTISRDNAKNSLNLQMNSLRDEDTAVYYCAR | [SEQ ID NO.219] |
| 1-0 | 3-49 | FIRSKAYGGTTEYTASVKG | [SEQ ID NO.220] | RFTISRDGSKSIAYLQMNSLKTEDTAVYYCTR | [SEQ ID NO.221] |
| 1-1 | 3-53 | VIY-----SGGSTYYADSVKG | [SEQ ID NO.222] | RFTISRDNSKNTLYLQMNSLRAEDTAVYYCAR | [SEQ ID NO.223] |
| 1-3 | 3-64 | AISS----NGGSTYYAMSVKG | [SEQ ID NO.224] | RFTISRDNSKNTLYLQMGSLRAEDMAVYYCAR | [SEQ ID NO.225] |
| 1-1 | 3-66 | VIY-----SGGSTYYADSVKG | [SEQ ID NO.226] | RFTISRDNSKNTLYLQMNSLRAEDTAVYYCAR | [SEQ ID NO.227] |
| 1-4 | 3-72 | RTRNKANSYTTEYAASVKG | [SEQ ID NO.228] | RFTISRDDSKNSLYLQMMSLKTEDTAVYYCAR | [SEQ ID NO.229] |
| 1-4 | 3-73 | RIRSKANSYATAYAASVKG | [SEQ ID NO.230] | RFTISRDDSKNTAYLQMNSLKTEDTAVYYCTR | [SEQ ID NO.231] |
| 1-3 | 3-74 | RINS----DGGSTYYADSVKG | [SEQ ID NO.232] | RFTISRDNAKMTLHLQMNSLRAEDTAVYYCKK | [SEQ ID NO.233] |
| 1-6 | 3-d | SI------SGGSTYYADSVRG | [SEQ ID NO.234] | RFTISRDNSKNTLHLQMNSLRAEDTAVYYCKK | [SEQ ID NO.235] |
| VH4 2-1/1-1 | 4-04 | EIY-----HSGSTNYNPSLKS | [SEQ ID NO.236] | RVTISVDKSKNQFSLKLSSVTAADTAVYYCAR | [SEQ ID NO.237] |
| 2-1 | 4-28 | YIY-----YSGSTYYNPSLKS | [SEQ ID NO.238] | RVTISVDTSKNQFSLKLSSVTAVDTAVYYCAR | [SEQ ID NO.239] |
| 3-1 | 4-30.1 | YIY-----HSGSTYYNPSLKS | [SEQ ID NO.240] | RVTMSVDTSKNQFSLKLSSVTAADTAVYYCAR | [SEQ ID NO.241] |
| 3-1 | 4-30.2 | YIY-----YSGSTYYNPSLKS | [SEQ ID NO.242] | RVTISVDRSKNQFSLKLSSVTAADTAVYYCAR | [SEQ ID NO.243] |
| 3-1 | 4-30.4 | YIY-----YSGSTYYNPSLKS | [SEQ ID NO.244] | RVTISVDTSKNQFSLKLSSVTAADTAVYYCAR | [SEQ ID NO.245] |
| 1-1 | 4-31 | YIY-----YSGSTYYNPSLKS | [SEQ ID NO.246] | RVTISVDTSKNQFSLKLSSVTAADTAVYYCAR | [SEQ ID NO.247] |
| 1-1 | 4-34 | EIN-----HSGSTNYNPSLKS | [SEQ ID NO.248] | RVTISVDTSKNQFSLKLSSVTAADTAVYYCAR | [SEQ ID NO.249] |
| 3-1 | 4-39 | SIY-----YSGSTNYNPSLKS | [SEQ ID NO.250] | RVTISVDTSKNQFSLKLSSVTAADTAVYYCAR | [SEQ ID NO.251] |
| 1-1 | 4-59 | YIY-----YSGSTYYNPSLKS | [SEQ ID NO.252] | RVTISVDTSKNQFSLKLSSVTAADTAVYYCAR | [SEQ ID NO.253] |
| 3-1 | 4-61 | YIY-----YSGSTYYNPSLKS | [SEQ ID NO.254] | RVTISVDTSKNQFSLKLSSVTAADTAVYYCAR | [SEQ ID NO.255] |
| 2-1 | 4-b | SIY-----HSGSTYYNPSLKS | [SEQ ID NO.256] | RVTISVDTSKNQFSLKLSSVTAADTAVYYCAR | [SEQ ID NO.257] |

*Figure 1 (con't)*

```
VH5  1-2   5-51   SIY---HSGSTYYNPSLKS  [SEQ ID NO.258]  RVTISVDTSKNQFSLKLSSVTAADTAVYYCAR  [SEQ ID NO.259]
     1-2   5-8    IIYP---GDSDTRYSPSFQG [SEQ ID NO.260]  QVTISADKSISTAYLQWSSLKASDTAMYYCAR  [SEQ ID NO.261]
VH6  3-5   6-01   RIDP---SDSYTNYSPSFQG [SEQ ID NO.262]  HVTISADKSISTAYLQWSSLKASDTAMYYCAR  [SEQ ID NO.263]
VH7  1-2   7-4.1  RTYYR--SKWYNDIAVSVKS [SEQ ID NO.264]  RITINPDTSKNQFSLQLNSVTEDTAVYYCAR   [SEQ ID NO.265]
                  WINT---NTGNPTYAQGFTG [SEQ ID NO.266]  RFVESLDTSVSTAYLQICSLKAEDTAVYYCAR  [SEQ ID NO.267]
```

```
        RF 1                              RF 2                       RF 3
D1  1-1   GTTGT   [SEQ ID NO.268]   VQLER    [SEQ ID NO.269]   YNWND     [SEQ ID NO.270]  [SEQ ID NO.271]
    1-7   GIYGT   [SEQ ID NO.271]   V*LEL    [SEQ ID NO.272]   YNWNY     [SEQ ID NO.273]
    1-20  GITGT   [SEQ ID NO.274]   V*LER    [SEQ ID NO.275]   YNWND     [SEQ ID NO.276]
    1-26  GIVGAT  [SEQ ID NO.277]   V*WELL   [SEQ ID NO.278]   YSGSYY    [SEQ ID NO.279]
D2  2-2   RIL**YQLLY [SEQ ID NO.280] GYCSSTSCYT [SEQ ID NO.281] DIVVVPAAI [SEQ ID NO.282]
    2-8   RILY*WCMLY [SEQ ID NO.283] GYCTNGVCYT [SEQ ID NO.284] DIVLMVYAI [SEQ ID NO.285]
    2-15  RIL*WW*LLL [SEQ ID NO.286] GYCSGGSCYS [SEQ ID NO.287] DIVVVVAAT [SEQ ID NO.288]
    2-21  SILWW*ILE  [SEQ ID NO.289] AYCGGDCYS  [SEQ ID NO.290] HIVVVTAI  [SEQ ID NO.291]
D3  3-3   VLRFLEWLLY [SEQ ID NO.292] YYDFWSGYVT [SEQ ID NO.293] ITIFGVVII [SEQ ID NO.294]
    3-9   VLRYFDWLL* [SEQ ID NO.295] YYDILTGYYN [SEQ ID NO.296] IYIF*LVII [SEQ ID NO.297]
    3-10  VLLWFGELL* [SEQ ID NO.298] YYYGSGSYYN [SEQ ID NO.299] TTMVRGVII [SEQ ID NO.300]
    3-16  VL*LRLGELSLY [SEQ ID NO.301] YYDYVWGSYRYT [SEQ ID NO.302] EMITFGGSYIVI [SEQ ID NO.303]
    3-22  VLL***WLLL [SEQ ID NO.304] YYYDSSGYYY [SEQ ID NO.305] ITMIVVVIT [SEQ ID NO.306]
D4  4-4   *LQ*L   [SEQ ID NO.307]   DYSNY    [SEQ ID NO.308]   TTVT      [SEQ ID NO.309]
    4-11  *LQ*L   [SEQ ID NO.310]   DYSNY    [SEQ ID NO.311]   IYVT      [SEQ ID NO.312]
    4-17  *LR*L   [SEQ ID NO.313]   DYGDY    [SEQ ID NO.314]   TTVT      [SEQ ID NO.315]
    4-23  *LRW*L  [SEQ ID NO.316]   DYGGNS   [SEQ ID NO.317]   ETVVT     [SEQ ID NO.318]
```

*Figure 1 (con't)*

Figure 1 (con't)

| | | | FR1 | | CDR1 | | FR2 | |
|---|---|---|---|---|---|---|---|---|
| | | | 1 2 | | 3 | | 4 | |
| | | | 1234567890123456789012 3 | | 4567890labcdef234 | | 567890123456789 | |
| VK1 | L1-L2-L3 | Locus | | | | | | |
| | 2-1-(1) | O12 | DIQMTQSPSSLSASVGDRVTITC | [SEQ ID NO.343] | RASQSISS-------YLN | [SEQ ID NO.344] | WYQQKPGKAPKLLIY | [SEQ ID NO.345] |
| | 2-1-(1) | O2 | DIQMTQSPSSLSASVGDRVTITC | [SEQ ID NO.346] | RASQSISS-------YLN | [SEQ ID NO.347] | WYQQKPGKAPKLLIY | [SEQ ID NO.348] |
| | 2-1-(1) | O18 | DIQMTQSPSSLSASVGDRVTITC | [SEQ ID NO.349] | QASQDISN-------YLN | [SEQ ID NO.350] | WYQQKPGKAPKLLIY | [SEQ ID NO.351] |
| | 2-1-(1) | O8 | DIQMTQSPSSLSASVGDRVTITC | [SEQ ID NO.352] | QASQDISN-------YLN | [SEQ ID NO.353] | WYQQKPGKAPKLLIY | [SEQ ID NO.354] |
| | 2-1-(0) | A20 | DIQMTQSPSSLSASVGDRVTITC | [SEQ ID NO.355] | RASQGISN-------YLA | [SEQ ID NO.356] | WYQQKPGKAPKLLIY | [SEQ ID NO.357] |
| | 2-1-(1) | A30 | DIQMTQSPSSLSASVGDRVTITC | [SEQ ID NO.258] | RASQGIRN-------DLG | [SEQ ID NO.259] | WYQQKPGKVPKLLIY | [SEQ ID NO.260] |
| | 2-1-(1) | L14 | NIQMTQSPSAMSASVGDRVTITC | [SEQ ID NO.361] | RASQGISN-------YLA | [SEQ ID NO.362] | WFQQKPGKVPKLLIY | [SEQ ID NO.363] |
| | 2-1-(1) | L1 | DIQMTQSPSSLSASVGDRVTITC | [SEQ ID NO.364] | RARQGISN-------YLA | [SEQ ID NO.365] | WYQQKPGKAPKSLIY | [SEQ ID NO.366] |
| | 2-1-(1) | L15 | AIQLTQSPSSLSASVGDRVTITC | [SEQ ID NO.367] | RASQGISS-------WLA | [SEQ ID NO.368] | WYQQKPGKAPKLLIY | [SEQ ID NO.369] |
| | 2-1-(1) | L4 | AIQLTQSPSSLSASVGDRVTITC | [SEQ ID NO.370] | RASQGISS-------ALA | [SEQ ID NO.371] | WYQQKPGKAPKLLIY | [SEQ ID NO.372] |
| | 2-1-(1) | L18 | AIQLTQSPSSLSASVGDRVTITC | [SEQ ID NO.373] | RASQGISS-------ALA | [SEQ ID NO.374] | WYQQKPGKAPKLLIY | [SEQ ID NO.375] |
| | 2-1-(1) | L5 | DIQMTQSPSSVSASVGDRVTITC | [SEQ ID NO.376] | RASQGISS-------WLA | [SEQ ID NO.377] | WYQQKPGKAPKLLIY | [SEQ ID NO.378] |
| | 2-1-(1) | L19 | DIQMTQSPSSVSASVGDRVTITC | [SEQ ID NO.379] | RASQGISS-------WLA | [SEQ ID NO.380] | WYQQKPGKAPKLLIY | [SEQ ID NO.381] |
| | 2-1-(1) | L8 | DIQLTQSPSFLSASVGDRVTITC | [SEQ ID NO.382] | WASQGISS-------YLA | [SEQ ID NO.383] | WYQQKPGKAPKLLIY | [SEQ ID NO.384] |
| | 2-1-(1) | L23 | AIRMTQSPFSLSASVGDRVTITC | [SEQ ID NO.385] | RASQGISS-------YLA | [SEQ ID NO.386] | WYQQKPAKAPKLFTY | [SEQ ID NO.387] |
| | 2-1-(1) | L9 | AIRMTQSPSSFSASTGDRVTITC | [SEQ ID NO.388] | RASQGISS-------YLA | [SEQ ID NO.389] | WYQQKPGKAPELLIY | [SEQ ID NO.390] |
| | 2-1-(1) | L24 | VIWMTQSPSLLSASTGDRVTITC | [SEQ ID NO.391] | RMSQGISS-------YLA | [SEQ ID NO.392] | WYQQKPGKAPELLIY | [SEQ ID NO.393] |
| | 0-1-(1) | L11 | AIQMTQSPSSLSASVGDRVTITC | [SEQ ID NO.394] | RASQGIRN-------DLG | [SEQ ID NO.395] | WYQQKPGKAPKLLIY | [SEQ ID NO.396] |
| | 2-1-(0) | L12 | DIQMTQSPSTLSASVGDRVTITC | [SEQ ID NO.397] | RASQSISS-------WLA | [SEQ ID NO.398] | WYQQKPGKAPKLLIY | [SEQ ID NO.399] |

*Figure 1 (con't)*

| | | | | | |
|---|---|---|---|---|---|
| VKII | O11 | 3-1-(1) | DIVMTQTPLSLPVTPGEPASISC [SEQ ID NO.400] | RSSQSLLDSDGNTYLD [SEQ ID NO.401] | WYLQKPGQSPQLLIY [SEQ ID NO.402] |
| | O1 | 3-1-(1) | DIVMTQTPLSLPVTPGEPASISC [SEQ ID NO.403] | RSSQSLLDSDGNTYLD [SEQ ID NO.404] | WYLQKPGQSPQLLIY [SEQ ID NO.405] |
| | A17 | 4-1-(1) | DVVMTQSPLSLPVTLGQPASISC [SEQ ID NO.406] | RSSQSLVYS-DGNTYLN [SEQ ID NO.407] | WHQQRPGQSPRRLIY [SEQ ID NO.408] |
| | A1 | 4-1-(1) | DVVMTQSPLSLPVTLGQPASISC [SEQ ID NO.409] | RSSQSLVYS-DGNTYLN [SEQ ID NO.410] | WFQQRPGQSPRRLIY [SEQ ID NO.411] |
| | A18 | 4-1-(1) | DIVMTQTPLSLSVTPGQPASISC [SEQ ID NO.412] | KSSQSLLHS-DGKTYLY [SEQ ID NO.413] | WYLQKPGQSPQLLIY [SEQ ID NO.414] |
| | A2 | 4-1-(1) | DIVMTQTPLSLSVTPGQPASISC [SEQ ID NO.415] | KSSQSLLHS-DGKTYLY [SEQ ID NO.416] | WYLQKPGQPFQLLIY [SEQ ID NO.417] |
| | A19 | 4-1-(1) | DIVMTQSPLSLPVTPGEPASISC [SEQ ID NO.418] | RSSQSLLHS-MGYNYLD [SEQ ID NO.419] | WYLQKPGQSPQLLIY [SEQ ID NO.420] |
| | A3 | 4-1-(1) | DIVMTQSPLSLPVTPGEPASISC [SEQ ID NO.421] | RSSQSLLHS-NGYNYLD [SEQ ID NO.422] | WYLQKPGQSPQLLIY [SEQ ID NO.423] |
| | A23 | 4-1-(1) | DIVMTQTPLSSPVTLGQPASISC [SEQ ID NO.424] | RSSQSLVHS-DGNTYLS [SEQ ID NO.425] | WLQQRPGQPPRRLIY [SEQ ID NO.426] |
| VKIII | A27 | 6-1-(1) | EIVLTQSPGTLSLSPGERATLSC [SEQ ID NO.427] | RASQSVSS------YLA [SEQ ID NO.428] | WYQQKPGQAPRLLIY [SEQ ID NO.429] |
| | A11 | 6-1-(1) | EIVLTQSPATLSLSPGERATLSC [SEQ ID NO.430] | GASQSVSS------YLA [SEQ ID NO.431] | WYQQKPGQAPRLLIY [SEQ ID NO.432] |
| | L2 | 2-1-(1) | EIVMTQSPATLSVSPGERATLSC [SEQ ID NO.433] | RASQSVSS------NLA [SEQ ID NO.434] | WYQQKPGQAPRLLIY [SEQ ID NO.435] |
| | L16 | 2-1-(1) | EIVMTQSPATLSVSPGERATLSC [SEQ ID NO.436] | RASQSVSS------NLA [SEQ ID NO.437] | WYQQKPGQAPRLLIY [SEQ ID NO.438] |
| | L6 | 2-1-(1) | EIVLTQSPATLSLSPGERATLSC [SEQ ID NO.439] | RASQSVGS------YLA [SEQ ID NO.440] | WYQQKPGQAPRLLIY [SEQ ID NO.441] |
| | L20 | 2-1-(0) | EIVMTQSPATLSLSPGERATLSC [SEQ ID NO.442] | RASQGVSS------YLA [SEQ ID NO.443] | WYQQKPGQAPRLLIY [SEQ ID NO.444] |
| | L25 | 6-1-(1) | EIVLTQSPATLSLSPGERATLSC [SEQ ID NO.445] | RASQSVSS------YLS [SEQ ID NO.446] | WYQQKPGQAPRLLIY [SEQ ID NO.447] |
| VKIV | B3 | 3-1-(1) | DIVMTQSPDSLAVSLGERATINC [SEQ ID NO.448] | KSSQSVLYSSNNKNYLA [SEQ ID NO.449] | WYQQKPGQPPKLLIY [SEQ ID NO.450] |
| VKV | B2 | 3-1-(1) | ETTLTQSPAFMSATPGDKVNISC [SEQ ID NO.451] | KASQDIDD------DMN [SEQ ID NO.452] | WYQQKPGEAAIFIIQ [SEQ ID NO.453] |
| VKVI | A26 | 2-1-(1) | EIVLTQSPDFQSPDEQSVTEKEKVTITC [SEQ ID NO.454] | RASQSIGS------SIH [SEQ ID NO.455] | WYQQKPDQSPKLLIK [SEQ ID NO.456] |
| | A10 | 2-1-(1) | EIVLTQSPDFQSVTPKEKVTITC [SEQ ID NO.457] | RASQSIGS------SLH [SEQ ID NO.458] | WYQQKPDQSPKLLIK [SEQ ID NO.459] |
| | A14 | 2-1-(1) | DVVMTQSPAFLSVTPGEKVTITC [SEQ ID NO.460] | QASEGIGN------YLY [SEQ ID NO.461] | WYQQKPDQAPKLLIK [SEQ ID NO.462] |

*Figure 1 (con't)*

*Figure 1 (con't)*

|  | L1-L2-L3 | Locus | CDR2<br>5<br>0123456 |  | FR3<br>6 7 8<br>7890123456789012345678901234567 8 |  | CDR3<br>9<br>9012345 |  |
|---|---|---|---|---|---|---|---|---|
| VKI | 2-1-(1) | O12 | AASSLQS | [SEQ ID NO.463] | GVPSRFSGSGSGTDFTLTISSLQPEDFATYYC | [SEQ ID NO.464] | QQSYSTP | [SEQ ID NO.465] |
|  | 2-1-(1) | O2 | AASSLQS | [SEQ ID NO.466] | GVPSRFSGSGSGTDFTLTISSLQPEDEATYYC | [SEQ ID NO.467] | QQSYSTP | [SEQ ID NO.468] |
|  | 2-1-(1) | O18 | DASNLET | [SEQ ID NO.469] | GVPSRFSGSGSGTDFTFTISSLQPEDIATYYC | [SEQ ID NO.470] | QQYDNLP | [SEQ ID NO.471] |
|  | 2-1-(1) | O8 | DASNLET | [SEQ ID NO.472] | GVPSRFSGSGSGTDFTFTISSLQPEDIATYYC | [SEQ ID NO.473] | QQYDNLP | [SEQ ID NO.474] |
|  | 2-1-(0) | A20 | AASTLQS | [SEQ ID NO.475] | GVPSRFSGSGSGTDFTLTISSLQREDVATYYC | [SEQ ID NO.476] | QKYNSAP | [SEQ ID NO.477] |
|  | 2-1-(1) | A30 | AASSLQS | [SEQ ID NO.478] | GVPSRFSGSGSGTDFTLTISSLQPEDFATYYC | [SEQ ID NO.479] | LQHNSYP | [SEQ ID NO.480] |
|  | 2-1-(1) | L14 | AASSLQS | [SEQ ID NO.481] | GVPSRFSGSGSGSGTEFTLTISSLQPEDFATYYC | [SEQ ID NO.482] | LQHNSYP | [SEQ ID NO.483] |
|  | 2-1-(1) | L1 | AASSLQS | [SEQ ID NO.484] | GVPSRFSGSGSGSGTDFTLTISSLQPEDFATYYC | [SEQ ID NO.485] | QQYNSYP | [SEQ ID NO.486] |
|  | 2-1-(1) | L15 | DASSLES | [SEQ ID NO.487] | GVPSRFSGSGSGTDFTLTISSLQPEDFATYYC | [SEQ ID NO.488] | QQYNSYP | [SEQ ID NO.489] |
|  | 2-1-(1) | L4 | DASSLES | [SEQ ID NO.490] | GVPSRFSGSGSGTDFTLTISSLQPEDFATYYC | [SEQ ID NO.491] | QQFNSYP | [SEQ ID NO.492] |
|  | 2-1-(1) | L18 | DASSLES | [SEQ ID NO.493] | GVPSRFSGSGSGTDFTLTITISSLQPEDEATYYC | [SEQ ID NO.494] | QQENSYP | [SEQ ID NO.495] |
|  | 2-1-(1) | L5 | AASSLQS | [SEQ ID NO.496] | GVPSRFSGSGSGTDFTLTISSLQPEDFATYYC | [SEQ ID NO.497] | QQANSFP | [SEQ ID NO.498] |
|  | 2-1-(1) | L19 | AASTLQS | [SEQ ID NO.499] | GVPSRFSGSGSGTDFTLTISSLQPEDFATYYC | [SEQ ID NO.500] | QQANSFP | [SEQ ID NO.501] |
|  | 2-1-(1) | L8 | YASSLQS | [SEQ ID NO.502] | GVPSRFSGSGSGSGTDYTFTISSLQPEDFATYYC | [SEQ ID NO.503] | QQHNSYP | [SEQ ID NO.504] |
|  | 2-1-(1) | L23 | AASSLQS | [SEQ ID NO.505] | GVPSRFSGSGSGTDFTLTISCLQSEDFATYYC | [SEQ ID NO.506] | QQYYSTP | [SEQ ID NO.507] |
|  | 2-1-(1) | L9 | AASSLQS | [SEQ ID NO.508] | GVPSRFSGSGSGTDFTLTISSLQPEDFATYYC | [SEQ ID NO.509] | QQYSYP | [SEQ ID NO.510] |
|  | 0-1-(0) | L24 | AASTLQS | [SEQ ID NO.511] | GVPSRFSGSGSGTDFTLTISCLQSEDFATYYC | [SEQ ID NO.512] | QQYYSEP | [SEQ ID NO.513] |
|  | 2-1-(1) | L11 | AASSLQS | [SEQ ID NO.514] | GVPSRFSGSGSGTDFTLTISSLQPEDFATYYC | [SEQ ID NO.515] | LQDYNYP | [SEQ ID NO.516] |
|  | 2-1-(0) | L12 | DASSLES | [SEQ ID NO.517] | GVPSRHSGSGSGTEFTLTISSLQPDDFATYYC | [SEQ ID NO.518] | QQYNSYS | [SEQ ID NO.519] |

| Group | Clone | | CDR-L2 | SEQ ID NO | Framework | SEQ ID NO | CDR-L3 | SEQ ID NO |
|---|---|---|---|---|---|---|---|---|
| VKII | O11 | 3-1-(1) | TLSYRAS | 520 | GVPDRFSGSGSGTDFTLKISRVEAEDVGVYYC | 521 | MQRIEFP | 522 |
| | O1 | 3-1-(1) | TLSYRAS | 523 | GVPDRFSGSGSGTDFTLKISRVEAEDVGVYYC | 524 | MQRIEFP | 525 |
| | A17 | 4-1-(1) | KVSNRDS | 526 | GVPDRFSGSGSGTDFTLKISRVEAEDVGVYYC | 527 | MQGTHWP | 528 |
| | A1 | 4-1-(1) | KVSNWDS | 529 | GVPDRFSGSGSGTDFTLKISRVEAEDVGVYYC | 530 | MQGTHWP | 531 |
| | A18 | 4-1-(1) | EVSSRFS | 532 | GVPDRFSGSGSGTDFTLKISRVEAEDVGVYYC | 533 | MQGIHLP | 534 |
| | A2 | 4-1-(1) | EVSNRFS | 535 | GVPDRFSGSGSGTDFTLKISRVEAEDVGVYYC | 536 | MQSIQLP | 537 |
| | A19 | 4-1-(1) | LGSNRAS | 538 | GVPDRFSGSGSGTDFTLKISRAEDVGVYYC | 539 | MQALQTP | 540 |
| | A3 | 4-1-(1) | LGSNRAS | 541 | GVPDRFSGSGSGTDFTLKISRVEAEDVGVYYC | 542 | MQALQTP | 543 |
| | A23 | 4-1-(1) | KISNRFS | 544 | GVPDRFSGSGSGAGTDFTLKISRVEAEDVGVYYC | 545 | MQATQEP | 546 |
| VKIII | A27 | 6-1-(1) | GASSRAT | 547 | GIPDRFSGSGSGTDFTLTISRLEPEDFAVYYC | 548 | QQYGSSP | 549 |
| | A11 | 6-1-(1) | DASSRAT | 550 | GIPDRFSGSGSGTDFTLTISRLEPEDFAVYYC | 551 | QQIGSSP | 552 |
| | L2 | 2-1-(1) | GASTRAT | 553 | GIPARFSGSGSGTEFTLTISSLQSEDFAVYYC | 554 | QQYNNWP | 555 |
| | L16 | 2-1-(1) | GASTRAT | 556 | GIPARFSGSGSGTEFTLTISSLQSEDFAVYYC | 557 | QQYNNWP | 558 |
| | L6 | 2-1-(1) | DASNRAT | 559 | GIPARFSGSGSGTDFTLTISSLEPEDFAVYYC | 560 | QQRSNWH | 561 |
| | L20 | 2-1-(0) | DASNRAT | 562 | GIPARFSGSGSGTDFTLTISSLEPEDFAVYYC | 563 | QQRSNWP | 564 |
| | L25 | 6-1-(1) | GASTRAT | 565 | GIPARFSGSGSGPGTDFTLTISSLQPEDFAVYYC | 566 | QQDVNLP | 567 |
| VKIV | B3 | 3-2-(1) | WASTRES | 568 | GVPDRFSGSGSGTDFTLTISSLQAEDVAVYYC | 569 | QQYYSTP | 570 |
| VKV | B2 | 2-1-(1) | EATLLVP | 571 | GIPDRFSGSGYGTDFTLIIMNIESEDAAYYFC | 572 | LQHDNFP | 573 |
| VKVI | A26 | 2-1-(1) | YASQSFS | 574 | GVPSRFSGSGSGSGTDFTLTINSLEAEDAATYYC | 575 | HQSSLFP | 576 |
| | A10 | 2-1-(1) | YASQSFS | 577 | GVPSRFSGSGSGSGTDFTLTINSLEAEDAATYYC | 578 | HQSSLFP | 579 |
| | A14 | 2-1-(1) | YASQSIS | 580 | GVPSRFSGSGSGTDFTFTISSLEAEDAATYYC | 581 | QQGNKHP | 582 |

*Figure 1 (con't)*

L3

CDR3
---|
 100
 |

JK1 WTFGQGTKVEIK [SEQ ID NO.583]
JK2 VTFGQGTKLEIK [SEQ ID NO.584]
JK3 FTFGPGTKVDIK [SEQ ID NO.585]
JK4 LTFGGGTKVEIK [SEQ ID NO.586]
JK5 ITFGQGTRLEIK [SEQ ID NO.587]

```
                                       FR1                              CDR1                          FR2
                       -----------------------------------    ----------------------    -----------------------
                                         2                              3                        4
           CDR1-2 Locus 123456789012345678901234567890123    4567890123456789abc234    567890123456789
    VL1    13-7(A)  1a  QSVLTQPPSVSEAPRQRVTISC[SEQ ID NO.588]  SGSSSNIGNM-AVN[SEQ ID NO.589]  WYQQLPGKAPKLLIY[SEQ ID NO.590]
           14-7(A)  1e  QSVLTQPPSVSGAPGQRVTISC[SEQ ID NO.591]  TGSSSNIGAGYDVH[SEQ ID NO.592]  WYQQLPGTAPKLLIY[SEQ ID NO.593]
           13-7(A)  1c  QSVLTQPPSASGTPGQRVTISC[SEQ ID NO.594]  SGSSSNIGSN-TVN[SEQ ID NO.595]  WYQQLPGTAPKLLIY[SEQ ID NO.596]
           13-7(A)  1g  QSVLTQPPSASGTPGQRVTISC[SEQ ID NO.597]  SGSSSNIGSN-YVY[SEQ ID NO.598]  WYQQLPGTAPKLLIY[SEQ ID NO.599]
           13-7(A)  1b  QSVLTQPPSVSAAPGQKVTISC[SEQ ID NO.600]  SGSSSNIGNN--YVS[SEQ ID NO.601]  WYQQLPGTAPKLLIY[SEQ ID NO.602]
    VL2    14-7(A)  2c  QSALTQPPSASGSPGQSVTISC[SEQ ID NO.603]  TGTSSDVGGYNYVS[SEQ ID NO.604]  WYQQHPGKAPKLMIY[SEQ ID NO.605]
           14-7(A)  2e  QSALTQPPSRSVSGSPGQSVTISC[SEQ ID NO.606] TGTSSDVGGYNYVS[SEQ ID NO.607]  WYQQHPGKAPKLMIY[SEQ ID NO.608]
           14-7(A)  2a2 QSALTQPASVSGSPGQSVTISC[SEQ ID NO.609]  TGTSSDVGSYNYVS[SEQ ID NO.610]  WYQQHPGKAPKLMIY[SEQ ID NO.611]
           14-7(A)  2d  QSALTQPPSASGSPGQSVTISC[SEQ ID NO.612]  TGTSSDVGSYNRVS[SEQ ID NO.613]  WYQQPPGTAPKLMIY[SEQ ID NO.614]
           14-7(A)  2b2 QSALHQPASVSGGSPGQSTTISC[SEQ ID NO.615] TGTSSDVGGYNLVS[SEQ ID NO.616]  WYQQHPGKAPKLMIY[SEQ ID NO.617]
```

*Figure 1 (con't)*

| | | | | |
|---|---|---|---|---|
| VL3 | 11-7 | 3r | SYELTQPPSVSVSPGQTASITC [SEQ ID NO.618] | SG-DK-LGDK-YAC [SEQ ID NO.619] | WYQQKPGQSPVLVIY [SEQ ID NO.620] |
| | 11-7 | 3j | SYELTQPLSVSVSVALGQTARITC [SEQ ID NO.621] | GG-NN-IGSK-NVH [SEQ ID NO.622] | WYQQKPGQAPVLVIY [SEQ ID NO.623] |
| | 11-7 | 3p | SYELTQPPSVSVSPGQTARITC [SEQ ID NO.624] | SG-DA-LPKK-YAY [SEQ ID NO.625] | WYQQKSGQAPVLVIY [SEQ ID NO.626] |
| | 11-7 | 3a | SYELTQPPSVSVSLGQMARITC [SEQ ID NO.627] | SG-EA-LPKK-YAY [SEQ ID NO.628] | WYQQKPGQEPPVLVIY [SEQ ID NO.629] |
| | 11-7 | 3i | SSELTQDPAVSVALGQTVRITC [SEQ ID NO.630] | QG-DS-LRSY-YAS [SEQ ID NO.631] | WYQQKPGQAPVLVLY [SEQ ID NO.632] |
| | 11-7 | 3h | SYVLTQPPSVSVAPGKTARITC [SEQ ID NO.633] | GG-NN-IGSK-SVH [SEQ ID NO.634] | WYQQKPGQAPVLVIY [SEQ ID NO.635] |
| | 11-7 | 3e | SYELTQLPSVSVSPGGTARITC [SEQ ID NO.636] | SG-DV-LGEM-YAD [SEQ ID NO.637] | WYQQKPGQAPELVIY [SEQ ID NO.638] |
| | 11-7 | 3m | SYELMQPPSVSVSPGQTARITC [SEQ ID NO.639] | SG-DA-LPKQ-YAY [SEQ ID NO.640] | WYQQKPGQAPVLVIY [SEQ ID NO.641] |
| | 11-7 | 2-19 | SYELTQPPSVSVSPGQTAMITC [SEQ ID NO.642] | SG-DV-LAKK-YAR [SEQ ID NO.643] | WFQQKPGQAPVLVIY [SEQ ID NO.644] |
| VL4 | 12-11 | 4c | LPVLTQPPSASALLGASIKLTC [SEQ ID NO.645] | TLSSEHSTY---TIE [SEQ ID NO.646] | WYQQRPGRSPQYIMK [SEQ ID NO.647] |
| | 12-11 | 4a | QPVLTQSSSASASIGSSVKLTC [SEQ ID NO.648] | TLSSGHSSY---IIA [SEQ ID NO.649] | WHQLQPGKAFPRYLMK [SEQ ID NO.650] |
| | 12-11 | 4b | QLVLTQSPSASASLGASVKLTC [SEQ ID NO.651] | TLSSGHSSY---AIA [SEQ ID NO.652] | WHQQQPEKGPRYLMK [SEQ ID NO.653] |
| VL5 | 14-11 | 5e | QFVLTQPSSSASPGESARLTC [SEQ ID NO.654] | TLPSDINVGSNIY [SEQ ID NO.655] | WYQQKPGSPPRYLLY [SEQ ID NO.656] |
| | 14-11 | 5c | QAVLTQPASLSASPGASASLTC [SEQ ID NO.657] | TLRSGINVGTYRIY [SEQ ID NO.658] | WYQQKPGSPPQYLLR [SEQ ID NO.659] |
| | 14-11 | 5b | QPVLTQPSSHSASSGASVRLTC [SEQ ID NO.660] | MLSSGFSVGDFWIR [SEQ ID NO.661] | WYQQKPGNEPRYLLY [SEQ ID NO.662] |
| VL6 | 13-7(B) | 6a | NFMLTQPSVSESPGKTVTLISC [SEQ ID NO.663] | TRSSGSIASN-YVQ [SEQ ID NO.664] | WYQRPGSSPTTVLY [SEQ ID NO.665] |
| VL7 | 14-7(B) | 7a | QTVVTQEPSLTVSPGGTVTLTC [SEQ ID NO.666] | ASSTGAVTSGYYPN [SEQ ID NO.667] | WFQQKPGQAPRALIY [SEQ ID NO.668] |
| | 14-7(B) | 7b | QAVVTQEPSLTVSPGGTVTLTC [SEQ ID NO.669] | GSSTGAVTSGHYPY [SEQ ID NO.670] | WFQQKPGQAPRLLY [SEQ ID NO.671] |
| VL8 | 14-7(B) | 8a | QTVVTQEPSFSVSPGGTVTLTC [SEQ ID NO.672] | GLSSGSVSTSYYPS [SEQ ID NO.673] | WYQQTPGQAPRTLLY [SEQ ID NO.674] |
| VL9 | 12-12 | 9a | QPVLTQPPSVSVSKGLRQTATLTC [SEQ ID NO.675] | TLSSGYSNY---KVD [SEQ ID NO.676] | WYQQRPGKGERFVMR [SEQ ID NO.677] |
| VL10 | 13-7(C) | 10a | QAGLTQPPSVSVSKGLRQTATILTC [SEQ ID NO.678] | TGMSMNVGMQ-GAA [SEQ ID NO.679] | WLQQHQGHPPKLLSY [SEQ ID NO.680] |

*Figure 1 (con't)*

Figure 1 (con't)

| | CDR1-2 | Locus | CDR2 | | FR3 | | CDR3 | |
|---|---|---|---|---|---|---|---|---|
| | | | 5 | | 6 7 8 | | 9 | |
| | | | 01abcde23456 | | 78901234567ab9012345678901234567890123456789012345678 | | 9012345abcde | |
| VL1 | 13-7(A) | 1a | YD------DLRPS | [SEQ ID NO.681] | GVSDRFSGSKSG---TSASLAISGLQSEDEADYYC | [SEQ ID NO.682] | AAWDDSLNG | [SEQ ID NO.683] |
| | 14-7(A) | 1e | GM------SNRPS | [SEQ ID NO.684] | GVPDRFSGSKSG---TSASLAITGLQAEDEADYYC | [SEQ ID NO.685] | QSYDSSLSG | [SEQ ID NO.686] |
| | 13-7(A) | 1c | SM------MQRPS | [SEQ ID NO.687] | GVPDRFSGSKSG---TSASLAISGLQSEDEADYYC | [SEQ ID NO.688] | AAWDDSLNG | [SEQ ID NO.689] |
| | 13-7(A) | 1g | RN------MQRPS | [SEQ ID NO.690] | GVPDRFSGSKSG---TSASLAISGLRSEDEADYYC | [SEQ ID NO.691] | AAWDDSL3G | [SEQ ID NO.692] |
| | 13-7(A) | 1b | DN------NKRPS | [SEQ ID NO.693] | GIPDRFSGSKSG---TSATLGITGLQTGDEADYYC | [SEQ ID NO.694] | GTWDSSLSA | [SEQ ID NO.695] |
| VL2 | 14-7(A) | 2c | EY------SKRPS | [SEQ ID NO.696] | GVPDRFSGSKSG---NTASLTISGLQAEDEADYYC | [SEQ ID NO.697] | SSYAGSNNF | [SEQ ID NO.698] |
| | 14-7(A) | 2e | DV------SKRPS | [SEQ ID NO.699] | GVPDRFSGSKSG---NTASLTISGLQAEDEADYYC | [SEQ ID NO.700] | CSYAGSYTF | [SEQ ID NO.701] |
| | 14-7(A) | 2a2 | EV------SNRPS | [SEQ ID NO.702] | GVSNRFSGSKSG---NTASLTISGLQAEDEADYYC | [SEQ ID NO.703] | SSYTSSSTL | [SEQ ID NO.704] |
| | 14-7(A) | 2h | EV------SNRPS | [SEQ ID NO.705] | GVSDRFSGSKSG---NTASLTISGLQAEDEADYYC | [SEQ ID NO.706] | SIYTSSSTF | [SEQ ID NO.707] |
| | 14-7(A) | 2b2 | EV------SKRPS | [SEQ ID NO.708] | GVSNRFSGSKSG---NTASLTITSGVQAMDEADYYC | [SEQ ID NO.709] | CSYAGSSTF | [SEQ ID NO.710] |
| VL3 | 11-7 | 3r | QD------SKRPS | [SEQ ID NO.711] | GIPERFSGSNSG---NTATLTISGAQAGDEADYYC | [SEQ ID NO.712] | QAMDSSTA | [SEQ ID NO.713] |
| | 11-7 | 3i | RD------SNRPS | [SEQ ID NO.714] | GIPERFSGSNSG---NTATLTISRAQAGDEADYYC | [SEQ ID NO.715] | QVMDSSTA | [SEQ ID NO.716] |
| | 11-7 | 3p | ED------SKRPS | [SEQ ID NO.717] | GIPERFSGSSSG---NTATLTISGAQVEDEADYYC | [SEQ ID NO.718] | YSTDSSGMH | [SEQ ID NO.719] |
| | 11-7 | 3a | KD------SERPS | [SEQ ID NO.720] | GIPERFSGSSSG---TIVTLTISGVQABDEADYYC | [SEQ ID NO.721] | LSADSSGTY | [SEQ ID NO.722] |
| | 11-7 | 3l | GK------BNRPS | [SEQ ID NO.723] | GIPDRFSGSSSG---NTASLTITYGAQAEDEADYYC | [SEQ ID NO.724] | NSRDSSGMH | [SEQ ID NO.725] |
| | 11-7 | 3h | YD------SDRPS | [SEQ ID NO.726] | GIPERESGSMSG---NTATLTISRVEAGDEADYYC | [SEQ ID NO.727] | QVMDSSSDH | [SEQ ID NO.728] |
| | 11-7 | 3e | ED------SEYP | [SEQ ID NO.729] | GIPERFSGSTSG---NTTTLTISRVLTEDEADYYC | [SEQ ID NO.730] | LSGEDM | [SEQ ID NO.731] |
| | 11-7 | 3m | KD------SERPS | [SEQ ID NO.732] | GIPERFSGSSSG---TTVTLTISGVQAEDEADYYC | [SEQ ID NO.733] | QSADSSGTY | [SEQ ID NO.734] |
| | 2-19 | 3l | KD------SERPS | [SEQ ID NO.735] | GIPERFSGSSSG---TTVTLTISGAQVEDEADYYC | [SEQ ID NO.736] | YSAADNN | [SEQ ID NO.737] |
| VL4 | 12-11 | 4c | VKS-DSHSRGD | [SEQ ID NO.738] | GIPDRFMGSSSG---ADRYLTPSMLQSDDEAEYHC | [SEQ ID NO.739] | GESHITHGQVc* | [SEQ ID NO.740] |
| | 12-11 | 4a | LEG-SGSYNKGS | [SEQ ID NO.741] | GVPDRFSGSSSG---ADRYLTISMLQLEDEADYYC | [SEQ ID NO.742] | ETWDSNT | [SEQ ID NO.743] |
| | 12-11 | 4b | LMS-DGSHSKGD | [SEQ ID NO.744] | GIPDRFSGSSSG---ABRYLTISSLQSEDEADYYC | [SEQ ID NO.745] | QTWGTGI | [SEQ ID NO.746] |

```
VL5   14-11   5a   YYS-DSDKGQGS  [SEQ ID NO.747]  GVPSRFSGSKDASANTGTLLISGLQSEDEADYYC  [SEQ ID NO.748]  MTWPSNRS      [SEQ ID NO.749]
      14-11   5c   YKS-DSDKQQGS  [SEQ ID NO.750]  GVPSRFSGSKDASANAGTLLISGLQSEDEADYYC  [SEQ ID NO.751]  MTWHSSAS      [SEQ ID NO.752]
      14-11   5b   YHS-DSNKSQGS  [SEQ ID NO.753]  GVPSRFSGSNDASANAGILRISGLQPEDEADYYC  [SEQ ID NO.754]  CTWHSNSKT     [SEQ ID NO.755]
VL6   13-7(B) 6a   BD------MQRPS [SEQ ID NO.756]  GVPDRFSGSIDSSNSASIFISGLKTEDEADYYC   [SEQ ID NO.757]  QSYDSSN       [SEQ ID NO.758]
VL7   14-7(B) 7a   ST------SNKHS [SEQ ID NO.759]  WTPARFSGSLLG---GKAAIHLSGVQPEDEARYYC [SEQ ID NO.760]  LLIYYGGAQ     [SEQ ID NO.761]
      14-7(B) 7b   DT------SNKHS [SEQ ID NO.762]  WTPARFSGSLLG---GKAAIHLSGAQPEDEAEYYC [SEQ ID NO.763]  LLSYSGAR      [SEQ ID NO.764]
VL8   14-7(B) 8a   ST------NTRSS [SEQ ID NO.765]  GVPDRFSGSTLG---NKAALETTGAQADDESDYYC [SEQ ID NO.766]  VLXMGSGI      [SEQ ID NO.767]
VL9   12-12   9a   VGTEGIVGSKGD  [SEQ ID NO.768]  GIPDRFSVLGSG---LMRYIHIRNIQEEDESDZHC [SEQ ID NO.769]  GADHGGSMFV*   [SEQ ID NO.770]
VL10  13-7(C) 10a  RW------MNRPS [SEQ ID NO.771]  GISERLSASRSG---NTASLTITGLQPEDEADYYC [SEQ ID NO.772]  SAWDSSLSA     [SEQ ID NO.773]

CDR3
      |                100
      |                 |
JL1   YVFGGGTKVTVL  [SEQ ID NO.774]
JL2   WFGGGTKLTVL   [SEQ ID NO.775]
JL3   YVFGGGTKLTVL  [SEQ ID NO.776]
JL7   AVFGGGTQLTVL  [SEQ ID NO.777]
```

*Figure 1 (con't)*

```
BC-1      EVQLVQSGADV--KKPGASVKVSCKASGYTFTNYVMHWVRQAPGQGLEWLGYINPYNDGTQ
C6.5      QVQLLQSGAEV--KKPGESLKISCKGSGYSFTSYWIAWVRQMPGKGLEYMGLIYPGDSDTK
BC-1-mut  EVQLVQSGADV--KQPGASVKVSCKASGYTFTNYVMHWVRQAPGKGLEWLGYINPYNDGTQ BC-1      YNERFKGRVTMTGDTSISTAYMELSRLRSDDTAVYYCAR-EVYG----------NYIWGN
C6.5      YSPSFQGQVTISVDKSVSTAYLQWSSLKPSDSAVYFCAR-HDVGYCSSNCAKWPEYFQH
BC-1-mut  YNERFKGRVTMTGDTSISTAYMELSRLKSDDTAVYYCAR-EVYG----------NYIWGN BC-1      WGQGTLVSVSSGGGGSGGGGSGGGGSGGSALEIVLTQS-PGTLSLSPGERATLSCSASSS--ISSN
C6.5      WGQGTLVTVSSGGGGSGGGGSGGGGSGGSQSVLTQP-P-SVSAAPGQKVTISCSGSSSNIGNN
BC-1-mut  WGQGTLVSVSSGGGGSGGGGSGGGGSGGSALEIVLTQS-PGTLSLSPGEKATLSCSASSS--ISSN BC-1      YLHWYQQKPGQAPRLLIYR-----TSNLASGIPDRFSGS---GSGTDFTLTISRLEPEDFAV
C6.5      YVSWYQQLPGTAPKLLIYG-----BTNRPAGVPDRFSGS---KSGTSASLAISGFRSEDEAD
BC-1-mut  YLHWYQQKPGQAPKLLIYR-----TSNLASGIPDRFSGS---KSGTDFTLTISRLEPEDFAV BC-1      YYCQQGSS--IPFTFGQGTKLEIN [SEQ ID NO.778]
C6.5      YYCAAWDDSLSGWVFGGGTKLTVL [SEQ ID NO.779]
BC-1-mut. YYCQQGSS--IPFTFGQGTKLEIN [SEQ ID NO.780]
```

*Figure 19*

| scFv | Variable-Heavy domain |
|---|---|
| GP6 | EVQLVESGGGL-VQPGGSLRLSCAASGFTFSSYWMHWVRQAPGKGLVWVSRINSDGSSAS |
| D1.3 | QVQLQESGPGL-VAPSQSLSITCTVSGFSLTGYGVNWVRQPPGKGLEWLGMI-WGDGNTD |
| HH10 | DIVLTQSPATLSVTPGNSVSLSCRAS-QSIGNN-LHWYQQKSHESPRLLIKY-----ASQ |
| MFE | QVKLQQSGAEL-VRSGTSVKLSCTASGFNIKDSYMHWLRQGPEQGLEWIGWIDPENGDTE |
| F1 | EVQLVQSGGGV-VQPGRSLRLSCAASGFTFDDYGMSWVRQAPGKGLEWVSGINWNGGSTG |
| BC-1 | EVQLVQSGADV-KKPGASVKVSCKASGYTFTNYVMHWVRQAPGQGLEWLGYINPYNDGTQ |
| C6.5 | QVQLLQSGAEV-KKPGESLKISCKGSGYSFTSYWIAWVRQMPGKGLEYMGLIYPGDSDTK |

| scFv | Variable-Heavy domain |
|---|---|
| GP6 | YADSVKGRFTISRDNAKNTLYLQMNSLRAEDTAVYYCAR-TVT----------ER |
| D1.3 | YNSALKSRLSISKDNSKSQVFLKMNSLHTDDTARYYCARERDYR----------LDY |
| HH10 | SISGIPSRFSGSG---SGTDFTLSINSVETEDFGMYFCQQ-SNSWP---------YT |
| MFE | YAPKFQGKATFTTDTSSNTAYLQLSSLTSEDTAVYYCNEGTPTG----------PYYFDY |
| F1 | YADSVKGRFTISRDNAKNSLFLQMNSLRAEDTALYYCAR-AIRSYSGS-----YGNAFDI |
| BC-1 | YNERFKGRVTMTGDTSISTAYMELSRLTSDDTAVYYCAR-EVYG----------NYIWGN |
| C6.5 | YSPSFQGQVTISVDKSVSTAYLQWSSLKPSDSAVYFCAR-HDVGYCSSSNCAKWPEYFQH |

| scFv | Var-Heavy | | Linker |
|---|---|---|---|
| GP6 | WGQGTLVTVSS [SEQ ID NO.781] | | GGGGSGGGGSGGSAL [SEQ ID NO.788] |
| D1.3 | WGQGTTVTVSS [SEQ ID NO.782] | | GGGGSGGGGSGGSAL [SEQ ID NO.789] |
| HH10 | FGGGTKLEIKS [SEQ ID NO.783] | | GGG--SGGGGSGGGGS [SEQ ID NO.790] |
| MFE | WGQGTTVTVSS [SEQ ID NO.784] | | GGGGSGGGGSGGGGS [SEQ ID NO.791] |
| F1 | WGKGTLVTVSS [SEQ ID NO.785] | | GGGGSGGGGSGGGGS [SEQ ID NO.792] |
| BC-1 | WGQGTLVSVSS [SEQ ID NO.786] | | GGGGSGGGGSGGSAL [SEQ ID NO.793] |
| C6.5 | WGQGTLVTVSS [SEQ ID NO.787] | | GGGGSGGGGSGGGGS [SEQ ID NO.794] |

| Variable-Light domain |
|---|
| SSELTQD-P--AVSVALGQTVRITCQGDSL---RSY |
| DIQMTQS-PASLSASVGETVTITCRASGN---IHN |
| DVQLQESGP-ELVK-PSQTLSLTCSVTGDSITSN |
| ENVLTQS-PAIMSASPGEKVTITCSASSS--VS---- |
| DIQMTQS-PSTLSASIGDRVTITCRASEG---IYH |
| EIVLTQS-PGTLSLSPGERATLSCSASSS--ISSN |
| QSVLTQP-P--SVSAAPGQKVTISCSGSSSNIGNN |

| scFv | Variable-Light domain |
|---|---|
| GP6 | YASWYQQKPGQAPVLVIYG-----KNNRPSGIPDRFSGS--SSGNTASLTITGAQAEDEAD |
| D1.3 | YLAWYQQKQGKSPQLLVYY-----TTTLADGVPSRFSGS--GSGTQYSLKINSLQPEDFGS |
| HH10 | YWSWIRKFPGNRLEYMGYVSYSGSTYYNPSLKSRISITRDTSKNQYYLDLNSVTTEDTAT |
| MFE | YMHWFQQKPGTSPKLWIYS-----TSNLASGVPARFSGS--GSGTSYSLTISRMEAEDAAT |
| F1 | WLAWYQQKPGKAPKLLIYK-----ASSLASGAPSRFSGS--GSGTDFTLTISSLQPDDFAT |
| BC-1 | YLHWYQQKPGQAPRLLIYR-----TSNLASGIPDRFSGS--GSGTDFTLTISRLEPEDFAV |
| C6.5 | YVSWYQQLPGTAPKLLIYG-----HTNRPAGVPDRFSGS--KSGTSASLAISGFKSEDEAD |

| scFv | Variable-Light domain |
|---|---|
| GP6 | YYCNSRDS---SGTVFGGGTKLTVL [SEQ ID NO.795] |
| D1.3 | YYCQHFWS---TPRTFGGGTKLEIQ [SEQ ID NO.796] |
| HH10 | YYCANWDG---TFDYWGQGTLVTVS [SEQ ID NO.797] |
| MFE | YYCQQRSS---YPLTFGAGTKLELK [SEQ ID NO.798] |
| F1 | YYCQQYSN---YPLTFGGGTVLEIK [SEQ ID NO.799] |
| BC-1 | YYCQQGSS---IPFTFGQGTKLEIN [SEQ ID NO.800] |
| C6.5 | YYCAAWDDSLSGWVFGGGTKLTVL [SEQ ID NO.801] |

*Figure 26*

Figure 28

SEQUENCE LISTING

```
<160> NUMBER OF SEQ ID NOS: 801

<210> SEQ ID NO 1
<211> LENGTH: 7
<212> TYPE: PRT
<213> ORGANISM: Artificial Sequence
<220> FEATURE:
<223> OTHER INFORMATION: SV40 large T

<400> SEQUENCE: 1

Lys Lys Lys Lys Arg Pro Arg
1               5

<210> SEQ ID NO 2
<211> LENGTH: 17
<212> TYPE: PRT
<213> ORGANISM: Homo sapiens

<400> SEQUENCE: 2

Lys Arg Pro Met Asn Ala Phe Ile Val Trp Ser Arg Asp Gln Arg Arg
1               5                   10                  15

Lys
```

-continued

```
<210> SEQ ID NO 3
<211> LENGTH: 55
<212> TYPE: PRT
<213> ORGANISM: Homo sapiens

<400> SEQUENCE: 3

Met Leu Val His Leu Phe Arg Val Gly Ile Arg Gly Gly Pro Phe Pro
1               5                   10                  15

Gly Arg Leu Leu Pro Pro Leu Arg Phe Gln Thr Phe Ser Ala Val Arg
            20                  25                  30

Tyr Ser Asp Gly Tyr Arg Ser Ser Ser Leu Leu Arg Ala Val Ala His
        35                  40                  45

Leu Pro Ser Gln Leu Trp Ala
    50                  55

<210> SEQ ID NO 4
<211> LENGTH: 4
<212> TYPE: PRT
<213> ORGANISM: Homo sapiens

<400> SEQUENCE: 4

Thr Met Gly Tyr
1

<210> SEQ ID NO 5
<211> LENGTH: 4
<212> TYPE: PRT
<213> ORGANISM: Homo sapiens

<400> SEQUENCE: 5

Thr Met Leu Ile
1

<210> SEQ ID NO 6
<211> LENGTH: 4
<212> TYPE: PRT
<213> ORGANISM: Homo sapiens

<400> SEQUENCE: 6

Lys Asp Glu Leu
1

<210> SEQ ID NO 7
<211> LENGTH: 23
<212> TYPE: PRT
<213> ORGANISM: Artificial Sequence
<220> FEATURE:
<223> OTHER INFORMATION: Influenza HA2

<400> SEQUENCE: 7

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 8
<211> LENGTH: 18
<212> TYPE: PRT
<213> ORGANISM: Artificial Sequence
<220> FEATURE:
<223> OTHER INFORMATION: Polio virus vp1
```

```
<400> SEQUENCE: 8

Gly Ile Glu Asp Leu Ile Ser Glu Val Ala Gln Gly Ala Leu Thr Leu
 1               5                  10                  15

Val Pro

<210> SEQ ID NO 9
<211> LENGTH: 30
<212> TYPE: PRT
<213> ORGANISM: Homo sapiens

<400> SEQUENCE: 9

Ala Cys Tyr Cys Arg Ile Pro Ala Cys Ile Ala Gly Glu Arg Arg Tyr
 1               5                  10                  15

Gly Thr Cys Ile Tyr Gln Gly Arg Leu Trp Ala Phe Cys Cys
             20                  25                  30

<210> SEQ ID NO 10
<211> LENGTH: 29
<212> TYPE: PRT
<213> ORGANISM: Artificial Sequence
<220> FEATURE:
<223> OTHER INFORMATION: Sendai virus F1

<400> SEQUENCE: 10

Phe Phe Gly Ala Val Ile Gly Thr Ile Ala Leu Gly Val Ala Thr Ser
 1               5                  10                  15

Ala Gln Ile Thr Ala Gly Ile Ala Leu Ala Glu Ala Arg
             20                  25

<210> SEQ ID NO 11
<211> LENGTH: 30
<212> TYPE: PRT
<213> ORGANISM: Homo sapiens

<400> SEQUENCE: 11

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr
             20                  25                  30

<210> SEQ ID NO 12
<211> LENGTH: 5
<212> TYPE: PRT
<213> ORGANISM: Homo sapiens

<400> SEQUENCE: 12

Gly Tyr Tyr Met His
 1               5

<210> SEQ ID NO 13
<211> LENGTH: 14
<212> TYPE: PRT
<213> ORGANISM: Homo sapiens

<400> SEQUENCE: 13

Trp Val Arg Gln Ala Pro Gly Gln Gly Leu Glu Trp Met Gly
 1               5                  10

<210> SEQ ID NO 14
<211> LENGTH: 30
<212> TYPE: PRT
<213> ORGANISM: Homo sapiens

<400> SEQUENCE: 14
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 15
<211> LENGTH: 5
<212> TYPE: PRT
<213> ORGANISM: Homo sapiens

<400> SEQUENCE: 15

Ser Tyr Ala Met His
1               5

<210> SEQ ID NO 16
<211> LENGTH: 14
<212> TYPE: PRT
<213> ORGANISM: Homo sapiens

<400> SEQUENCE: 16

Trp Val Arg Gln Ala Pro Gly Gln Arg Leu Glu Trp Met Gly
1               5                   10

<210> SEQ ID NO 17
<211> LENGTH: 30
<212> TYPE: PRT
<213> ORGANISM: Homo sapiens

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 18
<211> LENGTH: 5
<212> TYPE: PRT
<213> ORGANISM: Homo sapiens

<400> SEQUENCE: 18

Ser Tyr Asp Ile Asn
1               5

<210> SEQ ID NO 19
<211> LENGTH: 14
<212> TYPE: PRT
<213> ORGANISM: Homo sapiens

<400> SEQUENCE: 19

Trp Val Arg Gln Ala Thr Gly Gln Gly Leu Glu Trp Met Gly
1               5                   10

<210> SEQ ID NO 20
<211> LENGTH: 30
<212> TYPE: PRT
<213> ORGANISM: Homo sapiens

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

-continued

```
<210> SEQ ID NO 21
<211> LENGTH: 5
<212> TYPE: PRT
<213> ORGANISM: Homo sapiens

<400> SEQUENCE: 21

Ser Tyr Gly Ile Ser
1               5

<210> SEQ ID NO 22
<211> LENGTH: 14
<212> TYPE: PRT
<213> ORGANISM: Homo sapiens

<400> SEQUENCE: 22

Trp Val Arg Gln Ala Pro Gly Gln Gly Leu Glu Trp Met Gly
1               5                   10

<210> SEQ ID NO 23
<211> LENGTH: 30
<212> TYPE: PRT
<213> ORGANISM: Homo sapiens

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr
            20                  25                  30

<210> SEQ ID NO 24
<211> LENGTH: 5
<212> TYPE: PRT
<213> ORGANISM: Homo sapiens

<400> SEQUENCE: 24

Glu Leu Ser Met His
1               5

<210> SEQ ID NO 25
<211> LENGTH: 14
<212> TYPE: PRT
<213> ORGANISM: Homo sapiens

<400> SEQUENCE: 25

Trp Val Arg Gln Ala Pro Gly Lys Gly Leu Glu Trp Met Gly
1               5                   10

<210> SEQ ID NO 26
<211> LENGTH: 30
<212> TYPE: PRT
<213> ORGANISM: Homo sapiens

<400> SEQUENCE: 26

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr
            20                  25                  30

<210> SEQ ID NO 27
<211> LENGTH: 5
<212> TYPE: PRT
<213> ORGANISM: Homo sapiens

<400> SEQUENCE: 27

Tyr Arg Tyr Leu His
```

-continued

<210> SEQ ID NO 28
<211> LENGTH: 14
<212> TYPE: PRT
<213> ORGANISM: Homo sapiens

<400> SEQUENCE: 28

Trp Val Arg Gln Ala Pro Gly Gln Ala Leu Glu Trp Met Gly
1               5                   10

<210> SEQ ID NO 29
<211> LENGTH: 30
<212> TYPE: PRT
<213> ORGANISM: Homo sapiens

<400> SEQUENCE: 29

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr
            20                  25                  30

<210> SEQ ID NO 30
<211> LENGTH: 5
<212> TYPE: PRT
<213> ORGANISM: Homo sapiens

<400> SEQUENCE: 30

Ser Tyr Tyr Met His
1               5

<210> SEQ ID NO 31
<211> LENGTH: 14
<212> TYPE: PRT
<213> ORGANISM: Homo sapiens

<400> SEQUENCE: 31

Trp Val Arg Gln Ala Pro Gly Gln Gly Leu Glu Trp Met Gly
1               5                   10

<210> SEQ ID NO 32
<211> LENGTH: 30
<212> TYPE: PRT
<213> ORGANISM: Homo sapiens

<400> SEQUENCE: 32

Gln Met Gln Leu Val Gln Ser Gly Pro Glu Val Lys Lys Pro Gly Thr
1               5                   10                  15
Ser Val Lys Val Ser Cys Lys Ala Ser Gly Phe Thr Phe Thr
            20                  25                  30

<210> SEQ ID NO 33
<211> LENGTH: 5
<212> TYPE: PRT
<213> ORGANISM: Homo sapiens

<400> SEQUENCE: 33

Ser Ser Ala Val Gln
1               5

<210> SEQ ID NO 34
<211> LENGTH: 14
<212> TYPE: PRT
<213> ORGANISM: Homo sapiens -continued

```
<400> SEQUENCE: 34

Trp Val Arg Gln Ala Arg Gly Gln Arg Leu Glu Trp Ile Gly
1               5                   10

<210> SEQ ID NO 35
<211> LENGTH: 30
<212> TYPE: PRT
<213> ORGANISM: Homo sapiens

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 36
<211> LENGTH: 5
<212> TYPE: PRT
<213> ORGANISM: Homo sapiens

<400> SEQUENCE: 36

Ser Tyr Ala Ile Ser
1               5

<210> SEQ ID NO 37
<211> LENGTH: 14
<212> TYPE: PRT
<213> ORGANISM: Homo sapiens

<400> SEQUENCE: 37

Trp Val Arg Gln Ala Pro Gly Gln Gly Leu Glu Trp Met Gly
1               5                   10

<210> SEQ ID NO 38
<211> LENGTH: 30
<212> TYPE: PRT
<213> ORGANISM: Homo sapiens

<400> SEQUENCE: 38

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 39
<211> LENGTH: 5
<212> TYPE: PRT
<213> ORGANISM: Homo sapiens

<400> SEQUENCE: 39

Ser Tyr Ala Ile Ser
1               5

<210> SEQ ID NO 40
<211> LENGTH: 14
<212> TYPE: PRT
<213> ORGANISM: Homo sapiens

<400> SEQUENCE: 40

Trp Val Arg Gln Ala Pro Gly Gln Gly Leu Glu Trp Met Gly
1               5                   10

<210> SEQ ID NO 41
<211> LENGTH: 30
```

```
<212> TYPE: PRT
<213> ORGANISM: Homo sapiens

<400> SEQUENCE: 41

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr
            20                  25                  30

<210> SEQ ID NO 42
<211> LENGTH: 5
<212> TYPE: PRT
<213> ORGANISM: Homo sapiens

<400> SEQUENCE: 42

Asp Tyr Tyr Met His
1               5

<210> SEQ ID NO 43
<211> LENGTH: 14
<212> TYPE: PRT
<213> ORGANISM: Homo sapiens

<400> SEQUENCE: 43

Trp Val Gln Gln Ala Pro Gly Lys Gly Leu Glu Trp Met Gly
1               5                   10

<210> SEQ ID NO 44
<211> LENGTH: 30
<212> TYPE: PRT
<213> ORGANISM: Homo sapiens

<400> SEQUENCE: 44

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 45
<211> LENGTH: 7
<212> TYPE: PRT
<213> ORGANISM: Homo sapiens

<400> SEQUENCE: 45

Thr Ser Gly Val Gly Val Gly
1               5

<210> SEQ ID NO 46
<211> LENGTH: 14
<212> TYPE: PRT
<213> ORGANISM: Homo sapiens

<400> SEQUENCE: 46

Trp Ile Arg Gln Pro Pro Gly Lys Ala Leu Glu Trp Leu Ala
1               5                   10

<210> SEQ ID NO 47
<211> LENGTH: 30
<212> TYPE: PRT
<213> ORGANISM: Homo sapiens

<400> SEQUENCE: 47

Gln Val Thr Leu Lys Glu Ser Gly Pro Val Leu Val Lys Pro Thr Glu
1               5                   10                  15
```

Thr Leu Thr Leu Thr Cys Thr Val Ser Gly Phe Ser Leu Ser
            20                  25                  30

<210> SEQ ID NO 48
<211> LENGTH: 7
<212> TYPE: PRT
<213> ORGANISM: Homo sapiens

<400> SEQUENCE: 48

Asn Ala Arg Met Gly Val Ser
1               5

<210> SEQ ID NO 49
<211> LENGTH: 14
<212> TYPE: PRT
<213> ORGANISM: Homo sapiens

<400> SEQUENCE: 49

Trp Ile Arg Gln Pro Pro Gly Lys Ala Leu Glu Trp Leu Ala
1               5                   10

<210> SEQ ID NO 50
<211> LENGTH: 30
<212> TYPE: PRT
<213> ORGANISM: Homo sapiens

<400> SEQUENCE: 50

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 51
<211> LENGTH: 7
<212> TYPE: PRT
<213> ORGANISM: Homo sapiens

<400> SEQUENCE: 51

Thr Ser Gly Met Arg Val Ser
1               5

<210> SEQ ID NO 52
<211> LENGTH: 14
<212> TYPE: PRT
<213> ORGANISM: Homo sapiens

<400> SEQUENCE: 52

Trp Ile Arg Gln Pro Pro Gly Lys Ala Leu Glu Trp Leu Ala
1               5                   10

<210> SEQ ID NO 53
<211> LENGTH: 30
<212> TYPE: PRT
<213> ORGANISM: Homo sapiens

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 54
<211> LENGTH: 5
<212> TYPE: PRT
<213> ORGANISM: Homo sapiens

<400> SEQUENCE: 54

Ser Tyr Trp Met Ser
1               5

<210> SEQ ID NO 55
<211> LENGTH: 14
<212> TYPE: PRT
<213> ORGANISM: Homo sapiens

<400> SEQUENCE: 55

Trp Val Arg Gln Ala Pro Gly Lys Gly Leu Glu Trp Val Ala
1               5                   10

<210> SEQ ID NO 56
<211> LENGTH: 30
<212> TYPE: PRT
<213> ORGANISM: Homo sapiens

<400> SEQUENCE: 56

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp
            20                  25                  30

<210> SEQ ID NO 57
<211> LENGTH: 5
<212> TYPE: PRT
<213> ORGANISM: Homo sapiens

<400> SEQUENCE: 57

Asp Tyr Ala Met His
1               5

<210> SEQ ID NO 58
<211> LENGTH: 14
<212> TYPE: PRT
<213> ORGANISM: Homo sapiens

<400> SEQUENCE: 58

Trp Val Arg Gln Ala Pro Gly Lys Gly Leu Glu Trp Val Ser
1               5                   10

<210> SEQ ID NO 59
<211> LENGTH: 30
<212> TYPE: PRT
<213> ORGANISM: Homo sapiens

<400> SEQUENCE: 59

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 60
<211> LENGTH: 5
<212> TYPE: PRT
<213> ORGANISM: Homo sapiens

<400> SEQUENCE: 60

Asp Tyr Tyr Met Ser
1               5

<210> SEQ ID NO 61

```
<211> LENGTH: 14
<212> TYPE: PRT
<213> ORGANISM: Homo sapiens

<400> SEQUENCE: 61

Trp Ile Arg Gln Ala Pro Gly Lys Gly Leu Glu Trp Val Ser
1               5                   10

<210> SEQ ID NO 62
<211> LENGTH: 30
<212> TYPE: PRT
<213> ORGANISM: Homo sapiens

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 63
<211> LENGTH: 5
<212> TYPE: PRT
<213> ORGANISM: Homo sapiens

<400> SEQUENCE: 63

Ser Tyr Asp Met His
1               5

<210> SEQ ID NO 64
<211> LENGTH: 14
<212> TYPE: PRT
<213> ORGANISM: Homo sapiens

<400> SEQUENCE: 64

Trp Val Arg Gln Ala Thr Gly Lys Gly Leu Glu Trp Val Ser
1               5                   10

<210> SEQ ID NO 65
<211> LENGTH: 30
<212> TYPE: PRT
<213> ORGANISM: Homo sapiens

<400> SEQUENCE: 65

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 66
<211> LENGTH: 5
<212> TYPE: PRT
<213> ORGANISM: Homo sapiens

<400> SEQUENCE: 66

Asn Ala Trp Met Ser
1               5

<210> SEQ ID NO 67
<211> LENGTH: 14
<212> TYPE: PRT
<213> ORGANISM: Homo sapiens

<400> SEQUENCE: 67

Trp Val Arg Gln Ala Pro Gly Lys Gly Leu Glu Trp Val Gly
1               5                   10
```

```
<210> SEQ ID NO 68
<211> LENGTH: 30
<212> TYPE: PRT
<213> ORGANISM: Homo sapiens

<400> SEQUENCE: 68

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp
            20                  25                  30

<210> SEQ ID NO 69
<211> LENGTH: 5
<212> TYPE: PRT
<213> ORGANISM: Homo sapiens

<400> SEQUENCE: 69

Asp Tyr Gly Met Ser
1               5

<210> SEQ ID NO 70
<211> LENGTH: 14
<212> TYPE: PRT
<213> ORGANISM: Homo sapiens

<400> SEQUENCE: 70

Trp Val Arg Gln Ala Pro Gly Lys Gly Leu Glu Trp Val Ser
1               5                   10

<210> SEQ ID NO 71
<211> LENGTH: 30
<212> TYPE: PRT
<213> ORGANISM: Homo sapiens

<400> SEQUENCE: 71

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 72
<211> LENGTH: 5
<212> TYPE: PRT
<213> ORGANISM: Homo sapiens

<400> SEQUENCE: 72

Ser Tyr Ser Met Asn
1               5

<210> SEQ ID NO 73
<211> LENGTH: 14
<212> TYPE: PRT
<213> ORGANISM: Homo sapiens

<400> SEQUENCE: 73

Trp Val Arg Gln Ala Pro Gly Lys Gly Leu Glu Trp Val Ser
1               5                   10

<210> SEQ ID NO 74
<211> LENGTH: 30
<212> TYPE: PRT
<213> ORGANISM: Homo sapiens

<400> SEQUENCE: 74
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

```
<210> SEQ ID NO 75
<211> LENGTH: 5
<212> TYPE: PRT
<213> ORGANISM: Homo sapiens

<400> SEQUENCE: 75

Ser Tyr Ala Met Ser
1               5
```

```
<210> SEQ ID NO 76
<211> LENGTH: 14
<212> TYPE: PRT
<213> ORGANISM: Homo sapiens

<400> SEQUENCE: 76

Trp Val Arg Gln Ala Pro Gly Lys Gly Leu Glu Trp Val Ser
1               5                   10
```

```
<210> SEQ ID NO 77
<211> LENGTH: 30
<212> TYPE: PRT
<213> ORGANISM: Homo sapiens

<400> SEQUENCE: 77

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30
```

```
<210> SEQ ID NO 78
<211> LENGTH: 5
<212> TYPE: PRT
<213> ORGANISM: Homo sapiens

<400> SEQUENCE: 78

Ser Tyr Gly Met His
1               5
```

```
<210> SEQ ID NO 79
<211> LENGTH: 14
<212> TYPE: PRT
<213> ORGANISM: Homo sapiens

<400> SEQUENCE: 79

Trp Val Arg Gln Ala Pro Gly Lys Gly Leu Glu Trp Val Ala
1               5                   10
```

```
<210> SEQ ID NO 80
<211> LENGTH: 30
<212> TYPE: PRT
<213> ORGANISM: Homo sapiens

<400> SEQUENCE: 80

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30
```

```
<210> SEQ ID NO 81
<211> LENGTH: 5
<212> TYPE: PRT
<213> ORGANISM: Homo sapiens

<400> SEQUENCE: 81

Ser Tyr Ala Met His
1               5

<210> SEQ ID NO 82
<211> LENGTH: 14
<212> TYPE: PRT
<213> ORGANISM: Homo sapiens

<400> SEQUENCE: 82

Trp Val Arg Gln Ala Pro Gly Lys Gly Leu Glu Trp Val Ala
1               5                   10

<210> SEQ ID NO 83
<211> LENGTH: 30
<212> TYPE: PRT
<213> ORGANISM: Homo sapiens

<400> SEQUENCE: 83

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 84
<211> LENGTH: 5
<212> TYPE: PRT
<213> ORGANISM: Homo sapiens

<400> SEQUENCE: 84

Ser Tyr Gly Met His
1               5

<210> SEQ ID NO 85
<211> LENGTH: 14
<212> TYPE: PRT
<213> ORGANISM: Homo sapiens

<400> SEQUENCE: 85

Trp Val Arg Gln Ala Pro Gly Lys Gly Leu Glu Trp Val Ala
1               5                   10

<210> SEQ ID NO 86
<211> LENGTH: 30
<212> TYPE: PRT
<213> ORGANISM: Homo sapiens

<400> SEQUENCE: 86

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 87
<211> LENGTH: 5
<212> TYPE: PRT
<213> ORGANISM: Homo sapiens

<400> SEQUENCE: 87

Ser Tyr Gly Met His
```

```
<210> SEQ ID NO 88
<211> LENGTH: 14
<212> TYPE: PRT
<213> ORGANISM: Homo sapiens

<400> SEQUENCE: 88

Trp Val Arg Gln Ala Pro Gly Lys Gly Leu Glu Trp Val Ala
1               5                   10

<210> SEQ ID NO 89
<211> LENGTH: 30
<212> TYPE: PRT
<213> ORGANISM: Homo sapiens

<400> SEQUENCE: 89

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp
            20                  25                  30

<210> SEQ ID NO 90
<211> LENGTH: 5
<212> TYPE: PRT
<213> ORGANISM: Homo sapiens

<400> SEQUENCE: 90

Asp Tyr Thr Met His
1               5

<210> SEQ ID NO 91
<211> LENGTH: 14
<212> TYPE: PRT
<213> ORGANISM: Homo sapiens

<400> SEQUENCE: 91

Trp Val Arg Gln Ala Pro Gly Lys Gly Leu Glu Trp Val Ser
1               5                   10

<210> SEQ ID NO 92
<211> LENGTH: 30
<212> TYPE: PRT
<213> ORGANISM: Homo sapiens

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 93
<211> LENGTH: 5
<212> TYPE: PRT
<213> ORGANISM: Homo sapiens

<400> SEQUENCE: 93

Ser Tyr Ser Met Asn
1               5

<210> SEQ ID NO 94
<211> LENGTH: 14
<212> TYPE: PRT
<213> ORGANISM: Homo sapiens
```

-continued

<400> SEQUENCE: 94

Trp Val Arg Gln Ala Pro Gly Lys Gly Leu Glu Trp Val Ser
1               5                   10

<210> SEQ ID NO 95
<211> LENGTH: 30
<212> TYPE: PRT
<213> ORGANISM: Homo sapiens

<400> SEQUENCE: 95

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly
            20                  25                  30

<210> SEQ ID NO 96
<211> LENGTH: 5
<212> TYPE: PRT
<213> ORGANISM: Homo sapiens

<400> SEQUENCE: 96

Asp Tyr Ala Met Ser
1               5

<210> SEQ ID NO 97
<211> LENGTH: 14
<212> TYPE: PRT
<213> ORGANISM: Homo sapiens

<400> SEQUENCE: 97

Trp Phe Arg Gln Ala Pro Gly Lys Gly Leu Glu Trp Val Gly
1               5                   10

<210> SEQ ID NO 98
<211> LENGTH: 30
<212> TYPE: PRT
<213> ORGANISM: Homo sapiens

<400> SEQUENCE: 98

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser
            20                  25                  30

<210> SEQ ID NO 99
<211> LENGTH: 5
<212> TYPE: PRT
<213> ORGANISM: Homo sapiens

<400> SEQUENCE: 99

Ser Asn Tyr Met Ser
1               5

<210> SEQ ID NO 100
<211> LENGTH: 14
<212> TYPE: PRT
<213> ORGANISM: Homo sapiens

<400> SEQUENCE: 100

Trp Val Arg Gln Ala Pro Gly Lys Gly Leu Glu Trp Val Ser
1               5                   10

<210> SEQ ID NO 101
<211> LENGTH: 30

```
<212> TYPE: PRT
<213> ORGANISM: Homo sapiens

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 102
<211> LENGTH: 5
<212> TYPE: PRT
<213> ORGANISM: Homo sapiens

<400> SEQUENCE: 102

Ser Tyr Ala Met His
1               5

<210> SEQ ID NO 103
<211> LENGTH: 14
<212> TYPE: PRT
<213> ORGANISM: Homo sapiens

<400> SEQUENCE: 103

Trp Val Arg Gln Ala Pro Gly Lys Gly Leu Glu Tyr Val Ser
1               5                   10

<210> SEQ ID NO 104
<211> LENGTH: 30
<212> TYPE: PRT
<213> ORGANISM: Homo sapiens

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser
            20                  25                  30

<210> SEQ ID NO 105
<211> LENGTH: 5
<212> TYPE: PRT
<213> ORGANISM: Homo sapiens

<400> SEQUENCE: 105

Ser Asn Tyr Met Ser
1               5

<210> SEQ ID NO 106
<211> LENGTH: 14
<212> TYPE: PRT
<213> ORGANISM: Homo sapiens

<400> SEQUENCE: 106

Trp Val Arg Gln Ala Pro Gly Lys Gly Leu Glu Trp Val Ser
1               5                   10

<210> SEQ ID NO 107
<211> LENGTH: 30
<212> TYPE: PRT
<213> ORGANISM: Homo sapiens

<400> SEQUENCE: 107

Glu Val Gln Leu Val Glu Ser Gly Gly Gly Leu Val Gln Pro Gly Gly
1               5                   10                  15
```

-continued

Ser Leu Arg Leu Ser Cys Ala Ala Ser Gly Phe Thr Phe Ser
            20                  25                  30

<210> SEQ ID NO 108
<211> LENGTH: 5
<212> TYPE: PRT
<213> ORGANISM: Homo sapiens

<400> SEQUENCE: 108

Asp His Tyr Met Asp
1               5

<210> SEQ ID NO 109
<211> LENGTH: 14
<212> TYPE: PRT
<213> ORGANISM: Homo sapiens

<400> SEQUENCE: 109

Trp Val Arg Gln Ala Pro Gly Lys Gly Leu Glu Trp Val Gly
1               5                   10

<210> SEQ ID NO 110
<211> LENGTH: 30
<212> TYPE: PRT
<213> ORGANISM: Homo sapiens

<400> SEQUENCE: 110

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser
            20                  25                  30

<210> SEQ ID NO 111
<211> LENGTH: 5
<212> TYPE: PRT
<213> ORGANISM: Homo sapiens

<400> SEQUENCE: 111

Gly Ser Ala Met His
1               5

<210> SEQ ID NO 112
<211> LENGTH: 14
<212> TYPE: PRT
<213> ORGANISM: Homo sapiens

<400> SEQUENCE: 112

Trp Val Arg Gln Ala Ser Gly Lys Gly Leu Glu Trp Val Gly
1               5                   10

<210> SEQ ID NO 113
<211> LENGTH: 30
<212> TYPE: PRT
<213> ORGANISM: Homo sapiens

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 114
<211> LENGTH: 5
<212> TYPE: PRT
<213> ORGANISM: Homo sapiens

<400> SEQUENCE: 114

Ser Tyr Trp Met His
1               5

<210> SEQ ID NO 115
<211> LENGTH: 14
<212> TYPE: PRT
<213> ORGANISM: Homo sapiens

<400> SEQUENCE: 115

Trp Val Arg Gln Ala Pro Gly Lys Gly Leu Val Trp Val Ser
1               5                   10

<210> SEQ ID NO 116
<211> LENGTH: 30
<212> TYPE: PRT
<213> ORGANISM: Homo sapiens

<400> SEQUENCE: 116

Glu Val Gln Leu Val Glu Ser Arg Gly Val Leu Val Gln Pro Gly Gly
1               5                   10                  15

Ser Leu Arg Leu Ser Cys Ala Ala Ser Gly Phe Thr Val Ser
            20                  25                  30

<210> SEQ ID NO 117
<211> LENGTH: 5
<212> TYPE: PRT
<213> ORGANISM: Homo sapiens

<400> SEQUENCE: 117

Ser Asn Glu Met Ser
1               5

<210> SEQ ID NO 118
<211> LENGTH: 14
<212> TYPE: PRT
<213> ORGANISM: Homo sapiens

<400> SEQUENCE: 118

Trp Val Arg Gln Ala Pro Gly Lys Gly Leu Glu Trp Val Ser
1               5                   10

<210> SEQ ID NO 119
<211> LENGTH: 30
<212> TYPE: PRT
<213> ORGANISM: Homo sapiens

<400> SEQUENCE: 119

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser
            20                  25                  30

<210> SEQ ID NO 120
<211> LENGTH: 6
<212> TYPE: PRT
<213> ORGANISM: Homo sapiens

<400> SEQUENCE: 120

Ser Ser Asn Trp Trp Ser
1               5

<210> SEQ ID NO 121

<211> LENGTH: 14
<212> TYPE: PRT
<213> ORGANISM: Homo sapiens

<400> SEQUENCE: 121

Trp Val Arg Gln Pro Pro Gly Lys Gly Leu Glu Trp Ile Gly
1               5                   10

<210> SEQ ID NO 122
<211> LENGTH: 30
<212> TYPE: PRT
<213> ORGANISM: Homo sapiens

<400> SEQUENCE: 122

Gln Val Gln Leu Gln Glu Ser Gly Pro Gly Leu Val Lys Pro Ser Asp
1               5                   10                  15
Thr Leu Ser Leu Thr Cys Ala Val Ser Gly Tyr Ser Ile Ser
            20                  25                  30

<210> SEQ ID NO 123
<211> LENGTH: 6
<212> TYPE: PRT
<213> ORGANISM: Homo sapiens

<400> SEQUENCE: 123

Ser Ser Asn Trp Trp Gly
1               5

<210> SEQ ID NO 124
<211> LENGTH: 14
<212> TYPE: PRT
<213> ORGANISM: Homo sapiens

<400> SEQUENCE: 124

Trp Ile Arg Gln Pro Pro Gly Lys Gly Leu Glu Trp Ile Gly
1               5                   10

<210> SEQ ID NO 125
<211> LENGTH: 30
<212> TYPE: PRT
<213> ORGANISM: Homo sapiens

<400> SEQUENCE: 125

Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Ser
            20                  25                  30

<210> SEQ ID NO 126
<211> LENGTH: 7
<212> TYPE: PRT
<213> ORGANISM: Homo sapiens

<400> SEQUENCE: 126

Ser Gly Gly Tyr Tyr Trp Ser
1               5

<210> SEQ ID NO 127
<211> LENGTH: 14
<212> TYPE: PRT
<213> ORGANISM: Homo sapiens

<400> SEQUENCE: 127

Trp Ile Arg Gln His Pro Gly Lys Gly Leu Glu Trp Ile Gly
1               5                   10

<210> SEQ ID NO 128
<211> LENGTH: 30
<212> TYPE: PRT
<213> ORGANISM: Homo sapiens

<400> SEQUENCE: 128

Gln Leu Gln Leu Gln Glu Ser Gly Ser Gly Leu Val Lys Pro Ser Gln
1               5                   10                  15
Thr Leu Ser Leu Thr Cys Ala Val Ser Gly Gly Ser Ile Ser
            20                  25                  30

<210> SEQ ID NO 129
<211> LENGTH: 7
<212> TYPE: PRT
<213> ORGANISM: Homo sapiens

<400> SEQUENCE: 129

Ser Gly Gly Tyr Ser Trp Ser
1               5

<210> SEQ ID NO 130
<211> LENGTH: 14
<212> TYPE: PRT
<213> ORGANISM: Homo sapiens

<400> SEQUENCE: 130

Trp Ile Arg Gln Pro Pro Gly Lys Gly Leu Glu Trp Ile Gly
1               5                   10

<210> SEQ ID NO 131
<211> LENGTH: 30
<212> TYPE: PRT
<213> ORGANISM: Homo sapiens

<400> SEQUENCE: 131

Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Ser
            20                  25                  30

<210> SEQ ID NO 132
<211> LENGTH: 7
<212> TYPE: PRT
<213> ORGANISM: Homo sapiens

<400> SEQUENCE: 132

Ser Gly Asp Tyr Tyr Trp Ser
1               5

<210> SEQ ID NO 133
<211> LENGTH: 14
<212> TYPE: PRT
<213> ORGANISM: Homo sapiens

<400> SEQUENCE: 133

Trp Ile Arg Gln Pro Pro Gly Lys Gly Leu Glu Trp Ile Gly
1               5                   10

<210> SEQ ID NO 134
<211> LENGTH: 30
<212> TYPE: PRT
<213> ORGANISM: Homo sapiens

<400> SEQUENCE: 134

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser
            20                  25                  30
```

<210> SEQ ID NO 135
<211> LENGTH: 7
<212> TYPE: PRT
<213> ORGANISM: Homo sapiens

<400> SEQUENCE: 135

```
Ser Gly Gly Tyr Tyr Trp Ser
1               5
```

<210> SEQ ID NO 136
<211> LENGTH: 14
<212> TYPE: PRT
<213> ORGANISM: Homo sapiens

<400> SEQUENCE: 136

```
Trp Ile Arg Gln His Pro Gly Lys Gly Leu Glu Trp Ile Gly
1               5                   10
```

<210> SEQ ID NO 137
<211> LENGTH: 30
<212> TYPE: PRT
<213> ORGANISM: Homo sapiens

<400> SEQUENCE: 137

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser
            20                  25                  30
```

<210> SEQ ID NO 138
<211> LENGTH: 5
<212> TYPE: PRT
<213> ORGANISM: Homo sapiens

<400> SEQUENCE: 138

```
Gly Tyr Tyr Trp Ser
1               5
```

<210> SEQ ID NO 139
<211> LENGTH: 14
<212> TYPE: PRT
<213> ORGANISM: Homo sapiens

<400> SEQUENCE: 139

```
Trp Ile Arg Gln Pro Pro Gly Lys Gly Leu Glu Trp Ile Gly
1               5                   10
```

<210> SEQ ID NO 140
<211> LENGTH: 30
<212> TYPE: PRT
<213> ORGANISM: Homo sapiens

<400> SEQUENCE: 140

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30
```

```
<210> SEQ ID NO 141
<211> LENGTH: 7
<212> TYPE: PRT
<213> ORGANISM: Homo sapiens

<400> SEQUENCE: 141

Ser Ser Ser Tyr Tyr Trp Gly
1               5

<210> SEQ ID NO 142
<211> LENGTH: 14
<212> TYPE: PRT
<213> ORGANISM: Homo sapiens

<400> SEQUENCE: 142

Trp Ile Arg Gln Pro Pro Gly Lys Gly Leu Glu Trp Ile Gly
1               5                   10

<210> SEQ ID NO 143
<211> LENGTH: 30
<212> TYPE: PRT
<213> ORGANISM: Homo sapiens

<400> SEQUENCE: 143

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser
            20                  25                  30

<210> SEQ ID NO 144
<211> LENGTH: 5
<212> TYPE: PRT
<213> ORGANISM: Homo sapiens

<400> SEQUENCE: 144

Ser Tyr Tyr Trp Ser
1               5

<210> SEQ ID NO 145
<211> LENGTH: 14
<212> TYPE: PRT
<213> ORGANISM: Homo sapiens

<400> SEQUENCE: 145

Trp Ile Arg Gln Pro Pro Gly Lys Gly Leu Glu Trp Ile Gly
1               5                   10

<210> SEQ ID NO 146
<211> LENGTH: 30
<212> TYPE: PRT
<213> ORGANISM: Homo sapiens

<400> SEQUENCE: 146

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Val Ser
            20                  25                  30

<210> SEQ ID NO 147
<211> LENGTH: 7
<212> TYPE: PRT
<213> ORGANISM: Homo sapiens

<400> SEQUENCE: 147

Ser Gly Ser Tyr Tyr Trp Ser
```

```
<210> SEQ ID NO 148
<211> LENGTH: 14
<212> TYPE: PRT
<213> ORGANISM: Homo sapiens

<400> SEQUENCE: 148

Trp Ile Arg Gln Pro Pro Gly Lys Gly Leu Glu Trp Ile Gly
1               5                   10

<210> SEQ ID NO 149
<211> LENGTH: 30
<212> TYPE: PRT
<213> ORGANISM: Homo sapiens

<400> SEQUENCE: 149

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser
            20                  25                  30

<210> SEQ ID NO 150
<211> LENGTH: 6
<212> TYPE: PRT
<213> ORGANISM: Homo sapiens

<400> SEQUENCE: 150

Ser Gly Tyr Tyr Trp Gly
1               5

<210> SEQ ID NO 151
<211> LENGTH: 14
<212> TYPE: PRT
<213> ORGANISM: Homo sapiens

<400> SEQUENCE: 151

Trp Ile Arg Gln Pro Pro Gly Lys Gly Leu Glu Trp Ile Gly
1               5                   10

<210> SEQ ID NO 152
<211> LENGTH: 30
<212> TYPE: PRT
<213> ORGANISM: Homo sapiens

<400> SEQUENCE: 152

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 153
<211> LENGTH: 5
<212> TYPE: PRT
<213> ORGANISM: Homo sapiens

<400> SEQUENCE: 153

Ser Tyr Trp Ile Gly
1               5

<210> SEQ ID NO 154
<211> LENGTH: 14
<212> TYPE: PRT
<213> ORGANISM: Homo sapiens
```

<400> SEQUENCE: 154

Trp Val Arg Gln Met Pro Gly Lys Gly Leu Glu Trp Met Gly
1               5                   10

<210> SEQ ID NO 155
<211> LENGTH: 30
<212> TYPE: PRT
<213> ORGANISM: Homo sapiens

<400> SEQUENCE: 155

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr
            20                  25                  30

<210> SEQ ID NO 156
<211> LENGTH: 5
<212> TYPE: PRT
<213> ORGANISM: Homo sapiens

<400> SEQUENCE: 156

Ser Tyr Trp Ile Ser
1               5

<210> SEQ ID NO 157
<211> LENGTH: 14
<212> TYPE: PRT
<213> ORGANISM: Homo sapiens

<400> SEQUENCE: 157

Trp Val Arg Gln Met Pro Gly Lys Gly Leu Glu Trp Met Gly
1               5                   10

<210> SEQ ID NO 158
<211> LENGTH: 30
<212> TYPE: PRT
<213> ORGANISM: Homo sapiens

<400> SEQUENCE: 158

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser
            20                  25                  30

<210> SEQ ID NO 159
<211> LENGTH: 7
<212> TYPE: PRT
<213> ORGANISM: Homo sapiens

<400> SEQUENCE: 159

Ser Asn Ser Ala Ala Trp Asn
1               5

<210> SEQ ID NO 160
<211> LENGTH: 14
<212> TYPE: PRT
<213> ORGANISM: Homo sapiens

<400> SEQUENCE: 160

Trp Ile Arg Gln Ser Pro Ser Arg Gly Leu Glu Trp Leu Gly
1               5                   10

<210> SEQ ID NO 161
<211> LENGTH: 30

```
<212> TYPE: PRT
<213> ORGANISM: Homo sapiens

<400> SEQUENCE: 161

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 162
<211> LENGTH: 5
<212> TYPE: PRT
<213> ORGANISM: Homo sapiens

<400> SEQUENCE: 162

Ser Tyr Ala Met Asn
1               5

<210> SEQ ID NO 163
<211> LENGTH: 14
<212> TYPE: PRT
<213> ORGANISM: Homo sapiens

<400> SEQUENCE: 163

Trp Val Arg Gln Ala Pro Gly Gln Gly Leu Glu Trp Met Gly
1               5                   10

<210> SEQ ID NO 164
<211> LENGTH: 17
<212> TYPE: PRT
<213> ORGANISM: Homo sapiens

<400> SEQUENCE: 164

Trp Ile Asn Pro Asn Ser Gly Gly Thr Asn Tyr Ala Gln Lys Phe Gln
1               5                   10                  15

Gly

<210> SEQ ID NO 165
<211> LENGTH: 32
<212> TYPE: PRT
<213> ORGANISM: Homo sapiens

<400> SEQUENCE: 165

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 166
<211> LENGTH: 17
<212> TYPE: PRT
<213> ORGANISM: Homo sapiens

<400> SEQUENCE: 166

Trp Ile Asn Ala Gly Asn Gly Asn Thr Lys Tyr Ser Gln Lys Phe Gln
1               5                   10                  15

Gly

<210> SEQ ID NO 167
<211> LENGTH: 32
<212> TYPE: PRT
<213> ORGANISM: Homo sapiens

<400> SEQUENCE: 167
```

```
Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
                20                  25                  30
```

<210> SEQ ID NO 168
<211> LENGTH: 17
<212> TYPE: PRT
<213> ORGANISM: Homo sapiens

<400> SEQUENCE: 168

```
Trp Met Asn Pro Asn Ser Gly Asn Thr Gly Tyr Ala Gln Lys Phe Gln
1               5                   10                  15

Gly
```

<210> SEQ ID NO 169
<211> LENGTH: 32
<212> TYPE: PRT
<213> ORGANISM: Homo sapiens

<400> SEQUENCE: 169

```
Arg Val Thr Met Thr Arg Asn Thr Ser Ile Ser Thr Ala Tyr Met Glu
1               5                   10                  15

Leu Ser Ser Leu Arg Ser Glu Asp Thr Ala Val Tyr Tyr Cys Ala Arg
                20                  25                  30
```

<210> SEQ ID NO 170
<211> LENGTH: 17
<212> TYPE: PRT
<213> ORGANISM: Homo sapiens

<400> SEQUENCE: 170

```
Trp Ile Ser Ala Tyr Asn Gly Asn Thr Asn Tyr Ala Gln Lys Leu Gln
1               5                   10                  15

Gly
```

<210> SEQ ID NO 171
<211> LENGTH: 32
<212> TYPE: PRT
<213> ORGANISM: Homo sapiens

<400> SEQUENCE: 171

```
Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
                20                  25                  30
```

<210> SEQ ID NO 172
<211> LENGTH: 17
<212> TYPE: PRT
<213> ORGANISM: Homo sapiens

<400> SEQUENCE: 172

```
Gly Phe Asp Pro Glu Asp Gly Glu Thr Ile Tyr Ala Gln Lys Phe Gln
1               5                   10                  15

Gly
```

<210> SEQ ID NO 173
<211> LENGTH: 32
<212> TYPE: PRT
<213> ORGANISM: Homo sapiens

<400> SEQUENCE: 173

Arg Val Thr Met Thr Glu Asp Thr Ser Thr Ala Tyr Met Glu
1               5                   10                  15

Leu Ser Ser Leu Arg Ser Glu Asp Thr Ala Val Tyr Tyr Cys Ala Thr
                20                  25                  30

<210> SEQ ID NO 174
<211> LENGTH: 17
<212> TYPE: PRT
<213> ORGANISM: Homo sapiens

<400> SEQUENCE: 174

Trp Ile Thr Pro Phe Asn Gly Asn Thr Asn Tyr Ala Gln Lys Phe Gln
1               5                   10                  15

Asp

<210> SEQ ID NO 175
<211> LENGTH: 32
<212> TYPE: PRT
<213> ORGANISM: Homo sapiens

<400> SEQUENCE: 175

Arg Val Thr Ile Thr Arg Asp Arg Ser Met Ser Thr Ala Tyr Met Glu
1               5                   10                  15

Leu Ser Ser Leu Arg Ser Glu Asp Thr Ala Met Tyr Tyr Cys Ala Arg
                20                  25                  30

<210> SEQ ID NO 176
<211> LENGTH: 17
<212> TYPE: PRT
<213> ORGANISM: Homo sapiens

<400> SEQUENCE: 176

Ile Ile Asn Pro Ser Gly Gly Ser Thr Ser Tyr Ala Gln Lys Phe Gln
1               5                   10                  15

Gly

<210> SEQ ID NO 177
<211> LENGTH: 32
<212> TYPE: PRT
<213> ORGANISM: Homo sapiens

<400> SEQUENCE: 177

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 178
<211> LENGTH: 17
<212> TYPE: PRT
<213> ORGANISM: Homo sapiens

<400> SEQUENCE: 178

Trp Ile Val Val Gly Ser Gly Asn Thr Asn Tyr Ala Gln Lys Phe Gln
1               5                   10                  15

Glu

<210> SEQ ID NO 179
<211> LENGTH: 32
<212> TYPE: PRT
<213> ORGANISM: Homo sapiens

<400> SEQUENCE: 179

Arg Val Thr Ile Thr Arg Asp Met Ser Thr Ser Ala Tyr Met Glu
1               5                   10                  15

Leu Ser Ser Leu Arg Ser Glu Asp Thr Ala Val Tyr Tyr Cys Ala Ala
            20                  25                  30

<210> SEQ ID NO 180
<211> LENGTH: 17
<212> TYPE: PRT
<213> ORGANISM: Homo sapiens

<400> SEQUENCE: 180

Gly Ile Ile Pro Ile Phe Gly Thr Ala Asn Tyr Ala Gln Lys Phe Gln
1               5                   10                  15

Gly

<210> SEQ ID NO 181
<211> LENGTH: 32
<212> TYPE: PRT
<213> ORGANISM: Homo sapiens

<400> SEQUENCE: 181

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 182
<211> LENGTH: 17
<212> TYPE: PRT
<213> ORGANISM: Homo sapiens

<400> SEQUENCE: 182

Gly Ile Ile Pro Ile Phe Gly Thr Ala Asn Tyr Ala Gln Lys Phe Gln
1               5                   10                  15

Gly

<210> SEQ ID NO 183
<211> LENGTH: 32
<212> TYPE: PRT
<213> ORGANISM: Homo sapiens

<400> SEQUENCE: 183

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 184
<211> LENGTH: 17
<212> TYPE: PRT
<213> ORGANISM: Homo sapiens

<400> SEQUENCE: 184

Leu Val Asp Pro Glu Asp Gly Glu Thr Ile Tyr Ala Glu Lys Phe Gln
1               5                   10                  15

Gly

<210> SEQ ID NO 185
<211> LENGTH: 32
<212> TYPE: PRT

<213> ORGANISM: Homo sapiens

<400> SEQUENCE: 185

Arg Val Thr Ile Thr Ala Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
                20                  25                  30

<210> SEQ ID NO 186
<211> LENGTH: 16
<212> TYPE: PRT
<213> ORGANISM: Homo sapiens

<400> SEQUENCE: 186

Leu Ile Tyr Trp Asn Asp Asp Lys Arg Tyr Ser Pro Ser Leu Lys Ser
1               5                   10                  15

<210> SEQ ID NO 187
<211> LENGTH: 33
<212> TYPE: PRT
<213> ORGANISM: Homo sapiens

<400> SEQUENCE: 187

Arg Leu Thr Ile Thr Lys Asp Thr Ser Lys Asn Gln Val Val Leu Thr
1               5                   10                  15

Met Thr Asn Met Asp Pro Val Asp Thr Ala Thr Tyr Tyr Cys Ala His
                20                  25                  30

Arg

<210> SEQ ID NO 188
<211> LENGTH: 16
<212> TYPE: PRT
<213> ORGANISM: Homo sapiens

<400> SEQUENCE: 188

His Ile Phe Ser Asn Asp Glu Lys Ser Tyr Ser Thr Ser Leu Lys Ser
1               5                   10                  15

<210> SEQ ID NO 189
<211> LENGTH: 33
<212> TYPE: PRT
<213> ORGANISM: Homo sapiens

<400> SEQUENCE: 189

Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
                20                  25                  30

Ile

<210> SEQ ID NO 190
<211> LENGTH: 16
<212> TYPE: PRT
<213> ORGANISM: Homo sapiens

<400> SEQUENCE: 190

Arg Ile Asp Trp Asp Asp Asp Lys Phe Tyr Ser Thr Ser Leu Lys Thr
1               5                   10                  15

<210> SEQ ID NO 191
<211> LENGTH: 33
<212> TYPE: PRT
<213> ORGANISM: Homo sapiens

<400> SEQUENCE: 191

Arg Leu Thr Ile Ser Lys Asp Thr Ser Lys Asn Gln Val Val Leu Thr
1               5                   10                  15

Met Thr Asn Met Asp Pro Val Asp Thr Ala Tyr Tyr Cys Ala Arg
            20                  25                  30

Ile

<210> SEQ ID NO 192
<211> LENGTH: 17
<212> TYPE: PRT
<213> ORGANISM: Homo sapiens

<400> SEQUENCE: 192

Asn Ile Lys Gln Asp Gly Ser Glu Lys Tyr Tyr Val Asp Ser Val Lys
1               5                   10                  15

Gly

<210> SEQ ID NO 193
<211> LENGTH: 32
<212> TYPE: PRT
<213> ORGANISM: Homo sapiens

<400> SEQUENCE: 193

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 194
<211> LENGTH: 17
<212> TYPE: PRT
<213> ORGANISM: Homo sapiens

<400> SEQUENCE: 194

Gly Ile Ser Trp Asn Ser Gly Ser Ile Gly Tyr Ala Asp Ser Val Lys
1               5                   10                  15

Gly

<210> SEQ ID NO 195
<211> LENGTH: 33
<212> TYPE: PRT
<213> ORGANISM: Homo sapiens

<400> SEQUENCE: 195

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr Tyr Cys Ala Lys
            20                  25                  30

Asp

<210> SEQ ID NO 196
<211> LENGTH: 17
<212> TYPE: PRT
<213> ORGANISM: Homo sapiens

<400> SEQUENCE: 196

Tyr Ile Ser Ser Ser Gly Ser Thr Ile Tyr Tyr Ala Asp Ser Val Lys
1               5                   10                  15

Gly

```
<210> SEQ ID NO 197
<211> LENGTH: 32
<212> TYPE: PRT
<213> ORGANISM: Homo sapiens

<400> SEQUENCE: 197

Arg Phe Thr Ile Ser Arg Asp Asn Ala Lys Asn Ser Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 198
<211> LENGTH: 16
<212> TYPE: PRT
<213> ORGANISM: Homo sapiens

<400> SEQUENCE: 198

Ala Ile Gly Thr Ala Gly Asp Thr Tyr Tyr Pro Gly Ser Val Lys Gly
1               5                   10                  15

<210> SEQ ID NO 199
<211> LENGTH: 32
<212> TYPE: PRT
<213> ORGANISM: Homo sapiens

<400> SEQUENCE: 199

Arg Phe Thr Ile Ser Arg Glu Asn Ala Lys Asn Ser Leu Tyr Leu Gln
1               5                   10                  15
Met Asn Ser Leu Arg Ala Gly Asp Thr Ala Val Tyr Tyr Cys Ala Arg
            20                  25                  30

<210> SEQ ID NO 200
<211> LENGTH: 19
<212> TYPE: PRT
<213> ORGANISM: Homo sapiens

<400> SEQUENCE: 200

Arg Ile Lys Ser Lys Thr Asp Gly Gly Thr Thr Asp Tyr Ala Ala Pro
1               5                   10                  15
Val Lys Gly

<210> SEQ ID NO 201
<211> LENGTH: 32
<212> TYPE: PRT
<213> ORGANISM: Homo sapiens

<400> SEQUENCE: 201

Arg Phe Thr Ile Ser Arg Asp Asp Ser Lys Asn Thr Leu Tyr Leu Gln
1               5                   10                  15
Met Asn Ser Leu Lys Thr Glu Asp Thr Ala Val Tyr Tyr Cys Thr Thr
            20                  25                  30

<210> SEQ ID NO 202
<211> LENGTH: 17
<212> TYPE: PRT
<213> ORGANISM: Homo sapiens

<400> SEQUENCE: 202

Gly Ile Asn Trp Asn Gly Gly Ser Thr Gly Tyr Ala Asp Ser Val Lys
1               5                   10                  15
Gly
```

<210> SEQ ID NO 203
<211> LENGTH: 32
<212> TYPE: PRT
<213> ORGANISM: Homo sapiens

<400> SEQUENCE: 203

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Leu Tyr His Cys Ala Arg
            20                  25                  30

<210> SEQ ID NO 204
<211> LENGTH: 17
<212> TYPE: PRT
<213> ORGANISM: Homo sapiens

<400> SEQUENCE: 204

Ser Ile Ser Ser Ser Ser Ser Tyr Ile Tyr Tyr Ala Asp Ser Val Lys
1               5                   10                  15

Gly

<210> SEQ ID NO 205
<211> LENGTH: 32
<212> TYPE: PRT
<213> ORGANISM: Homo sapiens

<400> SEQUENCE: 205

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 206
<211> LENGTH: 17
<212> TYPE: PRT
<213> ORGANISM: Homo sapiens

<400> SEQUENCE: 206

Ala Ile Ser Gly Ser Gly Gly Ser Thr Tyr Tyr Ala Asp Ser Val Lys
1               5                   10                  15

Gly

<210> SEQ ID NO 207
<211> LENGTH: 32
<212> TYPE: PRT
<213> ORGANISM: Homo sapiens

<400> SEQUENCE: 207

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 208
<211> LENGTH: 17
<212> TYPE: PRT
<213> ORGANISM: Homo sapiens

<400> SEQUENCE: 208

Val Ile Ser Tyr Asp Gly Ser Asn Lys Tyr Tyr Ala Asp Ser Val Lys
1               5                   10                  15

Gly

<210> SEQ ID NO 209
<211> LENGTH: 32
<212> TYPE: PRT
<213> ORGANISM: Homo sapiens

<400> SEQUENCE: 209

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Lys
            20                  25                  30

<210> SEQ ID NO 210
<211> LENGTH: 17
<212> TYPE: PRT
<213> ORGANISM: Homo sapiens

<400> SEQUENCE: 210

Val Ile Ser Tyr Asp Gly Ser Asn Lys Tyr Tyr Ala Asp Ser Val Lys
1               5                   10                  15
Gly

<210> SEQ ID NO 211
<211> LENGTH: 32
<212> TYPE: PRT
<213> ORGANISM: Homo sapiens

<400> SEQUENCE: 211

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 212
<211> LENGTH: 17
<212> TYPE: PRT
<213> ORGANISM: Homo sapiens

<400> SEQUENCE: 212

Val Ile Ser Tyr Asp Gly Ser Asn Lys Tyr Tyr Ala Asp Ser Val Lys
1               5                   10                  15
Gly

<210> SEQ ID NO 213
<211> LENGTH: 32
<212> TYPE: PRT
<213> ORGANISM: Homo sapiens

<400> SEQUENCE: 213

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Lys
            20                  25                  30

<210> SEQ ID NO 214
<211> LENGTH: 17
<212> TYPE: PRT
<213> ORGANISM: Homo sapiens

<400> SEQUENCE: 214

Val Ile Trp Tyr Asp Gly Ser Asn Lys Tyr Tyr Ala Asp Ser Val Lys
1               5                   10                  15
Gly

<210> SEQ ID NO 215
<211> LENGTH: 32
<212> TYPE: PRT
<213> ORGANISM: Homo sapiens

<400> SEQUENCE: 215

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 216
<211> LENGTH: 17
<212> TYPE: PRT
<213> ORGANISM: Homo sapiens

<400> SEQUENCE: 216

Leu Ile Ser Trp Asp Gly Gly Ser Thr Tyr Tyr Ala Asp Ser Val Lys
1               5                   10                  15

Gly

<210> SEQ ID NO 217
<211> LENGTH: 33
<212> TYPE: PRT
<213> ORGANISM: Homo sapiens

<400> SEQUENCE: 217

Arg Phe Thr Ile Ser Arg Asp Asn Ser Lys Asn Ser Leu Tyr Leu Gln
1               5                   10                  15

Met Asn Ser Leu Arg Thr Glu Asp Thr Ala Leu Tyr Tyr Cys Ala Lys
            20                  25                  30

Asp

<210> SEQ ID NO 218
<211> LENGTH: 17
<212> TYPE: PRT
<213> ORGANISM: Homo sapiens

<400> SEQUENCE: 218

Tyr Ile Ser Ser Ser Ser Ser Thr Ile Tyr Tyr Ala Asp Ser Val Lys
1               5                   10                  15

Gly

<210> SEQ ID NO 219
<211> LENGTH: 32
<212> TYPE: PRT
<213> ORGANISM: Homo sapiens

<400> SEQUENCE: 219

Arg Phe Thr Ile Ser Arg Asp Asn Ala Lys Asn Ser Leu Tyr Leu Gln
1               5                   10                  15

Met Asn Ser Leu Arg Asp Glu Asp Thr Ala Val Tyr Tyr Cys Ala Arg
            20                  25                  30

<210> SEQ ID NO 220
<211> LENGTH: 19
<212> TYPE: PRT
<213> ORGANISM: Homo sapiens

<400> SEQUENCE: 220

Phe Ile Arg Ser Lys Ala Tyr Gly Gly Thr Thr Glu Tyr Thr Ala Ser

```
1               5                  10                  15

Val Lys Gly

<210> SEQ ID NO 221
<211> LENGTH: 32
<212> TYPE: PRT
<213> ORGANISM: Homo sapiens

<400> SEQUENCE: 221

Arg Phe Thr Ile Ser Arg Asp Gly Ser Lys Ser Ile Ala Tyr Leu Gln
1               5                  10                  15

Met Asn Ser Leu Lys Thr Glu Asp Thr Ala Val Tyr Tyr Cys Thr Arg
            20                  25                  30

<210> SEQ ID NO 222
<211> LENGTH: 16
<212> TYPE: PRT
<213> ORGANISM: Homo sapiens

<400> SEQUENCE: 222

Val Ile Tyr Ser Gly Gly Ser Thr Tyr Tyr Ala Asp Ser Val Lys Gly
1               5                  10                  15

<210> SEQ ID NO 223
<211> LENGTH: 32
<212> TYPE: PRT
<213> ORGANISM: Homo sapiens

<400> SEQUENCE: 223

Arg Phe Thr Ile Ser Arg Asp Asn Ser Lys Asn Thr Leu Tyr Leu Gln
1               5                  10                  15

Met Asn Ser Leu Arg Ala Glu Asp Thr Ala Val Tyr Tyr Cys Ala Arg
            20                  25                  30

<210> SEQ ID NO 224
<211> LENGTH: 17
<212> TYPE: PRT
<213> ORGANISM: Homo sapiens

<400> SEQUENCE: 224

Ala Ile Ser Ser Asn Gly Gly Ser Thr Tyr Tyr Ala Asn Ser Val Lys
1               5                  10                  15

Gly

<210> SEQ ID NO 225
<211> LENGTH: 32
<212> TYPE: PRT
<213> ORGANISM: Homo sapiens

<400> SEQUENCE: 225

Arg Phe Thr Ile Ser Arg Asp Asn Ser Lys Asn Thr Leu Tyr Leu Gln
1               5                  10                  15

Met Gly Ser Leu Arg Ala Glu Asp Met Ala Val Tyr Tyr Cys Ala Arg
            20                  25                  30

<210> SEQ ID NO 226
<211> LENGTH: 16
<212> TYPE: PRT
<213> ORGANISM: Homo sapiens

<400> SEQUENCE: 226

Val Ile Tyr Ser Gly Gly Ser Thr Tyr Tyr Ala Asp Ser Val Lys Gly
1               5                  10                  15
```

```
<210> SEQ ID NO 227
<211> LENGTH: 32
<212> TYPE: PRT
<213> ORGANISM: Homo sapiens

<400> SEQUENCE: 227

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 228
<211> LENGTH: 19
<212> TYPE: PRT
<213> ORGANISM: Homo sapiens

<400> SEQUENCE: 228

Arg Thr Arg Asn Lys Ala Asn Ser Tyr Thr Thr Glu Tyr Ala Ala Ser
1               5                   10                  15

Val Lys Gly

<210> SEQ ID NO 229
<211> LENGTH: 32
<212> TYPE: PRT
<213> ORGANISM: Homo sapiens

<400> SEQUENCE: 229

Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys Ala Arg
            20                  25                  30

<210> SEQ ID NO 230
<211> LENGTH: 19
<212> TYPE: PRT
<213> ORGANISM: Homo sapiens

<400> SEQUENCE: 230

Arg Ile Arg Ser Lys Ala Asn Ser Tyr Ala Thr Ala Tyr Ala Ala Ser
1               5                   10                  15

Val Lys Gly

<210> SEQ ID NO 231
<211> LENGTH: 32
<212> TYPE: PRT
<213> ORGANISM: Homo sapiens

<400> SEQUENCE: 231

Arg Phe Thr Ile Ser Arg Asp Asp Ser Lys Asn Thr Ala Tyr Leu Gln
1               5                   10                  15

Met Asn Ser Leu Lys Thr Glu Asp Thr Ala Val Tyr Tyr Cys Thr Arg
            20                  25                  30

<210> SEQ ID NO 232
<211> LENGTH: 17
<212> TYPE: PRT
<213> ORGANISM: Homo sapiens

<400> SEQUENCE: 232

Arg Ile Asn Ser Asp Gly Ser Ser Thr Ser Tyr Ala Asp Ser Val Lys
1               5                   10                  15
```

Gly

<210> SEQ ID NO 233
<211> LENGTH: 32
<212> TYPE: PRT
<213> ORGANISM: Homo sapiens

<400> SEQUENCE: 233

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 234
<211> LENGTH: 15
<212> TYPE: PRT
<213> ORGANISM: Homo sapiens

<400> SEQUENCE: 234

Ser Ile Ser Gly Gly Ser Thr Tyr Tyr Ala Asp Ser Arg Lys Gly
1               5                   10                  15

<210> SEQ ID NO 235
<211> LENGTH: 32
<212> TYPE: PRT
<213> ORGANISM: Homo sapiens

<400> SEQUENCE: 235

Arg Phe Thr Ile Ser Arg Asp Asn Ser Lys Asn Thr Leu His Leu Gln
1               5                   10                  15

Met Asn Ser Leu Arg Ala Glu Asp Thr Ala Val Tyr Tyr Cys Lys Lys
            20                  25                  30

<210> SEQ ID NO 236
<211> LENGTH: 16
<212> TYPE: PRT
<213> ORGANISM: Homo sapiens

<400> SEQUENCE: 236

Glu Ile Tyr His Ser Gly Ser Thr Asn Tyr Asn Pro Ser Leu Lys Ser
1               5                   10                  15

<210> SEQ ID NO 237
<211> LENGTH: 32
<212> TYPE: PRT
<213> ORGANISM: Homo sapiens

<400> SEQUENCE: 237

Arg Val Thr Ile Ser Val Asp Lys Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 238
<211> LENGTH: 16
<212> TYPE: PRT
<213> ORGANISM: Homo sapiens

<400> SEQUENCE: 238

Tyr Ile Tyr Tyr Ser Gly Ser Thr Tyr Tyr Asn Pro Ser Leu Lys Ser
1               5                   10                  15

<210> SEQ ID NO 239
<211> LENGTH: 32

<212> TYPE: PRT
<213> ORGANISM: Homo sapiens

<400> SEQUENCE: 239

```
Arg Val Thr Met Ser Val Asp Thr Ser Lys Asn Gln Phe Ser Leu Lys
1               5                   10                  15

Leu Ser Ser Val Thr Ala Val Asp Thr Ala Val Tyr Tyr Cys Ala Arg
            20                  25                  30
```

<210> SEQ ID NO 240
<211> LENGTH: 16
<212> TYPE: PRT
<213> ORGANISM: Homo sapiens

<400> SEQUENCE: 240

```
Tyr Ile Tyr Tyr Ser Gly Ser Thr Tyr Tyr Asn Pro Ser Leu Lys Ser
1               5                   10                  15
```

<210> SEQ ID NO 241
<211> LENGTH: 32
<212> TYPE: PRT
<213> ORGANISM: Homo sapiens

<400> SEQUENCE: 241

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 242
<211> LENGTH: 16
<212> TYPE: PRT
<213> ORGANISM: Homo sapiens

<400> SEQUENCE: 242

```
Tyr Ile Tyr His Ser Gly Ser Thr Tyr Tyr Asn Pro Ser Leu Lys Ser
1               5                   10                  15
```

<210> SEQ ID NO 243
<211> LENGTH: 32
<212> TYPE: PRT
<213> ORGANISM: Homo sapiens

<400> SEQUENCE: 243

```
Arg Val Thr Ile Ser Val Asp Arg Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 244
<211> LENGTH: 16
<212> TYPE: PRT
<213> ORGANISM: Homo sapiens

<400> SEQUENCE: 244

```
Tyr Ile Tyr Tyr Ser Gly Ser Thr Tyr Tyr Asn Pro Ser Leu Lys Ser
1               5                   10                  15
```

<210> SEQ ID NO 245
<211> LENGTH: 32
<212> TYPE: PRT
<213> ORGANISM: Homo sapiens

<400> SEQUENCE: 245

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 246
<211> LENGTH: 16
<212> TYPE: PRT
<213> ORGANISM: Homo sapiens

<400> SEQUENCE: 246

Tyr Ile Tyr Tyr Ser Gly Ser Thr Tyr Tyr Asn Pro Ser Leu Lys Ser
1               5                   10                  15

<210> SEQ ID NO 247
<211> LENGTH: 32
<212> TYPE: PRT
<213> ORGANISM: Homo sapiens

<400> SEQUENCE: 247

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 248
<211> LENGTH: 16
<212> TYPE: PRT
<213> ORGANISM: Homo sapiens

<400> SEQUENCE: 248

Glu Ile Asn His Ser Gly Ser Thr Asn Tyr Asn Pro Ser Leu Lys Ser
1               5                   10                  15

<210> SEQ ID NO 249
<211> LENGTH: 32
<212> TYPE: PRT
<213> ORGANISM: Homo sapiens

<400> SEQUENCE: 249

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 250
<211> LENGTH: 16
<212> TYPE: PRT
<213> ORGANISM: Homo sapiens

<400> SEQUENCE: 250

Ser Ile Tyr Tyr Ser Gly Ser Thr Tyr Tyr Asn Pro Ser Leu Lys Ser
1               5                   10                  15

<210> SEQ ID NO 251
<211> LENGTH: 32
<212> TYPE: PRT
<213> ORGANISM: Homo sapiens

<400> SEQUENCE: 251

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 252
<211> LENGTH: 16
<212> TYPE: PRT
<213> ORGANISM: Homo sapiens

<400> SEQUENCE: 252

Tyr Ile Tyr Tyr Ser Gly Ser Thr Asn Tyr Asn Pro Ser Leu Lys Ser
1               5                   10                  15

<210> SEQ ID NO 253
<211> LENGTH: 32
<212> TYPE: PRT
<213> ORGANISM: Homo sapiens

<400> SEQUENCE: 253

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 254
<211> LENGTH: 16
<212> TYPE: PRT
<213> ORGANISM: Homo sapiens

<400> SEQUENCE: 254

Tyr Ile Tyr Tyr Ser Gly Ser Thr Asn Tyr Asn Pro Ser Leu Lys Ser
1               5                   10                  15

<210> SEQ ID NO 255
<211> LENGTH: 32
<212> TYPE: PRT
<213> ORGANISM: Homo sapiens

<400> SEQUENCE: 255

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 256
<211> LENGTH: 16
<212> TYPE: PRT
<213> ORGANISM: Homo sapiens

<400> SEQUENCE: 256

Ser Ile Tyr His Ser Gly Ser Thr Tyr Tyr Asn Pro Ser Leu Lys Ser
1               5                   10                  15

<210> SEQ ID NO 257
<211> LENGTH: 32
<212> TYPE: PRT
<213> ORGANISM: Homo sapiens

<400> SEQUENCE: 257

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 258
<211> LENGTH: 16
<212> TYPE: PRT

<213> ORGANISM: Homo sapiens

<400> SEQUENCE: 258

Ser Ile Tyr His Ser Gly Ser Thr Tyr Tyr Asn Pro Ser Leu Lys Ser
1               5                   10                  15

<210> SEQ ID NO 259
<211> LENGTH: 32
<212> TYPE: PRT
<213> ORGANISM: Homo sapiens

<400> SEQUENCE: 259

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
                20                  25                  30

<210> SEQ ID NO 260
<211> LENGTH: 17
<212> TYPE: PRT
<213> ORGANISM: Homo sapiens

<400> SEQUENCE: 260

Ile Ile Tyr Pro Gly Asp Ser Asp Thr Arg Tyr Ser Pro Ser Phe Gln
1               5                   10                  15

Gly

<210> SEQ ID NO 261
<211> LENGTH: 32
<212> TYPE: PRT
<213> ORGANISM: Homo sapiens

<400> SEQUENCE: 261

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
                20                  25                  30

<210> SEQ ID NO 262
<211> LENGTH: 17
<212> TYPE: PRT
<213> ORGANISM: Homo sapiens

<400> SEQUENCE: 262

Arg Ile Asp Pro Ser Asp Ser Tyr Thr Asn Tyr Ser Pro Ser Phe Gln
1               5                   10                  15

Gly

<210> SEQ ID NO 263
<211> LENGTH: 32
<212> TYPE: PRT
<213> ORGANISM: Homo sapiens

<400> SEQUENCE: 263

His Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
                20                  25                  30

<210> SEQ ID NO 264
<211> LENGTH: 18
<212> TYPE: PRT
<213> ORGANISM: Homo sapiens

```
<400> SEQUENCE: 264

Arg Thr Tyr Tyr Arg Ser Lys Trp Tyr Asn Asp Tyr Ala Val Ser Val
1               5                   10                  15
Lys Ser

<210> SEQ ID NO 265
<211> LENGTH: 32
<212> TYPE: PRT
<213> ORGANISM: Homo sapiens

<400> SEQUENCE: 265

Arg Ile Thr Ile Asn Pro Asp Thr Ser Lys Asn Gln Phe Ser Leu Gln
1               5                   10                  15
Leu Asn Ser Val Thr Pro Glu Asp Thr Ala Val Tyr Tyr Cys Ala Arg
            20                  25                  30

<210> SEQ ID NO 266
<211> LENGTH: 17
<212> TYPE: PRT
<213> ORGANISM: Homo sapiens

<400> SEQUENCE: 266

Trp Ile Asn Thr Asn Thr Gly Asn Pro Thr Tyr Ala Gln Gly Phe Thr
1               5                   10                  15
Gly

<210> SEQ ID NO 267
<211> LENGTH: 32
<212> TYPE: PRT
<213> ORGANISM: Homo sapiens

<400> SEQUENCE: 267

Arg Phe Val Phe Ser Leu Asp Thr Ser Val Ser Thr Ala Tyr Leu Gln
1               5                   10                  15
Ile Cys Ser Leu Lys Ala Glu Asp Thr Ala Val Tyr Tyr Cys Ala Arg
            20                  25                  30

<210> SEQ ID NO 268
<211> LENGTH: 5
<212> TYPE: PRT
<213> ORGANISM: Homo sapiens

<400> SEQUENCE: 268

Gly Thr Thr Gly Thr
1               5

<210> SEQ ID NO 269
<211> LENGTH: 5
<212> TYPE: PRT
<213> ORGANISM: Homo sapiens

<400> SEQUENCE: 269

Val Gln Leu Glu Arg
1               5

<210> SEQ ID NO 270
<211> LENGTH: 5
<212> TYPE: PRT
<213> ORGANISM: Homo sapiens

<400> SEQUENCE: 270

Tyr Asn Trp Asn Asp
```

```
<210> SEQ ID NO 271
<211> LENGTH: 5
<212> TYPE: PRT
<213> ORGANISM: Homo sapiens

<400> SEQUENCE: 271

Gly Ile Thr Gly Thr
1               5

<210> SEQ ID NO 272
<211> LENGTH: 4
<212> TYPE: PRT
<213> ORGANISM: Homo sapiens

<400> SEQUENCE: 272

Val Leu Glu Leu
1

<210> SEQ ID NO 273
<211> LENGTH: 5
<212> TYPE: PRT
<213> ORGANISM: Homo sapiens

<400> SEQUENCE: 273

Tyr Asn Trp Asn Tyr
1               5

<210> SEQ ID NO 274
<211> LENGTH: 5
<212> TYPE: PRT
<213> ORGANISM: Homo sapiens

<400> SEQUENCE: 274

Gly Ile Thr Gly Thr
1               5

<210> SEQ ID NO 275
<211> LENGTH: 4
<212> TYPE: PRT
<213> ORGANISM: Homo sapiens

<400> SEQUENCE: 275

Val Leu Glu Arg
1

<210> SEQ ID NO 276
<211> LENGTH: 5
<212> TYPE: PRT
<213> ORGANISM: Homo sapiens

<400> SEQUENCE: 276

Tyr Asn Trp Asn Asp
1               5

<210> SEQ ID NO 277
<211> LENGTH: 6
<212> TYPE: PRT
<213> ORGANISM: Homo sapiens

<400> SEQUENCE: 277

Gly Ile Val Gly Ala Thr
1               5
```

```
<210> SEQ ID NO 278
<211> LENGTH: 5
<212> TYPE: PRT
<213> ORGANISM: Homo sapiens

<400> SEQUENCE: 278

Val Trp Glu Leu Leu
1               5

<210> SEQ ID NO 279
<211> LENGTH: 6
<212> TYPE: PRT
<213> ORGANISM: Homo sapiens

<400> SEQUENCE: 279

Tyr Ser Gly Ser Tyr Tyr
1               5

<210> SEQ ID NO 280
<211> LENGTH: 8
<212> TYPE: PRT
<213> ORGANISM: Homo sapiens

<400> SEQUENCE: 280

Arg Ile Leu Tyr Gln Leu Leu Tyr
1               5

<210> SEQ ID NO 281
<211> LENGTH: 10
<212> TYPE: PRT
<213> ORGANISM: Homo sapiens

<400> SEQUENCE: 281

Gly Tyr Cys Ser Ser Thr Ser Cys Tyr Thr
1               5                   10

<210> SEQ ID NO 282
<211> LENGTH: 9
<212> TYPE: PRT
<213> ORGANISM: Homo sapiens

<400> SEQUENCE: 282

Asp Ile Val Val Pro Ala Ala Ile
1               5

<210> SEQ ID NO 283
<211> LENGTH: 9
<212> TYPE: PRT
<213> ORGANISM: Homo sapiens

<400> SEQUENCE: 283

Arg Ile Leu Tyr Trp Cys Met Leu Tyr
1               5

<210> SEQ ID NO 284
<211> LENGTH: 10
<212> TYPE: PRT
<213> ORGANISM: Homo sapiens

<400> SEQUENCE: 284

Gly Tyr Cys Thr Asn Gly Val Cys Tyr Thr
1               5                   10

<210> SEQ ID NO 285
<211> LENGTH: 9
<212> TYPE: PRT
```

```
<213> ORGANISM: Homo sapiens

<400> SEQUENCE: 285

Asp Ile Val Leu Met Val Tyr Ala Ile
1               5

<210> SEQ ID NO 286
<211> LENGTH: 8
<212> TYPE: PRT
<213> ORGANISM: Homo sapiens

<400> SEQUENCE: 286

Arg Ile Leu Trp Trp Leu Leu Leu
1               5

<210> SEQ ID NO 287
<211> LENGTH: 10
<212> TYPE: PRT
<213> ORGANISM: Homo sapiens

<400> SEQUENCE: 287

Gly Tyr Cys Ser Gly Gly Ser Cys Tyr Ser
1               5                   10

<210> SEQ ID NO 288
<211> LENGTH: 9
<212> TYPE: PRT
<213> ORGANISM: Homo sapiens

<400> SEQUENCE: 288

Asp Ile Val Val Val Val Ala Ala Thr
1               5

<210> SEQ ID NO 289
<211> LENGTH: 8
<212> TYPE: PRT
<213> ORGANISM: Homo sapiens

<400> SEQUENCE: 289

Ser Ile Leu Trp Trp Leu Leu Phe
1               5

<210> SEQ ID NO 290
<211> LENGTH: 9
<212> TYPE: PRT
<213> ORGANISM: Homo sapiens

<400> SEQUENCE: 290

Ala Tyr Cys Gly Gly Asp Cys Tyr Ser
1               5

<210> SEQ ID NO 291
<211> LENGTH: 8
<212> TYPE: PRT
<213> ORGANISM: Homo sapiens

<400> SEQUENCE: 291

His Ile Val Val Val Thr Ala Ile
1               5

<210> SEQ ID NO 292
<211> LENGTH: 10
<212> TYPE: PRT
<213> ORGANISM: Homo sapiens

<400> SEQUENCE: 292
```

Val Leu Arg Phe Leu Glu Trp Leu Leu Tyr
1               5                   10

<210> SEQ ID NO 293
<211> LENGTH: 10
<212> TYPE: PRT
<213> ORGANISM: Homo sapiens

<400> SEQUENCE: 293

Tyr Tyr Asp Phe Trp Ser Gly Tyr Tyr Thr
1               5                   10

<210> SEQ ID NO 294
<211> LENGTH: 9
<212> TYPE: PRT
<213> ORGANISM: Homo sapiens

<400> SEQUENCE: 294

Ile Thr Ile Phe Gly Val Val Ile Ile
1               5

<210> SEQ ID NO 295
<211> LENGTH: 9
<212> TYPE: PRT
<213> ORGANISM: Homo sapiens

<400> SEQUENCE: 295

Val Leu Arg Tyr Phe Asp Trp Leu Leu
1               5

<210> SEQ ID NO 296
<211> LENGTH: 10
<212> TYPE: PRT
<213> ORGANISM: Homo sapiens

<400> SEQUENCE: 296

Tyr Tyr Asp Ile Leu Thr Gly Tyr Tyr Asn
1               5                   10

<210> SEQ ID NO 297
<211> LENGTH: 8
<212> TYPE: PRT
<213> ORGANISM: Homo sapiens

<400> SEQUENCE: 297

Ile Thr Ile Phe Leu Val Ile Ile
1               5

<210> SEQ ID NO 298
<211> LENGTH: 9
<212> TYPE: PRT
<213> ORGANISM: Homo sapiens

<400> SEQUENCE: 298

Val Leu Leu Trp Phe Gly Glu Leu Leu
1               5

<210> SEQ ID NO 299
<211> LENGTH: 10
<212> TYPE: PRT
<213> ORGANISM: Homo sapiens

<400> SEQUENCE: 299

Tyr Tyr Tyr Gly Ser Gly Ser Tyr Tyr Asn
1               5                   10

```
<210> SEQ ID NO 300
<211> LENGTH: 9
<212> TYPE: PRT
<213> ORGANISM: Homo sapiens

<400> SEQUENCE: 300

Ile Thr Met Val Arg Gly Val Ile Ile
1               5

<210> SEQ ID NO 301
<211> LENGTH: 11
<212> TYPE: PRT
<213> ORGANISM: Homo sapiens

<400> SEQUENCE: 301

Val Leu Leu Arg Leu Gly Glu Leu Ser Leu Tyr
1               5                   10

<210> SEQ ID NO 302
<211> LENGTH: 12
<212> TYPE: PRT
<213> ORGANISM: Homo sapiens

<400> SEQUENCE: 302

Tyr Tyr Asp Tyr Val Trp Gly Ser Tyr Arg Tyr Thr
1               5                   10

<210> SEQ ID NO 303
<211> LENGTH: 11
<212> TYPE: PRT
<213> ORGANISM: Homo sapiens

<400> SEQUENCE: 303

Ile Met Ile Thr Phe Gly Gly Val Ile Val Ile
1               5                   10

<210> SEQ ID NO 304
<211> LENGTH: 7
<212> TYPE: PRT
<213> ORGANISM: Homo sapiens

<400> SEQUENCE: 304

Val Leu Leu Trp Leu Leu Leu
1               5

<210> SEQ ID NO 305
<211> LENGTH: 10
<212> TYPE: PRT
<213> ORGANISM: Homo sapiens

<400> SEQUENCE: 305

Tyr Tyr Tyr Asp Ser Ser Gly Tyr Tyr Tyr
1               5                   10

<210> SEQ ID NO 306
<211> LENGTH: 9
<212> TYPE: PRT
<213> ORGANISM: Homo sapiens

<400> SEQUENCE: 306

Ile Thr Met Ile Val Val Val Ile Thr
1               5

<210> SEQ ID NO 307
```

```
<211> LENGTH: 5
<212> TYPE: PRT
<213> ORGANISM: Homo sapiens

<400> SEQUENCE: 307

Asp Tyr Ser Asn Tyr
1               5

<210> SEQ ID NO 308
<211> LENGTH: 4
<212> TYPE: PRT
<213> ORGANISM: Homo sapiens

<400> SEQUENCE: 308

Thr Thr Val Thr
1

<210> SEQ ID NO 309
<211> LENGTH: 5
<212> TYPE: PRT
<213> ORGANISM: Homo sapiens

<400> SEQUENCE: 309

Asp Tyr Ser Asn Tyr
1               5

<210> SEQ ID NO 310
<211> LENGTH: 4
<212> TYPE: PRT
<213> ORGANISM: Homo sapiens

<400> SEQUENCE: 310

Thr Thr Val Thr
1

<210> SEQ ID NO 311
<211> LENGTH: 5
<212> TYPE: PRT
<213> ORGANISM: Homo sapiens

<400> SEQUENCE: 311

Asp Tyr Gly Asp Tyr
1               5

<210> SEQ ID NO 312
<211> LENGTH: 4
<212> TYPE: PRT
<213> ORGANISM: Homo sapiens

<400> SEQUENCE: 312

Thr Thr Val Thr
1

<210> SEQ ID NO 313
<211> LENGTH: 4
<212> TYPE: PRT
<213> ORGANISM: Homo sapiens

<400> SEQUENCE: 313

Leu Arg Trp Leu
1

<210> SEQ ID NO 314
<211> LENGTH: 6
<212> TYPE: PRT
<213> ORGANISM: Homo sapiens
```

<400> SEQUENCE: 314

Asp Tyr Gly Gly Asn Ser
1               5

<210> SEQ ID NO 315
<211> LENGTH: 5
<212> TYPE: PRT
<213> ORGANISM: Homo sapiens

<400> SEQUENCE: 315

Thr Thr Val Val Thr
1               5

<210> SEQ ID NO 316
<211> LENGTH: 6
<212> TYPE: PRT
<213> ORGANISM: Homo sapiens

<400> SEQUENCE: 316

Val Asp Thr Ala Met Val
1               5

<210> SEQ ID NO 317
<211> LENGTH: 6
<212> TYPE: PRT
<213> ORGANISM: Homo sapiens

<400> SEQUENCE: 317

Trp Ile Gln Leu Trp Leu
1               5

<210> SEQ ID NO 318
<211> LENGTH: 6
<212> TYPE: PRT
<213> ORGANISM: Homo sapiens

<400> SEQUENCE: 318

Gly Tyr Ser Tyr Gly Tyr
1               5

<210> SEQ ID NO 319
<211> LENGTH: 7
<212> TYPE: PRT
<213> ORGANISM: Homo sapiens

<400> SEQUENCE: 319

Val Asp Ile Val Ala Thr Ile
1               5

<210> SEQ ID NO 320
<211> LENGTH: 6
<212> TYPE: PRT
<213> ORGANISM: Homo sapiens

<400> SEQUENCE: 320

Trp Ile Trp Leu Arg Leu
1               5

<210> SEQ ID NO 321
<211> LENGTH: 7
<212> TYPE: PRT
<213> ORGANISM: Homo sapiens

<400> SEQUENCE: 321

```
Gly Tyr Ser Gly Tyr Asp Tyr
1               5

<210> SEQ ID NO 322
<211> LENGTH: 6
<212> TYPE: PRT
<213> ORGANISM: Homo sapiens

<400> SEQUENCE: 322

Val Asp Thr Ala Met Val
1               5

<210> SEQ ID NO 323
<211> LENGTH: 6
<212> TYPE: PRT
<213> ORGANISM: Homo sapiens

<400> SEQUENCE: 323

Trp Ile Gln Leu Trp Leu
1               5

<210> SEQ ID NO 324
<211> LENGTH: 6
<212> TYPE: PRT
<213> ORGANISM: Homo sapiens

<400> SEQUENCE: 324

Gly Tyr Ser Tyr Gly Tyr
1               5

<210> SEQ ID NO 325
<211> LENGTH: 6
<212> TYPE: PRT
<213> ORGANISM: Homo sapiens

<400> SEQUENCE: 325

Val Glu Met Ala Thr Ile
1               5

<210> SEQ ID NO 326
<211> LENGTH: 5
<212> TYPE: PRT
<213> ORGANISM: Homo sapiens

<400> SEQUENCE: 326

Arg Trp Leu Gln Leu
1               5

<210> SEQ ID NO 327
<211> LENGTH: 6
<212> TYPE: PRT
<213> ORGANISM: Homo sapiens

<400> SEQUENCE: 327

Arg Asp Gly Tyr Asn Tyr
1               5

<210> SEQ ID NO 328
<211> LENGTH: 6
<212> TYPE: PRT
<213> ORGANISM: Homo sapiens

<400> SEQUENCE: 328

Glu Tyr Ser Ser Ser Ser
1               5
```

```
<210> SEQ ID NO 329
<211> LENGTH: 5
<212> TYPE: PRT
<213> ORGANISM: Homo sapiens

<400> SEQUENCE: 329

Ser Ile Ala Ala Arg
1               5

<210> SEQ ID NO 330
<211> LENGTH: 4
<212> TYPE: PRT
<213> ORGANISM: Homo sapiens

<400> SEQUENCE: 330

Val Gln Leu Val
1

<210> SEQ ID NO 331
<211> LENGTH: 7
<212> TYPE: PRT
<213> ORGANISM: Homo sapiens

<400> SEQUENCE: 331

Gly Tyr Ser Ser Ser Trp Tyr
1               5

<210> SEQ ID NO 332
<211> LENGTH: 6
<212> TYPE: PRT
<213> ORGANISM: Homo sapiens

<400> SEQUENCE: 332

Gly Ile Ala Ala Ala Gly
1               5

<210> SEQ ID NO 333
<211> LENGTH: 5
<212> TYPE: PRT
<213> ORGANISM: Homo sapiens

<400> SEQUENCE: 333

Val Gln Gln Leu Val
1               5

<210> SEQ ID NO 334
<211> LENGTH: 7
<212> TYPE: PRT
<213> ORGANISM: Homo sapiens

<400> SEQUENCE: 334

Gly Tyr Ser Ser Gly Trp Tyr
1               5

<210> SEQ ID NO 335
<211> LENGTH: 6
<212> TYPE: PRT
<213> ORGANISM: Homo sapiens

<400> SEQUENCE: 335

Gly Ile Ala Val Ala Gly
1               5

<210> SEQ ID NO 336
<211> LENGTH: 5
```

```
<212> TYPE: PRT
<213> ORGANISM: Homo sapiens

<400> SEQUENCE: 336

Val Gln Trp Leu Val
1               5

<210> SEQ ID NO 337
<211> LENGTH: 17
<212> TYPE: PRT
<213> ORGANISM: Homo sapiens

<400> SEQUENCE: 337

Ala Glu Tyr Phe Gln His Trp Gly Gln Gly Thr Leu Val Thr Val Ser
1               5                   10                  15

Ser

<210> SEQ ID NO 338
<211> LENGTH: 17
<212> TYPE: PRT
<213> ORGANISM: Homo sapiens

<400> SEQUENCE: 338

Tyr Trp Tyr Phe Asp Leu Trp Gly Arg Gly Thr Leu Val Thr Val Ser
1               5                   10                  15

Ser

<210> SEQ ID NO 339
<211> LENGTH: 15
<212> TYPE: PRT
<213> ORGANISM: Homo sapiens

<400> SEQUENCE: 339

Ala Phe Asp Ile Trp Gly Gln Gly Thr Met Val Thr Val Ser Ser
1               5                   10                  15

<210> SEQ ID NO 340
<211> LENGTH: 15
<212> TYPE: PRT
<213> ORGANISM: Homo sapiens

<400> SEQUENCE: 340

Tyr Phe Asp Tyr Trp Gly Gln Gly Thr Leu Val Thr Val Ser Ser
1               5                   10                  15

<210> SEQ ID NO 341
<211> LENGTH: 16
<212> TYPE: PRT
<213> ORGANISM: Homo sapiens

<400> SEQUENCE: 341

Asn Trp Phe Asp Pro Trp Gly Gln Gly Thr Leu Val Thr Val Ser Ser
1               5                   10                  15

<210> SEQ ID NO 342
<211> LENGTH: 20
<212> TYPE: PRT
<213> ORGANISM: Homo sapiens

<400> SEQUENCE: 342

Tyr Tyr Tyr Tyr Tyr Gly Met Asp Val Trp Gly Gln Gly Thr Thr Val
1               5                   10                  15

Thr Val Ser Ser
            20
```

<210> SEQ ID NO 343
<211> LENGTH: 23
<212> TYPE: PRT
<213> ORGANISM: Homo sapiens

<400> SEQUENCE: 343

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 344
<211> LENGTH: 11
<212> TYPE: PRT
<213> ORGANISM: Homo sapiens

<400> SEQUENCE: 344

Arg Ala Ser Gln Ser Ile Ser Ser Tyr Leu Asn
1               5                   10

<210> SEQ ID NO 345
<211> LENGTH: 15
<212> TYPE: PRT
<213> ORGANISM: Homo sapiens

<400> SEQUENCE: 345

Trp Tyr Gln Gln Lys Pro Gly Lys Ala Pro Lys Leu Leu Ile Tyr
1               5                   10                  15

<210> SEQ ID NO 346
<211> LENGTH: 23
<212> TYPE: PRT
<213> ORGANISM: Homo sapiens

<400> SEQUENCE: 346

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 347
<211> LENGTH: 11
<212> TYPE: PRT
<213> ORGANISM: Homo sapiens

<400> SEQUENCE: 347

Arg Ala Ser Gln Ser Ile Ser Ser Tyr Leu Asn
1               5                   10

<210> SEQ ID NO 348
<211> LENGTH: 15
<212> TYPE: PRT
<213> ORGANISM: Homo sapiens

<400> SEQUENCE: 348

Trp Tyr Gln Gln Lys Pro Gly Lys Ala Pro Lys Leu Leu Ile Tyr
1               5                   10                  15

<210> SEQ ID NO 349
<211> LENGTH: 23
<212> TYPE: PRT
<213> ORGANISM: Homo sapiens

<400> SEQUENCE: 349

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 350
<211> LENGTH: 11
<212> TYPE: PRT
<213> ORGANISM: Homo sapiens

<400> SEQUENCE: 350

```
Gln Ala Ser Gln Asp Ile Ser Asn Tyr Leu Asn
1               5                   10
```

<210> SEQ ID NO 351
<211> LENGTH: 15
<212> TYPE: PRT
<213> ORGANISM: Homo sapiens

<400> SEQUENCE: 351

```
Trp Tyr Gln Gln Lys Pro Gly Lys Ala Pro Lys Leu Leu Ile Tyr
1               5                   10                  15
```

<210> SEQ ID NO 352
<211> LENGTH: 23
<212> TYPE: PRT
<213> ORGANISM: Homo sapiens

<400> SEQUENCE: 352

```
Asp Ile Gln Met Thr Gln Ser Pro Ser Ser Leu Ser Ala Ser Val Gly
1               5                   10                  15

Asp Arg Val Thr Ile Thr Cys
            20
```

<210> SEQ ID NO 353
<211> LENGTH: 11
<212> TYPE: PRT
<213> ORGANISM: Homo sapiens

<400> SEQUENCE: 353

```
Gln Ala Ser Gln Asp Ile Ser Asn Tyr Leu Asn
1               5                   10
```

<210> SEQ ID NO 354
<211> LENGTH: 15
<212> TYPE: PRT
<213> ORGANISM: Homo sapiens

<400> SEQUENCE: 354

```
Trp Tyr Gln Gln Lys Pro Gly Lys Ala Pro Lys Leu Leu Ile Tyr
1               5                   10                  15
```

<210> SEQ ID NO 355
<211> LENGTH: 23
<212> TYPE: PRT
<213> ORGANISM: Homo sapiens

<400> SEQUENCE: 355

```
Asp Ile Gln Met Thr Gln Ser Pro Ser Ser Leu Ser Ala Ser Val Gly
1               5                   10                  15

Asp Arg Val Thr Ile Thr Cys
            20
```

```
<210> SEQ ID NO 356
<211> LENGTH: 11
<212> TYPE: PRT
<213> ORGANISM: Homo sapiens

<400> SEQUENCE: 356

Arg Ala Ser Gln Gly Ile Ser Asn Tyr Leu Ala
1               5                   10

<210> SEQ ID NO 357
<211> LENGTH: 15
<212> TYPE: PRT
<213> ORGANISM: Homo sapiens

<400> SEQUENCE: 357

Trp Tyr Gln Gln Lys Pro Gly Lys Val Pro Lys Leu Leu Ile Tyr
1               5                   10                  15

<210> SEQ ID NO 358
<211> LENGTH: 23
<212> TYPE: PRT
<213> ORGANISM: Homo sapiens

<400> SEQUENCE: 358

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 359
<211> LENGTH: 11
<212> TYPE: PRT
<213> ORGANISM: Homo sapiens

<400> SEQUENCE: 359

Arg Ala Ser Gln Gly Ile Arg Asn Asp Leu Gly
1               5                   10

<210> SEQ ID NO 360
<211> LENGTH: 15
<212> TYPE: PRT
<213> ORGANISM: Homo sapiens

<400> SEQUENCE: 360

Trp Tyr Gln Gln Lys Pro Gly Lys Ala Pro Lys Arg Leu Ile Tyr
1               5                   10                  15

<210> SEQ ID NO 361
<211> LENGTH: 23
<212> TYPE: PRT
<213> ORGANISM: Homo sapiens

<400> SEQUENCE: 361

Asn Ile Gln Met Thr Gln Ser Pro Ser Ala Met Ser Ala Ser Val Gly
1               5                   10                  15

Asp Arg Val Thr Ile Thr Cys
            20

<210> SEQ ID NO 362
<211> LENGTH: 11
<212> TYPE: PRT
<213> ORGANISM: Homo sapiens

<400> SEQUENCE: 362

Arg Ala Arg Gln Gly Ile Ser Asn Tyr Leu Ala
```

```
1               5                   10

<210> SEQ ID NO 363
<211> LENGTH: 15
<212> TYPE: PRT
<213> ORGANISM: Homo sapiens

<400> SEQUENCE: 363

Trp Phe Gln Gln Lys Pro Gly Lys Val Pro Lys His Leu Ile Tyr
1               5                   10                  15

<210> SEQ ID NO 364
<211> LENGTH: 23
<212> TYPE: PRT
<213> ORGANISM: Homo sapiens

<400> SEQUENCE: 364

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 365
<211> LENGTH: 11
<212> TYPE: PRT
<213> ORGANISM: Homo sapiens

<400> SEQUENCE: 365

Arg Ala Ser Gln Gly Ile Ser Asn Tyr Leu Ala
1               5                   10

<210> SEQ ID NO 366
<211> LENGTH: 15
<212> TYPE: PRT
<213> ORGANISM: Homo sapiens

<400> SEQUENCE: 366

Trp Phe Gln Gln Lys Pro Gly Lys Ala Pro Lys Ser Leu Ile Tyr
1               5                   10                  15

<210> SEQ ID NO 367
<211> LENGTH: 23
<212> TYPE: PRT
<213> ORGANISM: Homo sapiens

<400> SEQUENCE: 367

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 368
<211> LENGTH: 11
<212> TYPE: PRT
<213> ORGANISM: Homo sapiens

<400> SEQUENCE: 368

Arg Ala Ser Gln Gly Ile Ser Ser Trp Leu Ala
1               5                   10

<210> SEQ ID NO 369
<211> LENGTH: 15
<212> TYPE: PRT
<213> ORGANISM: Homo sapiens
```

<400> SEQUENCE: 369

Trp Tyr Gln Gln Lys Pro Glu Lys Ala Pro Lys Ser Leu Ile Tyr
1               5                   10                  15

<210> SEQ ID NO 370
<211> LENGTH: 23
<212> TYPE: PRT
<213> ORGANISM: Homo sapiens

<400> SEQUENCE: 370

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 371
<211> LENGTH: 11
<212> TYPE: PRT
<213> ORGANISM: Homo sapiens

<400> SEQUENCE: 371

Arg Ala Ser Gln Gly Ile Ser Ser Ala Leu Ala
1               5                   10

<210> SEQ ID NO 372
<211> LENGTH: 15
<212> TYPE: PRT
<213> ORGANISM: Homo sapiens

<400> SEQUENCE: 372

Trp Tyr Gln Gln Lys Pro Gly Lys Ala Pro Lys Leu Leu Ile Tyr
1               5                   10                  15

<210> SEQ ID NO 373
<211> LENGTH: 23
<212> TYPE: PRT
<213> ORGANISM: Homo sapiens

<400> SEQUENCE: 373

Ala Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 374
<211> LENGTH: 11
<212> TYPE: PRT
<213> ORGANISM: Homo sapiens

<400> SEQUENCE: 374

Arg Ala Ser Gln Gly Ile Ser Ser Ala Leu Ala
1               5                   10

<210> SEQ ID NO 375
<211> LENGTH: 15
<212> TYPE: PRT
<213> ORGANISM: Homo sapiens

<400> SEQUENCE: 375

Trp Tyr Gln Gln Lys Pro Gly Lys Ala Pro Lys Leu Leu Ile Tyr
1               5                   10                  15

<210> SEQ ID NO 376
<211> LENGTH: 23

```
<212> TYPE: PRT
<213> ORGANISM: Homo sapiens

<400> SEQUENCE: 376

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 377
<211> LENGTH: 11
<212> TYPE: PRT
<213> ORGANISM: Homo sapiens

<400> SEQUENCE: 377

Arg Ala Ser Gln Gly Ile Ser Ser Trp Leu Ala
1               5                   10

<210> SEQ ID NO 378
<211> LENGTH: 15
<212> TYPE: PRT
<213> ORGANISM: Homo sapiens

<400> SEQUENCE: 378

Trp Tyr Gln Gln Lys Pro Gly Lys Ala Pro Lys Leu Leu Ile Tyr
1               5                   10                  15

<210> SEQ ID NO 379
<211> LENGTH: 23
<212> TYPE: PRT
<213> ORGANISM: Homo sapiens

<400> SEQUENCE: 379

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 380
<211> LENGTH: 11
<212> TYPE: PRT
<213> ORGANISM: Homo sapiens

<400> SEQUENCE: 380

Arg Ala Ser Gln Gly Ile Ser Ser Trp Leu Ala
1               5                   10

<210> SEQ ID NO 381
<211> LENGTH: 15
<212> TYPE: PRT
<213> ORGANISM: Homo sapiens

<400> SEQUENCE: 381

Trp Tyr Gln Gln Lys Pro Gly Lys Ala Pro Lys Leu Leu Ile Tyr
1               5                   10                  15

<210> SEQ ID NO 382
<211> LENGTH: 23
<212> TYPE: PRT
<213> ORGANISM: Homo sapiens

<400> SEQUENCE: 382

Asp Ile Gln Leu Thr Gln Ser Pro Ser Phe Leu Ser Ala Ser Val Gly
1               5                   10                  15
```

```
Asp Arg Val Thr Ile Thr Cys
        20

<210> SEQ ID NO 383
<211> LENGTH: 11
<212> TYPE: PRT
<213> ORGANISM: Homo sapiens

<400> SEQUENCE: 383

Arg Ala Ser Gln Gly Ile Ser Ser Tyr Leu Ala
1               5                   10

<210> SEQ ID NO 384
<211> LENGTH: 15
<212> TYPE: PRT
<213> ORGANISM: Homo sapiens

<400> SEQUENCE: 384

Trp Tyr Gln Gln Lys Pro Gly Lys Ala Pro Lys Leu Leu Ile Tyr
1               5                   10                  15

<210> SEQ ID NO 385
<211> LENGTH: 23
<212> TYPE: PRT
<213> ORGANISM: Homo sapiens

<400> SEQUENCE: 385

Ala Ile Arg Met Thr Gln Ser Pro Phe Ser Leu Ser Ala Ser Val Gly
1               5                   10                  15

Asp Arg Val Thr Ile Thr Cys
        20

<210> SEQ ID NO 386
<211> LENGTH: 11
<212> TYPE: PRT
<213> ORGANISM: Homo sapiens

<400> SEQUENCE: 386

Trp Ala Ser Gln Gly Ile Ser Ser Tyr Leu Ala
1               5                   10

<210> SEQ ID NO 387
<211> LENGTH: 15
<212> TYPE: PRT
<213> ORGANISM: Homo sapiens

<400> SEQUENCE: 387

Trp Tyr Gln Gln Lys Pro Ala Lys Ala Pro Lys Leu Phe Ile Tyr
1               5                   10                  15

<210> SEQ ID NO 388
<211> LENGTH: 23
<212> TYPE: PRT
<213> ORGANISM: Homo sapiens

<400> SEQUENCE: 388

Ala Ile Arg Met Thr Gln Ser Pro Ser Ser Phe Ser Ala Ser Thr Gly
1               5                   10                  15

Asp Arg Val Thr Ile Thr Cys
        20

<210> SEQ ID NO 389
<211> LENGTH: 11
<212> TYPE: PRT
<213> ORGANISM: Homo sapiens
```

```
<400> SEQUENCE: 389

Arg Ala Ser Gln Gly Ile Ser Ser Tyr Leu Ala
1               5                   10

<210> SEQ ID NO 390
<211> LENGTH: 15
<212> TYPE: PRT
<213> ORGANISM: Homo sapiens

<400> SEQUENCE: 390

Trp Tyr Gln Gln Lys Pro Gly Lys Ala Pro Lys Leu Leu Ile Tyr
1               5                   10                  15

<210> SEQ ID NO 391
<211> LENGTH: 23
<212> TYPE: PRT
<213> ORGANISM: Homo sapiens

<400> SEQUENCE: 391

Val Ile Trp Met Thr Gln Ser Pro Ser Leu Ser Ala Ser Thr Gly
1               5                   10                  15

Asp Arg Val Thr Ile Ser Cys
            20

<210> SEQ ID NO 392
<211> LENGTH: 11
<212> TYPE: PRT
<213> ORGANISM: Homo sapiens

<400> SEQUENCE: 392

Arg Met Ser Gln Gly Ile Ser Ser Tyr Leu Ala
1               5                   10

<210> SEQ ID NO 393
<211> LENGTH: 15
<212> TYPE: PRT
<213> ORGANISM: Homo sapiens

<400> SEQUENCE: 393

Trp Tyr Gln Gln Lys Pro Gly Lys Ala Pro Glu Leu Leu Ile Tyr
1               5                   10                  15

<210> SEQ ID NO 394
<211> LENGTH: 23
<212> TYPE: PRT
<213> ORGANISM: Homo sapiens

<400> SEQUENCE: 394

Ala Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 395
<211> LENGTH: 11
<212> TYPE: PRT
<213> ORGANISM: Homo sapiens

<400> SEQUENCE: 395

Arg Ala Ser Gln Gly Ile Arg Asn Asp Leu Gly
1               5                   10

<210> SEQ ID NO 396
```

```
<211> LENGTH: 15
<212> TYPE: PRT
<213> ORGANISM: Homo sapiens

<400> SEQUENCE: 396

Trp Tyr Gln Gln Lys Pro Gly Lys Ala Pro Lys Leu Leu Ile Tyr
1               5                   10                  15

<210> SEQ ID NO 397
<211> LENGTH: 23
<212> TYPE: PRT
<213> ORGANISM: Homo sapiens

<400> SEQUENCE: 397

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 398
<211> LENGTH: 11
<212> TYPE: PRT
<213> ORGANISM: Homo sapiens

<400> SEQUENCE: 398

Arg Ala Ser Gln Ser Ile Ser Ser Trp Leu Ala
1               5                   10

<210> SEQ ID NO 399
<211> LENGTH: 15
<212> TYPE: PRT
<213> ORGANISM: Homo sapiens

<400> SEQUENCE: 399

Trp Tyr Gln Gln Lys Pro Gly Lys Ala Pro Lys Leu Leu Ile Tyr
1               5                   10                  15

<210> SEQ ID NO 400
<211> LENGTH: 23
<212> TYPE: PRT
<213> ORGANISM: Homo sapiens

<400> SEQUENCE: 400

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 401
<211> LENGTH: 17
<212> TYPE: PRT
<213> ORGANISM: Homo sapiens

<400> SEQUENCE: 401

Arg Ser Ser Gln Ser Leu Leu Asp Ser Asp Asp Gly Asn Thr Tyr Leu
1               5                   10                  15

Asp

<210> SEQ ID NO 402
<211> LENGTH: 15
<212> TYPE: PRT
<213> ORGANISM: Homo sapiens

<400> SEQUENCE: 402
```

```
Trp Tyr Leu Gln Lys Pro Gly Gln Ser Pro Gln Leu Leu Ile Tyr
1               5                   10                  15

<210> SEQ ID NO 403
<211> LENGTH: 23
<212> TYPE: PRT
<213> ORGANISM: Homo sapiens

<400> SEQUENCE: 403

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 404
<211> LENGTH: 17
<212> TYPE: PRT
<213> ORGANISM: Homo sapiens

<400> SEQUENCE: 404

Arg Ser Ser Gln Ser Leu Leu Asp Ser Asp Gly Asn Thr Tyr Leu
1               5                   10                  15

Asp

<210> SEQ ID NO 405
<211> LENGTH: 15
<212> TYPE: PRT
<213> ORGANISM: Homo sapiens

<400> SEQUENCE: 405

Trp Tyr Leu Gln Lys Pro Gly Gln Ser Pro Gln Leu Leu Ile Tyr
1               5                   10                  15

<210> SEQ ID NO 406
<211> LENGTH: 23
<212> TYPE: PRT
<213> ORGANISM: Homo sapiens

<400> SEQUENCE: 406

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 407
<211> LENGTH: 16
<212> TYPE: PRT
<213> ORGANISM: Homo sapiens

<400> SEQUENCE: 407

Arg Ser Ser Gln Ser Leu Val Tyr Ser Asp Gly Asn Thr Tyr Leu Asn
1               5                   10                  15

<210> SEQ ID NO 408
<211> LENGTH: 15
<212> TYPE: PRT
<213> ORGANISM: Homo sapiens

<400> SEQUENCE: 408

Trp Phe Gln Gln Arg Pro Gly Gln Ser Pro Arg Arg Leu Ile Tyr
1               5                   10                  15

<210> SEQ ID NO 409
<211> LENGTH: 23
```

```
<212> TYPE: PRT
<213> ORGANISM: Homo sapiens

<400> SEQUENCE: 409

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 410
<211> LENGTH: 16
<212> TYPE: PRT
<213> ORGANISM: Homo sapiens

<400> SEQUENCE: 410

Arg Ser Ser Gln Ser Leu Val Tyr Ser Asp Gly Asn Thr Tyr Leu Asn
1               5                   10                  15

<210> SEQ ID NO 411
<211> LENGTH: 15
<212> TYPE: PRT
<213> ORGANISM: Homo sapiens

<400> SEQUENCE: 411

Trp Phe Gln Gln Arg Pro Gly Gln Ser Pro Arg Arg Leu Ile Tyr
1               5                   10                  15

<210> SEQ ID NO 412
<211> LENGTH: 23
<212> TYPE: PRT
<213> ORGANISM: Homo sapiens

<400> SEQUENCE: 412

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 413
<211> LENGTH: 16
<212> TYPE: PRT
<213> ORGANISM: Homo sapiens

<400> SEQUENCE: 413

Lys Ser Ser Gln Ser Leu Leu His Ser Asp Gly Lys Thr Tyr Leu Tyr
1               5                   10                  15

<210> SEQ ID NO 414
<211> LENGTH: 15
<212> TYPE: PRT
<213> ORGANISM: Homo sapiens

<400> SEQUENCE: 414

Trp Tyr Leu Gln Lys Pro Gly Gln Ser Pro Gln Leu Leu Ile Tyr
1               5                   10                  15

<210> SEQ ID NO 415
<211> LENGTH: 23
<212> TYPE: PRT
<213> ORGANISM: Homo sapiens

<400> SEQUENCE: 415

Asp Ile Val Met Thr Gln Thr Pro Leu Ser Leu Ser Val Thr Pro Gly
1               5                   10                  15
```

```
Gln Pro Ala Ser Ile Ser Cys
            20

<210> SEQ ID NO 416
<211> LENGTH: 16
<212> TYPE: PRT
<213> ORGANISM: Homo sapiens

<400> SEQUENCE: 416

Lys Ser Ser Gln Ser Leu Leu His Ser Asp Gly Lys Thr Tyr Leu Tyr
1               5                   10                  15

<210> SEQ ID NO 417
<211> LENGTH: 15
<212> TYPE: PRT
<213> ORGANISM: Homo sapiens

<400> SEQUENCE: 417

Trp Tyr Leu Gln Lys Pro Gly Gln Pro Pro Gln Leu Leu Ile Tyr
1               5                   10                  15

<210> SEQ ID NO 418
<211> LENGTH: 23
<212> TYPE: PRT
<213> ORGANISM: Homo sapiens

<400> SEQUENCE: 418

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 419
<211> LENGTH: 16
<212> TYPE: PRT
<213> ORGANISM: Homo sapiens

<400> SEQUENCE: 419

Arg Ser Ser Gln Ser Leu Leu His Ser Asn Gly Tyr Asn Tyr Leu Asp
1               5                   10                  15

<210> SEQ ID NO 420
<211> LENGTH: 15
<212> TYPE: PRT
<213> ORGANISM: Homo sapiens

<400> SEQUENCE: 420

Trp Tyr Leu Gln Lys Pro Gly Gln Ser Pro Gln Leu Leu Ile Tyr
1               5                   10                  15

<210> SEQ ID NO 421
<211> LENGTH: 23
<212> TYPE: PRT
<213> ORGANISM: Homo sapiens

<400> SEQUENCE: 421

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 422
<211> LENGTH: 16
<212> TYPE: PRT
<213> ORGANISM: Homo sapiens
```

<400> SEQUENCE: 422

Arg Ser Ser Gln Ser Leu Leu His Ser Asn Gly Tyr Asn Tyr Leu Asp
1               5                   10                  15

<210> SEQ ID NO 423
<211> LENGTH: 15
<212> TYPE: PRT
<213> ORGANISM: Homo sapiens

<400> SEQUENCE: 423

Trp Tyr Leu Gln Lys Pro Gly Gln Ser Pro Gln Leu Leu Ile Tyr
1               5                   10                  15

<210> SEQ ID NO 424
<211> LENGTH: 23
<212> TYPE: PRT
<213> ORGANISM: Homo sapiens

<400> SEQUENCE: 424

Asp Ile Val Met Thr Gln Thr Pro Leu Ser Ser Pro Val Thr Leu Gly
1               5                   10                  15

Gln Pro Ala Ser Ile Ser Cys
            20

<210> SEQ ID NO 425
<211> LENGTH: 16
<212> TYPE: PRT
<213> ORGANISM: Homo sapiens

<400> SEQUENCE: 425

Arg Ser Ser Gln Ser Leu Val His Ser Asp Gly Asn Thr Tyr Leu Ser
1               5                   10                  15

<210> SEQ ID NO 426
<211> LENGTH: 15
<212> TYPE: PRT
<213> ORGANISM: Homo sapiens

<400> SEQUENCE: 426

Trp Leu Gln Gln Arg Pro Gly Gln Pro Pro Arg Leu Leu Ile Tyr
1               5                   10                  15

<210> SEQ ID NO 427
<211> LENGTH: 23
<212> TYPE: PRT
<213> ORGANISM: Homo sapiens

<400> SEQUENCE: 427

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 428
<211> LENGTH: 12
<212> TYPE: PRT
<213> ORGANISM: Homo sapiens

<400> SEQUENCE: 428

Arg Ala Ser Gln Ser Val Ser Ser Ser Tyr Leu Ala
1               5                   10

<210> SEQ ID NO 429

```
<211> LENGTH: 15
<212> TYPE: PRT
<213> ORGANISM: Homo sapiens

<400> SEQUENCE: 429

Trp Tyr Gln Gln Lys Pro Gly Gln Ala Pro Arg Leu Leu Ile Tyr
1               5                   10                  15

<210> SEQ ID NO 430
<211> LENGTH: 23
<212> TYPE: PRT
<213> ORGANISM: Homo sapiens

<400> SEQUENCE: 430

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 431
<211> LENGTH: 12
<212> TYPE: PRT
<213> ORGANISM: Homo sapiens

<400> SEQUENCE: 431

Gly Ala Ser Gln Ser Val Ser Ser Ser Tyr Leu Ala
1               5                   10

<210> SEQ ID NO 432
<211> LENGTH: 15
<212> TYPE: PRT
<213> ORGANISM: Homo sapiens

<400> SEQUENCE: 432

Trp Tyr Gln Gln Lys Pro Gly Leu Ala Pro Arg Leu Leu Ile Tyr
1               5                   10                  15

<210> SEQ ID NO 433
<211> LENGTH: 23
<212> TYPE: PRT
<213> ORGANISM: Homo sapiens

<400> SEQUENCE: 433

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 434
<211> LENGTH: 11
<212> TYPE: PRT
<213> ORGANISM: Homo sapiens

<400> SEQUENCE: 434

Arg Ala Ser Gln Ser Val Ser Ser Asn Leu Ala
1               5                   10

<210> SEQ ID NO 435
<211> LENGTH: 15
<212> TYPE: PRT
<213> ORGANISM: Homo sapiens

<400> SEQUENCE: 435

Trp Tyr Gln Gln Lys Pro Gly Gln Ala Pro Arg Leu Leu Ile Tyr
1               5                   10                  15
```

-continued

<210> SEQ ID NO 436
<211> LENGTH: 23
<212> TYPE: PRT
<213> ORGANISM: Homo sapiens

<400> SEQUENCE: 436

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 437
<211> LENGTH: 11
<212> TYPE: PRT
<213> ORGANISM: Homo sapiens

<400> SEQUENCE: 437

Arg Ala Ser Gln Ser Val Ser Ser Asn Leu Ala
1               5                   10

<210> SEQ ID NO 438
<211> LENGTH: 15
<212> TYPE: PRT
<213> ORGANISM: Homo sapiens

<400> SEQUENCE: 438

Trp Tyr Gln Gln Lys Pro Gly Gln Ala Pro Arg Leu Leu Ile Tyr
1               5                   10                  15

<210> SEQ ID NO 439
<211> LENGTH: 23
<212> TYPE: PRT
<213> ORGANISM: Homo sapiens

<400> SEQUENCE: 439

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 440
<211> LENGTH: 11
<212> TYPE: PRT
<213> ORGANISM: Homo sapiens

<400> SEQUENCE: 440

Arg Ala Ser Gln Ser Val Ser Ser Tyr Leu Ala
1               5                   10

<210> SEQ ID NO 441
<211> LENGTH: 15
<212> TYPE: PRT
<213> ORGANISM: Homo sapiens

<400> SEQUENCE: 441

Trp Tyr Gln Gln Lys Pro Gly Gln Ala Pro Arg Leu Leu Ile Tyr
1               5                   10                  15

<210> SEQ ID NO 442
<211> LENGTH: 23
<212> TYPE: PRT
<213> ORGANISM: Homo sapiens

<400> SEQUENCE: 442

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 443
<211> LENGTH: 11
<212> TYPE: PRT
<213> ORGANISM: Homo sapiens

<400> SEQUENCE: 443

Arg Ala Ser Gln Gly Val Ser Ser Tyr Leu Ala
1               5                   10

<210> SEQ ID NO 444
<211> LENGTH: 15
<212> TYPE: PRT
<213> ORGANISM: Homo sapiens

<400> SEQUENCE: 444

Trp Tyr Gln Gln Lys Pro Gly Gln Ala Pro Arg Leu Leu Ile Tyr
1               5                   10                  15

<210> SEQ ID NO 445
<211> LENGTH: 23
<212> TYPE: PRT
<213> ORGANISM: Homo sapiens

<400> SEQUENCE: 445

Glu Ile Val Met Thr Gln Ser Pro Ala Thr Leu Ser Leu Ser Pro Gly
1               5                   10                  15

Glu Arg Ala Thr Leu Ser Cys
            20

<210> SEQ ID NO 446
<211> LENGTH: 12
<212> TYPE: PRT
<213> ORGANISM: Homo sapiens

<400> SEQUENCE: 446

Arg Ala Ser Gln Ser Val Ser Ser Ser Tyr Leu Ser
1               5                   10

<210> SEQ ID NO 447
<211> LENGTH: 15
<212> TYPE: PRT
<213> ORGANISM: Homo sapiens

<400> SEQUENCE: 447

Trp Tyr Gln Gln Lys Pro Gly Gln Ala Pro Arg Leu Leu Ile Tyr
1               5                   10                  15

<210> SEQ ID NO 448
<211> LENGTH: 23
<212> TYPE: PRT
<213> ORGANISM: Homo sapiens

<400> SEQUENCE: 448

Asp Ile Val Met Thr Gln Ser Pro Asp Ser Leu Ala Val Ser Leu Gly
1               5                   10                  15

Glu Arg Ala Thr Ile Asn Cys
            20

```
<210> SEQ ID NO 449
<211> LENGTH: 17
<212> TYPE: PRT
<213> ORGANISM: Homo sapiens

<400> SEQUENCE: 449

Lys Ser Ser Gln Ser Val Leu Tyr Ser Ser Asn Asn Lys Asn Tyr Leu
1               5                   10                  15

Ala

<210> SEQ ID NO 450
<211> LENGTH: 15
<212> TYPE: PRT
<213> ORGANISM: Homo sapiens

<400> SEQUENCE: 450

Trp Tyr Gln Gln Lys Pro Gly Gln Pro Pro Lys Leu Leu Ile Tyr
1               5                   10                  15

<210> SEQ ID NO 451
<211> LENGTH: 23
<212> TYPE: PRT
<213> ORGANISM: Homo sapiens

<400> SEQUENCE: 451

Glu Thr Thr Leu Thr Gln Ser Pro Ala Phe Met Ser Ala Thr Pro Gly
1               5                   10                  15

Asp Lys Val Asn Ile Ser Cys
            20

<210> SEQ ID NO 452
<211> LENGTH: 11
<212> TYPE: PRT
<213> ORGANISM: Homo sapiens

<400> SEQUENCE: 452

Lys Ala Ser Gln Asp Ile Asp Asp Asp Met Asn
1               5                   10

<210> SEQ ID NO 453
<211> LENGTH: 15
<212> TYPE: PRT
<213> ORGANISM: Homo sapiens

<400> SEQUENCE: 453

Trp Tyr Gln Gln Lys Pro Gly Glu Ala Ala Ile Phe Ile Ile Gln
1               5                   10                  15

<210> SEQ ID NO 454
<211> LENGTH: 23
<212> TYPE: PRT
<213> ORGANISM: Homo sapiens

<400> SEQUENCE: 454

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 455
<211> LENGTH: 11
<212> TYPE: PRT
<213> ORGANISM: Homo sapiens

<400> SEQUENCE: 455
```

Arg Ala Ser Gln Ser Ile Gly Ser Ser Leu His
1               5                   10

<210> SEQ ID NO 456
<211> LENGTH: 15
<212> TYPE: PRT
<213> ORGANISM: Homo sapiens

<400> SEQUENCE: 456

Trp Tyr Gln Gln Lys Pro Asp Gln Ser Pro Lys Leu Leu Ile Lys
1               5                   10                  15

<210> SEQ ID NO 457
<211> LENGTH: 23
<212> TYPE: PRT
<213> ORGANISM: Homo sapiens

<400> SEQUENCE: 457

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 458
<211> LENGTH: 11
<212> TYPE: PRT
<213> ORGANISM: Homo sapiens

<400> SEQUENCE: 458

Arg Ala Ser Gln Ser Ile Gly Ser Ser Leu His
1               5                   10

<210> SEQ ID NO 459
<211> LENGTH: 15
<212> TYPE: PRT
<213> ORGANISM: Homo sapiens

<400> SEQUENCE: 459

Trp Tyr Gln Gln Lys Pro Asp Gln Ser Pro Lys Leu Leu Ile Lys
1               5                   10                  15

<210> SEQ ID NO 460
<211> LENGTH: 23
<212> TYPE: PRT
<213> ORGANISM: Homo sapiens

<400> SEQUENCE: 460

Asp Val Val Met Thr Gln Ser Pro Ala Phe Leu Ser Val Thr Pro Gly
1               5                   10                  15

Glu Lys Val Thr Ile Thr Cys
            20

<210> SEQ ID NO 461
<211> LENGTH: 11
<212> TYPE: PRT
<213> ORGANISM: Homo sapiens

<400> SEQUENCE: 461

Gln Ala Ser Glu Gly Ile Gly Asn Tyr Leu Tyr
1               5                   10

<210> SEQ ID NO 462
<211> LENGTH: 15
<212> TYPE: PRT

<213> ORGANISM: Homo sapiens

<400> SEQUENCE: 462

Trp Tyr Gln Gln Lys Pro Asp Gln Ala Pro Lys Leu Leu Ile Lys
1               5                   10                  15

<210> SEQ ID NO 463
<211> LENGTH: 7
<212> TYPE: PRT
<213> ORGANISM: Homo sapiens

<400> SEQUENCE: 463

Ala Ala Ser Ser Leu Gln Ser
1               5

<210> SEQ ID NO 464
<211> LENGTH: 32
<212> TYPE: PRT
<213> ORGANISM: Homo sapiens

<400> SEQUENCE: 464

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 465
<211> LENGTH: 7
<212> TYPE: PRT
<213> ORGANISM: Homo sapiens

<400> SEQUENCE: 465

Gln Gln Ser Tyr Ser Thr Pro
1               5

<210> SEQ ID NO 466
<211> LENGTH: 7
<212> TYPE: PRT
<213> ORGANISM: Homo sapiens

<400> SEQUENCE: 466

Ala Ala Ser Ser Leu Gln Ser
1               5

<210> SEQ ID NO 467
<211> LENGTH: 32
<212> TYPE: PRT
<213> ORGANISM: Homo sapiens

<400> SEQUENCE: 467

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 468
<211> LENGTH: 7
<212> TYPE: PRT
<213> ORGANISM: Homo sapiens

<400> SEQUENCE: 468

Gln Gln Ser Tyr Ser Thr Pro
1               5

<210> SEQ ID NO 469
<211> LENGTH: 7
<212> TYPE: PRT
<213> ORGANISM: Homo sapiens

<400> SEQUENCE: 469

Asp Ala Ser Asn Leu Glu Thr
1               5

<210> SEQ ID NO 470
<211> LENGTH: 32
<212> TYPE: PRT
<213> ORGANISM: Homo sapiens

<400> SEQUENCE: 470

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 471
<211> LENGTH: 7
<212> TYPE: PRT
<213> ORGANISM: Homo sapiens

<400> SEQUENCE: 471

Gln Gln Tyr Asp Asn Leu Pro
1               5

<210> SEQ ID NO 472
<211> LENGTH: 7
<212> TYPE: PRT
<213> ORGANISM: Homo sapiens

<400> SEQUENCE: 472

Asp Ala Ser Asn Leu Glu Thr
1               5

<210> SEQ ID NO 473
<211> LENGTH: 32
<212> TYPE: PRT
<213> ORGANISM: Homo sapiens

<400> SEQUENCE: 473

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 474
<211> LENGTH: 7
<212> TYPE: PRT
<213> ORGANISM: Homo sapiens

<400> SEQUENCE: 474

Gln Gln Tyr Asp Asn Leu Pro
1               5

<210> SEQ ID NO 475
<211> LENGTH: 7
<212> TYPE: PRT
<213> ORGANISM: Homo sapiens

<400> SEQUENCE: 475

Ala Ala Ser Thr Leu Gln Ser

-continued

<210> SEQ ID NO 476
<211> LENGTH: 32
<212> TYPE: PRT
<213> ORGANISM: Homo sapiens

<400> SEQUENCE: 476

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 477
<211> LENGTH: 7
<212> TYPE: PRT
<213> ORGANISM: Homo sapiens

<400> SEQUENCE: 477

Gln Lys Tyr Asn Ser Ala Pro
1               5

<210> SEQ ID NO 478
<211> LENGTH: 7
<212> TYPE: PRT
<213> ORGANISM: Homo sapiens

<400> SEQUENCE: 478

Ala Ala Ser Ser Leu Gln Ser
1               5

<210> SEQ ID NO 479
<211> LENGTH: 32
<212> TYPE: PRT
<213> ORGANISM: Homo sapiens

<400> SEQUENCE: 479

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 480
<211> LENGTH: 7
<212> TYPE: PRT
<213> ORGANISM: Homo sapiens

<400> SEQUENCE: 480

Leu Gln His Asn Ser Tyr Pro
1               5

<210> SEQ ID NO 481
<211> LENGTH: 7
<212> TYPE: PRT
<213> ORGANISM: Homo sapiens

<400> SEQUENCE: 481

Ala Ala Ser Ser Leu Gln Ser
1               5

<210> SEQ ID NO 482
<211> LENGTH: 32
<212> TYPE: PRT
<213> ORGANISM: Homo sapiens -continued

<400> SEQUENCE: 482

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 483
<211> LENGTH: 7
<212> TYPE: PRT
<213> ORGANISM: Homo sapiens

<400> SEQUENCE: 483

Leu Gln His Asn Ser Tyr Pro
1               5

<210> SEQ ID NO 484
<211> LENGTH: 7
<212> TYPE: PRT
<213> ORGANISM: Homo sapiens

<400> SEQUENCE: 484

Ala Ala Ser Ser Leu Gln Ser
1               5

<210> SEQ ID NO 485
<211> LENGTH: 32
<212> TYPE: PRT
<213> ORGANISM: Homo sapiens

<400> SEQUENCE: 485

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 486
<211> LENGTH: 7
<212> TYPE: PRT
<213> ORGANISM: Homo sapiens

<400> SEQUENCE: 486

Gln Gln Tyr Asn Ser Tyr Pro
1               5

<210> SEQ ID NO 487
<211> LENGTH: 7
<212> TYPE: PRT
<213> ORGANISM: Homo sapiens

<400> SEQUENCE: 487

Ala Ala Ser Ser Leu Gln Ser
1               5

<210> SEQ ID NO 488
<211> LENGTH: 32
<212> TYPE: PRT
<213> ORGANISM: Homo sapiens

<400> SEQUENCE: 488

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 489
<211> LENGTH: 7
<212> TYPE: PRT
<213> ORGANISM: Homo sapiens

<400> SEQUENCE: 489

Gln Gln Tyr Asn Ser Tyr Pro
1               5

<210> SEQ ID NO 490
<211> LENGTH: 7
<212> TYPE: PRT
<213> ORGANISM: Homo sapiens

<400> SEQUENCE: 490

Asp Ala Ser Ser Leu Glu Ser
1               5

<210> SEQ ID NO 491
<211> LENGTH: 32
<212> TYPE: PRT
<213> ORGANISM: Homo sapiens

<400> SEQUENCE: 491

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 492
<211> LENGTH: 7
<212> TYPE: PRT
<213> ORGANISM: Homo sapiens

<400> SEQUENCE: 492

Gln Gln Phe Asn Ser Tyr Pro
1               5

<210> SEQ ID NO 493
<211> LENGTH: 7
<212> TYPE: PRT
<213> ORGANISM: Homo sapiens

<400> SEQUENCE: 493

Asp Ala Ser Ser Leu Glu Ser
1               5

<210> SEQ ID NO 494
<211> LENGTH: 32
<212> TYPE: PRT
<213> ORGANISM: Homo sapiens

<400> SEQUENCE: 494

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 495
<211> LENGTH: 7
<212> TYPE: PRT
<213> ORGANISM: Homo sapiens

<400> SEQUENCE: 495

```
Gln Gln Phe Asn Ser Tyr Pro
1               5

<210> SEQ ID NO 496
<211> LENGTH: 7
<212> TYPE: PRT
<213> ORGANISM: Homo sapiens

<400> SEQUENCE: 496

Ala Ala Ser Ser Leu Gln Ser
1               5

<210> SEQ ID NO 497
<211> LENGTH: 32
<212> TYPE: PRT
<213> ORGANISM: Homo sapiens

<400> SEQUENCE: 497

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 498
<211> LENGTH: 7
<212> TYPE: PRT
<213> ORGANISM: Homo sapiens

<400> SEQUENCE: 498

Gln Gln Ala Asn Ser Phe Pro
1               5

<210> SEQ ID NO 499
<211> LENGTH: 7
<212> TYPE: PRT
<213> ORGANISM: Homo sapiens

<400> SEQUENCE: 499

Ala Ala Ser Ser Leu Gln Ser
1               5

<210> SEQ ID NO 500
<211> LENGTH: 32
<212> TYPE: PRT
<213> ORGANISM: Homo sapiens

<400> SEQUENCE: 500

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 501
<211> LENGTH: 7
<212> TYPE: PRT
<213> ORGANISM: Homo sapiens

<400> SEQUENCE: 501

Gln Gln Ala Asn Ser Phe Pro
1               5

<210> SEQ ID NO 502
<211> LENGTH: 7
<212> TYPE: PRT
<213> ORGANISM: Homo sapiens
```

<400> SEQUENCE: 502

Ala Ala Ser Thr Leu Gln Ser
1               5

<210> SEQ ID NO 503
<211> LENGTH: 32
<212> TYPE: PRT
<213> ORGANISM: Homo sapiens

<400> SEQUENCE: 503

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 504
<211> LENGTH: 7
<212> TYPE: PRT
<213> ORGANISM: Homo sapiens

<400> SEQUENCE: 504

Gln Gln Leu Asn Ser Tyr Pro
1               5

<210> SEQ ID NO 505
<211> LENGTH: 7
<212> TYPE: PRT
<213> ORGANISM: Homo sapiens

<400> SEQUENCE: 505

Tyr Ala Ser Ser Leu Gln Ser
1               5

<210> SEQ ID NO 506
<211> LENGTH: 32
<212> TYPE: PRT
<213> ORGANISM: Homo sapiens

<400> SEQUENCE: 506

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 507
<211> LENGTH: 7
<212> TYPE: PRT
<213> ORGANISM: Homo sapiens

<400> SEQUENCE: 507

Gln Gln Tyr Tyr Ser Thr Pro
1               5

<210> SEQ ID NO 508
<211> LENGTH: 7
<212> TYPE: PRT
<213> ORGANISM: Homo sapiens

<400> SEQUENCE: 508

Ala Ala Ser Thr Leu Gln Ser
1               5

<210> SEQ ID NO 509

<211> LENGTH: 32
<212> TYPE: PRT
<213> ORGANISM: Homo sapiens

<400> SEQUENCE: 509

Gly Val Pro Ser Arg Phe Ser Gly Ser Gly Ser Gly Thr Asp Phe Thr
1               5                   10                  15

Leu Thr Ile Ser Cys Leu Gln Ser Glu Asp Phe Ala Thr Tyr Tyr Cys
            20                  25                  30

<210> SEQ ID NO 510
<211> LENGTH: 7
<212> TYPE: PRT
<213> ORGANISM: Homo sapiens

<400> SEQUENCE: 510

Gln Gln Tyr Tyr Ser Tyr Pro
1               5

<210> SEQ ID NO 511
<211> LENGTH: 7
<212> TYPE: PRT
<213> ORGANISM: Homo sapiens

<400> SEQUENCE: 511

Ala Ala Ser Thr Leu Gln Ser
1               5

<210> SEQ ID NO 512
<211> LENGTH: 32
<212> TYPE: PRT
<213> ORGANISM: Homo sapiens

<400> SEQUENCE: 512

Gly Val Pro Ser Arg Phe Ser Gly Ser Gly Ser Gly Thr Asp Phe Thr
1               5                   10                  15

Leu Thr Ile Ser Cys Leu Gln Ser Glu Asp Phe Ala Thr Tyr Tyr Cys
            20                  25                  30

<210> SEQ ID NO 513
<211> LENGTH: 7
<212> TYPE: PRT
<213> ORGANISM: Homo sapiens

<400> SEQUENCE: 513

Gln Gln Tyr Tyr Ser Phe Pro
1               5

<210> SEQ ID NO 514
<211> LENGTH: 7
<212> TYPE: PRT
<213> ORGANISM: Homo sapiens

<400> SEQUENCE: 514

Ala Ala Ser Ser Leu Gln Ser
1               5

<210> SEQ ID NO 515
<211> LENGTH: 32
<212> TYPE: PRT
<213> ORGANISM: Homo sapiens

<400> SEQUENCE: 515

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 516
<211> LENGTH: 7
<212> TYPE: PRT
<213> ORGANISM: Homo sapiens

<400> SEQUENCE: 516

Leu Gln Asp Tyr Asn Tyr Pro
1               5

<210> SEQ ID NO 517
<211> LENGTH: 7
<212> TYPE: PRT
<213> ORGANISM: Homo sapiens

<400> SEQUENCE: 517

Asp Ala Ser Ser Leu Glu Ser
1               5

<210> SEQ ID NO 518
<211> LENGTH: 32
<212> TYPE: PRT
<213> ORGANISM: Homo sapiens

<400> SEQUENCE: 518

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

<210> SEQ ID NO 519
<211> LENGTH: 7
<212> TYPE: PRT
<213> ORGANISM: Homo sapiens

<400> SEQUENCE: 519

Gln Gln Tyr Asn Ser Tyr Ser
1               5

<210> SEQ ID NO 520
<211> LENGTH: 7
<212> TYPE: PRT
<213> ORGANISM: Homo sapiens

<400> SEQUENCE: 520

Thr Leu Ser Tyr Arg Ala Ser
1               5

<210> SEQ ID NO 521
<211> LENGTH: 32
<212> TYPE: PRT
<213> ORGANISM: Homo sapiens

<400> SEQUENCE: 521

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 522
<211> LENGTH: 7
<212> TYPE: PRT

<213> ORGANISM: Homo sapiens

<400> SEQUENCE: 522

Met Gln Arg Ile Glu Phe Pro
1               5

<210> SEQ ID NO 523
<211> LENGTH: 7
<212> TYPE: PRT
<213> ORGANISM: Homo sapiens

<400> SEQUENCE: 523

Thr Leu Ser Tyr Arg Ala Ser
1               5

<210> SEQ ID NO 524
<211> LENGTH: 32
<212> TYPE: PRT
<213> ORGANISM: Homo sapiens

<400> SEQUENCE: 524

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 525
<211> LENGTH: 7
<212> TYPE: PRT
<213> ORGANISM: Homo sapiens

<400> SEQUENCE: 525

Met Gln Arg Ile Glu Phe Pro
1               5

<210> SEQ ID NO 526
<211> LENGTH: 7
<212> TYPE: PRT
<213> ORGANISM: Homo sapiens

<400> SEQUENCE: 526

Lys Val Ser Asn Arg Asp Ser
1               5

<210> SEQ ID NO 527
<211> LENGTH: 32
<212> TYPE: PRT
<213> ORGANISM: Homo sapiens

<400> SEQUENCE: 527

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 528
<211> LENGTH: 7
<212> TYPE: PRT
<213> ORGANISM: Homo sapiens

<400> SEQUENCE: 528

Met Gln Gly Thr His Trp Pro
1               5

```
<210> SEQ ID NO 529
<211> LENGTH: 7
<212> TYPE: PRT
<213> ORGANISM: Homo sapiens

<400> SEQUENCE: 529

Lys Val Ser Asn Trp Asp Ser
1               5

<210> SEQ ID NO 530
<211> LENGTH: 32
<212> TYPE: PRT
<213> ORGANISM: Homo sapiens

<400> SEQUENCE: 530

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 531
<211> LENGTH: 7
<212> TYPE: PRT
<213> ORGANISM: Homo sapiens

<400> SEQUENCE: 531

Met Gln Gly Thr His Trp Pro
1               5

<210> SEQ ID NO 532
<211> LENGTH: 7
<212> TYPE: PRT
<213> ORGANISM: Homo sapiens

<400> SEQUENCE: 532

Glu Val Ser Ser Arg Phe Ser
1               5

<210> SEQ ID NO 533
<211> LENGTH: 32
<212> TYPE: PRT
<213> ORGANISM: Homo sapiens

<400> SEQUENCE: 533

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 534
<211> LENGTH: 7
<212> TYPE: PRT
<213> ORGANISM: Homo sapiens

<400> SEQUENCE: 534

Met Gln Gly Ile His Leu Pro
1               5

<210> SEQ ID NO 535
<211> LENGTH: 7
<212> TYPE: PRT
<213> ORGANISM: Homo sapiens

<400> SEQUENCE: 535

Glu Val Ser Asn Arg Phe Ser
```

<210> SEQ ID NO 536
<211> LENGTH: 32
<212> TYPE: PRT
<213> ORGANISM: Homo sapiens

<400> SEQUENCE: 536

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 537
<211> LENGTH: 7
<212> TYPE: PRT
<213> ORGANISM: Homo sapiens

<400> SEQUENCE: 537

Met Gln Ser Ile Gln Leu Pro
1               5

<210> SEQ ID NO 538
<211> LENGTH: 7
<212> TYPE: PRT
<213> ORGANISM: Homo sapiens

<400> SEQUENCE: 538

Leu Gly Ser Asn Arg Ala Ser
1               5

<210> SEQ ID NO 539
<211> LENGTH: 32
<212> TYPE: PRT
<213> ORGANISM: Homo sapiens

<400> SEQUENCE: 539

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 540
<211> LENGTH: 7
<212> TYPE: PRT
<213> ORGANISM: Homo sapiens

<400> SEQUENCE: 540

Met Gln Ala Leu Gln Thr Pro
1               5

<210> SEQ ID NO 541
<211> LENGTH: 7
<212> TYPE: PRT
<213> ORGANISM: Homo sapiens

<400> SEQUENCE: 541

Leu Gly Ser Asn Arg Ala Ser
1               5

<210> SEQ ID NO 542
<211> LENGTH: 32
<212> TYPE: PRT
<213> ORGANISM: Homo sapiens

<400> SEQUENCE: 542

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 543
<211> LENGTH: 7
<212> TYPE: PRT
<213> ORGANISM: Homo sapiens

<400> SEQUENCE: 543

Met Gln Ala Leu Gln Thr Pro
1               5

<210> SEQ ID NO 544
<211> LENGTH: 7
<212> TYPE: PRT
<213> ORGANISM: Homo sapiens

<400> SEQUENCE: 544

Lys Ile Ser Asn Arg Phe Ser
1               5

<210> SEQ ID NO 545
<211> LENGTH: 32
<212> TYPE: PRT
<213> ORGANISM: Homo sapiens

<400> SEQUENCE: 545

Gly Val Pro Asp Arg Phe Ser Gly Ser Gly Ala Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 546
<211> LENGTH: 7
<212> TYPE: PRT
<213> ORGANISM: Homo sapiens

<400> SEQUENCE: 546

Met Gln Ala Thr Gln Phe Pro
1               5

<210> SEQ ID NO 547
<211> LENGTH: 7
<212> TYPE: PRT
<213> ORGANISM: Homo sapiens

<400> SEQUENCE: 547

Gly Ala Ser Ser Arg Ala Thr
1               5

<210> SEQ ID NO 548
<211> LENGTH: 32
<212> TYPE: PRT
<213> ORGANISM: Homo sapiens

<400> SEQUENCE: 548

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 549
<211> LENGTH: 7
<212> TYPE: PRT
<213> ORGANISM: Homo sapiens

<400> SEQUENCE: 549

Gln Gln Tyr Gly Ser Ser Pro
1               5

<210> SEQ ID NO 550
<211> LENGTH: 7
<212> TYPE: PRT
<213> ORGANISM: Homo sapiens

<400> SEQUENCE: 550

Asp Ala Ser Ser Arg Ala Thr
1               5

<210> SEQ ID NO 551
<211> LENGTH: 32
<212> TYPE: PRT
<213> ORGANISM: Homo sapiens

<400> SEQUENCE: 551

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 552
<211> LENGTH: 7
<212> TYPE: PRT
<213> ORGANISM: Homo sapiens

<400> SEQUENCE: 552

Gln Gln Tyr Gly Ser Ser Pro
1               5

<210> SEQ ID NO 553
<211> LENGTH: 7
<212> TYPE: PRT
<213> ORGANISM: Homo sapiens

<400> SEQUENCE: 553

Gly Ala Ser Thr Arg Ala Thr
1               5

<210> SEQ ID NO 554
<211> LENGTH: 32
<212> TYPE: PRT
<213> ORGANISM: Homo sapiens

<400> SEQUENCE: 554

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 555
<211> LENGTH: 7
<212> TYPE: PRT
<213> ORGANISM: Homo sapiens

<400> SEQUENCE: 555

Gln Gln Tyr Asn Asn Trp Pro
1               5

<210> SEQ ID NO 556
<211> LENGTH: 7
<212> TYPE: PRT
<213> ORGANISM: Homo sapiens

<400> SEQUENCE: 556

Gly Ala Ser Thr Arg Ala Thr
1               5

<210> SEQ ID NO 557
<211> LENGTH: 32
<212> TYPE: PRT
<213> ORGANISM: Homo sapiens

<400> SEQUENCE: 557

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 558
<211> LENGTH: 7
<212> TYPE: PRT
<213> ORGANISM: Homo sapiens

<400> SEQUENCE: 558

Gln Gln Tyr Asn Asn Trp Pro
1               5

<210> SEQ ID NO 559
<211> LENGTH: 7
<212> TYPE: PRT
<213> ORGANISM: Homo sapiens

<400> SEQUENCE: 559

Asp Ala Ser Asn Arg Ala Thr
1               5

<210> SEQ ID NO 560
<211> LENGTH: 32
<212> TYPE: PRT
<213> ORGANISM: Homo sapiens

<400> SEQUENCE: 560

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 561
<211> LENGTH: 7
<212> TYPE: PRT
<213> ORGANISM: Homo sapiens

<400> SEQUENCE: 561

Gln Gln Arg Ser Asn Trp Pro
1               5

<210> SEQ ID NO 562
<211> LENGTH: 7
<212> TYPE: PRT
<213> ORGANISM: Homo sapiens

<400> SEQUENCE: 562

Asp Ala Ser Asn Arg Ala Thr
1               5

<210> SEQ ID NO 563
<211> LENGTH: 32
<212> TYPE: PRT
<213> ORGANISM: Homo sapiens

<400> SEQUENCE: 563

Gly Ile Pro Ala Arg Phe Ser Gly Ser Gly Pro Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 564
<211> LENGTH: 7
<212> TYPE: PRT
<213> ORGANISM: Homo sapiens

<400> SEQUENCE: 564

Gln Gln Arg Ser Asn Trp His
1               5

<210> SEQ ID NO 565
<211> LENGTH: 7
<212> TYPE: PRT
<213> ORGANISM: Homo sapiens

<400> SEQUENCE: 565

Gly Ala Ser Thr Arg Ala Thr
1               5

<210> SEQ ID NO 566
<211> LENGTH: 32
<212> TYPE: PRT
<213> ORGANISM: Homo sapiens

<400> SEQUENCE: 566

Gly Ile Pro Ala Arg Phe Ser Gly Ser Gly Ser Gly Thr Asp Phe Thr
1               5                   10                  15

Leu Thr Ile Ser Ser Leu Gln Pro Glu Asp Phe Ala Val Tyr Tyr Cys
            20                  25                  30

<210> SEQ ID NO 567
<211> LENGTH: 7
<212> TYPE: PRT
<213> ORGANISM: Homo sapiens

<400> SEQUENCE: 567

Gln Gln Asp Tyr Asn Leu Pro
1               5

<210> SEQ ID NO 568
<211> LENGTH: 7
<212> TYPE: PRT
<213> ORGANISM: Homo sapiens

<400> SEQUENCE: 568

Trp Ala Ser Thr Arg Glu Ser
1               5

<210> SEQ ID NO 569

```
<211> LENGTH: 32
<212> TYPE: PRT
<213> ORGANISM: Homo sapiens

<400> SEQUENCE: 569

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 570
<211> LENGTH: 7
<212> TYPE: PRT
<213> ORGANISM: Homo sapiens

<400> SEQUENCE: 570

Gln Gln Tyr Tyr Ser Thr Pro
1               5

<210> SEQ ID NO 571
<211> LENGTH: 7
<212> TYPE: PRT
<213> ORGANISM: Homo sapiens

<400> SEQUENCE: 571

Glu Ala Thr Thr Leu Val Pro
1               5

<210> SEQ ID NO 572
<211> LENGTH: 32
<212> TYPE: PRT
<213> ORGANISM: Homo sapiens

<400> SEQUENCE: 572

Gly Ile Pro Pro Arg Phe Ser Gly Ser Gly Tyr Gly Thr Asp Phe Thr
1               5                   10                  15

Leu Thr Ile Asn Asn Ile Glu Ser Glu Asp Ala Ala Tyr Tyr Phe Cys
            20                  25                  30

<210> SEQ ID NO 573
<211> LENGTH: 7
<212> TYPE: PRT
<213> ORGANISM: Homo sapiens

<400> SEQUENCE: 573

Leu Gln His Asp Asn Phe Pro
1               5

<210> SEQ ID NO 574
<211> LENGTH: 7
<212> TYPE: PRT
<213> ORGANISM: Homo sapiens

<400> SEQUENCE: 574

Tyr Ala Ser Gln Ser Phe Ser
1               5

<210> SEQ ID NO 575
<211> LENGTH: 32
<212> TYPE: PRT
<213> ORGANISM: Homo sapiens

<400> SEQUENCE: 575

Gly Val Pro Ser Arg Phe Ser Gly Ser Gly Ser Gly Thr Asp Phe Thr
1               5                   10                  15
```

Leu Thr Ile Asn Ser Leu Glu Ala Glu Asp Ala Ala Thr Tyr Tyr Cys
            20                  25                  30

<210> SEQ ID NO 576
<211> LENGTH: 7
<212> TYPE: PRT
<213> ORGANISM: Homo sapiens

<400> SEQUENCE: 576

His Gln Ser Ser Ser Leu Pro
1               5

<210> SEQ ID NO 577
<211> LENGTH: 7
<212> TYPE: PRT
<213> ORGANISM: Homo sapiens

<400> SEQUENCE: 577

Tyr Ala Ser Gln Ser Phe Ser
1               5

<210> SEQ ID NO 578
<211> LENGTH: 32
<212> TYPE: PRT
<213> ORGANISM: Homo sapiens

<400> SEQUENCE: 578

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 579
<211> LENGTH: 7
<212> TYPE: PRT
<213> ORGANISM: Homo sapiens

<400> SEQUENCE: 579

His Gln Ser Ser Ser Leu Pro
1               5

<210> SEQ ID NO 580
<211> LENGTH: 7
<212> TYPE: PRT
<213> ORGANISM: Homo sapiens

<400> SEQUENCE: 580

Tyr Ala Ser Gln Ser Ile Ser
1               5

<210> SEQ ID NO 581
<211> LENGTH: 32
<212> TYPE: PRT
<213> ORGANISM: Homo sapiens

<400> SEQUENCE: 581

Gly Val Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30

<210> SEQ ID NO 582
<211> LENGTH: 7
<212> TYPE: PRT

<213> ORGANISM: Homo sapiens

<400> SEQUENCE: 582

Gln Gln Gly Asn Lys His Pro
1               5

<210> SEQ ID NO 583
<211> LENGTH: 12
<212> TYPE: PRT
<213> ORGANISM: Homo sapiens

<400> SEQUENCE: 583

Trp Thr Phe Gly Gln Gly Thr Lys Val Glu Ile Lys
1               5                   10

<210> SEQ ID NO 584
<211> LENGTH: 12
<212> TYPE: PRT
<213> ORGANISM: Homo sapiens

<400> SEQUENCE: 584

Tyr Thr Phe Gly Gln Gly Thr Lys Leu Glu Ile Lys
1               5                   10

<210> SEQ ID NO 585
<211> LENGTH: 12
<212> TYPE: PRT
<213> ORGANISM: Homo sapiens

<400> SEQUENCE: 585

Phe Thr Phe Gly Pro Gly Thr Lys Val Asp Ile Lys
1               5                   10

<210> SEQ ID NO 586
<211> LENGTH: 12
<212> TYPE: PRT
<213> ORGANISM: Homo sapiens

<400> SEQUENCE: 586

Leu Thr Phe Gly Gly Gly Thr Lys Val Glu Ile Lys
1               5                   10

<210> SEQ ID NO 587
<211> LENGTH: 12
<212> TYPE: PRT
<213> ORGANISM: Homo sapiens

<400> SEQUENCE: 587

Ile Thr Phe Gly Gln Gly Thr Arg Leu Glu Ile Lys
1               5                   10

<210> SEQ ID NO 588
<211> LENGTH: 22
<212> TYPE: PRT
<213> ORGANISM: Homo sapiens

<400> SEQUENCE: 588

Gln Ser Val Leu Thr Gln Pro Pro Ser Val Ser Glu Ala Pro Arg Gln
1               5                   10                  15

Arg Val Thr Ile Ser Cys
            20

<210> SEQ ID NO 589
<211> LENGTH: 13
<212> TYPE: PRT

<213> ORGANISM: Homo sapiens

<400> SEQUENCE: 589

Ser Gly Ser Ser Ser Asn Ile Gly Asn Asn Ala Val Asn
1               5                   10

<210> SEQ ID NO 590
<211> LENGTH: 15
<212> TYPE: PRT
<213> ORGANISM: Homo sapiens

<400> SEQUENCE: 590

Trp Tyr Gln Gln Leu Pro Gly Lys Ala Pro Lys Leu Leu Ile Tyr
1               5                   10                  15

<210> SEQ ID NO 591
<211> LENGTH: 22
<212> TYPE: PRT
<213> ORGANISM: Homo sapiens

<400> SEQUENCE: 591

Gln Ser Val Leu Thr Gln Pro Pro Ser Val Ser Gly Ala Pro Gly Gln
1               5                   10                  15

Arg Val Thr Ile Ser Cys
            20

<210> SEQ ID NO 592
<211> LENGTH: 14
<212> TYPE: PRT
<213> ORGANISM: Homo sapiens

<400> SEQUENCE: 592

Thr Gly Ser Ser Ser Asn Ile Gly Ala Gly Tyr Asp Val His
1               5                   10

<210> SEQ ID NO 593
<211> LENGTH: 15
<212> TYPE: PRT
<213> ORGANISM: Homo sapiens

<400> SEQUENCE: 593

Trp Tyr Gln Gln Leu Pro Gly Thr Ala Pro Lys Leu Leu Ile Tyr
1               5                   10                  15

<210> SEQ ID NO 594
<211> LENGTH: 22
<212> TYPE: PRT
<213> ORGANISM: Homo sapiens

<400> SEQUENCE: 594

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 595
<211> LENGTH: 13
<212> TYPE: PRT
<213> ORGANISM: Homo sapiens

<400> SEQUENCE: 595

Ser Gly Ser Ser Ser Asn Ile Gly Ser Asn Thr Val Asn
1               5                   10

```
<210> SEQ ID NO 596
<211> LENGTH: 15
<212> TYPE: PRT
<213> ORGANISM: Homo sapiens

<400> SEQUENCE: 596

Trp Tyr Gln Gln Leu Pro Gly Thr Ala Pro Lys Leu Leu Ile Tyr
1               5                   10                  15

<210> SEQ ID NO 597
<211> LENGTH: 22
<212> TYPE: PRT
<213> ORGANISM: Homo sapiens

<400> SEQUENCE: 597

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 598
<211> LENGTH: 13
<212> TYPE: PRT
<213> ORGANISM: Homo sapiens

<400> SEQUENCE: 598

Ser Gly Ser Ser Ser Asn Ile Gly Ser Asn Tyr Val Tyr
1               5                   10

<210> SEQ ID NO 599
<211> LENGTH: 15
<212> TYPE: PRT
<213> ORGANISM: Homo sapiens

<400> SEQUENCE: 599

Trp Tyr Gln Gln Leu Pro Gly Thr Ala Pro Lys Leu Leu Ile Tyr
1               5                   10                  15

<210> SEQ ID NO 600
<211> LENGTH: 22
<212> TYPE: PRT
<213> ORGANISM: Homo sapiens

<400> SEQUENCE: 600

Gln Ser Val Leu Thr Gln Pro Pro Ser Val Ser Ala Ala Pro Gly Gln
1               5                   10                  15

Lys Val Thr Ile Ser Cys
            20

<210> SEQ ID NO 601
<211> LENGTH: 13
<212> TYPE: PRT
<213> ORGANISM: Homo sapiens

<400> SEQUENCE: 601

Ser Gly Ser Ser Ser Asn Ile Gly Asn Asn Tyr Val Ser
1               5                   10

<210> SEQ ID NO 602
<211> LENGTH: 15
<212> TYPE: PRT
<213> ORGANISM: Homo sapiens

<400> SEQUENCE: 602

Trp Tyr Gln Gln Leu Pro Gly Thr Ala Pro Lys Leu Leu Ile Tyr
```

```
1               5                  10                 15
```

<210> SEQ ID NO 603
<211> LENGTH: 22
<212> TYPE: PRT
<213> ORGANISM: Homo sapiens

<400> SEQUENCE: 603

```
Gln Ser Ala Leu Thr Gln Pro Pro Ser Ala Ser Gly Ser Pro Gly Gln
1               5                  10                 15

Ser Val Thr Ile Ser Cys
            20
```

<210> SEQ ID NO 604
<211> LENGTH: 14
<212> TYPE: PRT
<213> ORGANISM: Homo sapiens

<400> SEQUENCE: 604

```
Thr Gly Thr Ser Ser Asp Val Gly Gly Tyr Asn Tyr Val Ser
1               5                  10
```

<210> SEQ ID NO 605
<211> LENGTH: 15
<212> TYPE: PRT
<213> ORGANISM: Homo sapiens

<400> SEQUENCE: 605

```
Trp Tyr Gln Gln His Pro Gly Lys Ala Pro Lys Leu Met Ile Tyr
1               5                  10                 15
```

<210> SEQ ID NO 606
<211> LENGTH: 22
<212> TYPE: PRT
<213> ORGANISM: Homo sapiens

<400> SEQUENCE: 606

```
Gln Ser Ala Leu Thr Gln Pro Arg Ser Val Ser Gly Ser Pro Gly Gln
1               5                  10                 15

Ser Val Thr Ile Ser Cys
            20
```

<210> SEQ ID NO 607
<211> LENGTH: 14
<212> TYPE: PRT
<213> ORGANISM: Homo sapiens

<400> SEQUENCE: 607

```
Thr Gly Thr Ser Ser Asp Val Gly Gly Tyr Asn Tyr Val Ser
1               5                  10
```

<210> SEQ ID NO 608
<211> LENGTH: 15
<212> TYPE: PRT
<213> ORGANISM: Homo sapiens

<400> SEQUENCE: 608

```
Trp Tyr Gln Gln His Pro Gly Lys Ala Pro Lys Leu Met Ile Tyr
1               5                  10                 15
```

<210> SEQ ID NO 609
<211> LENGTH: 22
<212> TYPE: PRT
<213> ORGANISM: Homo sapiens

```
<400> SEQUENCE: 609

Gln Ser Ala Leu Thr Gln Pro Ala Ser Val Ser Gly Ser Pro Gly Gln
1               5                   10                  15

Ser Ile Thr Ile Ser Cys
            20

<210> SEQ ID NO 610
<211> LENGTH: 14
<212> TYPE: PRT
<213> ORGANISM: Homo sapiens

<400> SEQUENCE: 610

Thr Gly Thr Ser Ser Asp Val Gly Gly Tyr Asn Tyr Val Ser
1               5                   10

<210> SEQ ID NO 611
<211> LENGTH: 15
<212> TYPE: PRT
<213> ORGANISM: Homo sapiens

<400> SEQUENCE: 611

Trp Tyr Gln Gln His Pro Gly Lys Ala Pro Lys Leu Met Ile Tyr
1               5                   10                  15

<210> SEQ ID NO 612
<211> LENGTH: 22
<212> TYPE: PRT
<213> ORGANISM: Homo sapiens

<400> SEQUENCE: 612

Gln Ser Ala Leu Thr Gln Pro Pro Ser Val Ser Gly Ser Pro Gly Gln
1               5                   10                  15

Ser Val Thr Ile Ser Cys
            20

<210> SEQ ID NO 613
<211> LENGTH: 14
<212> TYPE: PRT
<213> ORGANISM: Homo sapiens

<400> SEQUENCE: 613

Thr Gly Thr Ser Ser Asp Val Gly Ser Tyr Asn Arg Val Ser
1               5                   10

<210> SEQ ID NO 614
<211> LENGTH: 15
<212> TYPE: PRT
<213> ORGANISM: Homo sapiens

<400> SEQUENCE: 614

Trp Tyr Gln Gln Pro Pro Gly Thr Ala Pro Lys Leu Met Ile Tyr
1               5                   10                  15

<210> SEQ ID NO 615
<211> LENGTH: 22
<212> TYPE: PRT
<213> ORGANISM: Homo sapiens

<400> SEQUENCE: 615

Gln Ser Ala Leu Thr Gln Pro Ala Ser Val Ser Gly Ser Pro Gly Gln
1               5                   10                  15

Ser Ile Thr Ile Ser Cys
            20
```

<210> SEQ ID NO 616
<211> LENGTH: 14
<212> TYPE: PRT
<213> ORGANISM: Homo sapiens

<400> SEQUENCE: 616

Thr Gly Thr Ser Ser Asp Val Gly Ser Tyr Asn Leu Val Ser
1               5                   10

<210> SEQ ID NO 617
<211> LENGTH: 15
<212> TYPE: PRT
<213> ORGANISM: Homo sapiens

<400> SEQUENCE: 617

Trp Tyr Gln Gln His Pro Gly Lys Ala Pro Lys Leu Met Ile Tyr
1               5                   10                  15

<210> SEQ ID NO 618
<211> LENGTH: 22
<212> TYPE: PRT
<213> ORGANISM: Homo sapiens

<400> SEQUENCE: 618

Ser Tyr Glu Leu Thr Gln Pro Pro Ser Val Ser Val Ser Pro Gly Gln
1               5                   10                  15

Thr Ala Ser Ile Thr Cys
            20

<210> SEQ ID NO 619
<211> LENGTH: 11
<212> TYPE: PRT
<213> ORGANISM: Homo sapiens

<400> SEQUENCE: 619

Ser Gly Asp Lys Leu Gly Asp Lys Tyr Ala Cys
1               5                   10

<210> SEQ ID NO 620
<211> LENGTH: 15
<212> TYPE: PRT
<213> ORGANISM: Homo sapiens

<400> SEQUENCE: 620

Trp Tyr Gln Gln Lys Pro Gly Gln Ser Pro Val Leu Val Ile Tyr
1               5                   10                  15

<210> SEQ ID NO 621
<211> LENGTH: 22
<212> TYPE: PRT
<213> ORGANISM: Homo sapiens

<400> SEQUENCE: 621

Ser Tyr Glu Leu Thr Gln Pro Leu Ser Val Ser Val Ala Leu Gly Gln
1               5                   10                  15

Thr Ala Arg Ile Thr Cys
            20

<210> SEQ ID NO 622
<211> LENGTH: 11
<212> TYPE: PRT
<213> ORGANISM: Homo sapiens

<400> SEQUENCE: 622

Gly Gly Asn Asn Ile Gly Ser Lys Asn Val His
1               5                   10

<210> SEQ ID NO 623
<211> LENGTH: 15
<212> TYPE: PRT
<213> ORGANISM: Homo sapiens

<400> SEQUENCE: 623

Trp Tyr Gln Gln Lys Pro Gly Gln Ala Pro Val Leu Val Ile Tyr
1               5                   10                  15

<210> SEQ ID NO 624
<211> LENGTH: 22
<212> TYPE: PRT
<213> ORGANISM: Homo sapiens

<400> SEQUENCE: 624

Ser Tyr Glu Leu Thr Gln Pro Pro Ser Val Ser Val Ser Pro Gly Gln
1               5                   10                  15

Thr Ala Arg Ile Thr Cys
            20

<210> SEQ ID NO 625
<211> LENGTH: 11
<212> TYPE: PRT
<213> ORGANISM: Homo sapiens

<400> SEQUENCE: 625

Ser Gly Asp Ala Leu Pro Lys Lys Tyr Ala Tyr
1               5                   10

<210> SEQ ID NO 626
<211> LENGTH: 15
<212> TYPE: PRT
<213> ORGANISM: Homo sapiens

<400> SEQUENCE: 626

Trp Tyr Gln Gln Lys Ser Gly Gln Ala Pro Val Leu Val Ile Tyr
1               5                   10                  15

<210> SEQ ID NO 627
<211> LENGTH: 22
<212> TYPE: PRT
<213> ORGANISM: Homo sapiens

<400> SEQUENCE: 627

Ser Tyr Glu Leu Thr Gln Pro Pro Ser Val Ser Val Ser Leu Gly Gln
1               5                   10                  15

Met Ala Arg Ile Thr Cys
            20

<210> SEQ ID NO 628
<211> LENGTH: 11
<212> TYPE: PRT
<213> ORGANISM: Homo sapiens

<400> SEQUENCE: 628

Ser Gly Glu Ala Leu Pro Lys Lys Tyr Ala Tyr
1               5                   10

<210> SEQ ID NO 629
<211> LENGTH: 15
<212> TYPE: PRT
<213> ORGANISM: Homo sapiens

<400> SEQUENCE: 629

Trp Tyr Gln Gln Lys Pro Gly Gln Phe Pro Val Leu Val Ile Tyr
1               5                   10                  15

<210> SEQ ID NO 630
<211> LENGTH: 22
<212> TYPE: PRT
<213> ORGANISM: Homo sapiens

<400> SEQUENCE: 630

Ser Ser Glu Leu Thr Gln Asp Pro Ala Val Ser Val Ala Leu Gly Gln
1               5                   10                  15

Thr Val Arg Ile Thr Cys
            20

<210> SEQ ID NO 631
<211> LENGTH: 11
<212> TYPE: PRT
<213> ORGANISM: Homo sapiens

<400> SEQUENCE: 631

Gln Gly Asp Ser Leu Arg Ser Tyr Tyr Ala Ser
1               5                   10

<210> SEQ ID NO 632
<211> LENGTH: 15
<212> TYPE: PRT
<213> ORGANISM: Homo sapiens

<400> SEQUENCE: 632

Trp Tyr Gln Gln Lys Pro Gly Gln Ala Pro Val Leu Val Ile Tyr
1               5                   10                  15

<210> SEQ ID NO 633
<211> LENGTH: 22
<212> TYPE: PRT
<213> ORGANISM: Homo sapiens

<400> SEQUENCE: 633

Ser Tyr Val Leu Thr Gln Pro Pro Ser Val Ser Val Ala Pro Gly Lys
1               5                   10                  15

Thr Ala Arg Ile Thr Cys
            20

<210> SEQ ID NO 634
<211> LENGTH: 11
<212> TYPE: PRT
<213> ORGANISM: Homo sapiens

<400> SEQUENCE: 634

Gly Gly Asn Asn Ile Gly Ser Lys Ser Val His
1               5                   10

<210> SEQ ID NO 635
<211> LENGTH: 15
<212> TYPE: PRT
<213> ORGANISM: Homo sapiens

<400> SEQUENCE: 635

Trp Tyr Gln Gln Lys Pro Gly Gln Ala Pro Val Leu Val Ile Tyr
1               5                   10                  15

<210> SEQ ID NO 636

```
<211> LENGTH: 22
<212> TYPE: PRT
<213> ORGANISM: Homo sapiens

<400> SEQUENCE: 636

Ser Tyr Glu Leu Thr Gln Leu Pro Ser Val Ser Val Ser Pro Gly Gln
1               5                   10                  15

Thr Ala Arg Ile Thr Cys
            20

<210> SEQ ID NO 637
<211> LENGTH: 11
<212> TYPE: PRT
<213> ORGANISM: Homo sapiens

<400> SEQUENCE: 637

Ser Gly Asp Val Leu Gly Glu Asn Tyr Ala Asp
1               5                   10

<210> SEQ ID NO 638
<211> LENGTH: 15
<212> TYPE: PRT
<213> ORGANISM: Homo sapiens

<400> SEQUENCE: 638

Trp Tyr Gln Gln Lys Pro Gly Gln Ala Pro Glu Leu Val Ile Tyr
1               5                   10                  15

<210> SEQ ID NO 639
<211> LENGTH: 22
<212> TYPE: PRT
<213> ORGANISM: Homo sapiens

<400> SEQUENCE: 639

Ser Tyr Glu Leu Met Gln Pro Pro Ser Val Ser Val Ser Pro Gly Gln
1               5                   10                  15

Thr Ala Arg Ile Thr Cys
            20

<210> SEQ ID NO 640
<211> LENGTH: 11
<212> TYPE: PRT
<213> ORGANISM: Homo sapiens

<400> SEQUENCE: 640

Ser Gly Asp Ala Leu Pro Lys Gln Tyr Ala Tyr
1               5                   10

<210> SEQ ID NO 641
<211> LENGTH: 15
<212> TYPE: PRT
<213> ORGANISM: Homo sapiens

<400> SEQUENCE: 641

Trp Tyr Gln Gln Lys Pro Gly Gln Ala Pro Val Leu Val Ile Tyr
1               5                   10                  15

<210> SEQ ID NO 642
<211> LENGTH: 22
<212> TYPE: PRT
<213> ORGANISM: Homo sapiens

<400> SEQUENCE: 642

Ser Tyr Glu Leu Thr Gln Pro Ser Ser Val Ser Val Ser Pro Gly Gln
1               5                   10                  15
```

Thr Ala Arg Ile Thr Cys
            20

<210> SEQ ID NO 643
<211> LENGTH: 11
<212> TYPE: PRT
<213> ORGANISM: Homo sapiens

<400> SEQUENCE: 643

Ser Gly Asp Val Leu Ala Lys Lys Tyr Ala Arg
1               5                   10

<210> SEQ ID NO 644
<211> LENGTH: 15
<212> TYPE: PRT
<213> ORGANISM: Homo sapiens

<400> SEQUENCE: 644

Trp Phe Gln Gln Lys Pro Gly Gln Ala Pro Val Leu Val Ile Tyr
1               5                   10                  15

<210> SEQ ID NO 645
<211> LENGTH: 22
<212> TYPE: PRT
<213> ORGANISM: Homo sapiens

<400> SEQUENCE: 645

Leu Pro Val Leu Thr Gln Pro Pro Ser Ala Ser Ala Leu Leu Gly Ala
1               5                   10                  15
Ser Ile Lys Leu Thr Cys
            20

<210> SEQ ID NO 646
<211> LENGTH: 12
<212> TYPE: PRT
<213> ORGANISM: Homo sapiens

<400> SEQUENCE: 646

Thr Leu Ser Ser Glu His Ser Thr Tyr Thr Ile Glu
1               5                   10

<210> SEQ ID NO 647
<211> LENGTH: 15
<212> TYPE: PRT
<213> ORGANISM: Homo sapiens

<400> SEQUENCE: 647

Trp Tyr Gln Gln Arg Pro Gly Arg Ser Pro Gln Tyr Ile Met Lys
1               5                   10                  15

<210> SEQ ID NO 648
<211> LENGTH: 22
<212> TYPE: PRT
<213> ORGANISM: Homo sapiens

<400> SEQUENCE: 648

Gln Pro Val Leu Thr Gln Ser Ser Ser Ala Ser Ala Ser Leu Gly Ser
1               5                   10                  15
Ser Val Lys Leu Thr Cys
            20

<210> SEQ ID NO 649
<211> LENGTH: 12
<212> TYPE: PRT

<213> ORGANISM: Homo sapiens

<400> SEQUENCE: 649

Thr Leu Ser Ser Gly His Ser Ser Tyr Ile Ile Ala
1               5                   10

<210> SEQ ID NO 650
<211> LENGTH: 15
<212> TYPE: PRT
<213> ORGANISM: Homo sapiens

<400> SEQUENCE: 650

Trp His Gln Gln Gln Pro Gly Lys Ala Pro Arg Tyr Leu Met Lys
1               5                   10                  15

<210> SEQ ID NO 651
<211> LENGTH: 22
<212> TYPE: PRT
<213> ORGANISM: Homo sapiens

<400> SEQUENCE: 651

Gln Leu Val Leu Thr Gln Ser Pro Ser Ala Ser Ala Ser Leu Gly Ala
1               5                   10                  15

Ser Val Lys Leu Thr Cys
            20

<210> SEQ ID NO 652
<211> LENGTH: 12
<212> TYPE: PRT
<213> ORGANISM: Homo sapiens

<400> SEQUENCE: 652

Thr Leu Ser Ser Gly His Ser Ser Tyr Ala Ile Ala
1               5                   10

<210> SEQ ID NO 653
<211> LENGTH: 15
<212> TYPE: PRT
<213> ORGANISM: Homo sapiens

<400> SEQUENCE: 653

Trp His Gln Gln Gln Pro Glu Lys Gly Pro Arg Tyr Leu Met Lys
1               5                   10                  15

<210> SEQ ID NO 654
<211> LENGTH: 22
<212> TYPE: PRT
<213> ORGANISM: Homo sapiens

<400> SEQUENCE: 654

Gln Pro Val Leu Thr Gln Pro Pro Ser Ser Ala Ser Pro Gly Glu
1               5                   10                  15

Ser Ala Arg Leu Thr Cys
            20

<210> SEQ ID NO 655
<211> LENGTH: 14
<212> TYPE: PRT
<213> ORGANISM: Homo sapiens

<400> SEQUENCE: 655

Thr Leu Pro Ser Asp Ile Asn Val Gly Ser Tyr Asn Ile Tyr
1               5                   10

```
<210> SEQ ID NO 656
<211> LENGTH: 15
<212> TYPE: PRT
<213> ORGANISM: Homo sapiens

<400> SEQUENCE: 656

Trp Tyr Gln Gln Lys Pro Gly Ser Pro Pro Arg Tyr Leu Leu Tyr
1               5                   10                  15

<210> SEQ ID NO 657
<211> LENGTH: 22
<212> TYPE: PRT
<213> ORGANISM: Homo sapiens

<400> SEQUENCE: 657

Gln Ala Val Leu Thr Gln Pro Ala Ser Leu Ser Ala Ser Pro Gly Ala
1               5                   10                  15

Ser Ala Ser Leu Thr Cys
            20

<210> SEQ ID NO 658
<211> LENGTH: 14
<212> TYPE: PRT
<213> ORGANISM: Homo sapiens

<400> SEQUENCE: 658

Thr Leu Arg Ser Gly Ile Asn Val Gly Thr Tyr Arg Ile Tyr
1               5                   10

<210> SEQ ID NO 659
<211> LENGTH: 15
<212> TYPE: PRT
<213> ORGANISM: Homo sapiens

<400> SEQUENCE: 659

Trp Tyr Gln Gln Lys Pro Gly Ser Pro Pro Gln Tyr Leu Leu Arg
1               5                   10                  15

<210> SEQ ID NO 660
<211> LENGTH: 22
<212> TYPE: PRT
<213> ORGANISM: Homo sapiens

<400> SEQUENCE: 660

Gln Pro Val Leu Thr Gln Pro Ser Ser His Ser Ala Ser Ser Gly Ala
1               5                   10                  15

Ser Val Arg Leu Thr Cys
            20

<210> SEQ ID NO 661
<211> LENGTH: 14
<212> TYPE: PRT
<213> ORGANISM: Homo sapiens

<400> SEQUENCE: 661

Met Leu Ser Ser Gly Phe Ser Val Gly Asp Phe Trp Ile Arg
1               5                   10

<210> SEQ ID NO 662
<211> LENGTH: 15
<212> TYPE: PRT
<213> ORGANISM: Homo sapiens

<400> SEQUENCE: 662

Trp Tyr Gln Gln Lys Pro Gly Asn Pro Pro Arg Tyr Leu Leu Tyr
```

<210> SEQ ID NO 663
<211> LENGTH: 22
<212> TYPE: PRT
<213> ORGANISM: Homo sapiens

<400> SEQUENCE: 663

Asn Phe Met Leu Thr Gln Pro His Ser Val Ser Glu Ser Pro Gly Lys
1               5                   10                  15

Thr Val Thr Ile Ser Cys
            20

<210> SEQ ID NO 664
<211> LENGTH: 13
<212> TYPE: PRT
<213> ORGANISM: Homo sapiens

<400> SEQUENCE: 664

Thr Arg Ser Ser Gly Ser Ile Ala Ser Asn Tyr Val Gln
1               5                   10

<210> SEQ ID NO 665
<211> LENGTH: 15
<212> TYPE: PRT
<213> ORGANISM: Homo sapiens

<400> SEQUENCE: 665

Trp Tyr Gln Gln Arg Pro Gly Ser Ser Pro Thr Thr Val Ile Tyr
1               5                   10                  15

<210> SEQ ID NO 666
<211> LENGTH: 22
<212> TYPE: PRT
<213> ORGANISM: Homo sapiens

<400> SEQUENCE: 666

Gln Thr Val Val Thr Gln Glu Pro Ser Leu Thr Val Ser Pro Gly Gly
1               5                   10                  15

Thr Val Thr Leu Thr Cys
            20

<210> SEQ ID NO 667
<211> LENGTH: 14
<212> TYPE: PRT
<213> ORGANISM: Homo sapiens

<400> SEQUENCE: 667

Ala Ser Ser Thr Gly Ala Val Thr Ser Gly Tyr Tyr Pro Asn
1               5                   10

<210> SEQ ID NO 668
<211> LENGTH: 15
<212> TYPE: PRT
<213> ORGANISM: Homo sapiens

<400> SEQUENCE: 668

Trp Phe Gln Gln Lys Pro Gly Gln Ala Pro Arg Ala Leu Ile Tyr
1               5                   10                  15

<210> SEQ ID NO 669
<211> LENGTH: 22
<212> TYPE: PRT
<213> ORGANISM: Homo sapiens

```
<400> SEQUENCE: 669

Gln Ala Val Val Thr Gln Glu Pro Ser Leu Thr Val Ser Pro Gly Gly
1               5                   10                  15

Thr Val Thr Leu Thr Cys
            20

<210> SEQ ID NO 670
<211> LENGTH: 14
<212> TYPE: PRT
<213> ORGANISM: Homo sapiens

<400> SEQUENCE: 670

Gly Ser Ser Thr Gly Ala Val Thr Ser Gly His Tyr Pro Tyr
1               5                   10

<210> SEQ ID NO 671
<211> LENGTH: 15
<212> TYPE: PRT
<213> ORGANISM: Homo sapiens

<400> SEQUENCE: 671

Trp Phe Gln Gln Lys Pro Gly Gln Ala Pro Arg Thr Leu Ile Tyr
1               5                   10                  15

<210> SEQ ID NO 672
<211> LENGTH: 22
<212> TYPE: PRT
<213> ORGANISM: Homo sapiens

<400> SEQUENCE: 672

Gln Thr Val Val Thr Gln Glu Pro Ser Phe Ser Val Ser Pro Gly Gly
1               5                   10                  15

Thr Val Thr Leu Thr Cys
            20

<210> SEQ ID NO 673
<211> LENGTH: 14
<212> TYPE: PRT
<213> ORGANISM: Homo sapiens

<400> SEQUENCE: 673

Gly Leu Ser Ser Gly Ser Val Ser Thr Ser Tyr Tyr Pro Ser
1               5                   10

<210> SEQ ID NO 674
<211> LENGTH: 15
<212> TYPE: PRT
<213> ORGANISM: Homo sapiens

<400> SEQUENCE: 674

Trp Tyr Gln Gln Thr Pro Gly Gln Ala Pro Arg Thr Leu Ile Tyr
1               5                   10                  15

<210> SEQ ID NO 675
<211> LENGTH: 22
<212> TYPE: PRT
<213> ORGANISM: Homo sapiens

<400> SEQUENCE: 675

Gln Pro Val Leu Thr Gln Pro Pro Ser Ala Ser Ala Ser Leu Gly Ala
1               5                   10                  15

Ser Val Thr Leu Thr Cys
            20
```

<210> SEQ ID NO 676
<211> LENGTH: 12
<212> TYPE: PRT
<213> ORGANISM: Homo sapiens

<400> SEQUENCE: 676

Thr Leu Ser Ser Gly Tyr Ser Asn Tyr Lys Val Asp
1               5                   10

<210> SEQ ID NO 677
<211> LENGTH: 15
<212> TYPE: PRT
<213> ORGANISM: Homo sapiens

<400> SEQUENCE: 677

Trp Tyr Gln Gln Arg Pro Gly Lys Gly Pro Arg Phe Val Met Arg
1               5                   10                  15

<210> SEQ ID NO 678
<211> LENGTH: 22
<212> TYPE: PRT
<213> ORGANISM: Homo sapiens

<400> SEQUENCE: 678

Gln Ala Gly Leu Thr Gln Pro Pro Ser Val Ser Lys Gly Leu Arg Gln
1               5                   10                  15

Thr Ala Thr Leu Thr Cys
            20

<210> SEQ ID NO 679
<211> LENGTH: 13
<212> TYPE: PRT
<213> ORGANISM: Homo sapiens

<400> SEQUENCE: 679

Thr Gly Asn Ser Asn Asn Val Gly Asn Gln Gly Ala Ala
1               5                   10

<210> SEQ ID NO 680
<211> LENGTH: 15
<212> TYPE: PRT
<213> ORGANISM: Homo sapiens

<400> SEQUENCE: 680

Trp Leu Gln Gln His Gln Gly His Pro Pro Lys Leu Leu Ser Tyr
1               5                   10                  15

<210> SEQ ID NO 681
<211> LENGTH: 7
<212> TYPE: PRT
<213> ORGANISM: Homo sapiens

<400> SEQUENCE: 681

Tyr Asp Asp Leu Leu Pro Ser
1               5

<210> SEQ ID NO 682
<211> LENGTH: 32
<212> TYPE: PRT
<213> ORGANISM: Homo sapiens

<400> SEQUENCE: 682

Gly Val Ser Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 683
<211> LENGTH: 9
<212> TYPE: PRT
<213> ORGANISM: Homo sapiens

<400> SEQUENCE: 683

Ala Ala Trp Asp Asp Ser Leu Asn Gly
1               5

<210> SEQ ID NO 684
<211> LENGTH: 7
<212> TYPE: PRT
<213> ORGANISM: Homo sapiens

<400> SEQUENCE: 684

Gly Asn Ser Asn Arg Pro Ser
1               5

<210> SEQ ID NO 685
<211> LENGTH: 32
<212> TYPE: PRT
<213> ORGANISM: Homo sapiens

<400> SEQUENCE: 685

Gly Val Pro Asp Arg Phe Ser Gly Ser Lys Ser Gly Thr Ser Ala Ser
1               5                   10                  15

Leu Ala Ile Thr Gly Leu Gln Ala Glu Asp Glu Ala Asp Tyr Tyr Cys
            20                  25                  30

<210> SEQ ID NO 686
<211> LENGTH: 9
<212> TYPE: PRT
<213> ORGANISM: Homo sapiens

<400> SEQUENCE: 686

Gln Ser Tyr Asp Ser Ser Leu Ser Gly
1               5

<210> SEQ ID NO 687
<211> LENGTH: 7
<212> TYPE: PRT
<213> ORGANISM: Homo sapiens

<400> SEQUENCE: 687

Ser Asn Asn Gln Arg Pro Ser
1               5

<210> SEQ ID NO 688
<211> LENGTH: 32
<212> TYPE: PRT
<213> ORGANISM: Homo sapiens

<400> SEQUENCE: 688

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 689
<211> LENGTH: 9
<212> TYPE: PRT
<213> ORGANISM: Homo sapiens

```
<400> SEQUENCE: 689

Ala Ala Trp Asp Asp Ser Leu Asn Gly
1               5

<210> SEQ ID NO 690
<211> LENGTH: 7
<212> TYPE: PRT
<213> ORGANISM: Homo sapiens

<400> SEQUENCE: 690

Arg Asn Asn Gln Arg Pro Ser
1               5

<210> SEQ ID NO 691
<211> LENGTH: 32
<212> TYPE: PRT
<213> ORGANISM: Homo sapiens

<400> SEQUENCE: 691

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 692
<211> LENGTH: 9
<212> TYPE: PRT
<213> ORGANISM: Homo sapiens

<400> SEQUENCE: 692

Ala Ala Trp Asp Asp Ser Leu Ser Gly
1               5

<210> SEQ ID NO 693
<211> LENGTH: 7
<212> TYPE: PRT
<213> ORGANISM: Homo sapiens

<400> SEQUENCE: 693

Asp Asn Asn Lys Arg Pro Ser
1               5

<210> SEQ ID NO 694
<211> LENGTH: 32
<212> TYPE: PRT
<213> ORGANISM: Homo sapiens

<400> SEQUENCE: 694

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Asp Tyr Tyr Cys
            20                  25                  30

<210> SEQ ID NO 695
<211> LENGTH: 9
<212> TYPE: PRT
<213> ORGANISM: Homo sapiens

<400> SEQUENCE: 695

Gly Thr Trp Asp Ser Ser Leu Ser Ala
1               5

<210> SEQ ID NO 696
```

```
<211> LENGTH: 7
<212> TYPE: PRT
<213> ORGANISM: Homo sapiens

<400> SEQUENCE: 696

Glu Val Ser Lys Arg Pro Ser
1               5

<210> SEQ ID NO 697
<211> LENGTH: 32
<212> TYPE: PRT
<213> ORGANISM: Homo sapiens

<400> SEQUENCE: 697

Gly Val Pro Asp Arg Phe Ser Gly Ser Lys Ser Gly Asn Thr Ala Ser
1               5                   10                  15

Leu Thr Val Ser Gly Leu Gln Ala Glu Asp Glu Ala Asp Tyr Tyr Cys
            20                  25                  30

<210> SEQ ID NO 698
<211> LENGTH: 9
<212> TYPE: PRT
<213> ORGANISM: Homo sapiens

<400> SEQUENCE: 698

Ser Ser Tyr Ala Gly Ser Asn Asn Phe
1               5

<210> SEQ ID NO 699
<211> LENGTH: 7
<212> TYPE: PRT
<213> ORGANISM: Homo sapiens

<400> SEQUENCE: 699

Asp Val Ser Lys Arg Pro Ser
1               5

<210> SEQ ID NO 700
<211> LENGTH: 32
<212> TYPE: PRT
<213> ORGANISM: Homo sapiens

<400> SEQUENCE: 700

Gly Val Pro Asp Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 701
<211> LENGTH: 9
<212> TYPE: PRT
<213> ORGANISM: Homo sapiens

<400> SEQUENCE: 701

Cys Ser Tyr Ala Gly Ser Tyr Thr Phe
1               5

<210> SEQ ID NO 702
<211> LENGTH: 7
<212> TYPE: PRT
<213> ORGANISM: Homo sapiens

<400> SEQUENCE: 702

Glu Val Ser Asn Arg Pro Ser
1               5
```

<210> SEQ ID NO 703
<211> LENGTH: 32
<212> TYPE: PRT
<213> ORGANISM: Homo sapiens

<400> SEQUENCE: 703

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 704
<211> LENGTH: 9
<212> TYPE: PRT
<213> ORGANISM: Homo sapiens

<400> SEQUENCE: 704

Ser Ser Tyr Thr Ser Ser Ser Thr Leu
1               5

<210> SEQ ID NO 705
<211> LENGTH: 7
<212> TYPE: PRT
<213> ORGANISM: Homo sapiens

<400> SEQUENCE: 705

Glu Val Ser Asn Arg Pro Ser
1               5

<210> SEQ ID NO 706
<211> LENGTH: 32
<212> TYPE: PRT
<213> ORGANISM: Homo sapiens

<400> SEQUENCE: 706

Gly Val Pro Asp Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 707
<211> LENGTH: 9
<212> TYPE: PRT
<213> ORGANISM: Homo sapiens

<400> SEQUENCE: 707

Ser Leu Tyr Thr Ser Ser Ser Thr Phe
1               5

<210> SEQ ID NO 708
<211> LENGTH: 7
<212> TYPE: PRT
<213> ORGANISM: Homo sapiens

<400> SEQUENCE: 708

Glu Val Ser Lys Arg Pro Ser
1               5

<210> SEQ ID NO 709
<211> LENGTH: 32
<212> TYPE: PRT
<213> ORGANISM: Homo sapiens

<400> SEQUENCE: 709

```
Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30
```

<210> SEQ ID NO 710
<211> LENGTH: 9
<212> TYPE: PRT
<213> ORGANISM: Homo sapiens

<400> SEQUENCE: 710

```
Cys Ser Tyr Ala Gly Ser Ser Thr Phe
1               5
```

<210> SEQ ID NO 711
<211> LENGTH: 7
<212> TYPE: PRT
<213> ORGANISM: Homo sapiens

<400> SEQUENCE: 711

```
Gln Asp Ser Lys Arg Pro Ser
1               5
```

<210> SEQ ID NO 712
<211> LENGTH: 32
<212> TYPE: PRT
<213> ORGANISM: Homo sapiens

<400> SEQUENCE: 712

```
Gly Ile Pro Glu Arg Phe Ser Gly Ser Asn Ser Gly Asn Thr Ala Thr
1               5                   10                  15

Leu Thr Ile Ser Gly Thr Gln Ala Met Asp Glu Ala Asp Tyr Tyr Cys
            20                  25                  30
```

<210> SEQ ID NO 713
<211> LENGTH: 8
<212> TYPE: PRT
<213> ORGANISM: Homo sapiens

<400> SEQUENCE: 713

```
Gln Ala Trp Asp Ser Ser Thr Ala
1               5
```

<210> SEQ ID NO 714
<211> LENGTH: 7
<212> TYPE: PRT
<213> ORGANISM: Homo sapiens

<400> SEQUENCE: 714

```
Arg Asp Ser Asn Arg Pro Ser
1               5
```

<210> SEQ ID NO 715
<211> LENGTH: 32
<212> TYPE: PRT
<213> ORGANISM: Homo sapiens

<400> SEQUENCE: 715

```
Gly Ile Pro Glu Arg Phe Ser Gly Ser Asn Ser Gly Asn Thr Ala Thr
1               5                   10                  15

Leu Thr Ile Ser Arg Ala Gln Ala Gly Asp Glu Ala Asp Tyr Tyr Cys
            20                  25                  30
```

```
<210> SEQ ID NO 716
<211> LENGTH: 8
<212> TYPE: PRT
<213> ORGANISM: Homo sapiens

<400> SEQUENCE: 716

Gln Val Trp Asp Ser Ser Thr Ala
1               5

<210> SEQ ID NO 717
<211> LENGTH: 7
<212> TYPE: PRT
<213> ORGANISM: Homo sapiens

<400> SEQUENCE: 717

Glu Asp Ser Lys Arg Pro Ser
1               5

<210> SEQ ID NO 718
<211> LENGTH: 32
<212> TYPE: PRT
<213> ORGANISM: Homo sapiens

<400> SEQUENCE: 718

Gly Ile Pro Glu Arg Phe Ser Gly Ser Ser Gly Thr Met Ala Thr
1               5                   10                  15

Leu Thr Ile Ser Gly Ala Gln Val Glu Asp Glu Ala Asp Tyr Tyr Cys
            20                  25                  30

<210> SEQ ID NO 719
<211> LENGTH: 9
<212> TYPE: PRT
<213> ORGANISM: Homo sapiens

<400> SEQUENCE: 719

Tyr Ser Thr Asp Ser Ser Gly Asn His
1               5

<210> SEQ ID NO 720
<211> LENGTH: 7
<212> TYPE: PRT
<213> ORGANISM: Homo sapiens

<400> SEQUENCE: 720

Lys Asp Ser Glu Arg Pro Ser
1               5

<210> SEQ ID NO 721
<211> LENGTH: 32
<212> TYPE: PRT
<213> ORGANISM: Homo sapiens

<400> SEQUENCE: 721

Gly Ile Pro Glu Arg Phe Ser Gly Ser Ser Gly Thr Ile Val Thr
1               5                   10                  15

Leu Thr Ile Ser Gly Val Gln Ala Glu Asp Glu Ala Asp Tyr Tyr Cys
            20                  25                  30

<210> SEQ ID NO 722
<211> LENGTH: 9
<212> TYPE: PRT
<213> ORGANISM: Homo sapiens

<400> SEQUENCE: 722

Leu Ser Ala Asp Ser Ser Gly Thr Tyr
```

-continued

<210> SEQ ID NO 723
<211> LENGTH: 7
<212> TYPE: PRT
<213> ORGANISM: Homo sapiens

<400> SEQUENCE: 723

Gly Lys Asn Asn Arg Pro Ser
1               5

<210> SEQ ID NO 724
<211> LENGTH: 32
<212> TYPE: PRT
<213> ORGANISM: Homo sapiens

<400> SEQUENCE: 724

Gly Ile Pro Asp Arg Phe Ser Gly Ser Ser Gly Asn Thr Ala Ser
1               5                   10                  15

Leu Thr Ile Thr Gly Ala Gln Ala Glu Asp Glu Ala Asp Tyr Tyr Cys
            20                  25                  30

<210> SEQ ID NO 725
<211> LENGTH: 9
<212> TYPE: PRT
<213> ORGANISM: Homo sapiens

<400> SEQUENCE: 725

Asn Ser Arg Asp Ser Ser Gly Asn His
1               5

<210> SEQ ID NO 726
<211> LENGTH: 7
<212> TYPE: PRT
<213> ORGANISM: Homo sapiens

<400> SEQUENCE: 726

Tyr Asp Ser Asp Arg Pro Ser
1               5

<210> SEQ ID NO 727
<211> LENGTH: 32
<212> TYPE: PRT
<213> ORGANISM: Homo sapiens

<400> SEQUENCE: 727

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 728
<211> LENGTH: 9
<212> TYPE: PRT
<213> ORGANISM: Homo sapiens

<400> SEQUENCE: 728

Gln Val Trp Asp Ser Ser Ser Asp His
1               5

<210> SEQ ID NO 729
<211> LENGTH: 7
<212> TYPE: PRT
<213> ORGANISM: Homo sapiens

<400> SEQUENCE: 729

Glu Asp Ser Glu Arg Tyr Pro
1               5

<210> SEQ ID NO 730
<211> LENGTH: 32
<212> TYPE: PRT
<213> ORGANISM: Homo sapiens

<400> SEQUENCE: 730

Gly Ile Pro Glu Arg Phe Ser Gly Ser Thr Ser Gly Asn Thr Thr Thr
1               5                   10                  15

Leu Thr Ile Ser Arg Val Leu Thr Glu Asp Glu Ala Asp Tyr Tyr Cys
            20                  25                  30

<210> SEQ ID NO 731
<211> LENGTH: 7
<212> TYPE: PRT
<213> ORGANISM: Homo sapiens

<400> SEQUENCE: 731

Leu Ser Gly Asp Glu Asp Asn
1               5

<210> SEQ ID NO 732
<211> LENGTH: 7
<212> TYPE: PRT
<213> ORGANISM: Homo sapiens

<400> SEQUENCE: 732

Lys Asp Ser Glu Arg Pro Ser
1               5

<210> SEQ ID NO 733
<211> LENGTH: 32
<212> TYPE: PRT
<213> ORGANISM: Homo sapiens

<400> SEQUENCE: 733

Gly Ile Pro Glu Arg Phe Ser Gly Ser Ser Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 734
<211> LENGTH: 9
<212> TYPE: PRT
<213> ORGANISM: Homo sapiens

<400> SEQUENCE: 734

Gln Ser Ala Asp Ser Ser Gly Thr Tyr
1               5

<210> SEQ ID NO 735
<211> LENGTH: 7
<212> TYPE: PRT
<213> ORGANISM: Homo sapiens

<400> SEQUENCE: 735

Lys Asp Ser Glu Arg Pro Ser
1               5

<210> SEQ ID NO 736
<211> LENGTH: 32

```
<212> TYPE: PRT
<213> ORGANISM: Homo sapiens

<400> SEQUENCE: 736

Gly Ile Pro Glu Arg Phe Ser Gly Ser Ser Gly Thr Thr Val Thr
1               5                   10                  15

Leu Thr Ile Ser Gly Ala Gln Val Glu Asp Glu Ala Asp Tyr Tyr Cys
                20                  25                  30

<210> SEQ ID NO 737
<211> LENGTH: 7
<212> TYPE: PRT
<213> ORGANISM: Homo sapiens

<400> SEQUENCE: 737

Tyr Ser Ala Ala Asp Asn Asn
1               5

<210> SEQ ID NO 738
<211> LENGTH: 11
<212> TYPE: PRT
<213> ORGANISM: Homo sapiens

<400> SEQUENCE: 738

Val Lys Ser Asp Gly Ser His Ser Lys Gly Asp
1               5                   10

<210> SEQ ID NO 739
<211> LENGTH: 32
<212> TYPE: PRT
<213> ORGANISM: Homo sapiens

<400> SEQUENCE: 739

Gly Ile Pro Asp Arg Phe Met Gly Ser Ser Gly Ala Asp Arg Tyr
1               5                   10                  15

Leu Thr Phe Ser Asn Leu Gln Ser Asp Asp Glu Ala Glu Tyr His Cys
                20                  25                  30

<210> SEQ ID NO 740
<211> LENGTH: 11
<212> TYPE: PRT
<213> ORGANISM: Homo sapiens

<400> SEQUENCE: 740

Gly Glu Ser His Thr Ile Asp Gly Gln Val Gly
1               5                   10

<210> SEQ ID NO 741
<211> LENGTH: 11
<212> TYPE: PRT
<213> ORGANISM: Homo sapiens

<400> SEQUENCE: 741

Leu Glu Gly Ser Gly Ser Tyr Asn Lys Gly Ser
1               5                   10

<210> SEQ ID NO 742
<211> LENGTH: 32
<212> TYPE: PRT
<213> ORGANISM: Homo sapiens

<400> SEQUENCE: 742

Gly Val Pro Asp Arg Phe Ser Gly Ser Ser Ser Gly Ala Asp Arg Tyr
1               5                   10                  15
```

```
Leu Thr Ile Ser Asn Leu Gln Leu Glu Asp Glu Ala Asp Tyr Tyr Cys
            20                  25                  30

<210> SEQ ID NO 743
<211> LENGTH: 7
<212> TYPE: PRT
<213> ORGANISM: Homo sapiens

<400> SEQUENCE: 743

Glu Thr Trp Asp Ser Asn Thr
1               5

<210> SEQ ID NO 744
<211> LENGTH: 11
<212> TYPE: PRT
<213> ORGANISM: Homo sapiens

<400> SEQUENCE: 744

Leu Asn Ser Asp Gly Ser His Ser Lys Gly Asp
1               5                   10

<210> SEQ ID NO 745
<211> LENGTH: 32
<212> TYPE: PRT
<213> ORGANISM: Homo sapiens

<400> SEQUENCE: 745

Gly Ile Pro Asp Arg Phe Ser Gly Ser Ser Gly Ala Glu Arg Tyr
1               5                   10                  15

Leu Thr Ile Ser Ser Leu Gln Ser Glu Asp Glu Ala Asp Tyr Tyr Cys
            20                  25                  30

<210> SEQ ID NO 746
<211> LENGTH: 7
<212> TYPE: PRT
<213> ORGANISM: Homo sapiens

<400> SEQUENCE: 746

Gln Thr Trp Gly Thr Gly Ile
1               5

<210> SEQ ID NO 747
<211> LENGTH: 11
<212> TYPE: PRT
<213> ORGANISM: Homo sapiens

<400> SEQUENCE: 747

Tyr Tyr Ser Asp Ser Asp Lys Gly Gln Gly Ser
1               5                   10

<210> SEQ ID NO 748
<211> LENGTH: 34
<212> TYPE: PRT
<213> ORGANISM: Homo sapiens

<400> SEQUENCE: 748

Gly Val Pro Ser Arg Phe Ser Gly Ser Lys Asp Ala Ser Ala Asn Thr
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 749
<211> LENGTH: 8
```

```
<212> TYPE: PRT
<213> ORGANISM: Homo sapiens

<400> SEQUENCE: 749

Met Ile Trp Pro Ser Asn Ala Ser
1               5

<210> SEQ ID NO 750
<211> LENGTH: 11
<212> TYPE: PRT
<213> ORGANISM: Homo sapiens

<400> SEQUENCE: 750

Tyr Lys Ser Asp Ser Asp Lys Gln Gln Gly Ser
1               5                   10

<210> SEQ ID NO 751
<211> LENGTH: 34
<212> TYPE: PRT
<213> ORGANISM: Homo sapiens

<400> SEQUENCE: 751

Gly Val Pro Ser Arg Phe Ser Gly Ser Lys Asp Ala Ser Ala Asn Ala
1               5                   10                  15

Gly Ile Leu Leu Ile Ser Gly Leu Gln Ser Glu Asp Glu Ala Asp Tyr
            20                  25                  30

Tyr Cys

<210> SEQ ID NO 752
<211> LENGTH: 8
<212> TYPE: PRT
<213> ORGANISM: Homo sapiens

<400> SEQUENCE: 752

Met Ile Trp His Ser Ser Ala Ser
1               5

<210> SEQ ID NO 753
<211> LENGTH: 11
<212> TYPE: PRT
<213> ORGANISM: Homo sapiens

<400> SEQUENCE: 753

Tyr His Ser Asp Ser Asn Lys Gly Gln Gly Ser
1               5                   10

<210> SEQ ID NO 754
<211> LENGTH: 34
<212> TYPE: PRT
<213> ORGANISM: Homo sapiens

<400> SEQUENCE: 754

Gly Val Pro Ser Arg Phe Ser Gly Ser Asn Asp Ala Ser Ala Asn Ala
1               5                   10                  15

Gly Ile Leu Arg Ile Ser Gly Leu Gln Pro Glu Asp Glu Ala Asp Tyr
            20                  25                  30

Tyr Cys

<210> SEQ ID NO 755
<211> LENGTH: 9
<212> TYPE: PRT
<213> ORGANISM: Homo sapiens

<400> SEQUENCE: 755
```

Gly Thr Trp His Ser Asn Ser Lys Thr
1               5

<210> SEQ ID NO 756
<211> LENGTH: 7
<212> TYPE: PRT
<213> ORGANISM: Homo sapiens

<400> SEQUENCE: 756

Glu Asp Asn Gln Arg Pro Ser
1               5

<210> SEQ ID NO 757
<211> LENGTH: 34
<212> TYPE: PRT
<213> ORGANISM: Homo sapiens

<400> SEQUENCE: 757

Gly Val Pro Asp Arg Phe Ser Gly Ser Ile Asp Ser Ser Asn Ser
1               5                   10                  15
Ala Ser Leu Thr Ile Ser Gly Leu Lys Thr Glu Asp Glu Ala Asp Tyr
            20                  25                  30
Tyr Cys

<210> SEQ ID NO 758
<211> LENGTH: 7
<212> TYPE: PRT
<213> ORGANISM: Homo sapiens

<400> SEQUENCE: 758

Gln Ser Tyr Asp Ser Ser Asn
1               5

<210> SEQ ID NO 759
<211> LENGTH: 7
<212> TYPE: PRT
<213> ORGANISM: Homo sapiens

<400> SEQUENCE: 759

Ser Thr Ser Asn Lys His Ser
1               5

<210> SEQ ID NO 760
<211> LENGTH: 32
<212> TYPE: PRT
<213> ORGANISM: Homo sapiens

<400> SEQUENCE: 760

Trp Thr Pro Ala Arg Phe Ser Gly Ser Leu Leu Gly Gly Lys Ala Ala
1               5                   10                  15
Leu Thr Leu Ser Gly Val Gln Pro Glu Asp Glu Ala Glu Tyr Tyr Cys
            20                  25                  30

<210> SEQ ID NO 761
<211> LENGTH: 8
<212> TYPE: PRT
<213> ORGANISM: Homo sapiens

<400> SEQUENCE: 761

Leu Leu Tyr Tyr Gly Gly Ala Gln
1               5

<210> SEQ ID NO 762

```
<211> LENGTH: 7
<212> TYPE: PRT
<213> ORGANISM: Homo sapiens

<400> SEQUENCE: 762

Asp Thr Ser Asn Lys His Ser
1               5

<210> SEQ ID NO 763
<211> LENGTH: 32
<212> TYPE: PRT
<213> ORGANISM: Homo sapiens

<400> SEQUENCE: 763

Trp Thr Pro Ala Arg Phe Ser Gly Ser Leu Leu Gly Gly Lys Ala Ala
1               5                   10                  15

Leu Thr Leu Ser Gly Ala Gln Pro Glu Asp Glu Ala Glu Tyr Tyr Cys
            20                  25                  30

<210> SEQ ID NO 764
<211> LENGTH: 8
<212> TYPE: PRT
<213> ORGANISM: Homo sapiens

<400> SEQUENCE: 764

Leu Leu Ser Tyr Ser Gly Ala Arg
1               5

<210> SEQ ID NO 765
<211> LENGTH: 7
<212> TYPE: PRT
<213> ORGANISM: Homo sapiens

<400> SEQUENCE: 765

Ser Thr Asn Thr Arg Ser Ser
1               5

<210> SEQ ID NO 766
<211> LENGTH: 32
<212> TYPE: PRT
<213> ORGANISM: Homo sapiens

<400> SEQUENCE: 766

Gly Val Pro Asp Arg Phe Ser Gly Ser Ile Leu Gly Asn Lys Ala Ala
1               5                   10                  15

Leu Thr Ile Thr Gly Ala Gln Ala Asp Asp Glu Ser Tyr Tyr Cys
            20                  25                  30

<210> SEQ ID NO 767
<211> LENGTH: 8
<212> TYPE: PRT
<213> ORGANISM: Homo sapiens

<400> SEQUENCE: 767

Val Leu Tyr Met Gly Ser Gly Ile
1               5

<210> SEQ ID NO 768
<211> LENGTH: 12
<212> TYPE: PRT
<213> ORGANISM: Homo sapiens

<400> SEQUENCE: 768

Val Gly Thr Gly Gly Ile Val Gly Ser Lys Gly Asp
1               5                   10
```

<210> SEQ ID NO 769
<211> LENGTH: 32
<212> TYPE: PRT
<213> ORGANISM: Homo sapiens

<400> SEQUENCE: 769

Gly Ile Pro Asp Arg Phe Ser Val Leu Gly Ser Gly Leu Asn Arg Tyr
1               5                   10                  15

Leu Thr Ile Lys Asn Ile Gln Glu Glu Asp Glu Ser Asp Tyr His Cys
            20                  25                  30

<210> SEQ ID NO 770
<211> LENGTH: 11
<212> TYPE: PRT
<213> ORGANISM: Homo sapiens

<400> SEQUENCE: 770

Gly Ala Asp His Gly Ser Gly Ser Asn Phe Val
1               5                   10

<210> SEQ ID NO 771
<211> LENGTH: 7
<212> TYPE: PRT
<213> ORGANISM: Homo sapiens

<400> SEQUENCE: 771

Arg Asn Asn Asn Arg Pro Ser
1               5

<210> SEQ ID NO 772
<211> LENGTH: 32
<212> TYPE: PRT
<213> ORGANISM: Homo sapiens

<400> SEQUENCE: 772

Gly Ile Ser Glu Arg Leu Ser Ala Ser Arg Ser Gly Asn Thr Ala Ser
1               5                   10                  15

Leu Thr Ile Thr Gly Leu Gln Pro Glu Asp Glu Ala Asp Tyr Tyr Cys
            20                  25                  30

<210> SEQ ID NO 773
<211> LENGTH: 9
<212> TYPE: PRT
<213> ORGANISM: Homo sapiens

<400> SEQUENCE: 773

Ser Ala Trp Asp Ser Ser Leu Ser Ala
1               5

<210> SEQ ID NO 774
<211> LENGTH: 12
<212> TYPE: PRT
<213> ORGANISM: Homo sapiens

<400> SEQUENCE: 774

Tyr Val Phe Gly Thr Gly Thr Lys Val Thr Val Leu
1               5                   10

<210> SEQ ID NO 775
<211> LENGTH: 12
<212> TYPE: PRT
<213> ORGANISM: Homo sapiens

<400> SEQUENCE: 775

Val Val Phe Gly Gly Gly Thr Lys Leu Thr Val Leu
1               5                   10

<210> SEQ ID NO 776
<211> LENGTH: 12
<212> TYPE: PRT
<213> ORGANISM: Homo sapiens

<400> SEQUENCE: 776

Val Val Phe Gly Gly Gly Thr Lys Leu Thr Val Leu
1               5                   10

<210> SEQ ID NO 777
<211> LENGTH: 12
<212> TYPE: PRT
<213> ORGANISM: Homo sapiens

<400> SEQUENCE: 777

Ala Val Phe Gly Gly Gly Thr Gln Leu Thr Val Leu
1               5                   10

<210> SEQ ID NO 778
<211> LENGTH: 242
<212> TYPE: PRT
<213> ORGANISM: Homo sapiens

<400> SEQUENCE: 778

Glu Val Gln Leu Val Gln Ser Gly Ala Asp Val Lys Lys Pro Gly Ala
1               5                   10                  15

Ser Val Lys Val Ser Cys Lys Ala Ser Gly Tyr Thr Phe Thr Asn Tyr
                20                  25                  30

Val Met His Trp Val Arg Gln Ala Pro Gly Gln Gly Leu Glu Trp Leu
            35                  40                  45

Gly Tyr Ile Asn Pro Tyr Asn Asp Gly Thr Gln Tyr Asn Glu Arg Phe
        50                  55                  60

Lys Gly Arg Val Thr Met Thr Gly Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Glu Val Tyr Gly Asn Tyr Ile Trp Gly Asn Trp Gly Gln Gly
            100                 105                 110

Thr Leu Val Ser Val Ser Ser Gly Gly Gly Ser Gly Gly Gly Gly
        115                 120                 125

Ser Gly Gly Ser Ala Leu Glu Ile Val Leu Thr Gln Ser Pro Gly Thr
130                 135                 140

Leu Ser Leu Ser Pro Gly Glu Arg Ala Thr Leu Ser Cys Ser Ala Ser
145                 150                 155                 160

Ser Ser Ile Ser Ser Asn Tyr Leu His Trp Tyr Gln Gln Lys Pro Gly
                165                 170                 175

Gln Ala Pro Arg Leu Leu Ile Tyr Arg Thr Ser Asn Leu Ala Ser Gly
            180                 185                 190

Ile Pro Asp Arg Phe Ser Gly Ser Gly Ser Gly Thr Asp Phe Thr Leu
        195                 200                 205

Thr Ile Ser Arg Leu Glu Pro Glu Asp Phe Ala Val Tyr Tyr Cys Gln
    210                 215                 220

Gln Gly Ser Ser Ile Pro Phe Thr Phe Gly Gln Gly Thr Lys Leu Glu
225                 230                 235                 240

Ile Asn

```
<210> SEQ ID NO 779
<211> LENGTH: 254
<212> TYPE: PRT
<213> ORGANISM: Homo sapiens

<400> SEQUENCE: 779

Gln Val Gln Leu Leu Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80

Leu Gln Trp Ser Ser Leu Lys Pro Ser Asp Ser Ala Val Tyr Phe Cys
                85                  90                  95

Ala Arg His Asp Val Gly Tyr Cys Ser Ser Asn Cys Ala Lys Trp
            100                 105                 110

Pro Glu Tyr Phe Gln His Trp Gly Gln Gly Thr Leu Val Thr Val Ser
        115                 120                 125

Ser Gly Gly Gly Gly Ser Gly Gly Gly Ser Gly Gly Gly Gly Ser
    130                 135                 140

Gln Ser Val Leu Thr Gln Pro Pro Ser Val Ser Ala Ala Pro Gly Gln
145                 150                 155                 160

Lys Val Thr Ile Ser Cys Ser Gly Ser Ser Asn Ile Gly Asn Asn
                165                 170                 175

Tyr Val Ser Trp Tyr Gln Gln Leu Pro Gly Thr Ala Pro Lys Leu Leu
            180                 185                 190

Ile Tyr Gly His Thr Asn Arg Pro Ala Gly Val Pro Asp Arg Phe Ser
        195                 200                 205

Gly Ser Lys Ser Gly Thr Ser Ala Ser Leu Ala Ile Ser Gly Phe Arg
    210                 215                 220

Ser Glu Asp Glu Ala Asp Tyr Tyr Cys Ala Ala Trp Asp Asp Ser Leu
225                 230                 235                 240

Ser Gly Trp Val Phe Gly Gly Gly Thr Lys Leu Thr Val Leu
                245                 250

<210> SEQ ID NO 780
<211> LENGTH: 242
<212> TYPE: PRT
<213> ORGANISM: Homo sapiens

<400> SEQUENCE: 780

Glu Val Gln Leu Val Gln Ser Gly Ala Asp Val Lys Gln Pro Gly Ala
1               5                   10                  15

Ser Val Lys Val Ser Cys Lys Ala Ser Gly Tyr Thr Phe Thr Asn Tyr
            20                  25                  30

Val Met His Trp Val Arg Gln Ala Pro Gly Lys Gly Leu Glu Trp Leu
        35                  40                  45

Gly Tyr Ile Asn Pro Tyr Asn Asp Gly Thr Gln Tyr Asn Glu Arg Phe
    50                  55                  60

Lys Gly Arg Val Thr Met Thr Gly Asp Thr Ser Ile Ser Thr Ala Tyr
65                  70                  75                  80

Met Glu Leu Ser Arg Leu Lys Ser Asp Asp Thr Ala Val Tyr Tyr Cys
                85                  90                  95
```

```
Ala Arg Glu Val Tyr Gly Asn Tyr Ile Trp Gly Asn Trp Gly Gln Gly
                100                 105                 110

Thr Leu Val Ser Val Ser Ser Gly Gly Gly Ser Gly Gly Gly
            115                 120                 125

Ser Gly Gly Ser Ala Leu Glu Ile Val Leu Thr Gln Ser Pro Gly Thr
130                 135                 140

Leu Ser Leu Ser Pro Gly Glu Lys Ala Thr Leu Ser Cys Ser Ala Ser
145                 150                 155                 160

Ser Ser Ile Ser Ser Asn Tyr Leu His Trp Tyr Gln Lys Pro Gly
                165                 170                 175

Gln Ala Pro Lys Leu Leu Ile Tyr Arg Thr Ser Asn Leu Ala Ser Gly
                180                 185                 190

Ile Pro Asp Arg Phe Ser Gly Ser Lys Ser Gly Thr Asp Phe Thr Leu
                195                 200                 205

Thr Ile Ser Arg Leu Glu Pro Glu Asp Phe Ala Val Tyr Tyr Cys Gln
            210                 215                 220

Gln Gly Ser Ser Ile Pro Phe Thr Phe Gly Gln Gly Thr Lys Leu Glu
225                 230                 235                 240

Ile Asn

<210> SEQ ID NO 781
<211> LENGTH: 114
<212> TYPE: PRT
<213> ORGANISM: Homo sapiens

<400> SEQUENCE: 781

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met His Trp Val Arg Gln Ala Pro Gly Lys Gly Leu Val Trp Val
            35                  40                  45

Ser Arg Ile Asn Ser Asp Gly Ser Ser Ala Ser Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Val Thr Glu Arg Trp Gly Gln Gly Thr Leu Val Thr Val
                100                 105                 110

Ser Ser

<210> SEQ ID NO 782
<211> LENGTH: 116
<212> TYPE: PRT
<213> ORGANISM: Homo sapiens

<400> SEQUENCE: 782

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
                20                  25                  30

Gly Val Asn Trp Val Arg Gln Pro Pro Gly Lys Gly Leu Glu Trp Leu
            35                  40                  45

Gly Met Ile Trp Gly Asp Gly Asn Thr Asp Tyr Asn Ser Ala Leu Lys
        50                  55                  60
```

Ser Arg Leu Ser Ile Ser Lys Asp Asn Ser Lys Ser Gln Val Phe Leu
65                  70                  75                  80

Lys Met Asn Ser Leu His Thr Asp Asp Thr Ala Arg Tyr Tyr Cys Ala
            85                  90                  95

Arg Glu Arg Asp Tyr Arg Leu Asp Tyr Trp Gly Gln Gly Thr Thr Val
        100                 105                 110

Thr Val Ser Ser
115

<210> SEQ ID NO 783
<211> LENGTH: 108
<212> TYPE: PRT
<213> ORGANISM: Homo sapiens

<400> SEQUENCE: 783

Asp Ile Val Leu Thr Gln Ser Pro Ala Thr Leu Ser Val Thr Pro Gly
1               5                   10                  15

Asn Ser Val Ser Leu Ser Cys Arg Ala Ser Gln Ser Ile Gly Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
            85                  90                  95

Thr Phe Gly Gly Gly Thr Lys Leu Glu Ile Lys Ser
        100                 105

<210> SEQ ID NO 784
<211> LENGTH: 120
<212> TYPE: PRT
<213> ORGANISM: Homo sapiens

<400> SEQUENCE: 784

Gln Val Lys Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
            20                  25                  30

Tyr Met His Trp Leu Arg Gln Gly Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
            85                  90                  95

Asn Glu Gly Thr Pro Thr Gly Pro Tyr Tyr Phe Asp Tyr Trp Gly Gln
        100                 105                 110

Gly Thr Thr Val Thr Val Ser Ser
        115                 120

<210> SEQ ID NO 785
<211> LENGTH: 124
<212> TYPE: PRT
<213> ORGANISM: Homo sapiens

```
<400> SEQUENCE: 785

Glu Val Gln Leu Val Gln Ser Gly Gly Val Val Gln Pro Gly Arg
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Leu Tyr Tyr Cys
                85                  90                  95

Ala Arg Ala Ile Arg Ser Tyr Ser Gly Ser Tyr Gly Asn Ala Phe Asp
            100                 105                 110

Ile Trp Gly Lys Gly Thr Leu Val Thr Val Ser Ser
            115                 120

<210> SEQ ID NO 786
<211> LENGTH: 119
<212> TYPE: PRT
<213> ORGANISM: Homo sapiens

<400> SEQUENCE: 786

Glu Val Gln Leu Val Gln Ser Gly Ala Asp Val Lys Lys Pro Gly Ala
1               5                   10                  15

Ser Val Lys Val Ser Cys Lys Ala Ser Gly Tyr Thr Phe Thr Asn Tyr
            20                  25                  30

Val Met His Trp Val Arg Gln Ala Pro Gly Gln Gly Leu Glu Trp Leu
        35                  40                  45

Gly Tyr Ile Asn Pro Tyr Asn Asp Gly Thr Gln Tyr Asn Glu Arg Phe
    50                  55                  60

Lys Gly Arg Val Thr Met Thr Thr Gly Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Glu Val Tyr Gly Asn Tyr Ile Trp Gly Asn Trp Gly Gln Gly
            100                 105                 110

Thr Leu Val Ser Val Ser Ser
        115

<210> SEQ ID NO 787
<211> LENGTH: 129
<212> TYPE: PRT
<213> ORGANISM: Homo sapiens

<400> SEQUENCE: 787

Gln Val Gln Leu Leu Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
65                  70                  75                  80
```

-continued

Leu Gln Trp Ser Ser Leu Lys Pro Ser Asp Ser Ala Val Tyr Phe Cys
                85                  90                  95

Ala Arg His Asp Val Gly Tyr Cys Ser Ser Asn Cys Ala Lys Trp
            100                 105                 110

Pro Glu Tyr Phe Gln His Trp Gly Gln Gly Thr Leu Val Thr Val Ser
        115                 120                 125

Ser

<210> SEQ ID NO 788
<211> LENGTH: 15
<212> TYPE: PRT
<213> ORGANISM: Homo sapiens

<400> SEQUENCE: 788

Gly Gly Gly Gly Ser Gly Gly Gly Gly Ser Gly Gly Ser Ala Leu
1               5                   10                  15

<210> SEQ ID NO 789
<211> LENGTH: 15
<212> TYPE: PRT
<213> ORGANISM: Homo sapiens

<400> SEQUENCE: 789

Gly Gly Gly Gly Ser Gly Gly Gly Gly Ser Gly Gly Ser Ala Leu
1               5                   10                  15

<210> SEQ ID NO 790
<211> LENGTH: 14
<212> TYPE: PRT
<213> ORGANISM: Homo sapiens

<400> SEQUENCE: 790

Gly Gly Gly Ser Gly Gly Gly Gly Ser Gly Gly Gly Gly Ser
1               5                   10

<210> SEQ ID NO 791
<211> LENGTH: 15
<212> TYPE: PRT
<213> ORGANISM: Homo sapiens

<400> SEQUENCE: 791

Gly Gly Gly Gly Ser Gly Gly Gly Ser Gly Gly Gly Gly Ser
1               5                   10                  15

<210> SEQ ID NO 792
<211> LENGTH: 15
<212> TYPE: PRT
<213> ORGANISM: Homo sapiens

<400> SEQUENCE: 792

Gly Gly Gly Gly Ser Gly Gly Gly Gly Ser Gly Gly Gly Gly Ser
1               5                   10                  15

<210> SEQ ID NO 793
<211> LENGTH: 15
<212> TYPE: PRT
<213> ORGANISM: Homo sapiens

<400> SEQUENCE: 793

Gly Gly Gly Gly Ser Gly Gly Gly Gly Ser Gly Gly Ser Ala Leu
1               5                   10                  15

<210> SEQ ID NO 794
<211> LENGTH: 15
<212> TYPE: PRT
<213> ORGANISM: Homo sapiens

<400> SEQUENCE: 794

Gly Gly Gly Gly Ser Gly Gly Gly Gly Ser Gly Gly Gly Gly Ser
1               5                   10                  15

<210> SEQ ID NO 795
<211> LENGTH: 106
<212> TYPE: PRT
<213> ORGANISM: Homo sapiens

<400> SEQUENCE: 795

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Thr Val
                85                  90                  95

Phe Gly Gly Gly Thr Lys Leu Thr Val Leu
            100                 105

<210> SEQ ID NO 796
<211> LENGTH: 107
<212> TYPE: PRT
<213> ORGANISM: Homo sapiens

<400> SEQUENCE: 796

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Tyr Thr Thr Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Ile Gln
            100                 105

<210> SEQ ID NO 797
<211> LENGTH: 114
<212> TYPE: PRT
<213> ORGANISM: Homo sapiens

<400> SEQUENCE: 797

Asp Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Asn
            20                  25                  30

Tyr Trp Ser Trp Ile Arg Lys Phe Pro Gly Asn Arg Leu Glu Tyr Met
        35                  40                  45

Gly Tyr Val Ser Tyr Ser Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Asp Leu Asn Ser Val Thr Thr Glu Asp Thr Ala Thr Tyr Tyr Cys Ala
                85                  90                  95

Asn Trp Asp Gly Thr Phe Asp Tyr Trp Gly Gln Gly Thr Leu Val Thr
            100                 105                 110

Val Ser

<210> SEQ ID NO 798
<211> LENGTH: 106
<212> TYPE: PRT
<213> ORGANISM: Homo sapiens

<400> SEQUENCE: 798

Glu Asn Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys
            100                 105

<210> SEQ ID NO 799
<211> LENGTH: 107
<212> TYPE: PRT
<213> ORGANISM: Homo sapiens

<400> SEQUENCE: 799

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Gly Ile Tyr His Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Ala Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Asp Asp Phe Ala Thr Tyr Tyr Cys Gln Gln Tyr Ser Asn Tyr Pro Leu
                85                  90                  95

Thr Phe Gly Gly Gly Thr Val Leu Glu Ile Lys
            100                 105

<210> SEQ ID NO 800
<211> LENGTH: 108
<212> TYPE: PRT
<213> ORGANISM: Homo sapiens

<400> SEQUENCE: 800

Glu Ile Val Leu Thr Gln Ser Pro Gly Thr Leu Ser Leu Ser Pro Gly
1               5                   10                  15

Glu Arg Ala Thr Leu Ser Cys Ser Ala Ser Ser Ser Ile Ser Ser Asn
                20                  25                  30

Tyr Leu His Trp Tyr Gln Gln Lys Pro Gly Gln Ala Pro Arg Leu Leu
            35                  40                  45

Ile Tyr Arg Thr Ser Asn Leu Ala Ser Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Ser Ile Pro
                85                  90                  95

Phe Thr Phe Gly Gln Gly Thr Lys Leu Glu Ile Asn
            100                 105

<210> SEQ ID NO 801
<211> LENGTH: 110
<212> TYPE: PRT
<213> ORGANISM: Homo sapiens

<400> SEQUENCE: 801

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Gly His Thr Asn Arg Pro Ala Gly Val Pro Asp Arg Phe Ser
50                  55                  60

Gly Ser Lys Ser Gly Thr Ser Ala Ser Leu Ala Ile Ser Gly Phe Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Leu Thr Val Leu
            100                 105                 110
```

BIOLOGICAL MATERIALS AND USES THEREOF

The invention relates to photodynamic therapy (PDT) for the selective destruction of malignant, diseased, or infected cells or infective agents without causing damage to normal cells. This may lead to a more effective clinical treatment.

Current treatment of disease is predominantly non-targeted. Drugs are administered systemically or orally which expose many other tissues as well as the tissues which are diseased. In cancer therapy, chemotherapeutic drugs are specific for cells which are growing and dividing rapidly as they work mainly by a mechanism which interferes with DNA replication [1] (For details of all references, see later references section). Other cells can take up the drug and also become intoxicated, such as rapidly dividing bone marrow stem cells, resulting in immunosuppression and sickness. In infectious diseases, the anti-bacterial drug is introduced into the blood (orally or by injection) and interferes with a particular bacterial metabolic pathway. Exposure of other tissues to the drug can result in side effects as well as the major problem of drug resistance. Virally-infected cells are difficult to treat as their metabolism is practically identical to uninfected human cells.

It is widely hypothesised that advances in medicine may be in the tailoring of drugs to the disease. This means, inter alia, delivering the therapeutic to the correct target tissue or organism, rather than the non-selective hit and miss approach of most of the conventional drugs used today. This will result in lower doses administered, lower side effects and toxicities and overall better responses. Advances in genomics will one day mean that drugs can be tailored to the individual, as breast cancer in one individual may differ from breast cancer in another individual.

There are many drugs used clinically today that are very good at destroying or treating the diseased cells, once the drug has accumulated in the correct tissue. Therefore the problem is with the specific targeting of drugs rather than their mechanism of action. Examples of this include targeted ionising radiation as opposed to external beam radiotherapy [2], targeted chemotherapy drugs (e.g. methotrexate or doxorubicin) as opposed to free drugs [3] and toxins [4]. PDT is a particularly good example as it is already well established in many treatments, but it is becoming apparent that a better therapeutic result, and in consequence greatly expanded clinical applications, would come from pre-targeting the sensitizing drug to the correct tissues in addition to targeting the light source, which is not accurate at the cell level [5,6].

Targeting drugs or other effectors to the desired cells is a well-established area. One of the main approaches to targeting is to use antibodies or cell-specific ligands as the targeting element of a multifunctional molecule [7,8]. A good design for such a multifunctional molecule would be one which is highly specific for diseased cells, able to carry many drugs with high capacity without compromising their function, and able to deposit the drug in the sub-cellular compartment which would primarily be affected.

Antibodies have naturally evolved to act as the first line of defense in the mammalian immune system. They are complex glycoproteins which have exquisite specificity and tremendous diversity. This diversity comes about from programmed gene shuffling and targeted mutagenesis, resulting in probably a trillion different antibody sequences [9]. This diversity means that antibodies can bind to practically any target molecule which is usually protein in nature. It is now possible to mimic antibody selection and production in vitro, selecting for recombinant human antibodies against virtually any desired target [10].

That antigenic selectivity is conferred by variable domains and is independent of the constant domains is known from experiments involving the bacterial expression of antibody fragments, all containing one or more variable domains. These molecules include Fab-like molecules (Better et al. (1988) *Science* 240, 1041); Fv molecules (Skerra et al. (1988) *Science* 240, 1038); single-chain Fv (ScFv) molecules where the $V_H$ and $V_L$ partner domains are linked via a flexible oligopeptide (Bird et al. (1988) *Science* 242, 423; Huston et al. (1988) *Proc. Natl. Acad. Sci. USA* 85, 5879) and single domain antibodies (dAbs) comprising isolated V domains (Ward et al. (1989) *Nature* 341, 544). A general review of the techniques involved in the synthesis of antibody fragments which retain their selective binding sites is to be found in Holliger and Hudson, *Nature Biotechnology* (2005) 23, 1126-36

A significant number of biotechnological drugs are in development are based on antibody targeting [7,11,12]. The most popular in vitro selection technique is antibody phage display, where antibodies are displayed and manipulated on the surface of viruses [10].

The display of proteins and polypeptides on the surface of bacteriophage (phage), fused to one of the phage coat proteins, provides a powerful tool for the selection of selective ligands. This 'phage display' technique was originally used by Smith in 1985 (*Science* 228, 1315-7) to create large libraries of peptides for the purpose of selecting those with high affinity for a particular antigen. More recently, the method has been employed to present antibodies at the surface of phage in order to identify ligands having desired properties (McCafferty et al., Nature, 1990, 552-554).

The use of phage display to isolate ligands that bind biologically relevant molecules has been reviewed in Felici et al. (1995) *Biotechnol. Annual Rev.* 1, 149-183, Katz (1997) *Annual Rev. Biophys. Biomol. Struct.* 26, 27-45 and Hoogenboom *Nature Biotechnology* (2005) 23, 1105-16

There are many therapeutic antibodies being developed for a range of diseases, primarily cancer, autoimmune diseases and prevention of allograft rejection. Table 1 lists some of these major antibodies.

TABLE 1

Therapeutic uses of Antibodies (adapted from [11, 12])

| Antibody | Target | Application |
|---|---|---|
| Herceptin (trastuzumab) | ErbB2 (Her 2) receptor | Breast cancer therapy |
| Rituxan (rituximab) | CD20 | Lymphoma |
| Theragyn (pemtumomab) | Muc-1 | Ovarian cancer |
| Remicade (infliximab) | TNF-alpha | Rheumatoid arthritis, Crohn's disease |
| Zenapax (daclizumab) | CD25 | Allograft rejection |
| Panorex (edrecolomab) | 17-1A surface antigen | Colorectal cancer |
| Vitaxin | alphaVbeta3 intergrin | Sarcoma |
| Protovir | Cytomegalovirus (CMV) | CMV infection |
| MFE-23 | Carcinoembryonic antigen | Colorectal cancer |
| Amevive (alefacept) | CD11a | Psoriasis |
| Bexxar ($I^{131}$-tositumomab) | CD-20 | Lymphoma |
| Mylotarg (gemtuzumab ozogamicin) | CD-33 | Leukaemia |

Antibodies can bind with a high degree of specificity to target cells expressing the appropriate receptor. The affinity of an antibody is a measure of how well an antibody binds to the target (antigen). It is usually described by an equilibrium dissociation constant (Kd). For antibodies that need to be internalised, the association rate is more important as the dissociation rate is not applicable if the antibody is taken into the cell. A variety of technology exists to select and manipulate antibodies which have desired structural and binding properties [13].

As with all biological molecules, the size of the antibody affects its pharmacokinetics in vivo [14,15]. Larger molecules persist longer in the circulation due to slow clearance (large glycoproteins are cleared through specific uptake by the liver). For whole antibodies (molecular weight 150 KDa) which recognise a cancer cell antigen in an experimental mouse model system, 30-40% can be taken up by the tumour, but because they persist longer in the circulation, it takes 1-2 days for a tumour:blood ratio of more than one to be reached. Typical tumour:blood ratios are 5-10 by about day 3 [16]. With smaller fragments of antibodies, which have been produced by in vitro techniques and recombinant DNA technology, the clearance from the circulation is faster (molecules smaller than about 50 KDa are excreted through the kidneys). Single-chain Fvs (about 30 KDa) are artificial binding molecules derived from whole antibodies, but contain the minimal part required to recognise antigen [17]). Again in mouse model systems, scFvs can deliver 1-2% of the injected dose, but with tumour:blood ratios better than 20:1, with some tumour:organ ratios even better [18]. As scFvs have only been developed over the last 10 years, there are not many examples in late clinical trials [19]. From clinical trials of whole antibodies, the amount actually delivered to tumours is about 1% of that seen in mouse models, but with similar tumour:organ ratios [20]. If another molecule is attached to the antibody, then the new size and chemico-physical properties determines the altered pharmacokinetics. Additionally, properties such as net charge and hydrophilicity can effect the targeting kinetics [21].

Some cell surface antigens are static or very slowly internalise when bound by a ligand such as an antibody. There are some which have a function that requires internalisation, such as cell signalling or uptake of metals and lipids. Antibodies can be used to deliver agents intracellularly through such antigens. These agents can be therapeutic-repairing or destroying diseased cells. Examples include gene delivery [22] the intracellular delivery of toxins (e.g. *Pseudomonas* exotoxin [4], enzymes (e.g. ribonuclease [23], deoxyribonuclease [24] and drugs (e.g. methotrexate [3]. Some of these agents need targeting to particular sub-cellular organelles in order to exert their effects [24]. Advances in cell biology have uncovered intracellular targeting 'codes'—these are amino acid sequences which direct intracellular proteins to certain sub-cellular compartments. There are specific sequences which have been discovered that target various proteins to the nucleus, endoplasmic reticulum, golgi, lysosomes and mitochondria ([25], Table 2). These are being developed as add-ons to improve drug action by localising therapeutic proteins to the target compartment.

TABLE 2

Peptide sequences which could be used for sub-cellular localisation

| Name of Sequence | Function | Amino Acid Sequence |
| --- | --- | --- |
| SV 40 large T nuclear localisation | Targets polypeptides to the nucleus | KKKKRPR [SEQ. ID. NO. 1] |
| Human SRY | Targets polypeptides to the nucleus | KRPMNAFIVWSRDQRRK [SEQ. ID. NO. 2] |

TABLE 2-continued

Peptide sequences which could be used for sub-cellular localisation

| Name of Sequence | Function | Amino Acid Sequence |
| --- | --- | --- |
| ATP-binding protein N-terminal peptide containing mitochondria targeting | Targets polypeptides to the mitochondria | MLVHLFRVGIRGGPFP GRLLPPLRFQTFSAVR YSDGYRSSSLLRAVAH LPSQLWAS [SEQ. ID. NO. 3] |
| Lysosomal membrane targeting | Targets polypeptides to the lysosomes | TMGY [SEQ. ID. NO. 4] or TMLI [SEQ. ID. NO. 5] |
| Endoplasmic reticulum (ER) Retention Signal | Allows proteins to traffic back to the ER | KDEL [SEQ. ID. NO. 6] |
| Influenza Haemaglutinin HA2 | Disrupts membrane | GLFGAIAGFIENGWEG MIDGWYG [SEQ. ID. NO. 7] |
| Polio virus vp1 | Disrupts membrane | GIEDLISEVAQGALTLV P [SEQ. ID. NO. 8] |
| Human defensin | Disrupts membrane | ACYCRIPACIAGERRY GTCIYQGRLWAFCC [SEQ. ID. NO. 9] |
| Sendai virus fusion protein F1 | Disrupts membrane | FFGAVIGTIALGVATSA QITAGIALAEAR [SEQ. ID. NO. 10] |

There has been much research into targetable therapeutic drugs where novel effector functions have been linked to antibodies or other targeting ligands. Some of these need to be internalised to successfully deliver a toxic agent. Many of these have shown good results in vitro and in vivo in animal models, but have been disappointing in the clinic. Immunotoxins have shown problems such as immune reactions and liver/kidney toxicity [26]. There have been developments with new 'humanised' immunotoxins based on enzymes such as ribonuclease [23] and deoxyribonuclease [24]. These potentially have lower side effects are more tolerable, but still do not have a bystander killing effect. Chemotherapy drugs tend to be much less active when linked to proteins as they do not get released effectively, thus requiring selectively cleavable chemical linkers. Radioimmunotherapy tends to irradiate other tissues en route to the tumour, giving bone marrow and liver toxicity. Photosensitising (PS) drugs are particularly attractive agents to link to proteins as the cytotoxic elements are the singlet oxygen and other reactive oxygen species generated from them and not the PS drugs themselves [5,6].

Although antibodies are the first choice when it comes to considering ligands for targeting or detection, there exist many alternative ligands, some of which have been exploited through phage (or other) display/selection techniques. These include natural ligands for receptors (e.g. interleukin-6 (IL-6) [27] and tissue necrosis factor (TNF) [8], peptides (e.g. neuropeptides [28]) immunoglobulin-like domains (such as fibronectin (fn3) domains [29], single immunoglobulin domains [30]), anticalins [31], ankyrin repeats [32], etc. Many of these can be engineered and optimised to improve their biological and therapeutic properties [33].

Photodynamic Therapy (PDT) is a minimally invasive treatment for a range of conditions where diseased cells and tissues need to be removed [6,34,35]. Unlike ionising radiation, it can be administered repeatedly at the same site. Its use in cancer treatment is attractive because the use of conventional modalities such as chemotherapy, radiotherapy or surgery do not preclude the use of PDT and vice versa. PDT is also finding other applications where specific cell populations must be destroyed, such as blood vessels (in age-related macular degeneration (AMD [36]) or in cancer), the treatment of immune disorders [37], cardiovascular disease [38], and microbial infections [39,40].

PDT is a two-step or binary process starting with the administration of the PS drug, by intravenous injection, or topical application for skin cancer. The physico-chemical nature of the drug causes it to be preferentially taken up by cancer cells or other target cells [41]. Once a favourable tumour (or other target):normal organ ratio is obtained, the second step is the activation of the PS drug with a specific dose of light, at a particular wavelength. The photosensitizer, in its ground or singlet state absorbs a photon of light at a specific wavelength. This results in a short-lived excited singlet state. This can be converted by intersystem crossing to a longer-lived triplet state. It is this form of the sensitizer which carries out various cytotoxic actions.

The main classes of reactions are photooxidation by radicals (type I reaction), photooxidation by singlet oxygen (type II reaction), and photoreaction not involving oxygen (type III reaction). The triplet state form of the sensitiser causes the conversion of molecular oxygen found in the cellular environment into reactive oxygen species (ROS) primarily singlet oxygen ($^1O_2$) via a Type II reaction. If an activated photosensitizer interacts with cellular components, a Type I reaction occurs where electrons or protons are abstracted forming radicals such as hydroxyl radicals (OH. and superoxide ($O_2^-$.). These molecular species cause damage to cellular components such as DNA, proteins and lipids [42]. A Type III mechanism has also been proposed where the triplet state photosensitier interacts with free radicals to cause cellular damage. The site of cellular damage depends upon the type of photosensitizer, length of incubation, type of cells and mode of delivery. Hydrophobic photosensitizers tend to damage cell membranes [42], whereas cationic photosensitizers localise within membrane vesicles such as mitochondria and cause damage there [43].

The light activation of ROS is highly cytotoxic. In fact some natural processes in the immune system utilise ROS as a way of destroying unwanted cells. These species have a short lifetime (<0.04 ms) and act in a short radius (<0.04 mm) from their point of origin. The destruction of cells leads to a necrotic-like area of tissue which eventually sloughs away or is resorbed. The remaining tissue heals naturally, usually without scarring. There is no tissue heating and connective tissue such as collagen and elastin are unaffected. This results in less risk to the underlying structures compared to thermal laser techniques, surgery or external beam radiotherapy. More detailed research has shown that PDT induces apoptosis (non-inflammatory cell death), and the resulting necrosis (inflammatory cell lysis) seen is due to the mass of dying cells which are not cleared away by the immune system [44]. Research on a number of PS drugs including silicon phthalocyanines has shown that PDT induces apoptosis-programmed cell death [45]. Apoptosis is the highly orchestrated and evolutionary conserved form of cell death in which cells neatly commit suicide by chopping themselves into membrane-packaged pieces [46]. These apoptotic bodies are marked for phagocytosis by the immune system. Usually, too much apoptosis in a small area 'overloads' the immune system and the area eventually becomes necrotic, with inflammatory consequences.

PDT is a cold photochemical reaction, i.e. the laser light used is not ionising and delivers low levels of thermal energy, and the PS drugs have very low systemic toxicity. The combination of PS drug and light result in low morbidity and minimal functional disturbance and offers many advantages in the treatment of diseases. There is growing evidence that PDT response rates and durability of responses are as good as or even superior to standard locoregional therapies [35,36].

Generally PS drugs are administered systemically, with some topical applications for skin lesions. When the PS drug has accumulated in the target tissue, with ratios typically 2-5:1 compared with normal surrounding tissues (except in the brain where the ratio can be up to 50:1), low power light of a particular wavelength is directed onto the tumour (or the eye in AMD treatment [37]). Because human tissue can transmit light most effectively in the red region of the visible light spectrum, PS drugs which can absorb red light (630 nm or above) can be activated up to a depth of about 1 cm. After treatment direct sunlight must be avoided until systemically administered PS drugs clear from the body, otherwise they may have skin photosensitivity, resulting in skin burn.

The newer generation of PS drugs have longer activation wavelengths thus allowing deeper tissue penetration by red light, higher quantum yield and better pharmacokinetics in terms of tumour selectivity and residual skin photosensitivity. These classes of PS drugs include the phthalocyanines, chlorins, texaphyrins and purpurins. The synthetic chlorin, Foscan™ is a very potent PS drug with a wavelength of activation of 652 nm, quantum yield of 0.43 and skin photosensitivity of about 2 weeks. There have been many clinical trials for a variety of cancers, with good results [35,36]. There are other PS drugs which have been developed and are in trials which can absorb at >700 nm, such as meta-tetrahydrophenyl bacteriochlorin (m-THPBC). A palladium-bacteriopheophorbide photosensitizer (TOOKAD) has been developed which shows promise in the treatment of prostate cancer with favourable, deep red absorption properties (763 nm absorption peak) [47].

Preclinical studies have shown that fractionating the light dose results in enhanced PDT effects, allowing oxygen to replenish the system prior to the next round of activation. This has been observed for the Miravant drug MV6401 in an orthotopic breast cancer model [48]. The literature describes other ways to enhance non-targeted PDT effects such as the use of vitamin analogues administered separately to modulate the free radical pathway [49], the coupling of photosensitizers (e.g. m-THPC) to polyethylene glycol carriers to increase their half-life [50], the use of polymeric micelle carriers [51] and the use of adjuvants to potentiate the immune response after PDT treatment [52].

The PDT treatment scheme is attractive to the clinician in that superficial diseases can usually be treated with local anaesthesia and sedation [35]. The generally low toxicity (with the possible exception of skin photosensitivity) limits the need for other medication. Topical treatments do not require sterile conditions and can be given in an outpatient clinic.

Photofrin™ (porfimer sodium), 5-aminolaevulinic acid (ALA) and Visudyne™ (verteporfin, BPD-MA benzoporphyrin derivative mono acid) are three PS drugs which have regulatory approval. A promising, potent second generation PS drug, Foscan™ (temoporfin; meta-tetrahydroxyphenyl chlorin) has recently been approved in Europe, as has methyl-5-aminolevullinate. Porfimer sodium, the first PS drug to be approved, is licensed for use in bladder, stomach, oesophagus, cervix and lung cancer. Its performance is moderate due to poor light absorption characteristics in the red end of the spectrum (activated at 630 nm), meaning it can only penetrate about 5 mm into tissues, and limited selectivity for target tumour tissue. It also persists in the body for weeks, leading to skin photosensitivity. However it has been effective in the treatment of bladder, stomach, oesophagus, cervix and lung cancers [35,36]. ALA is applied topically in the treatment of skin lesions and is converted endogenously to protoporphyrin IX, a naturally-occurring. PS molecule. This can be activated at many wavelengths and its depth of effect is less than 2 mm. Verteporfin also performs well in age-related macular degeneration AMD [37,53], without the issues of tissue penetration found in tumour applications. The TAP and VP Clinical trials showed that PDT with verteporfin was more effective at recovering vision loss associated with AMD compared to the placebo control [53].

PDT can achieve control rates similar to conventional techniques with lower morbidity rates, simplicity of use and improved functional and cosmetic outcome. PDT has mainly been used where conventional approaches have failed or are unsuitable. These include pre-malignant dysplastic lesions and non-invasive cancers which are commonly found in the mucosa of aerodigestive and urinary tracts (e.g. oral cavity, oesophagus and bladder). Current treatments for cancer at this stage are not very successful and good responses here would prevent larger solid tumours or metastatic spreads occurring. Treatment for Barrett's oesophagus usually means oesophagectomy, which requires general anaesthesia, has a risk of morbidity and loss of function and disfigurement. PDT is being seen as an attractive option because of the large area which can be treated superficially with less risk. Photofrin™, ALA and Foscan™ have produced good responses in these types of cancers in clinical trials (Table 3). Breast cancer chest wall recurrences have been successfully treated with Foscan™ [54] and Photofrin™ [55]

TABLE 3

Clinical Results with PDT in cancer (adapted from [34, 35])

| Disease | Photosensitiser | Result |
|---|---|---|
| Barrett's mucosal cancer | Porfimer sodium | 75% conversion to normal epithelium and tumours eliminated |
| Barrett's oesophagus cancer | Systemic ALA | High-grade dysplasia erradicated in all patients |
| Bladder cancer | Hematoporphyrin derivative | 74% complete response, 30% alive after 5 years |
| Basal cell cancer of skin | Topical ALA | 90% complete response |
| Oral cancer | Dihematoporphyrin ether | 87% complete response over 5-53 months |
| Chest wall recurrence in breast cancer | Dihematoporphyrin ether | 20% complete response, 45% partial response |

Due to the easy light accessibility, treatment of cutaneous disease such as skin cancer has produced good results with systemic and topical PS drugs (Table 3). Head, neck and oral lesions have also produced good results and are well suited due to the good cosmetic outcome of the treatment (Table 3). Treatment of other cancers are being tested as advances are being made in laser and light delivery technology. Endoscopes can be used to deliver the activating light dose to any hollow structure such as the oesophagus and bronchial cavity, thus expanding the treatment range to gastrointestinal and lung cancers (Table 3) with minimal surgery. Large areas such as the pleura and peritoneum can be treated, where radiotherapy would not be able to give a high enough curative dose. PDT has great promise in the treatment of these surface serosal cancers, in combination with debulking surgery. Light can be delivered to these large surfaces in a short time, through hollow cavities. The limited depth of activity would be an advantage as critical underlying organs would be spared (Table 3). Adjuvant therapy is also an option being investigated, where the solid tumour is surgically removed and any remaining tumour cells are destroyed by one round of PDT in the cavity formed.

Although surface cancers may be the most amenable to PDT, solid tumours may be able to undergo interstitial treatment, where the PS drug is administered systemically or by intra-tumour injection, followed by the insertion of laser fibres through needles equally spread throughout the tumour. This can result in necrosis of very large tumours [56,57] (Table 3).

Therefore, there are several advantages of PDT therapy. It offers non-invasive, low toxicity treatments which can be targeted by the light activation. The target cells cannot develop resistance to the cytotoxic species (ROS). Following treatment, little tissue scarring exists. However, PS drugs are not very selective for the target cells with target:blood ratios typically in single figures at best. In many situations this lack of selectivity leads to unacceptable damage to proximal normal tissues e.g. Photofrin™ [58,59] in oesophageal cancers [60,61], bladder cancer [62]. Because PS drugs "piggy-back" on blood proteins, they persist longer in the circulation than is desired, leaving the patient photosensitive for 2 weeks in the best of cases.

Unlike standard chemotherapeutics, photosensitiser drugs can still be active and functional while attached to carriers as the cytotoxic effect is a secondary effect resulting from light activation. This makes them amenable to specific drug delivery mechanisms involving conjugation to targeting molecules. Currently, the preferred approach to link photosensitizer drugs to targetable elements is the direct conjugation of derivatized photosensitizer drugs to whole monoclonal antibodies. Whole antibodies have a molecular weight of 150 KDa, resulting in very large photo-immunoconjugates with unfavourable pharmacokinetics, such as poor tumour:organ ratios (2:1) [63,64] which take a long time to achieve. Current literature suggest that photosensitizer drugs linked to residues on a monoclonal antibody can have a detrimental effect on each other, with quenching effects occurring due to poor spectroscopic properties [65]. In addition to this, it has been shown that poor, and unreliable, loading of photosensitizer onto the antibody is seen with ratios of 4:1 being typical before the antibody aggregates or loses function [63-69].

Coupling of photosensitisers has been tried using various strategies with various monoclonal antibodies. For example PPa has been coupled to anti-Her 2 monoclonal antibodies. In order to achieve good sensitiser:antibody coupling ratios (in the region of 10:1) the antibody had to be made more soluble by attaching chains of polyethylene glycol [68]. This PEGylation would have a detrimental effect on the conjugate pharmacokinetics resulting in poorer tumour:blood ratios. Furthermore, non-covalent binding of photosensitiser to antibody was also seen here. Such non-covalent binding has been a feature of most reported attempts to produce antibody-photosensitiser conjugates, and represents a major problem in reliably producing well characterised conjugates. In a further study, a porphyrin sensitiser was used with monoclonal antibodies 17.1A, FSP77 and 35A7 using a isothiocyanate coupling method resulting in sensitiser:antibody ratio no better than 2.8:1 [67]. Another example was verteporfin (benzoporphyrin derivative, BPD) with monoclonal antibody C225 (anti-EGFR). Here, coupling ratios of greater than 11:1 resulted in poor immunoreactivity and solubility [69]. The best ratios were about 7:1. These examples serve to illustrate the problems of producing well characterised conjugates with high photosensitiser:antibody ratios, and suggest that the use of fragments which are one third to one sixth smaller than whole antibodies would be even less successful given the solubility and loading problems seen with the larger protein species.

The work on PS drugs attached to monoclonal antibodies has shown that if too many PS molecules are attached to an individual monoclonal antibody the hydrophobicity can be affected and an adverse effect on the pharmacokinetics may result. Given the problems with whole monoclonal antibodies, it is widely believed that small fragments (such as a scFv, 30 KDa) would have very unfavourable coupling efficiencies, resulting in only one or two photosensitisers being coupled. Birchler et al [70] attempted to produce an effective ScFv—photosensitiser conjugate but were only able to couple a single photosensitizer through a site-specific cysteine residue to a scFv.

Other groups have tried to circumvent these problems by attempting to link PS drugs to designated 'carriers' such as branched carbohydrate [71] or polyethylene glycol chains [72] and poly-lysine [73] chains. These approaches all require additional conjugation steps as the ligand-carriers cannot be made entirely recombinantly. Using such polymers may also have problems such as proteolyic instability in vivo. It is known that when photosensitizers are attached in this way, they self-quench, destroying their photophysical properties and rely on degradation in lysozymes to 'de-quench' before they can become active photosensitizers [71]. Therefore, higher coupling ratios can be achieved, up to 10:1, but only with lower phototoxicity and lower singlet oxygen yield than the free photosensitizer. Studies by Roder et al. [71] showed that the photosensitising activity of pheophorbides when covalently linked in large numbers around the periphery of a dendrimer were dramatically reduced. This is a result of energy transfer processes mainly Forster energy transfer from dye to dye. Forster transfer is distance dependant and drops off rapidly with distance. The interaction of dye molecules leads to changes in the absorption spectrum, reduced fluorescence lifetimes and singlet oxygen quantum yields. Fusion proteins combining an antibody fragment with a protein carrier molecule have also been described by our group [74].

Glickman et al [75,76] describe monoclonal antibody targeted PDT against the VEGF vasculature target for ocular disease. This uses standard coupling conditions with no description of antibody:photosensitizer ratios. However Hasan et al [77] discloses a two-solvent system to improve upon the photosensitizer:antibody coupling ratios. Here, using very high concentrations of organic solvents (typically 40-60%) mixed with aqueous buffers, ratios of up to 11:1 have been reported. However, the high concentrations of solvent used are unlikely to be tolerated by all antibodies. No mention is made of using fragments, but given their greater sensitivity to organic solvents, they would not be expected to viable in this method. Also in Hasan et al [77], the large number of coupled photosensitizers are self-quenching, hence this system relies upon internalisation and lysozomal degradation to release phototoxic molecules. Photo-immunoconjugates bound to the cell surface are not expected to be exposed to degradation enzymes like those found in intracellular lysozomes. This may exclude the targeting of low/non-internalizing antigens such as CEA and matrix/stromal antigens.

By linking novel or established PS drugs to small, targetable carrier proteins, it is possible to deliver a highly specific dose of PS drug to a target tissue, which can later be activated by light. These carrier-PS drug conjugates have advantages over existing targeted and non-targeted PDT approaches in that a greater amount of PS drug can accumulate in the target tissue, with tissue to blood/normal organ ratios of 20:1 or better, in shorter time intervals. Additionally, these agents could have advantages over other targetable strategies with little or no immunogenicity and lower side effects. Smaller ligands have been used to deliver photosensitizers such as insulin [78], transferrin [79,80], albumin [81], annexins [82], toxins [83], estrogen [84], rhodamine derivatives [85], folate [86] and growth factors such as EGF [87] and VEGF [88]. None of these examples or anything else in the current literature proposes that such ligands can be engineered by protein evolution or rational mutagenesis to improve or enhance the photosensitizers attached to them.

SUMMARY OF THE INVENTION

The present invention provides a method for coupling photo-sensitisers to biological targeting proteins such as antibody fragments (e.g. scFvs) using previously unknown and optimised coupling conditions to ensure that the carrier remains functional and soluble. The conjugates preferably possess a high and consistent molar ratio of covalently attached photosensitisers without non-covalent binding. The invention also provides engineered recombinant antibody-photosensitiser conjugates with optimised photophysical and photodynamic properties, and methods to produce them. Furthermore the invention provides ways of coupling other 'non-photosensitising' molecules which enhance the photo-physical and photodynamic properties of the overall conjugate.

We describe compounds made by a process which produces very effective, potent targeted photodynamic therapy conjugates based on small recombinant antibody fragments, chemically coupled to photosensitising molecules and other modulating molecules. The use of such modulating molecules can alter the mechanism of reactive oxygen species generation resulting in more type I species (free radicals and superoxides) than type II ROS. This has important implications for PDT because when targeting non- or low-internalizing antigens such as matrix proteins, none or little of the photosensitizer is internalised, meaning that species which can damage surface cell membranes more effectively will be more potent than the type II singlet oxygen generators. Furthermore, targeting non-internalizing antigens may be preferable in some cases, particularly if the cancer cells have developed some form of drug resistance to reactive oxygen species, for example in the up-regulation of ROS scavenging enzymes (e.g. superoxide dismutase).

The biological nature of antibodies requires that they be maintained in mostly aqueous buffers in order to retain function and integrity. However, photosensitizers tend to be hydrophobic in nature and are poorly soluble in the buffer conditions normally used for antibodies. Coupling a photosensitizer to an antibody under aqueous conditions will result in poor photosensitizer:antibody ratios and in solvents will result in damaged antibody proteins. We describe a method utilizing a combination of organic solvents at low concentration.

We have developed a robust conjugation protocol which can efficiently couple a number of photosensitisers to antibody fragments whilst minimising non-covalent binding.

The hydrophobic and highly adsorptive nature of most photosensitisers and the water-soluble nature of antibodies and other biomolecules has made conjugation chemistry difficult and more importantly rendered almost impossible the removal of unconjugated photosensitiser impurities from such conjugations. These problems were overcome, surprisingly, by using (a) very pure monofunctional photosensitisers which enable us to use relatively small coupling ratios between antibody and photosensitiser, and (b) using a combination of 2 aprotic solvents with an aqueous component which can be water, phosphate buffered saline (PBS) or any other approximately neutral buffering solution known in the art.

In a first aspect of the invention there is provided a process of making a compound comprising a photosensitising agent coupled to a carrier molecule comprising the steps of:
 (i) providing a photosensitising agent;
 (ii) providing a carrier molecule;
 (iii) conjugating the photosensitizing agent and the carrier molecule in the presence of a first and a second polar aprotic solvent and an aqueous buffer.

Preferably, the compound comprises a ratio of photosensitising agent to carrier molecule of at least 3:1. More preferably, the functional and physical properties of the photosensitising agent and the carrier molecule are substantially unaltered after coupling.

Appropriate polar aprotic solvents from which the first and second polar aprotic solvent are selected from (but are not limited to) the group consisting of: dimethyl sulfoxide (DMSO); acetonitrile; N,N-dimethylformamide (DMF); HMPA; dioxane; tetrahydrofuran (THF); carbon disulfide; glyme and diglyme; 2-butanone (MEK); sulpholane; nitromethane; N-methylpyrrolidone; pyridine; and acetone. Other polar aprotic solvents which may be used are well known to those skilled in the art. The total amount of both polar aprotic solvents relative to the aqueous mixture should be about 50% by volume. The relative amounts of the 2 polar aprotic solvents to each other can vary from 1 to 49%: 49% to 1

Preferably, the first and second aprotic solvent are selected from the group consisting of: DMSO; DMF; and acetonitrile. More preferably, the first and second aprotic solvent are DMF and acetonitrile.

Even more preferably, the ratio of aqueous buffer to first aprotic solvent to second aprotic solvent is approximately 50%:1 to 49%:49 to 1%.

Even more preferably, the aprotic solvent mixture is 92% PBS:2% DMSO:6% acetonitrile and the step of conjugating the photosensitizing agent and the carrier molecule is conducted at a temperature between 0° C. and 5° C. The combination of solvents keeps the whole reaction homogeneous especially at these low temperatures and by carrying out the coupling for approximately only 30 min, we are able to achieve high coupling ratios and very low degrees of non-covalent binding.

The invention further provides a process wherein the carrier molecule is an antibody fragment and/or a derivative thereof. Preferably, the antibody fragment and/or derivative is a single-chain antibody, and may conveniently be an ScFv. The carrier molecule is preferably humanised or human.

Using the above protocol, photosensitisers with carboxylic acid groups derivatised to form active esters may be coupled efficiently and with high molar ratio to antibody fragments via surface-accessible lysine residues. Pyropheophorbide a (PPA) is a photosensitiser derived from natural products, and apart from excellent photophysics which makes it an ideal photosensitiser, it possesses a single propionic acid side chain. The PPA propionic acid function may be readily converted to the corresponding N-hydroxysuccinimide ester (NHS) or 'active ester' and purified through a combination of chromatography and recrystallisation to obtain very pure derivatives ready for conjugation, and thereafter coupled efficiently to antibody fragments.

Preferably, the photosensitising agent is a monofunctional photosensitiser. More preferably, the photosensitising group is at least one selected from the group (but not limited to) consisting of: haematoporphyrins, Photofrin™, naturally-occurring porphyrins, chlorins and bacteriochlorins, pheophorbides like pyropheophorbide a and its derivatives like Photochlor, chlorins, chlorin e6, mono-1-aspartyl derivative of chlorin e6, di-1-aspartyl derivative of chlorin e6, tin (IV) chlorin e6, the palladium derivatives of naturally occurring bacteriochlorophylls like TOOKAD (Pd-bacteriopheophorbide), synthetic chlorins and bacteriochlorins like meta-tetrahydroxyphenyl chlorin (Foscan) and bacteriochlorin, benzoporphyrin derivatives, monobenzoporphyrin derivatives like verteporfin, phthalocyanines, sulphonated aluminium phthalocyanines (disulphonated and tetrasulphonated), sulphonated aluminium naphthalocyanines and derivatives, purpurins like purpurin-18, tin and zinc derivatives of octaethylpurpurin, tin etiopurpurin, verdins, porphycenes, synthetic porphyrins, chlorins and bacteriochlorins, like the meso-triethynylporphyrins (WO2004/046151) both metal free and metallated, core-modified porphyrins (WO2004/076461), expanded porphyrins (texaphyrins) like motexafin lutetium and motexafin gadolinium.

Non-porphyrinic compounds can also be used as photosensitisers and include but are not limited to, phenothiazinium derivatives like methylene blue, toluidine blue, cyanines such as merocyanine-540, acridine dyes, BODIPY dyes and aza-BODIPY derivatives, hypericin, halogenated squarine dyes and halogenated xanthene dyes like eosin and rose Bengal.

Other suitable photosensitisers for conjugation to antibody fragments will readily occur to those skilled in the art. However, the presence of multiple reactive functionalities on the photosensitiser can lead to a number of problems. It is difficult to obtain sufficiently pure material to control the stoichiometry of the conjugation reaction and as a consequence reactions are carried out using large excesses of the reactive photosensitiser resulting in increased non-covalent binding. Intramolecular antibody cross-linking can also occur during conjugation resulting in low coupling yields and increased aggregate formation.

Our work with antibody fragments has shown that by controlling the stoichiometry of the photosensitiser during the conjugation and having lysine residues sufficiently spaced apart geometrically can lead to photoimmunoconjugates with high photosensitiser loadings and excellent PDT activity.

Conveniently, the process further comprises the following step performed after step (iii):
 (iv) coupling a modulating agent to the carrier molecule, wherein the modulating agent is capable of modulating the function of the photosensitising agent.

As well as coupling photosensitisers to ligands, it is also possible, using similar coupling chemistries to couple other molecules to the ligands in such a way that they modify the photophysical or photodynamic properties of the overall photo-immunoconjugate. These alternative molecules can be coupled to same residue type as the photosensitisers (i.e. before or after photosensitiser coupling) at stoichiometric ratios to allow both types of molecules to be coupled/accommodated or on different residue types (e.g. photosensitiser coupled onto lysines and subsequently modifying chemical coupled to aspartate/glutamate residues).

Photodynamic modulators may serve to alter the types and amounts of reactive oxygen species generated upon light illumination of the photosensitiser. For example photosensitisers which generate a more type II reaction (i.e. singlet oxygen) can be modulated to generate more type I reaction with high concentrations of superoxide and hydroxide radicals. This could have major implications on the PDT potency or therapeutic outcome. For example a photo-immunoconjugate targeting a non-internalising tumour antigen may be more potent if it generated a predominantly type I reaction at the surface of the cell, causing membrane damage and being less susceptible to anti-oxidant responses such as superoxide dismutase (which is generated intracellularly).

Preferably, the modulating agent is selected from the group consisting of: benzoic acid; benzoic acid derivatives containing an azide group like 4-azidotetrafluorophenylbenzoic acid and other aromatic or heteroaromatic groups containing an azide moiety ($N_3$) including polyfluorobenzenes, naphthalines, napthaquinones, anthracenes, anthraquinones, phenanthrenes, tetracenes, naphthacenediones, pyridines, quinolines, isoquinolines, indoles, isoindoles, pyrroles, imidazoles, pyrazoles, pyrazines, benzimidazoles, benzofurans, dibenzofurans, carbazoles, acridiens acridones, and phenanthridines, xanthines, xanthones, flavones and coumarins. Aromatic and heteroaromatic sulfenates derived from the aromatic/heteroaromatic groups above. Other specific modulating agents include vitamin E analogues like Trolox, butyl hydroxyl toluene, propyl gallate, deoxycholic acid and ursadeoxycholic acid One example of a chemical modifier which can be coupled to a ligand alongside the photosensitising agent is the succinimidyl ester of benzoic acid (BA).

This has been shown to result in more potent PDT cell killing in vitro when co-coupled with PPa to an anti-CEA scFv compared to the scFv coupled with PPa alone.

Preferably, the process further comprises the following step performed after step (iii) or (iv):

(v) combining the compound with a pharmaceutically-acceptable carrier to form a pharmaceutical formulation.

The process of the invention may also include the optional step of coupling a visualising agent to the conjugate. Alternatively the photosensitising agent forming part of the conjugate may also be used as a visualising agent.

The use of recombinant antibodies in immuno-assays or diagnostics is a well studied area. The exquisite specificity, high affinity and versatility of antibodies and antibody fragments make them ideal binding molecules as part of a detection system. For example, in medical imaging, antibodies have been linked to optically-active compounds such as fluorescent dyes and used to detect precancerous and cancerous lesions, measuring treatment response and early detection of recurrences [95] and in vitro, transmissible spongiform encephalopathies (prion diseases) have been detected with fluorescently labelled antibodies [96]

Clinically useful tumour imaging requires detection of small lesions. The benefits of detection can then be realised by early action. One of the problems associated with conventional imaging techniques is poor tumour to background contrast. Various strategies have been developed to increase the localization of targeting molecules in tumours and to reduce their uptake by normal tissue, thus improving tumour:tissue ratio. These approaches include developing small tumour specific peptide molecules with favourable pharmacokinetics [97], improved labelling techniques [98], using pre-targeting strategies, modifying tumour delivery and up-regulating of tumour marker expression. In addition, several new dyes have been developed [99]. Far-red fluorochromes have been synthesized that have many properties desirable for in vivo imaging. Far-red fluorochromes absorb and emit at wavelengths at which blood and tissue are relatively transparent, have high quantum yields, and have good solubility even at higher molar ratios of fluorochrome to antibody. Small antibody species such as single-chain Fv fragments possess pharmacokinetics which can result in good contrast ratios, but clear rapidly resulting in low absolute levels of reporter groups in the target tissue. Higher fluorescent yields can compensate for this lower deposition increasing the sensitivity of detection.

Other applications of imaging include the development of research tools. Antibodies labelled with dyes have been invaluable in visualising cell biological processes such as receptor trafficking [100]. Increased fluorescent yields would enable the detection and monitoring of low abundance molecules. The usual method for visualising labelled cells is immunofluorescent microscopy where multiply-labelled molecules can be simultaneously monitored using a range of specific antibodies possessing different and non-overlapping fluorescence emission spectra.

As described above, the coupling of dye molecules to antibody fragments or other appropriate ligands using our novel coupling conditions results in higher loading ratios. This can translate directly into enhanced photophysics. As well as higher singlet oxygen generation for improved PDT, superior photophysics can manifest as increased fluorescence. Antibody fragment photo-immunoconjugates with appropriate dye molecules can make more effective diagnostic reagents due to their favourable pharmacokinetics and enhanced fluorescence. Rapid clearance and low non-specific tissue binding will lead to very high contrast ratios and high fluorescence will allow more sensitive detection of the output signal. The use of antibody fragments, constructed, selected or engineered to contain favourably-spaced functional groups for coupling (e.g. lysine amino groups) as described above can lead to dyes with more favourable fluorescence yields due to reduced quenching and mis-interactions. This will have applications primarily in medical imaging, but can also be used to make more sensitive reagents for diagnostic kits or cellular imaging and by coupling fluorescent dyes and photosensitisers to the same antibody fragments a bifunctional agent can be produced, allowing both tumour imaging and phototherapy.

In a second aspect of the invention there is provided a compound comprising a photosensitising agent coupled to a carrier molecule obtainable by the process of the invention.

In a third aspect of the invention there is provided a compound comprising a photosensitising agent coupled to a carrier molecule with a minimum coupling ratio of 3:1 wherein the carrier molecule binds selectively to a target cell.

Preferably the carrier molecule has an upper size limit of 3:1 when compared to the photosensitiser, typically an upper limit of 30 kDa. An example of such a carrier is an ScFv.

Advantageously the functional and physical properties of the photosensitising agent and the carrier molecule are substantially unaltered in the coupled form in comparison to the properties when in an uncoupled form.

Preferably, the carrier molecule is selected from the group consisting of: an antibody fragment and/or a derivative thereof, or a non-immunogenic peptide ligand.

Conveniently the antibody fragment and/or derivative thereof is a single-chain antibody fragment, in particular an ScFv.

Alternatively the carrier molecule is humanised or human.

Conveniently the photosensitising agent is a monofunctional photosensitiser. Preferably the photosensitising agent is at least one selected from the group consisting of: haematoporphyrins, Photofrin™, naturally occurring porphyrins, chlorins and bacteriochlorins, pheophorbides like pyropheophorbide a and its derivatives like Photochlor, chlorins (e.g. chlorin e6), mono-1-aspartyl derivative of chlorin e6, di-1-aspartyl derivative of chlorin e6, tin (IV) chlorin e6, the palladium derivatives of naturally occurring bacteriochlorphylls like TOOKAD (Pd-bacteriopheophorbide), synthetic chlorins and bacteriochlorins like meta-tetrahydroxyphenyl chlorin (Foscan) and bacteriochlorin, benzoporphyrin derivatives, monobenzoporphyrin derivatives like verteporfin, phthalocyanines, sulphonated aluminium phthalocyanines (disulphonated and tetrasulphonated), sulphonated aluminium naphthalocyanines and derivatives, purpurins like purpurin-18, tin and zinc derivatives of octaethylpurpurin, tin etiopurpurin, verdins, porphycenes, synthetic porphyrins, chlorins and bacteriochlorins, like the meso-triethynylporphyrins, metal-free and metallated core-modified porphyrins, expanded porphyrins (texaphyrins) like motexafin lutetium and motexafin gadolinium and non-porphyrinic compounds such as phenothiazinium derivatives like methylene blue, toluidine blue, cyanines such as merocyanine-540, acridine dyes, BODIPY dyes and aza-BODIPY derivatives, hypericin, halogenated squarine dyes and halogenated xanthene dyes like eosin and rose Bengal.

Conveniently the photosensitising agent is coupled to the carrier molecule at an amino acid residue or a sugar molecule on the carrier molecule.

Preferably the amino acid residue is at least one selected from the group consisting of: lysine; cysteine; tyrosine; serine; glutamate; aspartate; and arginine. Alternatively, the sugar molecule is selected from at least one of the group consisting of: sugars comprising an hydroxyl group; sugars comprising an aldehyde group; sugars comprising an amino group; and sugars comprising a carboxylic acid group.

Although coupling photosensitisers to lysine residues is generally straightforward, the above conjugation methodology can also apply to the coupling of photosensitisers to antibody fragments via other amino acid residues or sugar molecules attached to the protein by N- or O-linked glycosylation using different functional groups on the photosensitiser moieties. Table 4 lists these residues and the other possible coupling chemistries which can be used with this coupling method.

TABLE 4

Functional groups for coupling photosensitizers onto antibodies

| Residue(s) | Functional group | Coupling chemistry | Resulting bond |
|---|---|---|---|
| Lysine | Amine | Active-ester | Amide |
| | | Isothiocyanate | Isothiourea |
| | | Isocyanates | Isourea |
| | | Acyl azides | Amide |
| | | Sulphonyl chloride | Sulphonamide |
| | | Carbonyl, reduce. | Schiff Base, 2° amine |
| | | Epoxide | 2° Amine |
| | | Carbonates | Carbamate |
| | | Fluorobenzene deriv. | Arylamine |
| | | Imidoesters | Amidine |
| | | Carbodiimides | Amide |
| | | Anhydrides | Amide |
| Cysteine | Thiol | Haloacetyl | Thioether |
| | | Maleimides | Thioether |
| | | Acryloyl | Thioether |
| | | Activated aryl deriv. | Arylthioether |
| | | Active-ester | Thioester |
| | | Carbodiimide | Thioester |
| | | Redox reactions | Disulphide |
| Tyrosine, serine | Hydroxyl | Diazonium | Diazo |
| | | Mannich | 2°amine |
| | | Active-ester | Ester |
| | | Active Alkylation | Ether |
| | | Isocyanates | Carbamate |
| Glutamate, aspartate | Carboxylic acid | Diazoalkyl | Ester |
| | | Carbodiimides | Amide, Ester, Thioester |
| | | Acylimidazole | Amide, Ester, Thioester |
| Arginine | Guanidinyl | Dicarbonyl | Schiff base |
| Sugars | Hydroxyl (e.g. glucose) | Acylation | Ester |
| | | Alkylation | Ether |
| | | Oxidative cleavage to the aldehyde | Schiff base, mild redn. to the 2° amine |
| Sugars | Aldehyde (e.g. mannose) | Reductive amination | Schiff base, 2° amine |
| Sugars | Amino (e.g. b-D-mannosamine) | See reactions for lysine | See reactions for lysine |
| Sugars | Carboxylic acid (e.g. sialic acid) | See reactions for glutamate | See reactions for glutamate |

Antibody fragments vary in amino acid sequence and the number and spacing of functional groups to couple photosensitizers to. The most common frequently used functional group for conjugation is the primary amine found at the N-terminus and on lysine residues, as described above. We have found, surprisingly, that a major determinant of the effectiveness of a particular photosensitiser-antibody fragment conjugate is the spatial separation of the residues to which photosensitiser molecules are attached. These residues must be distinct and topologically separated on the surface of the antibody for effective coupling and optimal photophysics of the resulting conjugate.

Generally, proteins fold to form a hydrophobic core at the centre of the molecule with a hydrophilic surface to enable solubility in physiological solvents. Basic residues such as lysines and arginines, acidic residues such as glutamates and aspartates, polar residues such as serines (and sometimes tyrosines), cysteines, glutamines and asparagines are commonly found on the surface of proteins. In many examples these residues are involved in maintaining the structure and function of that protein.

In the example of antibody fragments such as single-chain Fv each domain is made up of a variable heavy (VH) and variable light (VL) domain. These can be one of any family of VH and VL domains. An alignment of the families of VH and VL genes (FIG. 1) shows that generally, many residues can be tolerated at any position. In the case of the antigen binding loops (complementarity determining regions-CDRs), these sequences are specific to the ability of that antibody to recognise its cognate antigen. These can be manipulated to alter the specificity or affinity of the antibody but for no other reasons. The major part of the domain sequence is the framework region. FIG. 1 indicates which areas tend to be present at the surface of the antibody and which areas tend to be interior as part of the core. Given the high degree of structural and sequence homology between antibodies, these regions can generally be applied to all antibody sequences. The surface framework regions tend to contain the charged or polar residues, evenly spaced out (i.e. no particular requirement at any particular position).

Taking lysine residues as one example. These are commonly found at the surface of antibody domains. In the case of members of the germline human VH1 family, there are 5-6 lysine residues, only one or two of which are close to each other. A definition of a residue being close to another can be one that is adjacent in the primary sequence hence adjacent in the 3-dimensional structure. Alternatively, a residue may be separated according to the primary sequence, but adjacent in space due to the structure of the fold of the antibody domain. A directly adjacent residue can be defined as 3-4 angstroms apart in space.

We have found that the coupling of photosensitizers onto lysine residues which are directly adjacent will result in photophysical quenching and poorer photodynamic effects (such as increased aggregation and poorer solubility of photo-immuno conjugates). Coupling is more effective when lysine residues are further separated, preferably two amino acids apart (3.5 to 7.5 angstroms), more preferably three amino acids apart (9 to 12 angstroms), more preferably four amino acids apart (10-15 angstroms), even more preferably five amino acids apart (15-20 angstroms), yet even more preferably six amino acids apart (20-25 angstroms). Antibodies should be chosen, selected or engineered to possess these properties. The more lysine residues an antibody possess, with more optimal separation, the better that antibody will be at forming effective and potent photo-immuno conjugates with optimal photophysical and photodynamic effects.

Methods of determining whether amino acid residues for photosensitiser coupling are close or adjacent to one another are well known in the art. Clustal sequence alignment (using web resources such as http://www.ebi.ac.uk/clustalw/ European bioinformatics Institute) is a well established tool for comparing primary amino-acid sequence. Furthermore, in the absence of full 3 dimensional structural data for an antibody fragment, it is possible to use well-established techniques such as homology modelling using known structures (for example that of a murine scFv [89] to deduce probable structure of the antibody fragment, and thereby to identify whether residues for coupling are close or adjacent in space. The high degree of homology exhibited by antibodies and antibody fragments means these techniques can be applied with a high degree of confidence. Web resources for homology modelling are available, such as the Expert Bioinformatics Analysis System from the Swiss Institute of Bioinformatics (http://us.expasy.org) which also provides the free desktop modelling programme SwissPDB Viewer.

Figure 2:
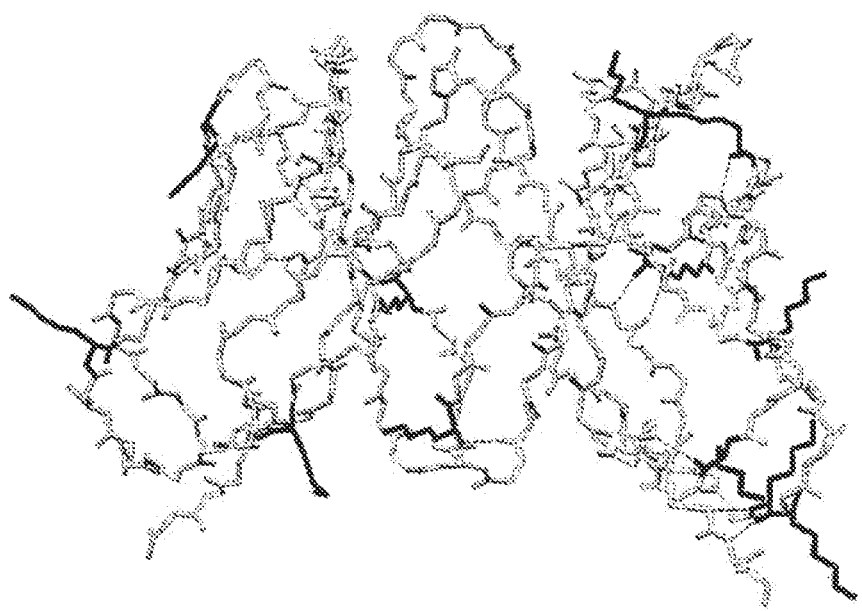

An example of such a favourable distribution of lysine residues on a scFv is shown in FIG. 2 (a scFv derived from human VH1-VK3). If the distribution of lysine residues is less favourable for conjugation and optimal photophysics, the antibody fragment may be altered using standard molecular biological techniques, such as site directed mutagenesis to remove poorly spaced (too closely positioned) or introduce well-spaced residues.

The above concept can also apply to the spacing and coupling to other amino acid residues other than lysine or to sugar molecules attached to the protein by N- or O-linked glycosylation. Table 4 lists these residues and the possible coupling chemistries which can be used.

The above concept can also be applied to non-antibody based ligands. Examples of ligands which can be used to target photosensitisers which can also be influenced by amino acid spacing are listed in Table 5.

TABLE 5

List of antibody and non-antibody based ligands which could be used in targeted photodynamic therapy

| Type | Ligand name | Reference |
|---|---|---|
| Immunoglobin-based | Domain antibodies | 30 |
| | Single chain Fvs | 70 |
| | Fab fragment | 90 |
| | Fn3 domains | 29 |
| | Protein L | 91 |
| | T cell receptors | 92 |
| Non-immunoglobin | Peptides | 88 |
| | Ankyrin repeats | 32 |
| | Anticalin | 31 |

This will lead to coupled photosensitizers retaining their photophysical properties and therefore good photodynamic therapy function. There are many examples of antibodies where many of the lysine residues are adjacent in primary sequence or in 3-dimensional space. By molecular modelling and site-directed mutagenesis, we are able to engineer the position of these lysine residues, adding additional ones if there are too few, removing adjacent residues or increasing the distance between others.

This leads to antibody fragments which are more amenable to photosensitizer coupling, capable of achieving higher loading (increased photosensitizer:antibody ratios) and more potent PDT effects. One indirect measurement of enhanced photophysics is increased fluorescence.

Advantageously the compound further comprises a modulating agent wherein the modulating agent capable of modulating the function of the photosensitising agent coupled to the carrier molecule. Preferably the modulating agent is selected from the group of benzoic acid, benzoic acid derivatives containing an azide group like 4-azidotetrafluorophenylbenzoic acid and other aromatic or heteroaromatic groups containing an azide moiety ($N_3$) including polyfluorobenzenes, naphthalines, napthaquinones, anthracenes, anthraquinones, phenanthrenes, tetracenes, naphthacenediones, pyridines, quinolines, isoquinolines, indoles, isoindoles, pyrroles, imidazoles, pyrazoles, pyrazines, benzimidazoles, benzofurans, dibenzofurans, carbazoles, acridiens acridones, and phenanthridines, xanthines, xanthones, flavones and coumarins. Aromatic and heteroaromatic sulfenates derived from the aromatic/heteroaromatic groups above. Other specific modulating agents include vitamin E analogues like Trolox, butyl hydroxyl toluene, propyl gallate, deoxycholic acid and ursadeoxycholic acid.

Conveniently, the compound further comprises a visualising agent, for example a fluorescent or luminescent dyes (see above).

Preferred examples of conjugates are:

(a) wherein the carrier molecule is an ScFv and the photosensitising agent is Pyropheophorbide a.

(b) wherein the carrier molecule is an ScFv and the photosensitising agent is benzoporphyrin derivative mono acid (Verteporfin, Visudyne™)

(c) wherein the carrier molecule is an ScFv and the photosensitising agent is palladium-bacteriopheophorbide (TOOKAD™).

(d) wherein the carrier molecule is an ScFv and the photosensitising agent is mono-l-aspartyl derivative of chlorin e6.

(e) wherein the carrier molecule is an ScFv and the photosensitising agent is meta-tetrahydroxyphenyl chlorin (Foscan™)

(f) wherein the carrier molecule is an ScFv and the photosensitising agent is tin etiopurpurin (rostaporfin).

In a fourth aspect of the invention there is provided a use of the compound in the treatment and/or prevention of a disease requiring the destruction of a target cell.

There is also provided the use of the compound in the manufacture of a medicament for the diagnosis, treatment and/or prevention of a disease requiring the destruction of a target cell.

Preferably, the disease to be treated is selected from the group consisting of: cancer; age-related macular degeneration; immune disorders; cardiovascular disease; and microbial infections including viral, bacterial or fungal infections, prion diseases such as BSE, and oral/dental diseases such as gingivitis.

Most preferably the disease to be treated is cancer of the colon, lung, breast, Head and neck, prostate, skin, stomach/gastrointestinal, bladder and precancerous lesions such as Barretts oesophagus.

Conveniently the diagnosis of diseases is conducted by visualisation of either the photosensitising agent or an optional visualisation agent such as a fluorescent or luminescent dye.

Advantageously the compound or composition is administered to a patient prior to light exposure.

In fifth aspect of the invention there is provided a composition comprising the compound of the invention and a pharmaceutically acceptable carrier, excipient or diluent

MEANINGS OF TERMS USED

The term "antibody fragment" shall be taken to refer to any one of an antibody, an antibody fragment, or antibody derivative. It is intended to embrace wildtype antibodies (i.e. a molecule comprising four polypeptide chains), synthetic antibodies, recombinant antibodies or antibody hybrids, such as, but not limited to, a single-chain modified antibody molecule produced by phage-display of immunoglobulin light and/or heavy chain variable and/or constant regions, or other immunointeractive molecule capable of binding to an antigen in an immunoassay format that is known to those skilled in the art.

The term "antibody derivative" refers to any modified antibody molecule that is capable of binding to an antigen in an immunoassay format that is known to those skilled in the art, such as a fragment of an antibody (e.g. Fab or Fv fragment), or a modified antibody molecule that is modified by the addition of one or more amino acids or other molecules to facilitate coupling the antibodies to another peptide or polypeptide, to a large carrier protein or to a solid support (e.g. the amino acids tyrosine, lysine, glutamic acid, aspartic acid, cysteine and derivatives thereof, $NH_2$-acetyl groups or COOH-terminal amido groups, amongst others).

The term "ScFv molecule" refers to any molecules wherein the $V_H$ and $V_L$ partner domains are linked via a flexible oligopeptide.

The terms "nucleotide sequence" or "nucleic acid" or "polynucleotide" or "oligonucleotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material. In the sequences herein A is adenine, C is cytosine, T is thymine, G is guanine and N is A, C, G or T (U). It is contemplated that where the polynucleotide is RNA, the T (thymine) in the sequences provided herein is substituted with U (uracil). Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "polypeptide" or "peptide" or "amino acid sequence" refer to an oligopeptide, peptide, polypeptide or protein sequence or fragment thereof and to naturally occurring or synthetic molecules. A polypeptide "fragment," "portion," or "segment" is a stretch of amino acid residues of at least about 5 amino acids, preferably at least about 7 amino acids, more preferably at least about 9 amino acids and most preferably at least about 17 or more amino acids. To be active, any polypeptide must have sufficient length to display biological and/or immunological activity.

The terms "purified" or "substantially purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "recombinant," when used herein to refer to a polypeptide or protein, means that a polypeptide or protein is derived from recombinant (e.g., microbial, insect, or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. coli*, will be free of glycosylation modifications; polypeptides or proteins expressed in yeast will have a glycosylation pattern in general different from those expressed in mammalian cells.

The term "expression vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters and often enhancers, (2) a structural or coding sequence which is transcribed into mRNA and translated into protein, and (3) appropriate transcription and translation initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an amino terminal methionine residue. This residue may or may not be subsequently cleaved from the expressed recombinant protein to provide a final product.

The terms "selective binding" and "binding selectivity" indicates that the variable regions of the antibodies of the invention recognise and bind polypeptides of the invention exclusively (i.e., able to distinguish the polypeptide of the invention from other similar polypeptides despite sequence identity, homology, or similarity found in the family of polypeptides), but may also interact with other proteins (for example, S. aureus protein A or other antibodies in ELISA techniques) through interactions with sequences outside the variable region of the antibodies, and in particular, in the constant region of the molecule. Screening assays to determine binding selectivity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies that recognise and bind fragments of the polypeptides of the invention are also contemplated, provided that the antibodies are first and foremost selective for, as defined above, full-length polypeptides of the invention. As with antibodies that are selective for full length polypeptides of the invention, antibodies of the invention that recognise fragments are those which can distinguish polypeptides from the same family of polypeptides despite inherent sequence identity, homology, or similarity found in the family of proteins.

The term "binding affinity" includes the meaning of the strength of binding between an antibody molecule and an antigen.

The term "coupling ratio" means the number of molecules of photosensitising agent coupled to one carrier molecule.

The term "carrier molecule" includes the meaning of any agent to which the photosensitising agent is coupled. In particular, the carrier molecule may be a small compound including but not limited to antibody fragments and non-immunogenic peptides.

The term "monofunctional photosensitiser" or "monofunctional phosensitising agent" means—a photosenstiser like PPa which contains a single propionic acid side chain which can be activated and coupled or by the use of chemistry known in the art a senstiser can be modified through protection/deprotection chemistry to possess a group that can be activated/coupled.

The term "aprotic solvent" means a solvent that has no OH groups and therefore cannot donate a hydrogen bond.

PREFERRED EMBODIMENTS

Examples embodying certain preferred aspects of the invention will now be described with reference to the following figures in which:—

FIG. 1—Alignment of human immunoglobin variable genes, with lysine residues highlighted in bold. [SEQ. ID NO. 11]-[SEQ. ID NO. 777] Certain families such as human VH-1 contain more and favourably separated lysine residues making scFvs (or other antibody formats) derived from them more effective for photosensitizing coupling. FR=framework, CDR=complementary determining regions.

FIG. 2—Structural representation of a scFv from the human VH1-VK3 family with naturally occurring lysine residues highlighted in black. The lysine residues are favourably placed for efficient photosensitizer coupling and good photophysics.

Figure 3:
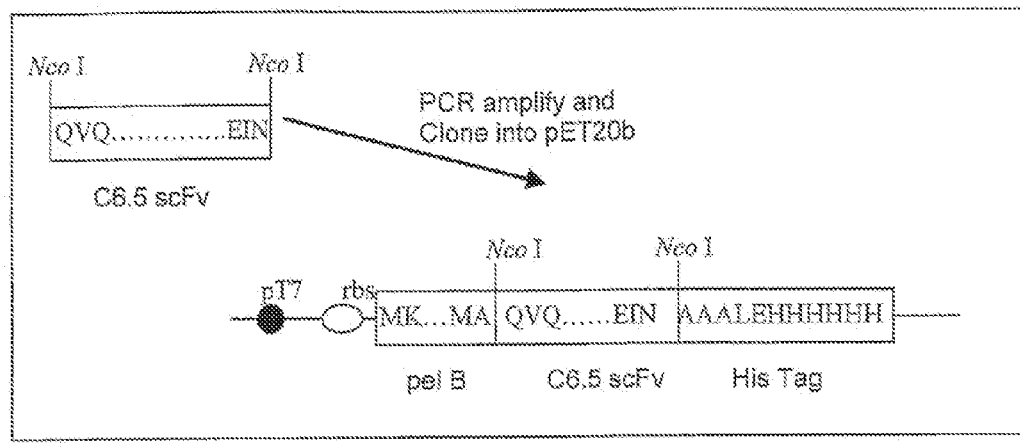

FIG. 3—Cloning of a scFv into a pET expression system

Figure 4:
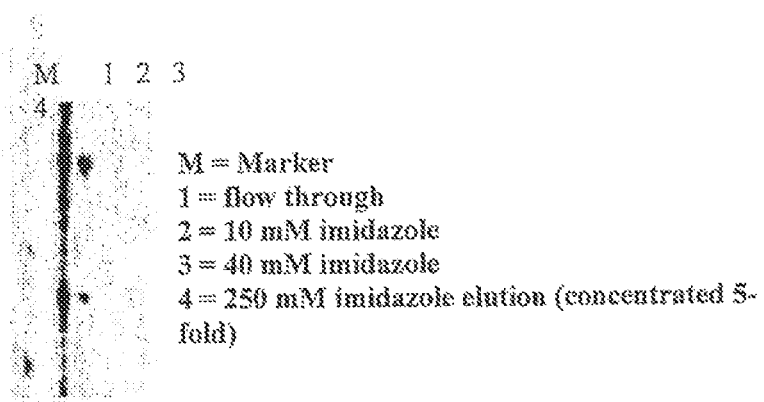

FIG. 4—Purification of C6.5 by immobilised metal affinity chromatography (IMAC) using nickel chloride-charged resin. C6.5 was eluted from the column using 250 mM imidazole Lane 4 shows C6 eluted from the column and concentrated 5-fold using a spin column.

Figure 5:
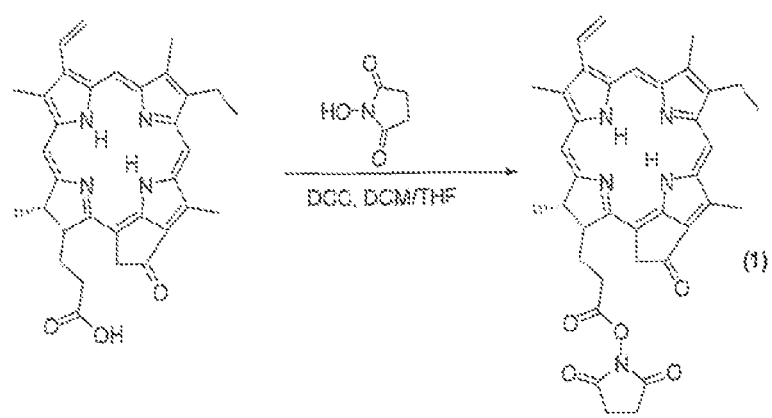

FIG. 5—Preparation of PPa succinimidyl ester

Figure 6:
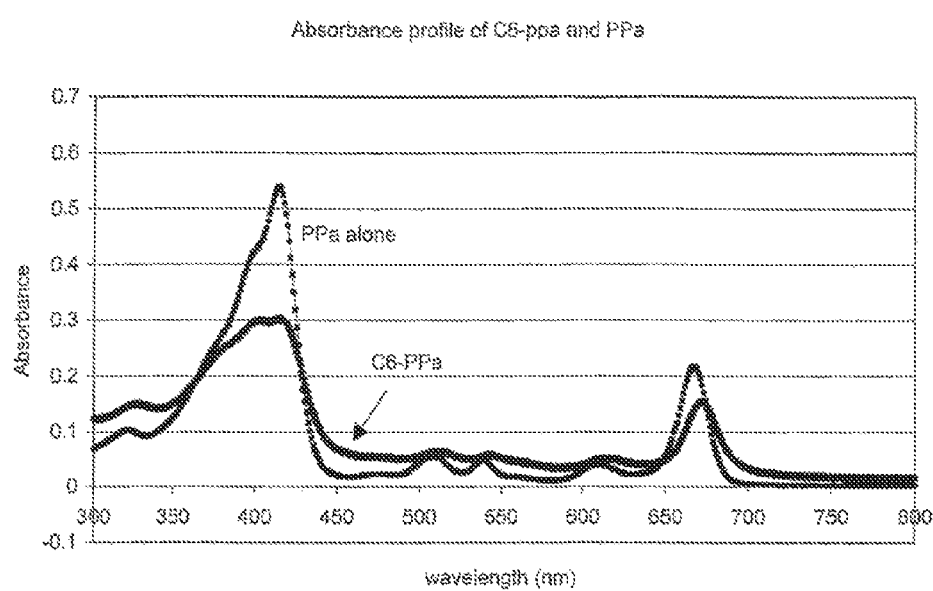

FIG. 6—Absorbance profile of C6.5 scFv conjugated to PPa (bold line) and free PPa (thin line), in PBS buffer. The absorbance peaks are used to determine the PPa:scFv ratio as described in the examples.

Figure 7:
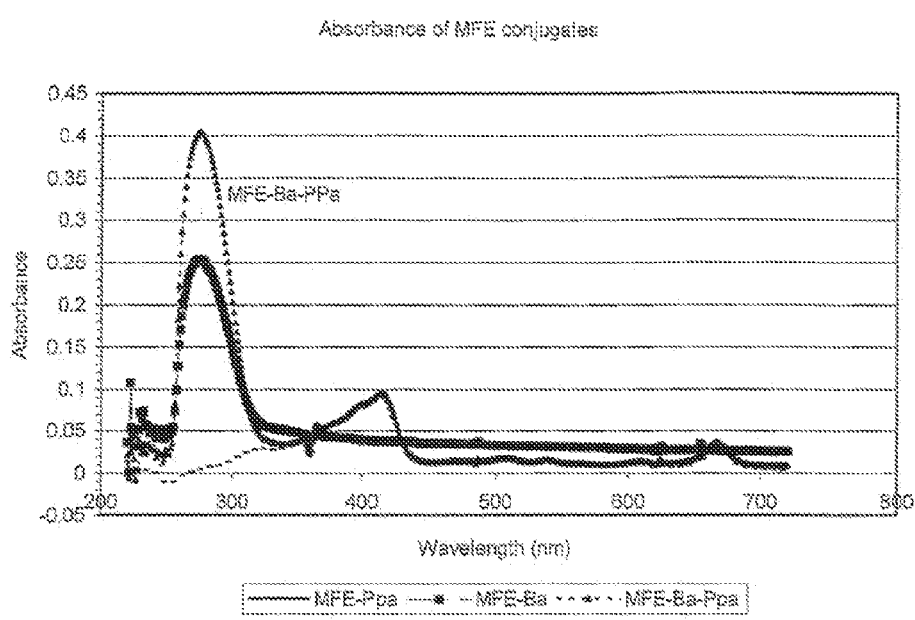

FIG. 7—Absorbance profile of MFE-23 scFv conjugated to PPa and PPa/benzoic acid (Ba) and free PPa, in PBS buffer. The absorbance peaks are used to determine the PPa:scFv ratio as described in the examples.

Figure 8:
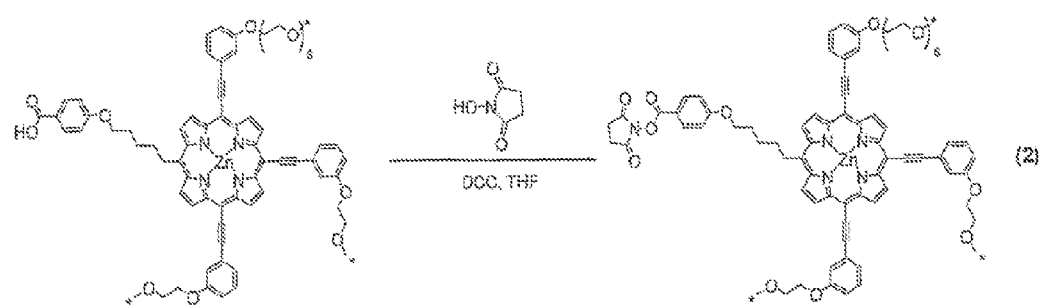

FIG. 8—Preparation of PB1 succinimidyl ester

Figure 9:
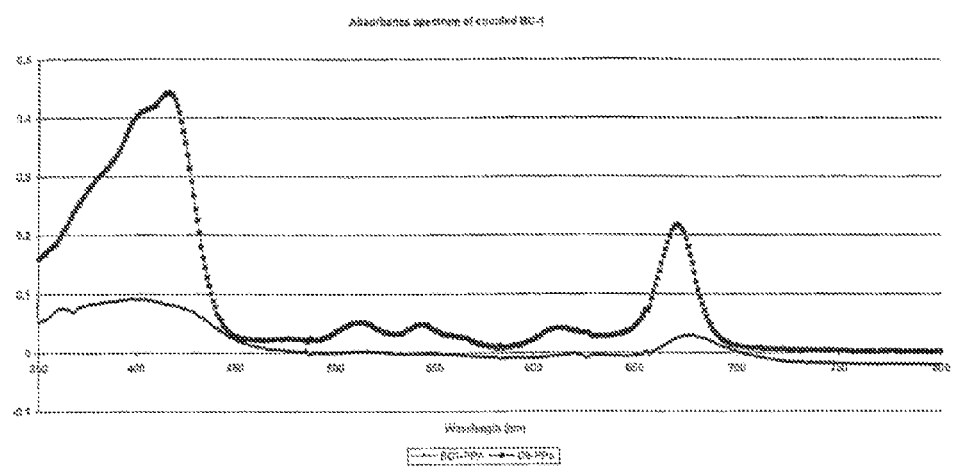

FIG. 9—Absorbance profile of HuBC-1 scFv conjugated to PPa. The absorbance peaks are used to determine the PPa:scFv ratio as described in the examples. The poor structure of HuBC-1 results in poor absorbance properties of the scFv-PPa conjugate compared to C6.5 scFv FIG. 10—Absorbance profile of C6.5 scFv coupled to Pyropheophorbide-a and Chlorin e6 photosensitisers FIG. 11—Fluorescence profiles of various concentrations of C6.5 scFv-PPa conjugate and free PPa measured in PBS buffer. Free PPA does not fluoresce significantly in aqueous buffers, but when conjugated to an scFv retains good photophysical properties.

Figure 12:
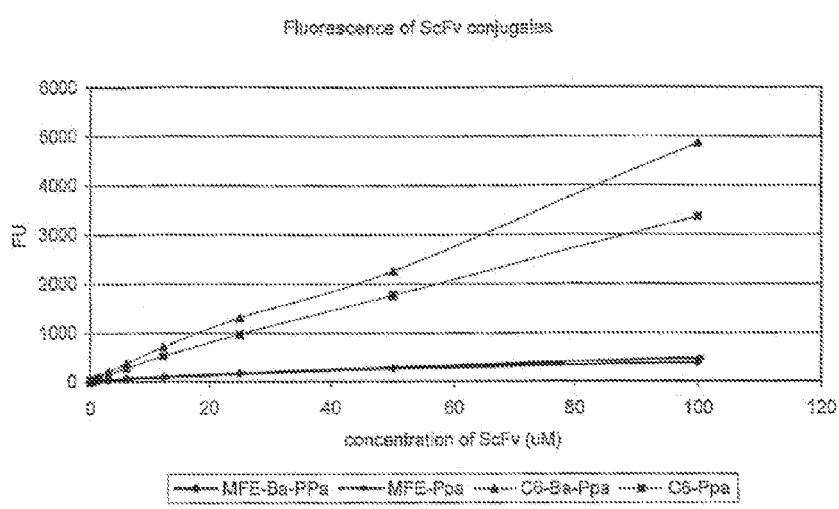

FIG. 12—Fluorescence profiles of various concentrations of C6.5 scFv-PPa, MFE-23 scFv-PPA and NFE-23 scFv-PPa/Ba (benzoic acid) conjugates measured in PBS buffer. Free PPA does not fluoresce significantly in aqueous buffers (FIG. 7), but when conjugated to an scFv retains good photophysical properties. The C6.5 scFv is better at retaining fluorescence (hence photophysics including singlet oxygen generation) than the MFE-23 scFv.

Figure 13:
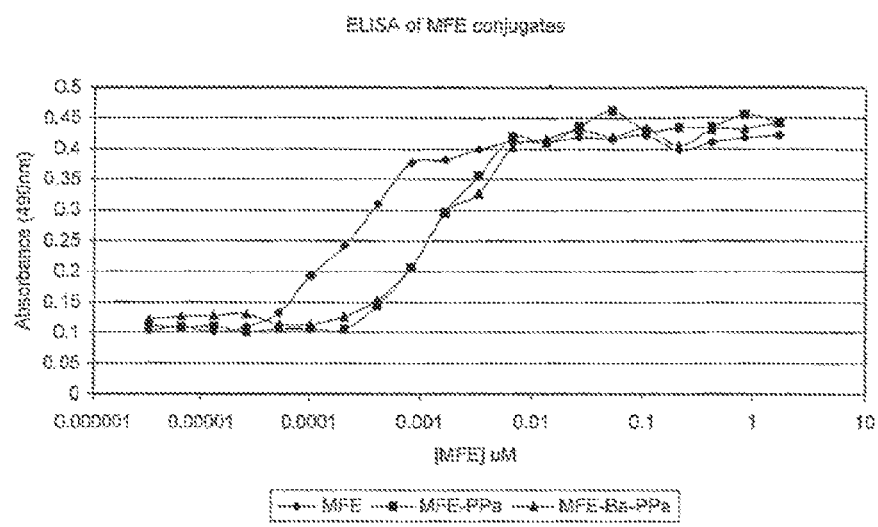

FIG. 13—CEA antigen ELISA of MFE-23 scFv, MFE-23 scFv-PPa and MFE-23 scFv-PPa/Ba. A small decrease in binding affinity is observed upon coupling.

Figure 14:
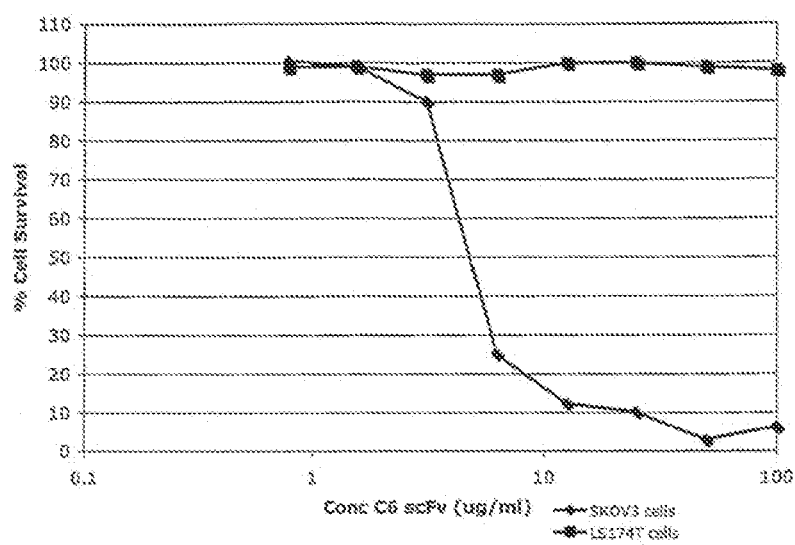

FIG. 14—In vitro PDT cell killing of C6.5 scFv-PPa on antigen-positive cells (SKOV-3) and antigen negative cells (LS174T).

Figure 15:
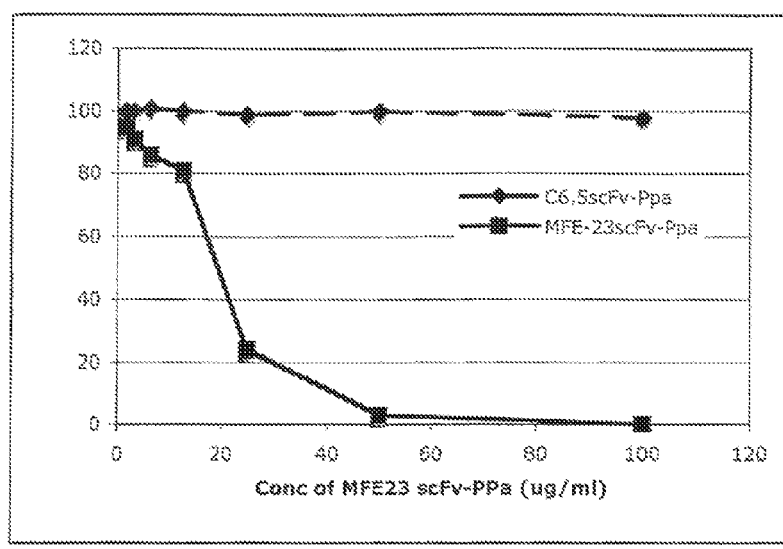

FIG. 15—In vitro PDT cell killing of C6.5 scFv-PPa on antigen-positive cells (LS174T) and antigen negative cells (SKOV-3).

Figure 16:
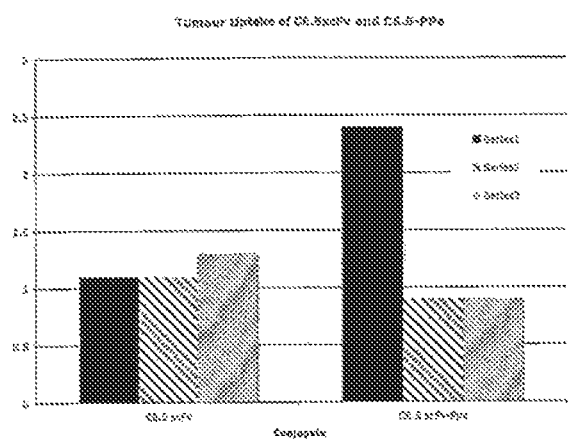

FIG. 16—In vivo tumour:blood ratios of C6.5 scFv compare to C6.5-PPa conjugate after 24 hr in a SKOV-3 human tumour xenograft model (upper) and percentage tumour uptake after 24 hr (lower)

Figure 17:
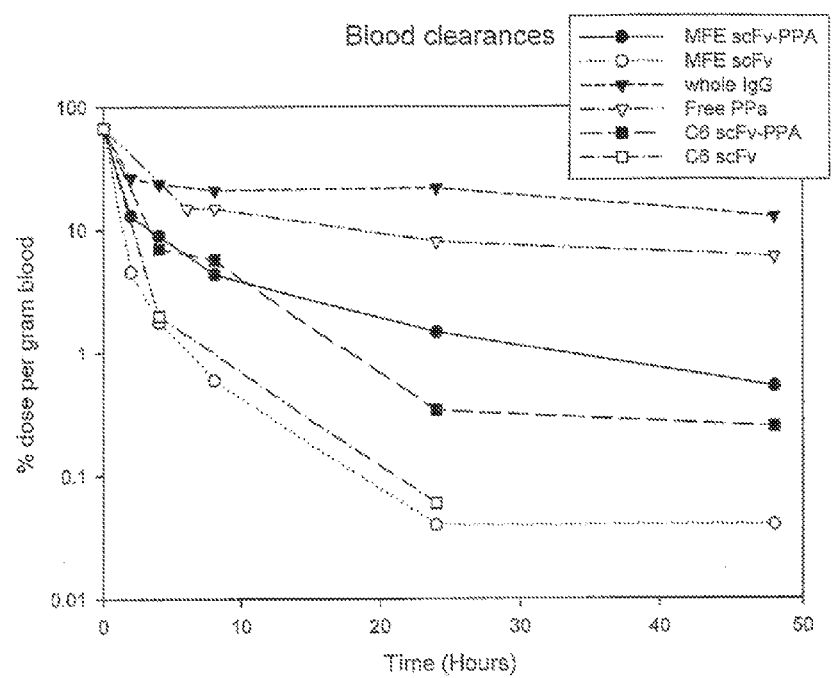
Figure 18:
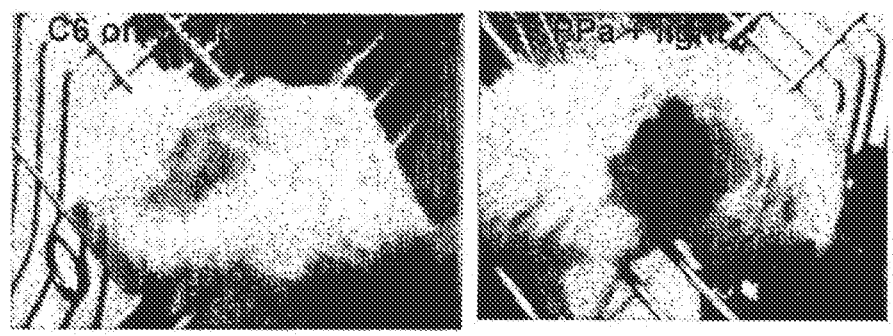

FIG. 17—In vivo pharmacokinetics (blood clearance profiles) of scFvs and scFv-Ppa conjugates in nude mice FIG. 18—In vivo PDT therapy of tumour-bearing nude mice results in necrosis of a human SKOV-3 xenografted tumour. Left panel, C6.5 alone plus light, right panel, C6.5-PPa plus light FIG. 19—Alignment of an optimal 'PDT' scFv such as C6.5 (a VH1-VK3 scFv) with HuBC-1 reveals changes which can be made by mutagenesis. [SEQ. ID NO. 778]-[SEQ. ID NO. 781] These 6 changes are made which can result in a HuBC-1 scFv (BC-1-mut) with more favourable photosensitiser coupling properties. These changes are K13Q, Q43K, T87K, R152K, R180K and G210K).

Figure 20:
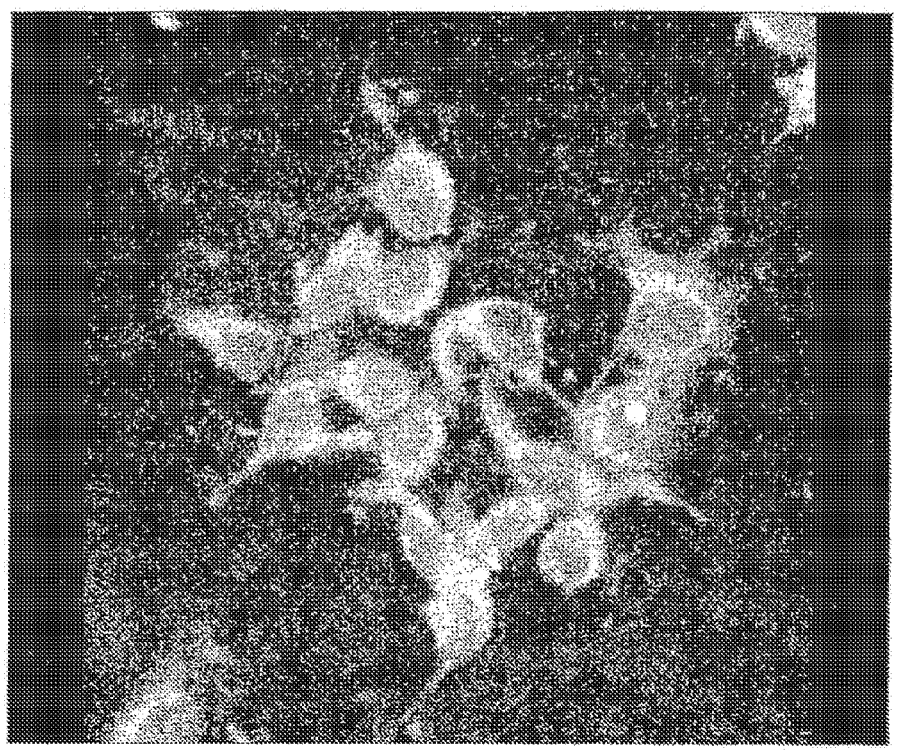

FIG. 20—SKOV3 cells labelled with C6.5scFV-PPa allows the sensitive visualization of the Her-2 receptor which is seen to effectively internalised.

Figure 21:
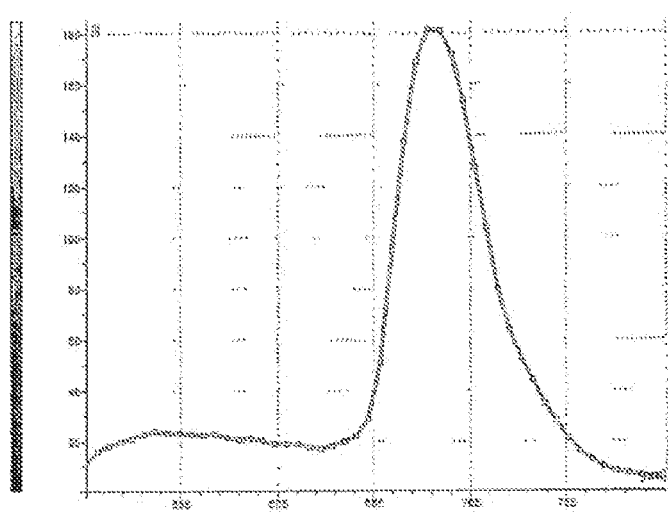

FIG. 21—Emission spectrum of PPa from SKOV-3 cells.

Figure 22:
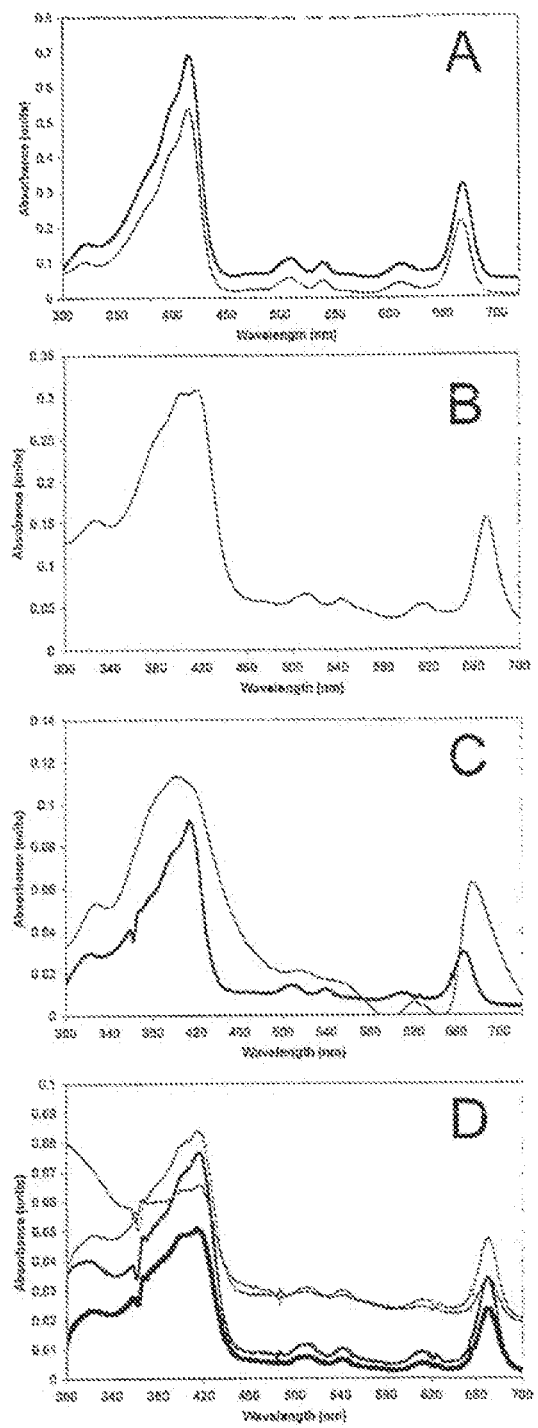

FIG. 22—Absorbance spectra of PPa and scFv-PPa photo-immunoconjugates (A) PPa (14 mg/ml) in PBS/1.9% DMSO [1] and 100% DMSO [2]. (B) 50 mg/ml of C6.5-PPa (C) 10 mg/ml each of MFE-PPa from frozen material [1] and fresh material [2]. (D) A panel of alternative scFv-PPa photo-immunoconjugates all at 10 mg/ml, D1.3 [1], F1 [2], GP6 [3], and HuBC-1 [4].

Figure 23:
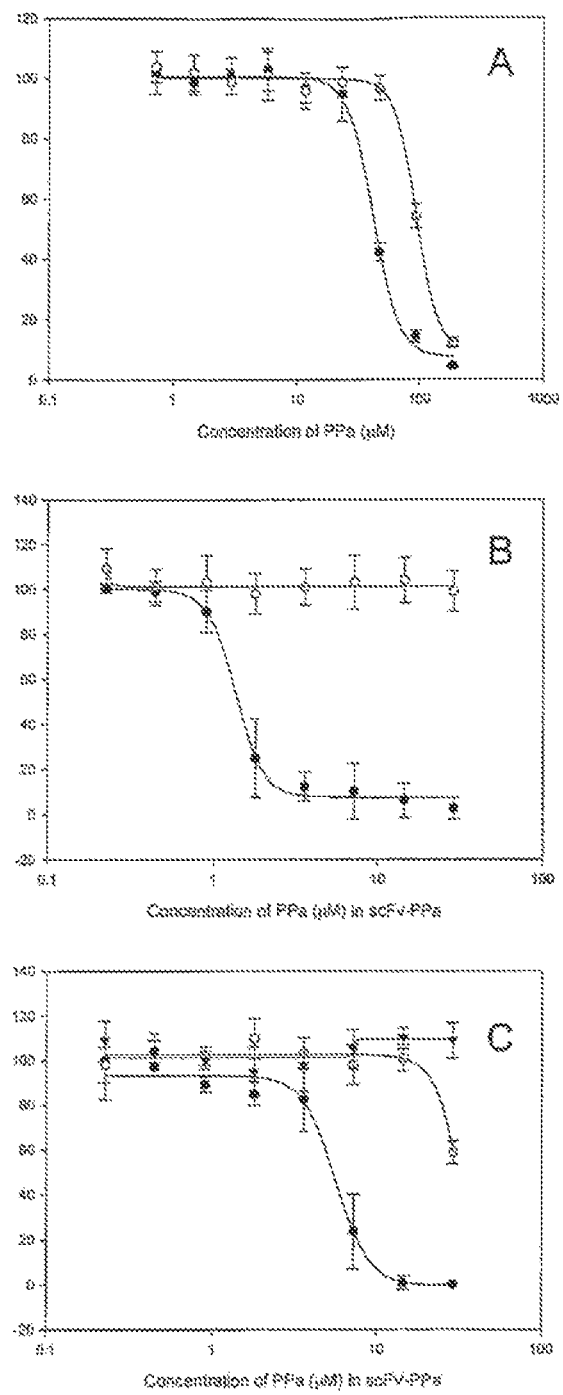

FIG. 23—In vitro cytotoxicity of C6.5-PPa and MFE-PPa photo-immunoconjugates
(A) LoVo (●), SKOV3 (○) exposed to free PPa (B) C6.5-PPa exposed to SKOV3 cells (●) and LoVo cells (○) (C) MFE scFv (fresh material)-PPa exposed to LoVo cells (●), MFE scFv (frozen material)-PPa exposed to LoVo cells (○), MFE scFv (fresh material)-PPa exposed to SKOV3 cells (▼)

Figure 24:
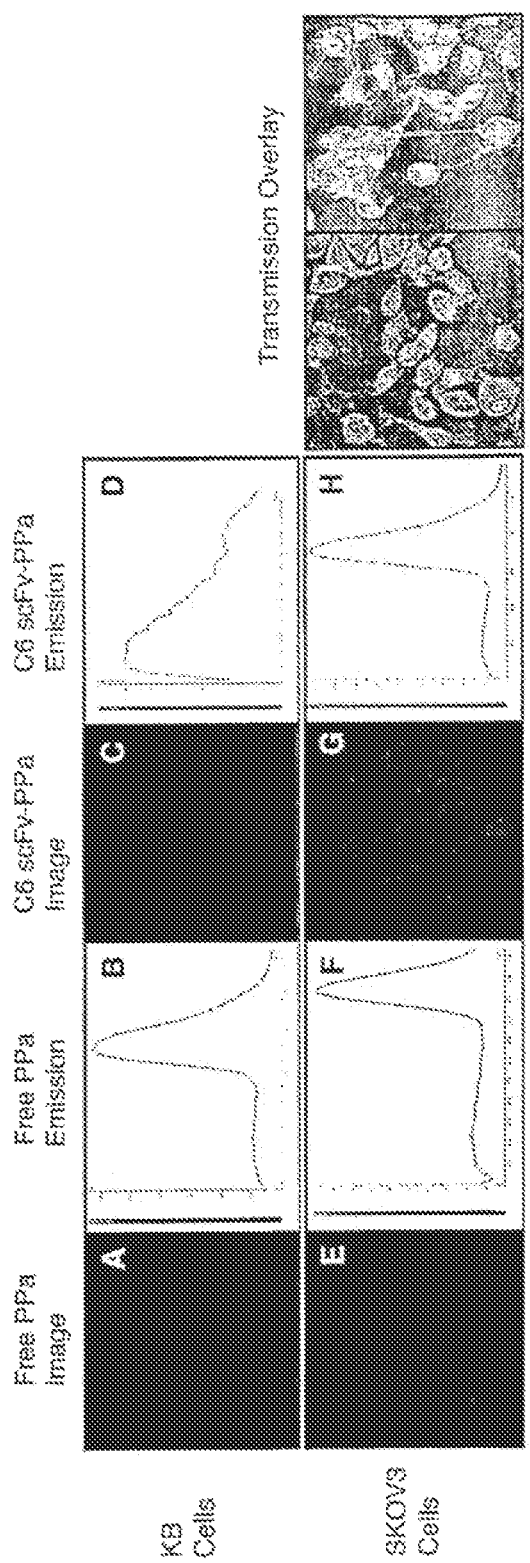

FIG. 24—Immunofluorescent microscopy of C6.5-PPa photo-immunoconjugate Antigen negative KB cells (A-D) or antigen positive SKOV3 cells (E-J) were incubated with free PPa or C6.5-PPa photo-immunoconjugate for 1 hour. Images and emission spectra were recorded.

Figure 25:
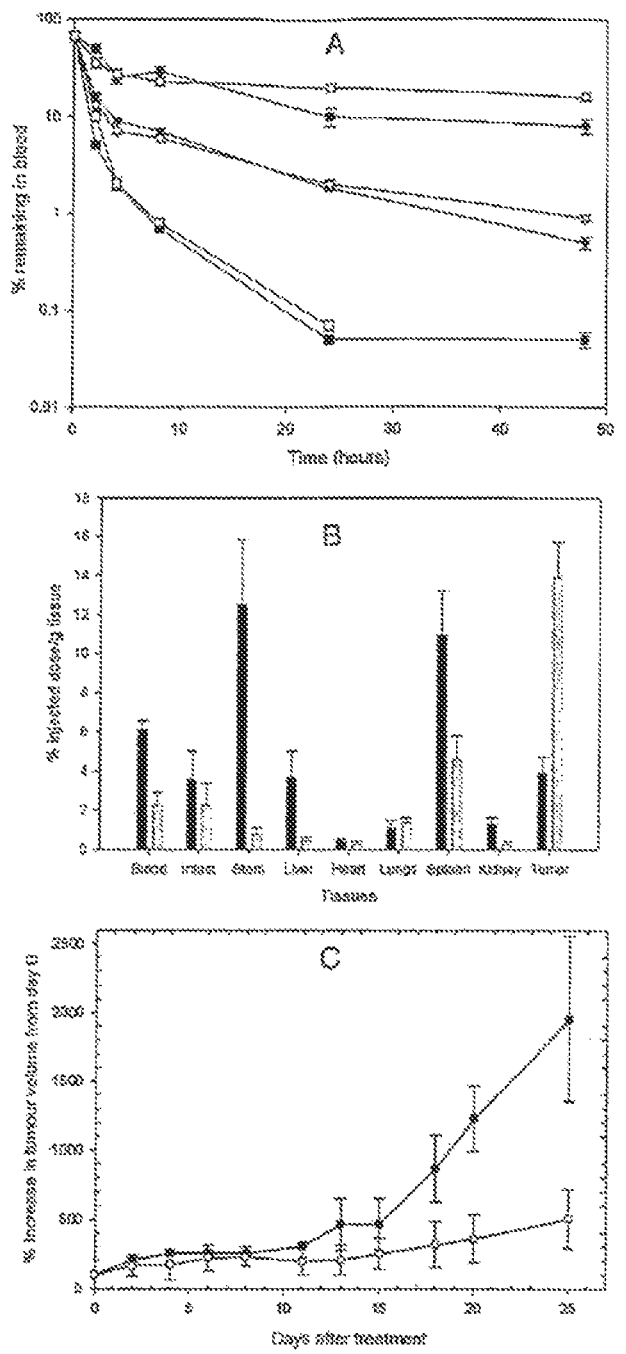

FIG. 25—in vivo analyses of C6.5-PPa PICs
(a) Blood pharmacokinetics—the fraction remaining in the blood over a period of 24 hr was measured for antibodies, PPa and photo-immunoconjugates. Whole IgG (○), free PPa (●), C6.5-PPa (Δ), MFE-PPa (▼), free C6.5 scFv (□), free MFE scFv (■)
(b) Biodistribution of the C6.5 scFv-PPa PIC in tumor-bearing nude mice at 8 hr (black bars) and 24 hr (grey bars). The tumor:blood ratio at 24 hr was chosen as a good value to perform the therapy study.
(c) Two sets of SKOV3 tumor-bearing nude mice were treated with PBS-saline (●) and 40 mg C6.5-PPa photo-immunoconjugate (○) followed by laser illumination. The tumor growth progress was recorded for the following 25 days. Significant growth delay was seen (p=0.0075).

FIG. 26—Amino acid alignment of scFvs The variable heavy-linker light domains are shown with lysine residues highlighted in bold to illustrate the variability in number and position which may influence PDT coupling efficiency and photo-immunoconjugate potency. [SEQ. ID NO. 781]-[SEQ. ID NO. 801]

Figure 27:
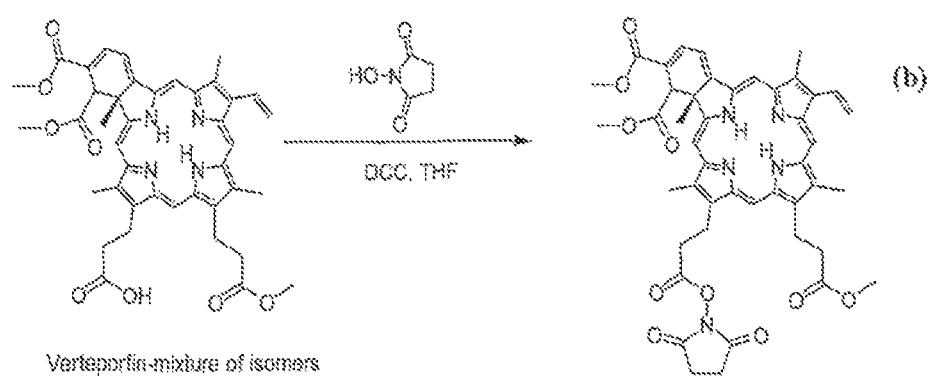

FIG. 27—Preparation of Verteporfin (Visudyne™) succinimidyl ester

Figure 28:
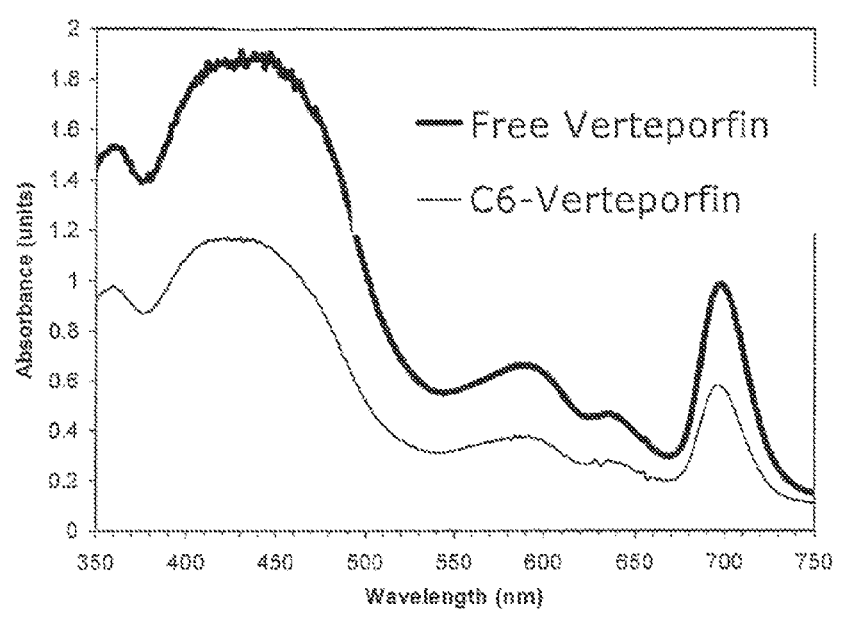

FIG. 28—Absorbance profiles of various concentrations of C6.5 scFv-Verteporfin (Visudyne™) conjugate and free Verteporfin (Visudyne™) measured in PBS buffer.

Figure 29:
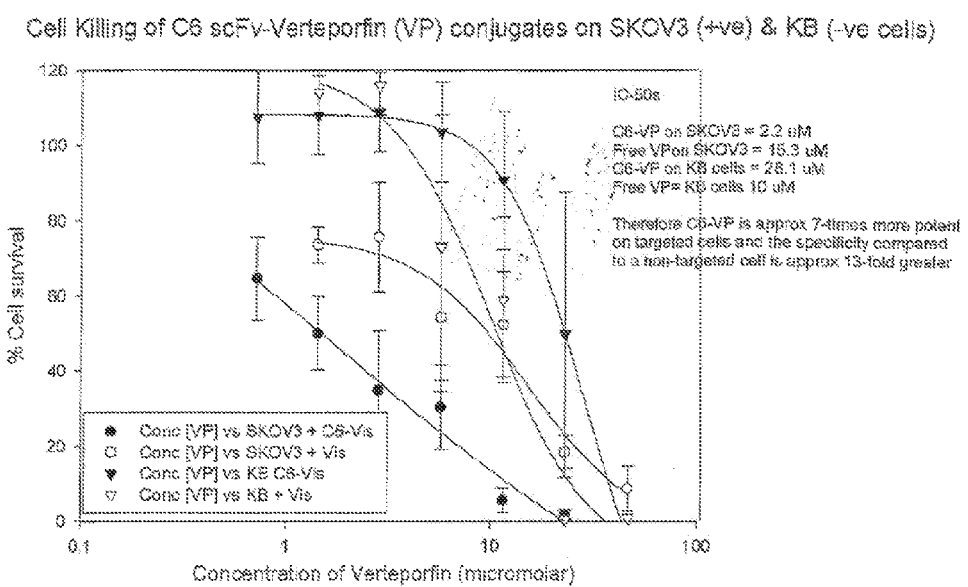

FIG. 29—In vitro PDT cell killing of C6.5 scFv-Verteporfin (Visudyne™) conjugate and free Verteporfin (Visudyne™) on antigen-negative cells (KB) and antigen-positive cells (SKOV-3). Percentage (%) cell survival was determined for:
C6.5 scFv-Verteporfin (Visudyne™) conjugate on SKOV3 cells (●);
free Verteporfin (Visudyne™) on SKOV3 cells (○);
C6.5 scFv-Verteporfin (Visudyne™) conjugate on KB cells (▼);
free Verteporfin (Visudyne™) on KB cells (Δ).

MATERIALS

All chemicals were purchased from Sigma-Aldrich UK unless stated. PPa was from Frontier Scientific, UK, C6.5 scFv was a gift from Prof. Marks (University of California, San Francisco, USA), MFE-23 scFv was a gift from Dr Chester (Royal Free Hospital, University College London, UK), HuBC-1 scFv was a gift from Antisoma Research Ltd (London, UK). Molecular biology reagents and bacteria were from Stratagene, Human cell lines were from the ECACC, UK, Chromatography media was from Amersham Biosciences, UK, Mice were from Harlan, UK, Light sources were from Phototherapeutics, UK and High Powered Devices, New Jersey, USA

Example 1

Preparation of an Anti-Her 2 scFv

1. A chosen, well characterised, anti-cancer scFv for example c6.5 (anti-Her2) was PCR amplified and cloned as an Nco I/Not I fragment into the bacterial expression vector (e.g. pET20b, Novagen) to create pETC6.5scFv (FIG. 3).
2. The vector pETc6.5scFv was transformed into *E. coli* BL21 (DE3) (Novagen) by the calcium chloride method (Sambrook et al, 1990) and plated onto 2TY agar plates containing 100 mg/ml ampicillin (Sambrook et al, 1990). Single colony transformants were picked and re-streaked onto fresh 2TY Agar plates containing ampicillin.
3. A single colony was picked and grown in 5 ml of 2TY media containing 100 mg/ml ampicillin at 30° C., in a shaking incubator (250 rpm) for 8-16 hr. This culture was then used to inoculate a culture of 500 ml 2TY media containing 100 mg/ml ampicillin and grown under similar conditions for a further 3-16 hr.
4. The culture supernatant was harvested and concentrated using an Amicon ultrafiltration stirred cell with a 30 KDa cut-off membrane to a final volume of 10 ml. Alternatively, the bacterial periplasm can be prepared using the sucrose osmotic shock method in a volume of 10 ml.
5. The concentrated supernatant or periplasmic extract was dialysed for 16 hr against 5 L of phosphate-buffered saline (PBS) containing 0.5 M NaCl and 2 mM $MgCl_2$. This was then applied to a copper (II) or nickel (II)-charged chelating sepharose column (Amersham-Pharmacia Biotech) and purified by immobilised metal affinity chromatography (IMAC) for example as described in [14]. The recombinant protein eluted in an imidazole gradient at between 40 and 150 mM imidazole (FIG. 4).
6. The eluted fusion protein is further purified by gel filtration on a superdex-75 column (Amersham-Pharmacia Biotech) equilibrated in PBS. The resulting protein is called c6.5 scFv.

Example 2

Preparation of PPa Succinimidyl Ester (FIG. 5)

1. To a light protected solution of the pyropheophorbide a (50 mg, 0.094 mmol) in a mixture of dry DCM/THF (9:1) N-hydroxysuccinimide (12.9 mg, 0.11 mmol) was added followed by dicyclohexylcarbodiimide (DCC) (23.2 mg, 0.11 mmol).
2. After stirring for 12 h, the precipitated dicyclohexylurea was filtered off and the solvents removed. The crude product was taken up in a small volume of chloroform and precipitated by the addition of hexane. The precipitate was collected, washed well with hexane and the resulting crude product purified by column chromatography on silica gel eluting with 2% hexane in ethyl acetate ($R_f$ 0.66).
3. The isolated product was recrystallised from DCM/hexane to give pure pyropheophorbide a succinimidyl ester (1) in 70% yield. MS (FAB$^+$) 631 (M$^+$, 100%)
4. A stock solution of C6.5 scFv at 500 μg/ml was defrosted at room temperature and 200 μl added to 706 μl of PBS. Acetonitrile (60 μl) was added to the solution. The solution was stirred on ice until cool.

Example 3

Conjugation of c6.5 scFv to PPa—Solvent System 1

1. Pyropheophorbide a succinimidyl ester made up in 100% DMSO was then added (34 μl) from a stock solution of 1.58 mM to the C6.5 scFv with continuous stirring (to give 16 equivalents of PPa). The mixture was kept on ice and in the dark, with stirring for 30 mins, after which time the solution was placed in dialysis tubing and dialysed against 5 L of PBS at 4° C. overnight in the dark.
2. Each sample of the conjugate was placed in a quartz cuvette and an absorbance profile was run against a blank containing PBS (FIG. 6). The absorbance value at 410 nm was measured and the concentration of PS in g/ml was determined by comparing to a standard curve of PPa.
3. For example, if the concentration of PPa found in the coupling reactions was 0.0000159 g/ml. The number of molecules of PPa in 0.0000159 g/ml was $1.4 \times 10^{16}$. The number of molecules of C6 in 100 ug/ml was $2 \times 10^{15}$. The ratio therefore of PPa:C6.5 was 8:1.

Example 4

Conjugation of MFE-23 (anti-CEA) scFv to PPa—Solvent System 2

1. A stock solution of MFE-23 at 500 μg/ml was defrosted at room temperature and 200 μl added to 706 μl of PBS. Acetonitrile (60 μl) was added to the solution. The solution was stirred on ice until cool.
2. Pyropheophorbide a succinimidyl ester was then added (34 μl) from a stock solution of DMSO 1.58 mM to the MFE-23 with continuous stirring (to give 16 equivalents of PPa). The mixture was kept on ice and in the dark, with stirring for 30 mins, after which time the solution was placed in dialysis tubing and dialysed against 5 L of PBS at 4° C. overnight in the dark.
3. Each sample of the conjugate was placed in a quartz cuvette and an absorbance profile run against a blank containing PBS (FIG. 7). The absorbance value at 410 nm was measured and the concentration of PS in g/ml determined by comparing to a standard curve of PPa. For example, if the concentration of PPa found in the coupling reactions was 0.0000129 g/ml. The number of molecules of PPa in 0.0000129 g/ml was $1.4 \times 10^{16}$. The number of molecules of MFE in 100 ug/ml was $2 \times 10^{15}$. The ratio therefore of PPa:MFE-23 was 6:1

Example 5

Preparation of PB1 Succinimidyl Ester (FIG. 8)

1. To a light-protected solution of the benzoic acid derivative of PB1 (20 mg, 0.01136 mmol) in anhydrous THF, N-hydroxysuccinimide (2 mg, 0.017 mmol) was added followed by dicyclohexylcarbodiimide (DCC) (3.5 mg, 0.017 mmol). After stirring for 12 h, the precipitated dicyclohexylurea was filtered off and the solvents removed. The resulting crude product was purified by column chromatography on silica gel eluting with THF (Rf 0.79) to give the desired compound (2) as dark-green solid in 65% yield. MS (FAB$^+$) 1860 (M+2, 80%).

Example 6

Conjugation of c6.5 scFV to PB1—Solvent System 1

1. A stock solution of C6.5 at 500 μg/ml was defrosted at room temperature and 200 μl added to 706 μl of PBS. Acetonitrile (60 μl) was added to the solution. The solution was stirred on ice until cool.
2. PB1 (see [94]) made up in 100% DMSO was then added (34 μl) from a stock solution of 1.58 mM to the C6.5 with continuous stirring (to give 16 equivalents of PB1). The mixture was kept on ice and in the dark, with stirring for 30 mins, after which time the solution was placed in dialysis tubing and dialysed against 5 L of PBS at 4° C. overnight in the dark.
3. Analysis of conjugate. Each sample of the conjugate was placed in a quartz cuvette and an absorbance profile was run against a blank containing PBS. The absorbance value at 460 nm was measured and the concentration of PS in g/ml was determined by comparing to a standard curve of PB1.

Example 7

Coupling of BA Modulator to a scFv or scFv-PPa Conjugate

1. A stock solution of MFE-23 at 500 μg/ml was defrosted at room temperature and 200 μl added to 690.8 μl of PBS. Acetonitrile (60 μl) was added to the solution.
2. The solution was stirred and 15.2 ul of 0.491 μM solution of the benzoyl succinimidyl ester (prepared by the reaction of benzoic acid with N-hydroxysuccinimide and DCC in dry dichloromethane), dissolved in DMSO was added (to give 16 equivalents of benzoic acid). The solution was stirred at room temperature for 30 minutes, after which time, the flask was cooled on ice with continuous stirring.
3. Pyropheophorbide a succinimidyl ester made up in 100% DMSO was then added (34 μl) from a stock solution of 1.58 mM (to give 16 equivalents of PPa). The mixture was kept on ice and in the dark, with stirring for 30 mins, after which time the solution was placed in dialysis tubing and dialysed against 5 L of PBS at 4° C. overnight in the dark.
4. Each sample of the conjugate was placed in a quartz cuvette and an absorbance profile run against a blank containing PBS (FIG. 7). The absorbance value at 410 nm was measured and the concentration of PS in g/ml determined by comparing to a standard curve of PPa. For example, if the concentration of PPa found in the coupling reactions was 0.0000129 g/ml. The number of molecules of PPa in 0.0000129 g/ml was $1.4 \times 10^{16}$. The number of molecules of MFE in 100 ug/ml was $2 \times 10^{15}$. The ratio therefore of PPa:MFE-23 was 6:1

Example 8

Conjugation of HuBC-1 scFv to PPa (a Poor scFv for PDT)

1. To a light protected solution of the pyrppheophorbide a (50 mg, 0.094 mmol) in a mixture of dry DCM/THF (9:1) N-hydroxysuccinimide (12.9 mg, 0.11 mmol) was added followed by dicyclohexylcarbodiimide (DCC) (23.2 mg, 0.11 mmol).
2. After stirring for 12 h, the precipitated dicyclohexylurea was filtered off and the solvents removed. The crude product was taken up in a small volume of chloroform and precipitated by the addition of hexane. The precipitate was collected, washed well with hexane and the resulting crude product purified by column chromatography on silica gel eluting with 2% hexane in ethyl acetate ($R_f$ 0.66).
3. The isolated product was recrystallised from DCM/hexane to give pure pyropheophorbide a succinimidyl ester (1) in 70% yield. MS (FAB$^+$) 631 (M$^+$, 100%)
4. A stock solution of HuBC-1 scFv at 500 µg/ml was defrosted at room temperature and 200 µl added to 706 µl of PBS. Acetonitrile (60 µl) was added to the solution. The solution was stirred on ice until cool.
5. Pyropheophorbide a succinimidyl ester made up in 100% DMSO was then added (34 µl) from a stock solution of 1.58 mM to the HuBC-1 scFv with continuous stirring (to give 16 equivalents of PPa). The mixture was kept on ice and in the dark, with stirring for 30 mins, after which time the solution was placed in dialysis tubing and dialysed against 5 L of PBS at 4° C. overnight in the dark.
6. Each sample of the conjugate was placed in a quartz cuvette and an absorbance profile was run against a blank containing PBS (FIG. 9). The absorbance value at 410 nm was measured and the concentration of PS in g/ml was determined by comparing to a standard curve of PPa.
7. The low absorbance peak at 410 nm means that it was not possible to determine the degree of PPA coupling.

Example 9

Conjugation of C6.5 scFv to Chlorin (e6)

Figure 10:
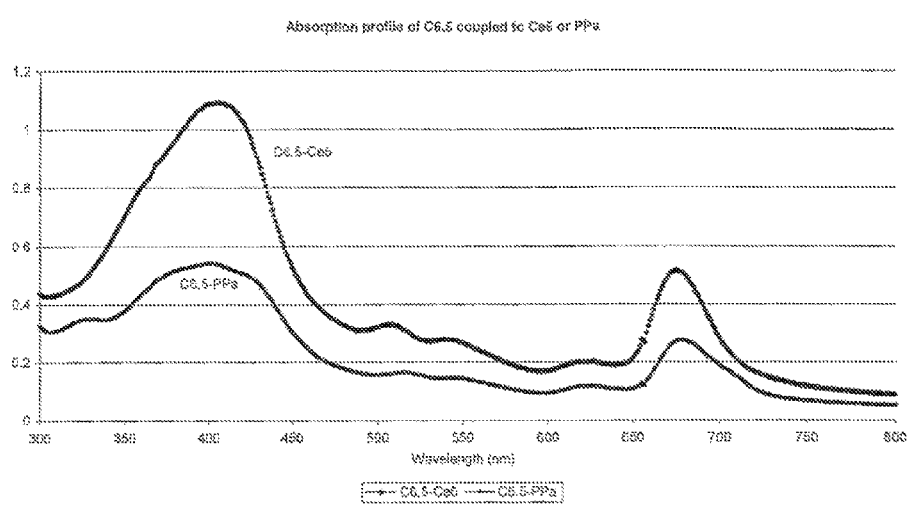
Figure 11:
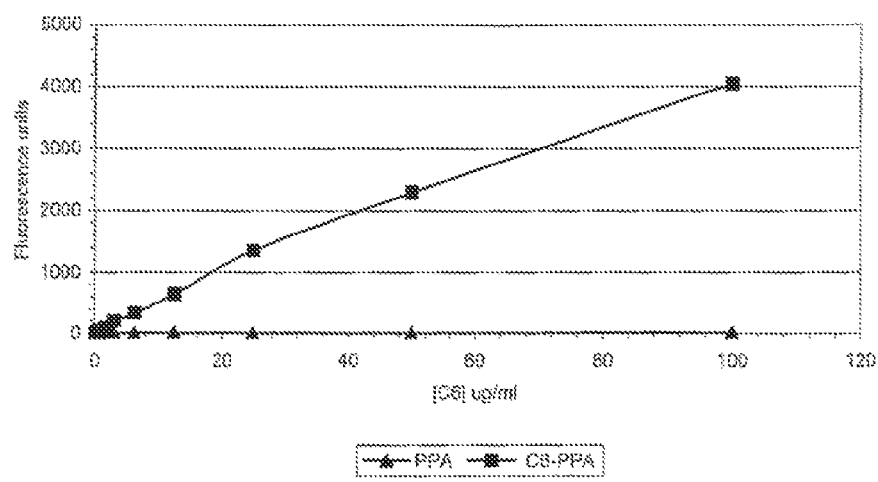

1. To a light-protected solution of chlorin e6 (0.00184 mmol) in anhydrous DMF equimolar amounts of both N-hydroxysuccinimide and dicyclohexyl carbodiimide were added and the mixture stirred for 12 h under argon.
2. The resulting mixture was briefly cooled in ice-water and then filtered to remove the dicyclohexyl urea by-product and evaporated to dryness to give the chlorin e6 succinimidyl ester as a dark-green-solid.
3. A stock solution of C6.5 scFv at 500 µg/ml was defrosted at room temperature and 200 µl added to 706 µl of PBS. Acetonitrile (60 µl) was added to the solution. The solution was stirred on ice until cool.
4. Chlorin e6 succinimidyl ester made up in 100% DMSO was then added (34 µl) from a stock solution of 1.58 mM to the C6.5 scFv with continuous stirring (to give 16 equivalents of Ce6). The mixture was kept on ice and in the dark, with stirring for 30 mins, after which time the solution was placed in dialysis tubing and dialysed against 5 L of PBS at 4° C. overnight in the dark.
5. Each sample of the conjugate was placed in a quartz cuvette and an absorbance profile was run against a blank containing PBS (FIG. 10). The absorbance value at 410 nm was measured and the concentration of PS in g/ml was determined by comparing to a standard curve of Ce6.
6. For example, if the concentration of Ce6 found in the coupling reactions was 0.000034 g/ml. The number of molecules of Ce6 in 0.000034 g/ml was 3.43×10$^{16}$. The number of molecules of C6 in 100 ug/ml was 2×10$^{15}$. The ratio therefore of Ce6:C6.5 was 9:1.

Example 10

Conjugation of C6.5 scFv to a Hydrazine Derivative of PPa

1. Preparation of the Hydrazide Derivative of PPa. The propionic acid side chain of pyropheophorbide a was converted to the acyl chloride by standard literature procedures (oxally chloride in DCM). The acid chloride was obtained as a sticky green residue and used without further purification.
2. A solution of the acid chloride in anhydrous DCM was added drop-wise to an excess of 98% hydrazine in anhydrous DCM, the reaction was monitored by TLC and was over in less than 1 h. The excess solvent and reagent was evaporated and the residue purified by chromatography. A stock solution of the PPa hydrazide was then made up in DMSO.
3. A scFv, e.g. C6.5 was engineered to possess carbohydrate chains as follows: Site-directed mutagenesis was used to incorporate N-linked glycosylation sites across the surface of the scFv, at positions which are all well-separated, according to the concept already described for Lysine residue spacing. This clone was placed in an expression vector suitable for a host cell which can carry out glycosylation (e.g. pPIC vector for expression in *Pichia pastoris* yeast).
4. The scFv was expressed and purified according to the manufacturer's instructions, using NTA-Nickel chromatography.
5. The derivatized PPa was coupled to the aldehyde residues on the glycosylated scfv. Coupling to the aldehyde residues proceed rapidly in buffered environments with the formation of a hydrazone linkage.

Example 11

Photophysical Characterisation of a scFV-PPa Conjugate

1. Serial dilutions (halving concentrations) of the conjugates were made in PBS and the fluorescence was measured at an excitation wavelength of 410 nm and an emission wavelength of 680 nm.
2. These were compared to free PPa in PBS. Examples are shown for c6.5 scFv-PPa (FIG. 11) and MFE scFv-PPA (+/− benzoic acid) (FIG. 12)

Example 12

Biochemical characterisation of a scFV-PPa and scFv-PPa/BA Conjugate

1. In vitro binding characteristics of the anti-CEA scFv-PPa molecule was carried out by ELISA (Lane, 1990) or by BIACore surface plasmon resonance using published methods Lipschultz et. al. 'Experimental Design For Analysis of Complex Kinetics Using Surface Plasmon Resonance' Methods (2000) 20, 3180, compared to the unmodified scFv. Cell binding of the scFv-PPa/BA can also be compared to the unmodified proteins can be determined by Fluorescently Activated Cell Sorting (FACS), Confocal fluorescence microscopy.
2. As an example, a 96-well ELISA plate was coated with 1 µg/ml carcinoembryonic antigen (CEA) in PBS and incubated overnight at 4° C. The next day the plate was washed three times in PBS-0.1% tween and three times PBS.
3. The ELISA plate was then incubated in blocking buffer (10% Marvel™ in PBS-0.1% tween) for 60 min at 37° C.
4. The blocking buffer was removed from the wells and 50 µl of conjugate or unconjugated MFE diluted in blocking buffer to give halving dilutions of MFE from 100-1.9×10⁴ µg/ml was added to each well. The plate was incubated as above and the wells washed as described above.
5. Primary antibody (50 µl, rabbit anti-MFE; diluted in blocking buffer at 1:40 000) was added into each well. The plate was incubated and washed as described above.
6. Secondary antibody (50 µl, anti-rabbit horse-radish peroxidase conjugate; diluted in blocking buffer at 1:10 000) was added to each well. Plates were incubated and washed as above. BM blue (50 µl) was added to each well and incubated at room temperature, in the dark, until a blue colour developed.
7. The reaction was stopped by adding 50 µl of 0.5M hydrochloric acid. Samples were then read at 460 nm (FIG. 13).

Example 13

In vitro Cytotoxicity of a c6.5 scFv-PPa Conjugate

1. In vitro cell cytotoxicity was be measured as followed: The target cells (in this example LoVo and LS17T) were maintained at 37° C., 5% $CO_2$ in media (DMEM) supplemented with 10% foetal calf serum and 5 mM penicillin/streptomycin in a 75 cm² flask. For SkoV3 cells, the medium used was McCoy's 5A medium supplemented with 15% FBS, 5 mM penicillin/streptomycin.
2. When 70-80% confluent, the cells were washed in PBS and 5 ml trypsin added. The flask was incubated at 37° C., 5% $CO_2$ for 15 mins or until the cells had detached from the flask. The cells were then placed in a 50 ml Falcon tube and the trypsin deactivated by adding 15 ml DMEM or McCoy's medium.
3. Cells (20 µl) were taken out of the tube and placed on a haemocytometer for counting. The remaining cells were harvested at 1800 g for 10 min at room temperature and the pellet gently resuspended in 1 ml of DMEM or McCoy's medium. The cells were thoroughly resuspended and a further 19 ml of DMEM or McCoy's medium added. The cells were diluted in DMEM or McCoy's medium accordingly to give 2×10⁶ cells/ml. Cells (50 µl) were then added to each well of a 96 well plate and incubated overnight at 37° C. and 5% $CO_2$.
4. The following procedure was carried out in subdued lighting: The next day, the conjugate was diluted in PBS to give C6.5 concentrations equivalent to 100, 50, 25, 12.5, 6.25, 3.125, 1.56 and 0.78 µg/ml. Cells were washed once with PBS and 50 µl of the conjugate added to wells in quadruplicate. Control wells were also included (wells with conjugate added but not exposed to light, and wells with neither conjugate added nor exposed to light). It was ascertained in previous experiments that laser light alone had no affect on the cell viability, so no 'light alone' controls are included unless the light source, or energy dose of the light is changed.
5. Cells were incubated in the conjugate or free PS (concentration varies) for 30 min at 37° C., 5% $CO_2$ and then washed 3 times with PBS. PBS (50 µl) was added to each well and quadruplicate wells exposed to laser light for 2 min (energy dose=4.2 J; energy density=1.4 J/cm²).
6. The PBS was removed from each well and 100 µl of DMEM or McCoy's medium added. The plates were loosely wrapped in foil, but covered adequately so that no ambient light could enter. The plates were then incubated as above for 48 hours, after which time a cell kill assay was carried out.
7. Cell kills assays were carried out using the Cytotox-96 kits (according to the Promega protocol). Cells were washed 3 times with PBS and 50 µl of cell lysis solution added. Plates were incubated for 60 minutes at 37° C. in the dark. After this time, 50 µl of substrate solution was added (which indicates the amount of lactate dehydrogenase in cells). This was incubated at room temperature for 30 min, after which time, 50 µl of stop solution (0.5M acetic acid) was added. The cell suspensions were removed from the wells and placed in a fresh microtitre plate. The absorbance was then measured at 490 nm in a microtitre plate reader.
8. Cell kills were determined and expressed as a percentage of controls (FIG. 14).

Example 14

In Vitro Cytotoxicity of a MFEscFv scFv-PPa/BA Conjugate

1. In vitro cell cytotoxicity was be measured as followed: The target cells (in this example, LoVo, LS17T or Skov3) were maintained at 37° C., 5% $CO_2$ in media (DMEM) supplemented with 10% foetal calf serum and 5 mM penicillin/streptomycin in a 75 cm² flask. For SkoV3 cells, the medium used was McCoy's 5A medium supplemented with 15% FBS, 5 mM penicillin/streptomycin.
2. When 70-80% confluent, the cells were washed in PBS and 5 ml trypsin added. The flask was incubated at 37° C., 5% $CO_2$ for 15 mins or until the cells detached from the flask. The cells were then placed in a 50 ml Falcon tube and the trypsin deactivated by adding 15 ml DMEM or McCoy's medium.
3. Cells (20 µl) were taken out of the tube and placed on a haemocytometer for counting. The remaining cells were harvested at 1800 g for 10 min at room temperature and the pellet gently resuspended in 1 ml of DMEM or McCoy's medium. The cells were thoroughly resuspended and a further 19 ml of DMEM or McCoy's added. The cells were diluted in DMEM or McCoy's medium accordingly to give 2×10⁶ cells/ml. Cells (50 µl) are then added to each well of a 96 well plate and incubated overnight at 37° C. and 5% $CO_2$.
4. The following procedure is carried out in subdued lighting: The next day, the conjugate was diluted in PBS to give MFE concentrations equivalent to 100, 50, 25, 12.5, 6.25, 3.125, 1.56 and 0.78 µg/ml. Cells were washed once with PBS and 50 µl of the conjugate added to wells in quadruplicate. Control wells were also included (wells with conjugate added but not exposed to light, and wells with neither conjugate added nor exposed to light). It was ascertained in previous experiments that laser light alone has no affect on the cell viability, so no 'light alone' controls are included unless the light source, or energy dose of the light is changed.
5. Cells were incubated in the conjugate or free PS (concentration varies) for 30 min at 37° C., 5% $CO_2$ and then washed 3 times with PBS. PBS (50 μl) was added to each well and quadruplicate wells were exposed to laser light for 2 min (energy dose=4.2 J; energy density=1.4 $J/cm^2$).
6. The PBS was removed from each well and 100 μl of DMEM was added. The plates were loosely wrapped in foil, but covered adequately so that no ambient light entered. The plates were then incubated as above for 48 hours, after which time a cell kill assay was carried out.
7. Cell kills assays were carried out using the Cytotox-96 kits (according to the Promega protocol). Cells were washed 3 times with PBS and 50 μl of cell lysis solution added. Plates were incubated for 60 min at 37° C. in the dark. After this time, 50 μl of substrate solution was added (which indicates the amount of lactate dehydrogenase in cells). This was incubated at room temperature for 30 min, after which time, 50 μl of stop solution (0.5M acetic acid) was added. The cell suspensions were removed from the wells and placed in a fresh microtitre plate. The absorbance was then measured at 490 nm in a microtitre plate reader.
8. Cell kills were determined and expressed as a percentage of controls (FIG. 15).

Example 15

In Vivo Targeting of a scFv-PPa Conjugate

1. In vivo tumour eradication can be demonstrated as follows: Approx 1×10⁷ SKOV-3 cells was injected s.c. into the flank of a nude BALB/C mouse and tumours are allowed to establish for 4-6 weeks.
2. Ten-50 μg of 125-Iodine radiolabelled (using Iodogen method, Pierce Chemical Co.) scFv-PPa was injected i.v. into the tail vein of tumour-bearing mice and allowed to accumulate in the tumour over a period of 1-48 hrs.
3. Groups of three or more mice from each time point analysed were culled under terminal anaesthesia, dissected and the tumour, blood and various organs were analysed for uptake of the scFv-PPa. Control experiments with PPa alone and scFv are carried out.
4. As an example, the tumour targeting of c6.5-PPa is shown compared to the scFv and PPa alone in FIG. 16. The blood circulation time of the hydrophobic photosensitiser was seen to decrease after attaching to a hydrophilic scFv (FIG. 17).

Example 16

In Vivo Photodynamic Therapy of a scFv-PPa Conjugate

1. In vivo tumour eradication can be demonstrated as follows: Approx 1×10⁷ SKOV-3 cells are injected s.c. into the flank of a nude BALB/C mouse and tumours are allowed to establish for 4-6 weeks.
2. Fifty-200 μg of scFv-PPa is injected i.v. into the tail vein of tumour-bearing mice and allowed to accumulate in the tumour over a period of 12-24 hrs.
3. At a time when the tumour:normal organ ratio is high (5:1 or better e.g. 16 hr), light is irradiated onto the tumours at 2.4 W per $cm^2$.
4. The size of the tumours is measured using calipers and compared to mice treated with saline only. The tumours were observed for PDT-induced necrosis (FIG. 18).

Example 17

Engineering a scFv (e.g. HuBC-1) to have Optimised Functional Groups for Photosensitizer Coupling 1. A scFv which has shown in practice to display very poor photophysical properties (such as fluorescence, singlet oxygen generation and in vitro photo-cytotoxicity) is analysed at the primary structure and tertiary structure level. This can be done by amino acid alignment to a scFv which is known to be a good one for coupling to photosensitizers or examination of the three-dimensional structure.
2. Residues which are going to be used to couple with activated photosensitizers are identified, for example lysine residues
3. Ones which are adjacent to each other, either in the primary sequence or topologically from a three-dimensional model (or actual structure) are manipulated by site directed mutagenesis. The alteration can be the introduction of a optimally spaced lysine residue, the removal of a lysine which is too close to another or the replacement of an unwanted lysine with another similar but non-conjugatable residue (such as arginine or glutamine).
4. In this example, the anti-fibronectin scFv HuBC-1 was aligned to c6.5 and lysine positions identified. Six changes were identified (FIG. 10) which converted the lysine positioning to look more like that found in c6.5 (FIG. 19).
5. Each possible change (6 in all in this example) identified is made in the antibody fragment as a single mutation in the antibody gene. Mutagenesis was done using the Stratagene Quick Change system.
6. Each mutant antibody from (4) is tested to see whether any of the antibody properties have been altered or destroyed upon mutagenesis. Expression of the antibody protein in the host cell (e.g. *E. coli*), purification, antigen binding (by ELISA and BIACore surface plasmon resonance), cell binding (by ELISA, FACS and immunomicroscopy), stability assays (temperature, urea-induced unfolding and serum stability) are all carried out.
7. Mutations which do not significantly alter the stability and function of the antibody are retained, ones which are detrimental are discarded.
8. All the mutations are combined into one antibody gene, forming a protein which has newly positioned lysine residues for optimised photosensitizer coupling.
9. This antibody is used as in Examples 1-11 to make a antibody-photosensitizer conjugate.

Example 18

Antimicrobial Targeting with a scFv-Photosensitizer Conjugate

1. A well-characterised anti-microbial antibody is cloned, expressed and purified using the same techniques as described in Example 1 (above).

2. Photosensitisers are attached as described in Examples 2-5 (above).
3. Anti-bacterial cell killing. Initially a quick method to screen a number of photosensitiser conjugates against a number of bacterial species was carried out. An overnight culture of the bacteria was harvested by centrifugation and resuspended in PBS. The bacterial culture (1 ml) was spread onto an agar plate and allowed to dry for 30 minutes.
4. After this time, 5 ul of the photosensitizer was placed onto the spread bacteria and exposed to light from a laser diode (35 mW, 675 nm) for 2 minutes (energy density=1.4 J/cm$^2$). The plates were incubated overnight at 37° C.
5. The next day, a lawn of bacteria should have grown on the plate except for where the photosensitiser conjugate and light was applied. If bacterial growth was found to occur here, the corresponding photosensitiser conjugate was not investigated further. Those photosensitiser conjugate/bacterial combinations that were found to be successful were further analysed as follows (modified method from [93,94]):
6. An overnight culture of bacteria was harvested and resuspended in PBS. An aliquot (100 ul) of the bacteria was taken and added to wells of a 24-well plate. Then, 100 ul of serially diluted photosensitiser conjugate was added to each well in triplicate. The suspensions were stirred for a specific length of time (usually between 1 and 30 minutes) after which time the bacteria were harvested by centrifugation and washed 4 times with PBS or 0.15M NaCl. Bacterial pellets were resuspended in PBS or 0.15M NaCl and placed into a 24-well plate. Wells were then exposed to light from a laser diode (energy density=1.4 j/cm$^2$). The entire suspension was removed from each well and serially diluted in 2TY broth. An aliquot (25 μl) was removed from each dilution and placed on one half of an agar plate. The suspension was then spread across one half of the agar plate and the plates incubated overnight at 37° C.
7. The following day, the number of colonies present on the plates was counted (i.e. plates that had between 20-200 colonies). Bacterial cell survival was then calculated by comparing to colonies from suspensions that had no photo sensitiser or light treatment.

Example 19

Cellular Imaging of SKOV3 Cells with C6.5 scFv-PPa

1. Round coverslips were washed in ethanol and rinsed in PBS. Coverslips were then placed in 12-well tissue culture plates.
2. SKOV3 cells were trypsinised and washed with PBS. The cell pellet was resuspended in McCoy's media and cells were seeded onto the coverslips at 2×105 cells/ml. The cells were incubated overnight at 37° C. and 5% CO2.
3. The coverslips with the adherent cells were rinsed carefully in PBS and either C6-PPa or PBS was added to the wells. The cells were incubated at 37° C. and 5% CO2 for 30 minutes after which time they were washed carefully with PBS.
4. The cells were fixed onto the coverslips by incubating in 2 ml 4% paraformaldehyde for 60 minutes at room temperature. After this time, the coverslips were washed with PBS and inverted cell-side down onto glass slides. The edges of the coverslips were then sealed using nail varnish.
5. Fluorescence imaging was then performed using an Ar+ laser (418 nm) as excitation source, using a Leica laser scanning confocal microscope, images are shown in FIGS. 20 and 24, and the emission spectrum is shown in FIGS. 21 and 24.

FIGS. 24a & 24e respectively show the HER-2-negative and HER-2-positive cell lines incubated with the same amount of free PPa with corresponding respective emission spectra in FIGS. 24b & 24f. The images and emission spectra show that the KB cells take up the PPa just over 2-fold better than the SKOV3 cells. FIGS. 24c and 24g shows the HER-2-negative and -positive cell lines incubated with C6-PPa (equivalent amount of PPa to FIG. 24a, b, e, f) and the corresponding emission spectra are shown in FIGS. 24d & 24h.

The C6.5 scFv clearly has influenced the targeting of the PPa with very weak fluorescence, not associated with the emission wavelength of PPa, being observed in the KB cells. However strong PPa-based fluorescence is seen in the SKOV3 cell line. The transmission overlays (FIGS. 24i & 24j) show more clearly that the PPa is spread throughout the cell with punctuate, endosomal-like staining.

Example 20

F1, GP6 and D1.3 Antibody Conjugates Compared to C6.5

F1 and GP6 (anti-human placental alkaline phosphatase) and D1.3 (31) were expressed in pHEN2. The expression and purification of all scFvs was the same as described above for C6.5.

Coupling of Pyropheophorbide-a Photosensitizer to scFvs.

Pyropheophorbide-a succinimidyl ester was synthesised for coupling to the scFv as follows. To a light protected solution of the pyropheophorbide-a (50 mg, 0.094 mmol) in a mixture of dry DCM/THF (9:1) N-hydroxysuccinimide (12.9 mg, 0.11 mmol) was added followed by dicyclohexylcarbodiimide (DCC) (23.2 mg, 0.11 mmol).

After stirring for 12 h (at room temperature), the precipitated dicyclohexylurea was filtered off and the solvents removed. The crude product was taken up in a small volume of chloroform and precipitated by the addition of hexane. The precipitate was collected, washed well with hexane and the resulting crude product purified by column chromatography on silica gel eluting with 2% hexane in ethyl acetate (Rf 0.66). The isolated product was re-crystallised from DCM/hexane to give pure succinimidyl ester in 70% yield.

The pyropheophorbide-a succinimidyl ester was resuspended in 100% DMSO and added at a concentration of 52.8 mM to 3.3 mM MFE-23, C6.5 or HuBC1 in PBS containing 6% acetonitrile and with continuous stirring at 40 C for 30 min. The photoimmunoconjugates (PICs) were then dialysed against PBS with one buffer change.

For comparison of C6.5, F1, GP6 and D1.3, the concentrations of all the scFvs were adjusted so as to be the same as GP6 which gave the poorest expression of all the scFvs. The scFvs were coupled to PPa at a concentration of 0.3 mM. There was no precipitation of the protein before coupling and the scFv-PPa conjugate remained soluble at concentrations of 0.5 mg/ml or below.

SDS-PAGE was carried out as described for C6.5 above and stained with coomassie blue. Non-stained gels were transferred using a semi-dry blotting apparatus (Biorad) onto nitrocellulose and gently dried.

Fluorescence was visualised by exciting the PPa on the blot on a short wavelength UV-transilluminator. As an example of a calculation to determine the Ppa:scFv ratio, the absorbance of 65 mg/ml PPa give 1 AU at 670 nm. Thus 0.2 AU is equal to 13 mg/ml PPa which is equal to $2.4 \times 10^{-5}$ M PPa (MW=535). This was found coupled to a scFv at a concentration of 50 mg/ml (see FIG. 1B), which is equal to $1.7 \times 10^{-6}$ M (MW=30,000). The ratio works out to be 14.1:1, which becomes 9.9:1 after correcting for 30% non-covalent binding.

Results

The absorbance profile of free PPa in 100% DMSO and PBS/1.9% DMSO is shown in FIG. 22A. Both show the characteristic peaks around 400 nm (Soret peal), minor peaks between 500-630 nm and the Q-band at 670 nm. FIG. 22B shows the profile for the C6.5 scFv coupled to PPa. The peaks remain sharp and similar to that of free PPa. The absorbance at 670 nm was used to determine the concentration of PPa and used to calculate the PPa:scFv ratio which was 11.92±1 (mean of 5 independent coupling reactions. This gives an effective ratio approximately 8:1 after correction for a small amount (30%) of non-covalent binding. The profile of PPa when attached to the MFE scFv is shown in FIG. 22C.

Four other scFvs were coupled to PPa in order to understand those factors important in obtaining good coupling ratios (FIG. 22D). D1.3 scFv-PPa gives close to the 'ideal' absorbance pattern exemplified by the C6.5 scFv, F1 scFv-PPa is slightly less effective.

However, GP6 scFv-PPa and HuBC-1 scFv-PPa show poor profiles with broadened peaks, indicating possible aggregation. The ratio of PPa:scFv for all scFv coupling experiments are shown in Table 6.

TABLE 6

PPa:scFv coupling ratios

| ScFv | PPa:scFv ratio |
|---|---|
| C6.5 | 8.3 |
| MFE-23 (fresh) | 6.0 |
| MFE-23 (frozen) | 3.0 |
| D1.3 | 6.1 |
| F1 | 5.1 |
| GP6 | 3.1 |
| HuBC-1 | 2.1 |

Effective PPa:scFv coupling ratios determined by comparison to a PPa standard curve and correcting for 30% non-covalent binding.

Sequence alignment (FIG. 26) of the scFvs used in this study revealed that C6.5, which gives reproducible coupling and good singlet oxygen yields has more lysines which are predicted to be spatially separated compared with scFvs which make poorer PICs (HuBC-1, GP6 and F1).

Example 21

Preparation of Verteporfin (Visudyne™) Succinimidyl Ester (FIG. 27)

Verteporfin was obtained as described in Scherrer et al. (1986) *J. Org. Chem.* 51: 1094-1100.

1. The Verteporfin succinimidyl ester (FIG. 27; Compound 'b') was prepared as described for PPa. To a light-protected solution of verteporfin (6 mg) in dry THF (5 ml), N-hydroxysuccinimde (3 mg) was added followed by dicyclohexylcarbodiimide (DCC, 6 mg).
2. The reaction mixture was stirred for 12 h at room temperature under nitrogen at which point all starting material had been consumed.
3. The solvent was evaporated and the crude product purified by column chromatography on silica gel, loaded as a solution in DCM and eluting with ethyl acetate (Rf 0.74) to give pure verteporfin succinimidyl ester in 75% yield. MS (FAB+) 832 (M+).
4. A stock solution of C6.5 scFv at 500 μg/ml was defrosted at room temperature and 200 μl added to 706 μl of PBS. Acetonitrile (60 μl) was added to the solution. The solution was stirred on ice until cool.

Example 22

Conjugation of c6.5 scFv to Verteporfin (Visudyne™)—Solvent System 1

1. Verteporfin (Visudyne™) succinimidyl ester made up in 100% DMSO was then added (34 μl) from a stock solution of 1.58 mM to the C6.5 scFv with continuous stirring (to give 16 equivalents of Verteporfin (Visudyne™)). The mixture was kept on ice and in the dark, with stirring for 30 mins, after which time the solution was placed in dialysis tubing and dialysed against 5 L of PBS at 4° C. overnight in the dark.
2. Each sample of the conjugate was placed in a quartz cuvette and an absorbance profile was run against a blank containing PBS. The absorbance value at 410 nm was measured and the concentration of PS in g/ml was determined by comparing to a standard curve of Verteporfin (Visudyne™).

Example 23

Conjugation of MFE-23 (anti-CEA) scFv to Verteporfin (Visudyne™)—Solvent System 2

1. A stock solution of MFE-23 at 500 μg/ml was defrosted at room temperature and 200 μl added to 706 μl of PBS. Acetonitrile (60 μl) was added to the solution. The solution was stirred on ice until cool.
2. Verteporfin (Visudyne™) succinimidyl ester was then added (34 μl) from a stock solution of DMSO 1.58 mM to the MFE-23 with continuous stirring (to give 16 equivalents of Verteporfin (Visudyne™)). The mixture was kept on ice and in the dark, with stirring for 30 mins, after which time the solution was placed in dialysis tubing and dialysed against 5 L of PBS at 4° C. overnight in the dark.
3. Each sample of the conjugate was placed in a quartz cuvette and an absorbance profile run against a blank containing PBS. The absorbance value at 410 nm was measured and the concentration of PS in g/ml determined by comparing to a standard curve of Verteporfin (Visudyne™). The ratio therefore of Verteporfin (Visudyne™)):MFE-23 was between 8:1 and 10:1.

Example 24

Photophysical Characterisation of a scFV-Verteporfin (Visudyne™) Conjugate (FIG. 28)

1. Serial dilutions (halving concentrations) of the conjugates were made in PBS and the absorbance was measured at an excitation wavelength of 690 nm and an emission wavelength of 680 nm.
2. These were compared to free Verteporfin (Visudyne™) in PBS (FIG. 28).

Example 25

In Vitro Cytotoxicity of a c6.5 scFv-Verteporfin (Visudyne™) Conjugate (FIG. 29)

1. In vitro cell cytotoxicity was be measured as followed: The target cells (in this example, SKOV3 cells were used as antigen-positive cells and KB cells were used as antigen-negative cells) were maintained at 37° C., 5% $CO_2$ in media (DMEM) supplemented with 10% foetal calf serum and 5 mM penicillin/streptomycin in a 75 $cm^2$ flask. For SKOV3 cells, the medium used was McCoy's 5A medium supplemented with 15% FBS, 5 mM penicillin/streptomycin.
2. When 70-80% confluent, the cells were washed in PBS and 5 ml trypsin added. The flask was incubated at 37° C., 5% $CO_2$ for 15 mins or until the cells had detached from the flask. The cells were then placed in a 50 ml Falcon tube and the trypsin deactivated by adding 15 ml DMEM or McCoy's medium.
3. Cells (20 µl) were taken out of the tube and placed on a haemocytometer for counting. The remaining cells were harvested at 1800 g for 10 min at room temperature and the pellet gently resuspended in 1 ml of DMEM or McCoy's medium. The cells were thoroughly resuspended and a further 19 ml of DMEM or McCoy's medium added. The cells were diluted in DMEM or McCoy's medium accordingly to give $2\times10^6$ cells/ml. Cells (50 µl) were then added to each well of a 96 well plate and incubated overnight at 37° C. and 5% $CO_2$.
4. The following procedure was carried out in subdued lighting: The next day, the conjugate was diluted in PBS to give C6.5 concentrations equivalent to 100, 50, 25, 12.5, 6.25, 3.125, 1.56 and 0.78 µg/ml. Cells were washed once with PBS and 50 µl of the conjugate added to wells in quadruplicate. Control wells were also included (wells with conjugate added but not exposed to light, and wells with neither conjugate added nor exposed to light). It was ascertained in previous experiments that laser light alone had no affect on the cell viability, so no 'light alone' controls are included unless the light source, or energy dose of the light is changed.
6. Cells were incubated in the conjugate or free PS (concentration varies) for 30 min at 37° C., 5% $CO_2$ and then washed 3 times with PBS. PBS (50 µl) was added to each well and quadruplicate wells exposed to laser light for 2 min (energy dose=4.2 J; energy density=1.4 $J/cm^2$).
7. The PBS was removed from each well and 100 µl of DMEM or McCoy's medium added. The plates were loosely wrapped in foil, but covered adequately so that no ambient light could enter. The plates were then incubated as above for 48 hours, after which time a cell kill assay was carried out.
8. Cell kills assays were carried out using the Cytotox-96 kits (according to the Promega protocol). Cells were washed 3 times with PBS and 50 µl of cell lysis solution added. Plates were incubated for 60 minutes at 37° C. in the dark. After this time, 50 µl of substrate solution was added (which indicates the amount of lactate dehydrogenase in cells). This was incubated at room temperature for 30 min, after which time, 50 µl of stop solution (0.5M acetic acid) was added. The cell suspensions were removed from the wells and placed in a fresh microtitre plate. The absorbance was then measured at 690 nm in a microtitre plate reader.
9. Cell kills were determined and expressed as a percentage of controls (FIG. 29).

Results: The IC50s are as follows:
C6.5-Verteporfin (Visudyne™) conjugate on SKOV3 cells=2.2 µM;
C6.5-Verteporfin (Visudyne™) conjugate on KB cells=28.1 µM;
Verteporfin (Visudyne™) on SKOV3 cells=15.3 µM;
Verteporfin (Visudyne™) on KB cells=10 µM.

Thus, when targeted using the C6.5 scFv, Verteporfin (Visudyne™) is 7-fold more potent and 13-fold more specific.

Example 26

Pharmaceutical Formulations and Administration

A further aspect of the invention provides a pharmaceutical formulation comprising a compound according to the first aspect of the invention in admixture with a pharmaceutically or veterinarily acceptable adjuvant, diluent or carrier.

Preferably, the formulation is a unit dosage containing a daily dose or unit, daily sub-dose or an appropriate fraction thereof, of the active ingredient.

The compounds of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the compounds of the invention can be administered alone but will generally be administered in admixture with a suitable pharmaceutical excipient diluent or carrier selected with regard to the intended route of administration and standard pharmaceutical practice.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the compounds of the invention will usually be from 1 mg/kg to 30 mg/kg. Thus, for example, the tablets or capsules of the compound of the invention may contain a dose of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" delivers an appropriate dose of a compound of the invention for delivery to the patient. It will be appreciated that the overall daily dose with an aerosol will vary from patient to patient, and may be administered in a single dose or, more usually, in divided doses throughout the day.

Alternatively, the compounds of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route, particularly for treating diseases of the eye.

For ophthalmic use, the compounds of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or topical administration of the compounds of the invention is the preferred route, being the most convenient. In circumstances where the recipient suffers from a swallowing disorder or from impairment of drug absorption after oral administration, the drug may be administered parenterally, e.g. sublingually or buccally.

For veterinary use, a compound of the invention is administered as a suitably acceptable formulation in accordance with normal veterinary practice and the veterinary surgeon will determine the dosing regimen and route of administration which will be most appropriate for a particular animal.

REFERENCES

[1] Price & Sikora (eds). Treatment of Cancer. Chapman & Hall 1995
[2] Press, O W & Rasey, J (2000). Semin Oncol. 6, 62-73. Priciples of Radioimmunotherapy for hematologists and oncologists
[3] Affleck, K et al (1992). Br. J. Cancer 65, 838-844. Monoclonal antibody targeting of methotrexate (MTX) against MTX-resistant tumour cell lines.
[4] Beers R et al. (2000). Clin Cancer Res. 6, 2835-43. Immunotoxins with increased activity against epidermal growth factor receptor vIII-expressing cells produced by antibody phage display.
[5] Rosenkranz, A. A et al (2000). Immunol. And Cell Biol. 78, 452-64. Targeted intracellular delivery of photosensitizers to enhance photodynamic therapy.
[6] Dolmans et al. (2003). Nature Rev. Cancer 3, 380-386. Photodynamic therapy for cancer.
[7] Hudson P J. (2000). Expert Opin Investig Drugs 9, 1231-42 Recombinant antibodies: a novel approach to cancer diagnosis and therapy.
[8] Borsi L, Balza E, Carnemolla B, Sassi F, Castellani P, Berndt A, Kosmehl H, Biro A, Siri A, Orecchia P, Grassi J, Neri D & Zardi L (2003) Blood. 102, 4384-92. Selective targeted delivery of TNFalpha to tumor blood vessels.
[9] Kuby (2000). Immunology, 4$^{th}$ Ed. W. H. Freeman.
[10] Hoogenboom H R. Selecting and screening recombinant antibody libraries. Nature Biotechnology (2005) 23, 1105-16

[11] Milenic D E, Brady E D & Brechbiel M W (2004) Nat Rev Drug Discov. 3, 488-99. Antibody-targeted radiation cancer therapy.

[12] Harris M (2004) *Lancet Oncol.* 5, 292-302. Monoclonal antibodies as therapeutic agents for cancer.

[13] Wu A M and senter P D. Arming antibodies: Prospects and challenges for Immunoconjugates Nature Biotechnology (2005) 23, 1137-46 Improving the efficacy of antibody-based cancer therapies.

[14] Deonarain, M P, Rowlinson-Busza, G, George, A J & Epenetos, A A, (1997) Protein Eng. 10, 89-98. Redesigned anti-human placental alkaline phosphatase single-chain Fv: soluble expression, characterization and in vivo tumour targeting.

[15] Batra S K, Jain M, Wittel U A, Chauhan S C & Colcher D (2002) *Curr Opin Biotechnol.* 13, 603-8. Pharmacokinetics and biodistribution of genetically engineered antibodies.

[16] Boxer G M et al. (1994). Br. J. Cancer 69, 307-14. Localisation of monoclonal antibodies reacting with different epitopes on carcinoembryonic antigen (CEA)—implications for targeted therapy.

[17] Little M, Kyprianov S M, LeGall F & Moldenhauer G (2000). Immunol Today 21, 364-70. Of mice and men: hybridoma and recombinant antibodies.

[18] Verhaar M J et al. (1995). Int J Cancer 61, 497-501 A single chain Fv derived from a filamentous phage library has distinct tumor targeting advantages over one derived from a hybridoma.

[19] Begent, R H et al. (1996). Nat. Med. 2, 979-84 Clinical evidence of efficient tumor targeting based on single-chain Fv antibody selected from a combinatorial library.

[20] Epenetos A A, Snook D, Durbin H, Johnson P M, Taylor-Papadimitriou (1986). Cancer Res. 46, 3183-91. Limitations of radiolabeled monoclonal antibodies for localization of human neoplasms.

[21] Gangopadhyay, A et al. (1996). Nucl. Med. Biol. 23, 257-61 Modification of antibody isoelectric point affects biodistribution of 111-indium-labeled antibody.

[22] Chen S Y et al. (1995). Gene Ther. 2, 116-23. Design of a genetic immunotoxin to eliminate toxin immunogenicity.

[23] Deonarain M P & Epenetos A A (1998) Br. J. Cancer. 77, 537-46 Design, characterization and anti-tumour cytotoxicity of a panel of recombinant, mammalian ribonuclease-based immunotoxins.

[24] Linardou, H. et al. (2000). Int. J. Cancer 86, 561-569 A recombinant cytotoxic chimera based on mammalian deoxyribonuclease.

[25] Bonifacino J S & Traub L M (2003) Annu Rev Biochem. 72, 395-447. Signals for sorting of transmembrane proteins to endosomes and lysosomes.

[26] Ghettie, V. & Vitetta, E. (1994) *Pharmacol. Ther.* 63, 209-34. Immunotoxins in the therapy of cancer: from bench to clinic.

[27] Ancey C, Kuster A, Haan S, Herrmann A, Heinrich P C & Muller-Newen G (2003) *J. Biol. Chem.* 278, 16968-72. A fusion protein of the gp130 and interleukin-6Ralpha ligand-binding domains acts as a potent interleukin-6 inhibitor.

[28] Komer M, Waser B & Reubi J C (2005) *Int J Cancer* 115, 734-41. Neuropeptide Y receptors in renal cell carcinomas and nephroblastomas.

[29] Koide A, Bailey C W, Huang X & Koide S (1998) J Mol. Biol. 284, 1141-51. The fibronectin type III domain as a scaffold for novel binding proteins.

[30] Holt L J, Herring C, Jespers L S, Woolven B P & Tomlinson I M (2003) *Trends Biotechnol.* 21, 484-90. Domain antibodies: proteins for therapy.

[31] Schlehuber S & Skerra A (2001) *Biol. Chem.* 382, 1335-42. Duocalins: engineered ligand-binding proteins with dual specificity derived from the lipocalin fold.

[32] Binz H K, Amstutz P, Kohl A, Stumpp M T, Briand C, Forrer P, Grutter M G & Pluckthun A (2004) *Nat. Biotechnol.* 22, 575-82. High-affinity binders selected from designed ankyrin repeat protein libraries.

[33] Vasserot, A P et al (2003) Drug Discovery Today 8, 118-126. Optimization of protein therapeutics by directed evolution

[34] Hopper, C. (2000). Lancet Oncology 1, 212-219. Photodynamic therapy: a clinical reality in the treatment of cancer.

[35] Brown, S, Brown, E & Walker, I (2004) Lancet Oncology 5, 497-508. The present and future of photodynamic therapy in cancer treatment.

[36] Schmidt-Erfurth U. et al. (1999). Arch. Opthalmol. 117, 1329-1345. Treatment of Age-related Macular degeneration with photodynamic therapy (TAP) study group. Photodynamic therapy of subfoveal neovascularization in age-related macular degeneration with verteporfin.

[37] Leman J A & Morton C A (2002) Expert Opin Biol Ther. 2, 45-53. Photodynamic therapy: applications in dermatology.

[38] Yamaguchi A, Woodburn K W, Hayase M, Hoyt G, Robbins R C. (2001). Transplantation 71, 1526-32. Photodynamic therapy with motexafin lutetium (Lu-Tex) reduces experimental graft coronary artery disease.

[39] Pfitzner A, Sigusch B W, Albrecht V, Gloclmann E. (2004). J. Periodontol. 75, 1343-9. Killing of periodontopathogenic bacteria by photodynamic therapy.

[40] Demidova T N, Hamblin M R. (2004). Int J Immunopathol Pharmacol. 17, 245-54. Photodynamic therapy targeted to pathogens.

[41] Polo, L. et al. (1992). Cancer Letts 66, 217-23. The distribution of the tumour photosensitizers Zn(II)-phthalocyanine and Sn (IV)-etiopurpurin among rabbit plasma proteins.

[42] Moan J and Berg K (1992). Photochemotherapy of cancer-experimental research. Photochem. Photobiol. 55, 931-948

[43] Kessel D et al (2003). Localization and photodynamic efficacy of two cationic porphyins varying in charge distributions. Photochem. photobiol. 78, 431-435

[44] Dellinger, M et al. (1996). Photochem. Photobiol. 64, 182-7 Apoptosis or necrosis following Photfrin photosensitization: Influence of the incubation protocol.

[45] Ahmad, N. et al (1998). PNAS USA 95, 6977-6982. Photodynamic therapy results in induction of WAF1/CIP1/P21 leading to cell cycle arrest and apoptosis.

[46] Fiers, W. et al. (1998). Oncogene 18, 7719-7730. More than one way to die: apoptosis, necrosis and reactive oxygen species.

[47] Koudinova et al (2003) Int J. Cancer 104, 782-789. TOOKAD (Pd-bacteriopheophorbide)

[48] Dolmans D E, Kadambi A, Hill J S, Flores K R, Gerber J N, Walker J P, Rinkes I H, Jain R K, Fukumura D. (2002). Cancer Res. 62, 4289-94. Targeting tumor vasculature and cancer cells in orthotopic breast tumor by fractionated photosensitizer dosing photodynamic therapy.

[49] Melnikova V O, Bezdetnaya L N, Brault D, Potapenlo A Y, Guillemin F. (2000). Int J Cancer 88, 798-803. Enhancement of meta-tetrahydroxyphenylchlorin-sensitized photodynamic treatment on human tumor xenografts using a water-soluble vitamin E analogue, Trolox.
[50] Westerman et al. (1998) Int J. Cancer 76, 842-50. Long circulating half-life and high tumor selectivity of the photosensitizermeta tetrahydroxyphenylchlorin conjugated to polyethylene glycol in nude mice grafted with a human colon carcinoma
[51] van Nostrum (2004) Advances in Drug Delivery Rev. 56, 9-16. Polymeric micelles as carriers.
[52] Nordquist, R E & Chen W E (1996) WO9631237. Cancer treatment by photodynamic therapy in combination with an immunoadjuvant.
[53] Meade C & Hyde C (2004) Br. J. Opthal. 88, 212-217. Photodynamic therapy with verteporfin is effective, but how big is its effect? Results of a systematic review.
[54] Wyss P, Schwarz V, Dobler-Girdziunaite D, Hornung R, Walt H, Degen A, Fehr M. (2001) Int J Cancer 93, 720-24. Photodynamic therapy of locoregional breast cancer recurrences using a chlorin-type photosensitizer.
[55] Cuenca R E, Allison R R, Sibata C, Downie G H. (2004) Annals Surg. Oncol. 11, 322-27. Breast cancer with chest wall progression: treatment with photodynamic therapy
[56] Lou P J, Jager H R, Jones L, Theodossy T, Bown S G, Hopper C (2004). Br J. Cancer. 91, 441-6. Interstitial photodynamic therapy as salvage treatment for recurrent head and neck cancer.
[57] Jager H R, Taylor M N, Theodossy T, Hopper C. (2005). MR imaging-guided interstitial photodynamic laser therapy for advanced head and neck tumors. AJNR Am J. Neuroradiol. 26, 1193-200.
[58] Wagnieres G, Hadjur C, Grosjean P, Braichotte D, Savary J F, Monnier P & van den Bergh H (1998) Photochem Photobiol. 68, 382-7. Clinical evaluation of the cutaneous phototoxicity of 5,10,15,20-tetra(m-hydroxyphenyl)chlorin.
[59] Moriwaki S I, Misawa J, Yoshinari Y, Yamada I, Takigawa M, Tokura Y (2001) Photodermatol Photoimmunol Photomed. 17, 241-3. Analysis of photosensitivity in Japanese cancer-bearing patients receiving photodynamic therapy with porfimer sodium (Photofrin™).
[60] Murrer L H, Hebeda K M, Marijnissen J P & Star W M (1999) Br J Cancer 80, 744-55. Short- and long-term normal tissue damage with photodynamic therapy in pig trachea: a fluence-response pilot study comparing Photofrin™ and mTHPC.
[61] Baas P, van Mansom I, van Tinteren H, Stewart F A, van Zandwijk N (1995) Lasers Surg Med. 16, 359-67. Effect of N-acetylcysteine on Photofrin™-induced skin photosensitivity in patients.
[62] Nseyo U O, Shumaker B, Klein E A, Sutherland K (1998) J. Urol. 160, 39-44. Photodynamic therapy using porfimer sodium as an alternative to cystectomy in patients with refractory transitional cell carcinoma in situ of the bladder.
[63] Vrouenraets, M B, Visser G W, Stewart F A, Stigter M, Oppelaar H, Postmus P E, Snow G B, van Dongen G A. (1999). Cancer Res. 59, 1505-1513. Development of metatetrahydroxyphenylchlorin-monoclonal antibody conjugates for photoimmunotherapy.
[64] Vrouenraets, M B, Visser G W, Loup C, Meunier B, Stigter M, Oppelaar H, Stewart F A, Snow G B, van Dongen G A. (2000). Int. J. Cancer 88, 108-114. Targeting of a hydrophilic photosensitizer by use of internalizing monoclonal antibodies: A new possibility for use in photodynamic therapy.
[65] van Dougen G A M S, Visser G W M & Vrouenraets, M B (2004). Adv. Drug Del. Rev 56, 31-52. Photosensitizer-antibody conjugates for detection and therapy of cancer.
[66] Vrouenraets, M B, Visser G W M, Stigter M, Oppelaar H, Snow G & van Dongen G A M S (2001). Targeting pf aluminium (III) phthalocyanine tetrasulfonate by use of internalizing monoclonal antibodies: Improved efficacy in photodynamic therapy.
[67] Hudson, R, et al (2005). Br. J. Cancer 92, 1442-1449. The development and characterisation of porphyrin isothiocyanate-monoclonal antibody conjugates for photo-immunotherapy.
[68] Savellano M D, Pogue B W, Hoopes P J, Vitetta E S & Paulsen K D (2005). Cancer Res. 65, 6371-9. Multiepitope Her2 targeting enhances photoimmunotherapy of Her2 expressing cancer cells with pyropheophorbide-a immunoconjugates.
[69] Savellano M D & Hasan T (2005). Clin. Cancer. Res 11, 1658-1668. Photochemical targeting of epidermal growth factor receptor: a mechanistic study.
[70] Birchler M, Viti F, Zardi L, Spiess B, Neri D (1999). Nat. Biotechnol. 17, 984-8. Selective targeting and photocoagulation of ocular angiogenesis mediated by a phage-derived human antibody fragment.
[71] Roder B & Hackbarth S (2001). WO0108704. Dendrimer-photosensitizer complexes for medical applications.
[72] Westerman P, Glanzmann T, Andrejevic S, Braichotte D R, Forrer M, Wagnieres G A, Monnier P, van den Bergh H, Mach J P, Folli S (1998) Int J Cancer 76, 842-50. Long circulating half-life and high tumor selectivity of the photosensitizer meta-tetrahydroxyphenylchlorin conjugated to polyethylene glycol in nude mice grafted with a human colon carcinoma.
[73] Demidova T N, Hamblin M R (2004) Int J Immunopathol Pharmacol. 17, 245-5. Photodynamic therapy targeted to pathogens.
[74] Deonarain M P & Stafford S (2003). WO03015825. Conjugate
[75] Glickman R D, Mayo G L, Mckinnon S J, Melendez R E & Kumar N C (2004). WO 080284 A2. Antibody targeted photodynamic therapy
[76] Mayo G L, Melendez R F, Kumar N, McKinnon S J & Glickman R D (2003). Am. J. Opthalmol. 136, 1151-2. Antibody-targeted photodynamic therapy
[77] Hasan T, Savellano M D & Skobe M (2002) WO 02100326. Photoimmunotherapies for cancer using photosensitizer immunoconjugates and combination therapies
[78] Akhlynina T V, Jans D A, Rosenkranz A A, Statsyuk N V, Balashova I Y, Toth G, Pavo I, Rubin A B, Sobolev A S (1997). J. Biol. Chem. 272, 20328-20331. Nuclear targeting of chlorin e6 enhances its photosensitizing activity.
[79] Cavanaugh P G (2002) Breast Cancer Res Treat. 72, 117-30. Synthesis of chlorin e6-transferrin and demonstration of its light-dependent in vitro breast cancer cell killing ability.
[80] Cavanaugh P G (2002) US 20021337901. Synthesis and photodynamic therapy-mediated anti-cancer and other used of chlorin e6-transferrin.
[81] Khadem J, Veloso A A Jr, Tolentino F, Hasan T, Hamblin M R (1999). Invest Opthalmol V is Sci. 40, 3132-7. Photodynamic tissue adhesion with chlorin(e6) protein conjugates.
[82] Green A M (2002). WO 02/080754 A2. Methods for using annexin for detecting cell death in vivo and treating associate conditions.
[83] Storrie B, Tarrago-Trani S (2002). B/B-like fragment for the purposes of photodynamic therapy and medical imaging WO 02/067850

[84] Ray R & Mohr S. (2001) WO 0178606. Selective nuclear receptor-targeted systems for delivery of cytotoxins to cancer cells for targeted photodynamic therapy

[85] Gaboury L & Villeneuve L (1996) U.S. Pat. No. 5,556,992. Novel rhodamine derivatives for photodynamic therapy of cancer and in vitro purging of the leukemias

[86] Schneider R, Schmitt F, Frochot C, Fort Y, Lourette N, Guillemin F, Muller J F, Barberi-Heyob M. (2005). Bioorgan. Med chem. 13, 2799-2808. Design, synthesis, and biological evaluation of folic acid targeted tetraphenylporphyrin as novel photosensitizers for selective photodynamic therapy.

[87] Lutsenko S V, Feldman N B, Finakova G V, Posypanova G A, Severin S E, Skryabin K G, Kirpichnikov M P, Lukyanets E A, Vorozhtsov G N (1999). Tumour Biol. 20, 218-24. Targeting phthalocyanines to tumor cells using epidermal growth factor conjugates.

[88] Renno R Z, Terada Y, Haddadin M J, Michaud N A, Gragoudas E S, Miller J W. (2004). Arch Opthamol. 122, 1002-1011. Selective photodynamic therapy by targeted verteporfin delivery to experimental choroidal neovascularization mediated by a homing peptide to vascular endothelial growth factor receptor-2.

[89] Boehm M K, Corper A L, Wan T, Sohi M K, Sutton B J, Thornton J D, Keep P A, Chester K A, Begent R H, Perkins S J. (2000). Crystal structure of the anti-(carcinoembryonic antigen) single-chain Fv antibody MFE-23 and a model for antigen binding based on intermolecular contacts. Biochem J. 346, 519-28.

[90] Hoogenboom H R, Griffiths A D, Johnson K S, Chiswell D J, Hudson P & Winter G (1991) *Nucleic Acids Res.* 19, 4133-7. Multi-subunit proteins on the surface of filamentous phage: methodologies for displaying antibody (Fab) heavy and light chains.

[91] Enever C, Tomlinson I M, Lund J, Levens M & Holliger P (2005) *J. Mol. Biol.* 347, 107-20. Engineering high affinity superantigens by phage display.

[92] Li Y, Moysey R, Molloy P E, Vuidepot A L, Mahon T, Baston E, Dunn S, Liddy N, Jacob J, Jakobsen B K & Boulter J M (2005) *Nat. Biotechnol.* 23, 349-54. Directed evolution of human T-cell receptors with picomolar affinities by phage display.

[93] Embleton M L, Nair S P, Cookson B D & Wilson M (2002) J. Antimicrob. Chemother. 50, 857-864. Selective lethal photosensitization of methicillin-resistant *Staphylococcus aureus* using an IgG-tin(IV) chlorin e6 conjugate

[94] Garcia D I & Yahioglu, G (WO2004/046151). Porphyrin derivatives

[95] Sokous N S, Hamblin M R, Deutsch T F & Hasan T (2001). Monoclonal antibody tagged receptor targeted contrast agents for detection of cancer. Proceedings of SPIE, 4259, 115. Biomarkers and Biological Spectral imaging, Eds. Bearman G H, Levenson R M and Bornhop D J.

[96] Kim J I, Wang C, Kuizon S, Xu J, Barengolts D, Gray P C, Rubenstein R (2005). Simple and specific detection of abnormal prion protein by a magnetic bead-based immunoassay coupled with laser-induced fluorescence spectrofluorometry. J Neuroimmunol 158, 112-9.

[97] Pasqualini R, Koivunen E, Ruoslahti E. (1997). Alpha v integrins as receptors for tumor targeting by circulating ligands. Nat. Biotechnol. 15, 542-6.

[98] Rusckowski M, Qu T, Chang F, Hnatowich D J. (1997). Technetium-99m labeled epidermal growth factor-tumor imaging in mice. J Pept Res. 50, 393-401.

[99] Weissleder R, Tung C H, Mahmood U, Bogdanov A Jr. (1999). In vivo imaging of tumors with protease-activated near-infrared fluorescent probes. Nat. Biotechnol. 17, 375-8.

[100] Pericleous, L M, Richards, J, Epenetos, A A, Courtenay-Luck, N & Deonarain M P (2005). Characterisation and internalization of recombinant humanized HMFG1 antibodies against MUC1. Br J. Cancer. 93 pp 1257-66

[101] Ward E S. Antibody engineering: the use of *Escherichia coli* as an expression host. FASEB J. 1992; 6: 2422-7.

The invention claimed is:

1. A compound comprising a plurality of photosensitizing agents coupled to a carrier molecule obtainable by the process of
  (i) providing a photosensitizing agent;
  (ii) providing a carrier molecule;
  (iii) conjugating the photosensitizing agent and the carrier molecule in the presence of a first and a second polar aprotic solvent and an aqueous buffer,
  wherein the carrier molecule is a human or humanized scFv
  wherein the photosensitising agents are directly coupled at an amino acid residue of the carrier molecule so as to not sterically, chemically or photophysically interfere with each other when participating in chemical or photochemical reactions and which are coupled 3.5 to 7.5 angstroms, or 9 to 12 angstroms or 10-15 angstroms or 15-20 angstroms or 20-25 angstroms apart; and
  wherein the ratio of photosensitizing agent to carrier molecules is at least 3:1.

2. The compound of claim 1, wherein the carrier molecule binds selectively a target cell.

3. The compound according to claim 1 wherein the functional and physical properties of the photosensitizing agent and the carrier molecule are substantially unaltered in the coupled form in comparison, to the properties when in an uncoupled form.

4. The compound according to claim 1 wherein the photosensitizing agent is a monofunctional photosensitizer.

5. The compound according to claim 4 wherein the photosensitizing agent is at least one selected from the group consisting of: naturally-occurring chlorins; naturally-occurring bacteriochlorins; pheophorbides; palladium derivatives of naturally-occurring bacteriochlorophylls; palladium derivatives of palladium-bacteriopheophorbide; synthetic chlorins; synthetic bacteriochlorins; benzoporphyrin derivatives; monobenzoporphyrin derivatives; purpurins; and synthetic porphyrins.

6. The compound according to claim 4 wherein the photosensitizing agent is at least one selected from the group consisting of: pyropheophorbide a and derivatives thereof, chlorine e6, photochlor, mono-1-aspartyl derivatives of chlorin e6, di-1-aspartyl derivative of chlorine e6, tin(IV) chlorin e6, metatetrahydroxyphenyl chlorin, metatetrahydroxyphenyl, bacteriochlorin, verteporfin, and purpurin-18.

7. The compound according to claim 1 wherein the amino acid residue is selected from the group consisting of: lysine; cysteine; tyrosine; serine; glutamate; aspartate; and arginine.

8. The compound according to claim 1 wherein the distance between photosensitizing agents coupled to the carrier molecule is between 3.5 angstroms and 25 angstroms.

9. The compound according to claim 8 wherein the distance between photosensitizing agents coupled to the carrier molecule is between 20 and 25 angstroms.

10. The compound according to claim 1 wherein the photosensitizing agent is Pyropheophorbide a.

11. The compound according to claim 1 wherein the photosensitizing agent is benzoporphyrin derivative mono acid (Verteporfin).

12. The compound according to claim 1 wherein the photosensitizing agent is palladium-bacteriopheophorbide.

13. The compound according to claim 1 wherein the photosensitizing agent is mono-1-aspartyl derivative of chlorin e6.

14. The compound according to claim 1 wherein the photosensitizing agent is meta-tetrahydroxyphenyl chlorin.

15. The compound according to claim 1 wherein the photosensitizing agent is tin etiopurpurin (rostaporfin).

16. A pharmaceutical composition comprising the compound of claim 1 and a pharmaceutically-acceptable carrier, excipient or diluent.

* * * * *

UNITED STATES PATENT AND TRADEMARK OFFICE
CERTIFICATE OF CORRECTION

PATENT NO. : 8,703,427 B2  Page 1 of 1
APPLICATION NO. : 12/089406
DATED : April 22, 2014
INVENTOR(S) : Deonarain et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 838 days.

Signed and Sealed this

Twenty-ninth Day of September, 2015

Michelle K. Lee
*Director of the United States Patent and Trademark Office*